US008163938B2

(12) United States Patent
Jung et al.

(10) Patent No.: US 8,163,938 B2
(45) Date of Patent: *Apr. 24, 2012

(54) AMINOCYCLOHEXYL ETHER COMPOUNDS AND USES THEREOF

(75) Inventors: Grace Jung, New Westminster (CA); Bertrand M. C. Plouvier, Vancouver (CA); Yuzhong Liu, Vancouver (CA); Jeff Jiqun Zhu, High Point, NC (US); Tao Sheng, Westwood, MA (US); Anthony G. M. Barrett, Chiswick (GB); Lewis Siu Leung Choi, Burnaby (CA); Doug Ta Hung Chou, Vancouver (CA)

(73) Assignee: Cardiome Pharma Corp., Vancouver, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/833,423

(22) Filed: Jul. 9, 2010

(65) Prior Publication Data
US 2011/0004006 A1 Jan. 6, 2011

Related U.S. Application Data

(63) Continuation of application No. 11/690,361, filed on Mar. 23, 2007, now Pat. No. 7,767,830, which is a continuation of application No. 10/555,364, filed as application No. PCT/US03/34655 on Oct. 31, 2003, now abandoned.

(60) Provisional application No. 60/467,159, filed on May 2, 2003, provisional application No. 60/476,083, filed on Jun. 4, 2003, provisional application No. 60/475,884, filed on Jun. 5, 2003, provisional application No. 60/475,912, filed on Jun. 5, 2003, provisional application No. 60/476,447, filed on Jun. 5, 2003, provisional application No. 60/489,659, filed on Jul. 23, 2003, provisional application No. 60/493,392, filed on Aug. 7, 2003.

(51) Int. Cl.
C07D 207/12 (2006.01)
A61K 31/40 (2006.01)

(52) U.S. Cl. ........................................ 548/541; 514/424

(58) Field of Classification Search .................. 548/541; 514/424
See application file for complete search history.

(56) References Cited

U.S. PATENT DOCUMENTS

| 2,954,380 | A | 9/1960 | Shapiro et al. ............... 260/268 |
| 3,218,328 | A | 11/1965 | Shapiro et al. ............... 260/294 |
| 4,145,435 | A | 3/1979 | Szmuszkovicz ............... 424/274 |
| 4,179,501 | A | 12/1979 | Szmuszkovicz ............... 424/226 |
| 4,598,087 | A | 7/1986 | Horwell ........................ 514/429 |
| 4,656,182 | A | 4/1987 | Horwell ........................ 514/324 |
| 4,663,343 | A | 5/1987 | Horwell et al. ............... 514/429 |
| 4,855,316 | A | 8/1989 | Horwell et al. ............... 514/422 |
| 4,880,800 | A | 11/1989 | Wallis et al. .................. 514/211 |
| 4,906,655 | A | 3/1990 | Horwell et al. ............... 514/422 |
| 5,019,588 | A | 5/1991 | Horwell et al. ............... 514/409 |
| 5,051,428 | A | 9/1991 | Horwell et al. ............... 514/320 |
| 5,059,620 | A | 10/1991 | Stout et al. .................... 514/422 |
| 5,492,825 | A | 2/1996 | Jan et al. ..................... 435/240.2 |
| 5,506,257 | A | 4/1996 | MacLeod et al. ............. 514/422 |
| 5,597,818 | A | 1/1997 | Sanguinetti et al. .......... 514/221 |
| 5,637,583 | A | 6/1997 | MacLeod et al. ............. 514/212 |
| 5,670,335 | A | 9/1997 | Jan et al. ........................ 435/29 |
| 5,728,535 | A | 3/1998 | Lester et al. ................... 435/7.2 |
| 5,734,021 | A | 3/1998 | Lester et al. .................. 530/350 |
| 5,750,537 | A | 5/1998 | Nomura et al. ............... 514/304 |
| 5,817,698 | A | 10/1998 | Brown et al. ................. 514/646 |
| 5,885,984 | A | 3/1999 | MacLeod et al. ............. 514/211 |
| 6,150,357 | A | 11/2000 | Salata et al. .................. 514/221 |
| 6,174,879 | B1 | 1/2001 | MacLeod et al. ......... 514/212.01 |
| 6,180,632 | B1 | 1/2001 | Myers et al. ................ 514/252.1 |
| 6,210,809 | B1 | 4/2001 | Okutomi et al. .............. 428/546 |
| 6,214,810 | B1 | 4/2001 | Fermini et al. .................. 514/75 |
| 6,399,618 | B1 | 6/2002 | Zolotoy et al. ............ 514/255.01 |
| 6,451,819 | B2 | 9/2002 | Alanine et al. ................ 514/326 |
| 6,521,619 | B2 | 2/2003 | Link et al. ................... 514/237.2 |
| 6,649,603 | B2 | 11/2003 | Sum ........................ 514/210.01 |
| 6,979,685 | B1 | 12/2005 | Beatch et al. ............... 514/231.2 |
| 7,053,087 | B1 | 5/2006 | Beatch et al. ............... 514/237.8 |
| 7,101,877 | B2 | 9/2006 | Bain et al. .................. 514/231.2 |
| 7,259,184 | B2 | 8/2007 | Beatch et al. ................ 514/424 |
| 7,345,087 | B2 | 3/2008 | Beatch et al. ................ 514/424 |
| 2004/0049049 | A1* | 3/2004 | Jurayj et al. .................. 546/329 |
| 2005/0026993 | A1 | 2/2005 | Beatch et al. ................ 514/424 |
| 2005/0038256 | A1 | 2/2005 | Barrett et al. ................ 546/236 |
| 2005/0070552 | A1 | 3/2005 | Fedida et al. ............. 514/255.06 |
| 2005/0119315 | A1 | 6/2005 | Fedida et al. ................ 514/355 |
| 2005/0209307 | A1 | 9/2005 | Bain et al. ......................... 514/1 |
| 2006/0247300 | A1 | 11/2006 | Beatch et al. ................ 548/557 |

(Continued)

FOREIGN PATENT DOCUMENTS

CA 1234808 4/1988

(Continued)

OTHER PUBLICATIONS

Adcock et al., "RSD931, a novel anti-tussive agent acting on airway sensory nerves", Br J Pharm 138(3):407-416, 2003.
Altria et al., "Capillary Electrophoresis as a Routine Analytical Tool in Pharmaceutical Analysis", LCGC 19(9): 972-985, Sep. 2001.
Amin et al., "RPR 101821, a New Potent Cholesterol-lowering Agent. Inhibition of Squalene Synthase and 7-Dehydrocholesterol Reductase", Naunyn-Schmiedeberg's Arch Pharmacol 353:233-240, 1996.
Alzheimer's Disease Information Page [online], [retrieved on Oct. 3, 2006]. Retrieved from the Internet, URL: <http://www.ninds.nih.gov/disorders/alzheimersdisease/alzheimersdisease.htm>.
Bain et al., "Better Antiarrhythmics? Development of Antiarrhythmic Drugs Selective for Ischaemia-Dependent Arrhythmias", Drug Development Research 42:198-210, 1997.

(Continued)

Primary Examiner — Robert Havlin
(74) Attorney, Agent, or Firm — Seed IP Law Group PLLC

(57) ABSTRACT

Aminocyclohexyl ether compounds are disclosed. The compounds of the present invention may be incorporated in compositions and kits. The present invention also discloses uses for the compounds and compositions, including the treatment of arrhythmia.

5 Claims, 165 Drawing Sheets

U.S. PATENT DOCUMENTS

| | | | |
|---|---|---|---|
| 2006/0252753 A1 | 11/2006 | Beatch et al. | 514/237.5 |
| 2007/0004718 A1 | 1/2007 | Bain et al. | 514/232.2 |
| 2007/0099983 A1 | 5/2007 | Barrett et al. | 514/424 |
| 2007/0190156 A1 | 8/2007 | Beatch et al. | 424/489 |
| 2007/0197632 A1 | 8/2007 | Beatch et al. | 514/424 |

FOREIGN PATENT DOCUMENTS

| | | |
|---|---|---|
| CA | 1235122 | 4/1988 |
| CA | 2004575 | 6/1990 |
| CA | 2058502 | 6/1993 |
| CA | 2172513 | 3/1995 |
| CA | 2244209 A1 | 7/1997 |
| CA | 2240728 | 9/1997 |
| CA | 2008391 | 12/1997 |
| CA | 2289055 | 1/1999 |
| CA | 2268590 | 10/2000 |
| CA | 2132841 | 3/2001 |
| CN | 1303364 | 7/2001 |
| DE | 2 259 260 | 6/1974 |
| DE | 2 658 401 | 7/1978 |
| DE | 3 517 901 | 12/1985 |
| EP | 222533 A1 | 5/1987 |
| EP | 147085 A2 | 3/1990 |
| EP | 147085 B1 | 3/1990 |
| EP | 372466 A2 | 6/1990 |
| EP | 372466 A3 | 6/1990 |
| EP | 380063 A1 | 8/1990 |
| EP | 380063 B1 | 8/1990 |
| EP | 552386 A1 | 7/1993 |
| EP | 720605 | 7/1996 |
| HU | 215963 B | 2/1995 |
| JP | 02-270864 | 11/1990 |
| WO | WO 93/19056 | 9/1993 |
| WO | WO 94/07843 | 4/1994 |
| WO | WO 94/14435 | 7/1994 |
| WO | WO 95/08544 | 3/1995 |
| WO | WO 95/28155 | 10/1995 |
| WO | WO 96/18615 | 6/1996 |
| WO | WO 96/23894 | 8/1996 |
| WO | WO 97/32857 | 9/1997 |
| WO | WO 97/49680 | 12/1997 |
| WO | WO 99/02159 | 1/1999 |
| WO | WO 99/03468 | 1/1999 |
| WO | WO 99/11252 | 3/1999 |
| WO | WO 99/16431 | 4/1999 |
| WO | WO 99/50205 | 10/1999 |
| WO | WO 99/50225 | 10/1999 |
| WO | WO 00/47547 | 8/2000 |
| WO | WO 00/51981 | 9/2000 |
| WO | WO 01/96335 | 12/2001 |
| WO | WO 03/105756 | 12/2003 |
| WO | WO 2004/008103 | 1/2004 |
| WO | WO 2004/098525 | 11/2004 |
| WO | WO 2004/099137 | 11/2004 |

OTHER PUBLICATIONS

Barrett and Walker, "Glibenclamide Possesses Transient, Ischaemia Selective Class III Antiarrhythmic Actions But Does Not Prevent Ischaemic Arrhythmias", BPS Proceedings 116P, 1996.

Barrett et al., "A Model of Myocardial Ischemia for the Simultaneous Assessment of Electrophysiological Changes and Arrhythmias in Intact Rabbits", J Pharmacol Toxicol Methods 37(1):27-36, 1997.

Barrett et al., "Ischaemia selectivity confers efficacy for suppression of ischaemia-induced arrhythmias in rats", Eur J Pharm 398:365-374, 2000.

Barrett et al., "Atypical Dose Response Curves for Antiarrhythmic Drugs", BPS Proceedings 115P, 1996.

Barrett, "Ischemia Selective Electrophysiological and Antiarrhythmic Actions of RSD1019 in Ischemic Cardiac Tissue", J Mol Cell Cardiol 29:197, 1997.

Barrett et al., "RSD1019 suppresses ischaemia-induced monophasic action potential shortening and arrhythmias in anaesthetized rabbits", Br J Pharm 131(3):405-414, 2000.

Beatch et al., "RSD1235 Selectively Prolongs Atrial Refractoriness and Terminates AF in Dogs with Electrically Remodelled Atria", Pharmacologist 44(2) (Supp I), A15: XIVth World Congress of Pharmacology: Meeting Abstracts, 2002. Abstract No. 22.11.

Beatch et al., "Effect of a Novel Anti-tussive Compound CP1 Against Citric Acid Induced Cough in Guinea-Pigs", Proc West Pharmacol Soc, 44:252, 2001.

Beatch et al., "Electrophysiological Profile of RSD1235, a New Drug for Conversion of Atrial Fibrillation", Abstract of U.S. Appl. No. 10/674,684, filed Sep. 29, 2003, now U.S. Patent No. 7,101,877 issued Sep. 5, 2006.

Beatch et al., "RSD1235 Rapidly and Effectively Terminates Atrial Fibrillation", Abstract submission ESC Congress Aug. 30-Sep. 3, 2003, in Vienna, Austria.

Beatch et al., "RSD1235, a Novel Atrial-Selective Antiarrhythmic Drug, Shows Rapid and Extensive Oral Absorption in Man", 12th International Congress on Cardiovascular Pharmacotherapy, May 7-10, 2003, Barcelona, Spain.

Beatch et al., "Ventricular Fibrillation, an Uncontrolled Arrhythmia Seeking New Targets", Drug Develop Res 55:45-52, 2002.

Beatch, "Antihistamine-induced Ventricular Arrhythmias", BPS Proceedings 120P, 1996.

Beatch et al., "Characterization of a Non-Human Primate Model of Drug-Induced Torsades De Pointes", Proc West Pharmacol Soc 40:13-16, 1997.

Beatch et al., "RSD1235 Selectively Prolongs Atrial Refractoriness and Terminates AF in Dogs with Electrically Remodelled Atria", PACE 24(Part II):698. Abstract 702, May 10, 2002.

Beatch et al., SIPO English Abstract for CN 1303364 issued Jul. 11, 2001.

Bian et al., "Effects of Kappa-opioid receptor stimulation in the heart and the involvement of protein kinase C", Brit J Pharmacol 124:600-606, 1998.

Billman, "RSD-1235", Curr Opin Investigational Drugs 4(3):352-354, 2003.

Boiadjiev and Lightner, "pH-Sensitive Exciton Chirality Chromophore. Solvatochromic Effects on Circular Dichroism Spectra", Tetrahedron: Asymmetry 7(10):2825-2832, 1996.

Bowen et al., "Characterization of the Enantiomers of cis-N-[2-(3,4-Dichlorophenyl)Ethyl]-N-Methy1-2-(1-Pyrrolidinyl)Cyclohexylamine (BD737 and BD738): Novel Compounds with High Affinity, Selectivity and Biological Efficacy at Sigma Receptors", J Pharmacol Exp Ther 262(1):32-40, 1992.

Cardiome Pharma Corp. (Jan. 31, 2001). "Nortran Drug Effective in Atrial Arrhythmia Model" (http://cardiome.com/wordpress/?p=104). Press Release.

Cardiome Pharma Corp. (Jun. 21, 2001). "Nortran Antiarrhythmia Drug Demonstrates Oral Bioavailability" (http://cardiome.com/wordpress/?p=99). Press Release.

Cardiome Pharma Corp. (Jul. 30, 2001). "Cardiome Pharma Completes Phase I Safety Study" (http://cardiome.com/wordpress/?p=97). Press Release.

Cardiome Pharma Corp. (Jan. 17, 2002). "Cardiome Reports Dosing of First Patient in Pivotal Phase II Study" (http://cardiome.com/wordpress/?p=90). Press Release.

Cardiome Pharma Corp. (Sep. 3, 2002). "Cardiome Drug Effective for Heart Patients" (http://cardiome.com/wordpress/?p=75). Press Release.

Cardiome Pharma Corp. (Dec. 5, 2002). "Cardiome Reports Oral Absorption of RSD1235 in Humans" (http://cardiome.com/wordpress/?p=72). Press Release.

Cardiome Pharma Corp. (Dec. 20, 2004). "Cardiome's Pivotal AF Study Achieves Primary Endpoint" (http://cardiome.com/wordpress/? p=14). Press Release.

Cardiome Pharma Corp. (Feb. 4, 2005). "Cardiome Reports Additional ACT 1 Clinical Results" (http://cardiome.com/wordpress/?p=2). Press Release.

Cardiome Pharma Corp. (Apr. 25, 2005). "Cardiome Successfully Completes Second Phase 1 Trial" (http://cardiome.com/wordpress/?p=230). Press Release.

Cardiome Pharma Corp. (Aug. 31, 2005). "Cardiome Successfully Completes RSD1235 Oral Phase 1 Trial" (http://cardiome.com/wordpress/?p=255). Press Release.

Cardiome Pharma Corp. (Sep. 29, 2005). "Cardiome and Astellas Announce Positive Results from Second Phase 3 Trial" (http://cardiome.com/wordpress/?p=262). Press Release.
Cardiome Pharma Corp. (May 5, 2006). "Cardiome Reports Additional Phase 1 Trial Data for Oral RSD1235" (http://cardiome.com/wordpress/?=291). Press Release.
Cardiome Pharma Corp. (Jul. 24, 2006). "Cardiome Announces Interim Phase 2A Results for Oral RSD1235" (http://cardiome.com/wordpress/?p=312). Press Release.
Cardiome Pharma Corp. (Sep. 13, 2006). "Cardiome Announces Positive Phase 2A Results for Oral RSD1235" (http://cardiome.com/wordpress/?p=321). Press Release.
Cardiome Pharma Corp. Healthcare (Underweight) Company Report Dec. 12, 2002. 26 pages.
Clohs and Wong, "Validation of a capillary electrophoresis assay for assessing the metabolic stability of verapamil in human liver microsomes", J Cap Elec & Microchip Tech. 007(5/6):113-117, 2002.
Clohs, "Capillary Electrophoresis and its Applications in The Pharmaceutical Industry—Short Course: One Platform Fits Many Applications", CSC 2002, 52 pages.
Clohs, "Capillary Electrophoresis as an Analytical Tool in the Drug Discovery Process", Presentation CE Symposium, Aug. 2000, 40 pages.
Clohs, "The Versatility of CE for Drug Pharmacokinetics and Metabolism Studies", CE in the Biotechnology & Pharmaceutical Industries (Symposium), Boston, Aug. 2001, 46 pages.
Clohs, "Pharmacokinetics profiling of new drug candidates: a key process in drug discovery", Beckman Coulter P/ACE Setter 4(1):6, Jun. 2000.
Clohs and Winstanley, "CE Analysis of Propranolol in Human Serum Using Dynamic Capillary Coating", CE Currents: LCGC Europe, Reader Service 14, pp. 289-293, May 2002.
Clohs, "Bio-Analytical Applications of Capillary Electrophoresis in a Drug Discovery Setting", CSC Seminar, Jun. 5, 2002, 29 pages.
Clohs, "CE and Drug Metabolism Studies: A Powerful Combination in Drug Discovery", CE in the Biotechnology and Pharmaceutical Industries (Symposium), Washington, DC, Aug. 2002, 31 pages.
Crotti et al., "Regiochemical control of the ring-opening of epoxides by means of chelating processes Part 13 . . . ", Chemical Abstracts 129(17):662-663, Abstract No. 216472k, 1998.
Crotti et al., "Synthesis and Ring-Opening Reactions of the Diastereoisomeric cis- and trans-Epoxides Derived from 3-(Benzyloxy)cyclopentene and 2-(Benzyloxy)-2,5-dihydrofuran", Eur J Org Chem 8:1675-1686, 1998.
De Costa et al., "Synthesis and Evaluation of N-Substituted cis-N-Methyl-2-(1-pyrrolidinyl)cyclohexylamines as High Affinity a Receptor Ligands. Identification of a New Class of Highly Potent and Selective σ Receptor Probes", J Med Chem 33:3100-3110, 1990.
Doci et al., "Local Anesthetic Effects of Intradermal RSD921 in Healthy Subjects", Proceedings of the 100th Annual Meeting of the American Society for Clinical Pharmacology and Therapeutics, San Antonio, Texas, Mar. 18-20, 1999, Abstract PIII-2 in Clin Pharm & Therap 65(2):177, Feb. 1999.
Duan et al., "Potassium Channel Blocking Properties of Propafenone in Rabbit Atrial Myocytes", J Pharm Exp Ther 264(3): 1113-1123, 1993.
Ezrin et al., "Safety and Pharmacokinetics of RSD1235, a Novel Atrial Fibrillation Converting Drug, in Healthy Volunteers", Abstracts: 11th Int. Congress Cardiovasc. Pharmacother. 16 Abstract P297, 2002.
Ezrin et al., "A Dose-Ranging Study of RSD1235, A Novel Antiarrhythmic Agent, In Healthy Volunteers", Pharmacologist, 44(2) (Supplement I), A15: XIVth World Congress of Pharmacology: Meeting Abstracts, 2002. Abstract No. 22.10.
Fedida et al., "Kv1.5 is an Important Component of Repolarizing K$^+$ Current in Canine Atrial Myocytes", Circulation Research Peer Review Plus Manuscript PDF, 38 pages, 2002.
Franciosi et al., "Phase II Clinical Trial of RSD921 as a Local Anaesthetic in Patients Undergoing Venous Cannulation for Elective Treatment", in Proceedings of the 28th Annual ACCP Meeting Abstract 32, p. 977, Feb. 2000.

Franciosi and McLarnon, "pH-dependent blocking actions of three novel antiarrhythmic compounds on K$^+$ and Na$^+$ currents in rat ventricular myocytes", Eur J Pharm 425:95-107, 2001.
Franqueza et al., "Effects of propafenone and 5-hydroxy-propafenone on hKv1.5 channels", Br J Pharm 125:969-978, 1998.
Friess et al., "Central Activity Evoked in the Cat by Cis-Trans Isomers of 1,2-Aminocyclohexanol Dervivatives", Taxicol Appl Pharmacol 3:638-653, 1961.
Grant, "Mechanisms of Atrial Fibrillation and Action of Drugs Used in its Management", Am J Cardiol 82:43N-49N, Oct. 16, 1998.
Halfpenny et al., "Highly Selective k-Opioid Analgesics. 3. Synthesis and Structure-Activity Relationships of Novel N-[2-(1-Pyrrolidinyl)-4- or -5-substituted-cyclohexyl]arylacetamide Derivatives", J Med Chem 33:286-291, 1990.
Halfpenny et al., "Highly Selective k-Opioid Analgesics. 2. Synthesis and Structure-Activity Relationships of Novel N-[(2-Aminocyclohexyl)aryl]acetamide Derivatives", J Med Chem 32:1620-1626, 1989.
Hanson, "Protecting Groups in Organic Synthesis," Blackwell Science, Inc., Malden, MA, 1999, pp. 10-11.
Hayes et al., "RSD 992 Enhances Erection and Copulation in Rats and Erection in Primates", Int J Impotence Res, p. 189 (Abstract P24), 1996.
Hayes et al., "Actions of Arylpiperazines on Corpus Cavernosum Smooth Muscle In Vitro", Asia Pac J Pharmacol 12:97-103, 1997.
Hayes et al., "Direct Actions of Arylpiperazines on Rabbit and Human Corpus Caversonal Smooth Muscle In Vitro", Asia Par J Pharmacol, Abstract S15, 1997.
Hesketh et al., "Safety of RSD1235 in a rabbit Purkinje fiber model", in Proceedings of the XIVth World Congress of Phar. Meeting, Abstract No. 22.12, 2002.
Keefe et al., "New Antiarrhythmic Drugs: Their Place in Therapy", Drugs 22:363-400, 1981.
Kertesz et al., "The Electrophysiological and Antiarrhythmic Actions of RSD Analogs of U50,488H in Rats", in Proceedings of the West Pharmacol Soc. 9 pages, 1994.
Lang et al., "Clinical Evaluation of RSD921 as a Local Anaesthetic in Patients Undergoing Venous Cannulation for Elective Treatment", Clin Pharm & Therapeutics, p. 142, Feb. 2000. Abstract PIII-1.
Lewis et al., "Enzyme inhibition during the conversion of squalene to cholesterol", Steroids 60:475-483, Jul. 1995.
Li et al., "Adrenergic Modulation of Ultrarapid Delayed Rectifier K$^+$ Current in Human Atrial Myocytes", Circ Res 78(5):903-915, May 1996.
Malayev et al., "Mechanism of Clofilium Block of the Human Kv1.5 Delayed Rectifier Potassium Channel", Mol Pharm 47:198-205, 1995.
Martens et al., "Einfache Synthese neuer anellierter Pyrrole", J Synth Org Chem 12:965-967, Dec. 1989.
Matyus et al., "Antiarrhythmic Agents: Current Status and Perspectives", Medicinal Research Reviews 17(5):427-451, 1997.
McLarnon et al., "Mixed Block of K$^+$ and Na$^+$ Currents by KC8851, A Structural Analogue of Tedisamil In Vitro and In Vivo Studies", BPS Proceedings 114P, 1996.
Moorman et al., "pK$_a$ Does Not Predict pH Potentiation of Sodium Channel Blockade by Lidocaine and W6211 in Guinea Pig Ventricular Myocardium", The Journal of Pharmacology and Experimental Therapeutics 238(1):159-166, 1986.
Morisawa et al., "Preparation of fluorocarbocyclic nucleosides as antitumor agents", Chemical Abstracts 115(5):904-905, abstract No. 50215n, 1991.
Nakashima et al., "Angiotensin II Type I Receptor Antagonist Prevents the Promotion of Atrial Fibrillation", PACE 24(Part II):698, May 10, 2002. Abstract 701.
Nattel et al., "Effects of the novel antiarrhythmic agent azimilide on experimental atrial fibrillation and atrial electrophysiologic properties", Cardiovascular Research 37:627-635, 1998.
Nattel et al., "RSD1235: a novel antiarrhythmic agent with a unique electrophysiological profile that terminates AF in dogs", Eur. Heart J 22(Suppl):448 (Abstract P2362), 2001.
Nattel, "Experimental evidence for proarrhythmic mechanisms of antiarrhythmic drugs", Cardiovascular Research 37:567-577, 1998.

Nattel et al., "The Role of Channel Opening in Transient Outward Current Block by Quinidine, Flecainide, and 4-Aminopyridine in Human Atrial Myocytes", K Channels II: Regulation and Block, Abstract No. Tu-Pos403, 1994.

Nishi et al., "Studies on 2-Oxoquinoline Derivatives as Blood Platelet Aggregation Inhibitors. IV. Synthesis and Biological Activity of the Metabolites of 6-[4-(1-Cyclohexyl-1H-5-tetrazolyl)butoxy]-2-oxo-1,2,3,4-tetrahydroquinoline (OPC-13013)", Chem. Pharm. Bull 33(3):1140-1147, 1985.

Orth et al., "Cyclopentane-1-amines", Chemical Abstracts 89(15):555, Abstract No. 129113f, 1978.

Orth et al., "The Novel AF Conversion Agent RSD1235 Preferentially Blocks a Late Component of the Human Heart (hH1) $Na^+$ Current Active During Repolarization", EP abstracts Oct. 3, 2003.

Plouvier et al., "Synthesis and Structure Activity Relationships of a Series of 2-Aminocyclohexyl ..as Potential Ischaemia Selective Ventricular Antiarrhythmics", BMPS 994.

Pugsley and Goldin, "Molecular analysis of the $Na^+$ channel blocking actions of the novel class I antiarrhythmic", Br J Pharm 127:9-18, 1999.

Pugsley et al., "A Characterization of the Antiarrhythmic and Electrophysiological Properties of RSD992, A Novel Arylpiperazine Drug", XIVth World Congress of Pharmacology: Meeting Abstract 22.8, in Pharmacologist 44(2, Supp 1):A15, 2002.

Pugsley et al., "Electropharmacology of Two New Class 1 agents", Heart and Stroke Annual Conference, p. 12, 1995.

Pugsley et al., "Sodium Channel-Blocking Properties of Spiradoline, a Kappa Receptor Agonist, are Responsible for its Antiarrhythmic Action in the Rat", J Cardiovas Pharmacol 32:863-874, 1998.

Pugsley et al., "Are the arrhythmias due to myocardial ischaemia and infarction dependent upon the sympathetic system?", Cardiol Res 43:830-831, 1999.

Ribeiro et al., "Determination of RSD921 in human plasma by high-performance liquid chromatography-tandem mass spectrometry using tri-deuterated RSD921 as internal standard: application to a phase I clinical trial", J Mass Spectrom 36:1133-1139, 2001.

Rich et al., "Quinidine Block of the Human Cardiac hKv1.5 Channel in Inside-Out Patches, K Channels II: Regulation and Block", Abstract No. Tu-Pos404, p. A209, 1999.

Roden and George, "The Cardiac Ion Channels: Relevance to Management of Arrhythmias", Annu Rev Med 47:135-148, 1996.

Roy et al., "RSD1235 Rapidly and Effectively Terminates Atrial Fibrillation", Eur Heart J, p. 3699, 2003.

Rynbrandt et al., "Cis-1-[2-(p-Anisidinomethyl)cyclohexyl]piperidine and Related Compounds. Oral Hypoglycemic Agents", J Med Chem 14(10): 985-987, 1971.

Sanguinetti, "Modulation of Potassium Channels by Antiarrhythmic and Antihypertensive Drugs", Hypertension 19(3):228-236, Mar. 1992.

Singh, "Antiarrhythmic Drugs: A Reorientation in Light of Recent Developments in the Control of Disorders of Rhythm", Am J Cardiol 81(6A):3D-13D, Mar. 19, 1998.

Singh, "Atrial Fibrillation: Epidemiologic Considerations and Rationale for Conversion and Maintenance of Sinus Rhythm", J Cardiovasc Pharmacol Therapeut 8(Supp 1):S13-S26, 2003.

Snyders et al., "A Rapidly Activating and Slowly Inactivating Potassium Channel Cloned from Human Heart", J. Gen. Physiol. 101:513-543, Apr. 1993.

Snyders and Yeola, "Determinants of Antiarrhythmic Drug Action—Electrostatic and Hydrophobic Components of Block of the Human Cardiac hKv1.5 Channel", Circ Res 77(3):575-583, Sep. 1995.

Srilatha et al., "Alterations in Rabbit Corpus Cavernosal Pharmacology by High Cholesterol Diet", Asia Par J Pharmacol, Abstract S15, 1997.

Steinbeck, "Proarrhythmische Wirkungen von Antiarrhythmika—Theoretische and Klinische Aspekte", Z Kardiol 81(Supp 4):139-143, 1992.

Stevenson, Atrial Fibrillation and Heart Failure—Five More Years, N Engl J Med 351(23):2437-2440, Dec. 2, 2004.

Tong et al., "Determination of an arylether antiarrhythmic and its N-dealkyl metabolite in rat plasma and hepatic microsomal incubates using liquid chromatography-tandem mass spectrometry", J Chromatog B 759:259-266, 2001.

Valenzuela et al., "Comparative effects of nonsedating histamine $H_1$ receptor antagonists, ebastine and terfenadine, on human Kv1.5 channels", Eur J Pharm 326:257-263, 1997.

Valenzuela et al., "Effects of Ropivacaine on a Potassium Channel (hKv1.5) Cloned from Human Ventricle", Anesthesiology 86:718-728, 1997.

Walker, "Antiarrhythmic Drug Development—Illusion and Disillusion?", Drug Develop Res 55:1-2, 2002.

Walker et al., "Determination of an arylacetamide antiarrhythmic in rat blood and tissues using reversed-phase high-performance liquid chromatography", J Chromatog B 675:257-263, 1996.

Walker et al., "Increased Electrophysiological Activity in Raised $K^+$ and low pH Improves Antiarrhythmic Efficacy for a Group of Morpholinocyclohexyl Derivatives", BPS Proceedings 118P, 1996.

Walker and Guppy, "Targeting Ischemic Ventricular Arrhythmias", Cardiac Drug Development Guide, Humana Press Inc., Totowa, NJ, pp. 175-201, 2003.

Wang et al., "Effects of Flecainide, Quinidine, and 4-Aminopyridine on Transient Outward and Ultrarapid Delayed Rectifier Currents in Human Atrial Myocytes", J Pharm Exp Ther 272(1):184-196, 1995.

Wang et al., "Sustained Depolarization-Induced Outward Current in Human Atrial Myocytes", Circ. Res. 73(6):1061-1076, Dec. 1993.

Wat et al., "Effects of Arylbenzacetamides on Neuromuscular Preparation", Proc West Pharmacol Soc 1994.

Wolf et al., "Impact of Atrial Fibrillation on Mortality, Stroke, and Medical Costs", Arch Intern Med 158: 229-234, Feb. 9, 1998.

Wong and Clohs, "Protein Binding Study of AA5, a New Antiarrhythmic Drug", Nortran Pharmaceuticals Inc., Vancouver, BC, Poster Conference, Aug. 2000.

Wong and Clohs, "Capillary Electrophoresis Assay to Assess In Vitro Metabolic Stability of Novel Compounds in Human Liver Microsomes", Cardiome Pharma Corp., Vancouver, BC, AAPS Poster, Oct. 2001.

Yeola et al., "Molecular Analysis of a Binding Site for Quinidine in a Human Cardiac Delayed Rectifier $K^+$ Channel—Role of S6 in Antiarrhythmic Drug Binding", Circ Res 78(6): 1105-1114, Jun. 1996.

Yong et al., "Low pKa Predicts Antiarrhythmic Efficacy in a Series of Aminocyclohexyl Esters", J Mol Cell Cardiol. Abstract 057, 1997.

Yong et al., "RSD1000: A Novel Antiarrhythmic Agent with Increased Potency Under Acidic and High-Potassium Conditions", J Pharm Exp Ther 289(1):236-244, 1999.

Yong et al., "RSD1000: A Novel Antiarrhythmic Agent with an Improved Therapeutic Index", BPS Proceedings 119P, 1996.

Yong et al., "SAR Evidence that Antiarrhythmic Activity is Unrelated to Opioid Kappa Agonist Activity", BPS Proceedings 117P, 1996.

Zhang et al., "Inhibition of [$^3$H]-U69593 binding and the cardiac effects of U50, 488H by calcium channel blockers in the rat heart", Brit J Pharmacol 120:827-832, 1997.

Zolotoy et al., "Physicochemical Determinants for Drug Induced Blockade of HERG Potassium Channels: Effect of Charge and Charge Shielding", Curr Med Chem 1(3): 1-17, 2003.

* cited by examiner

AMINOCYCLOHEXYL ETHER COMPOUNDS AND USES THEREOF

CROSS-REFERENCE TO RELATED APPLICATIONS

This application is a continuation of U.S. application Ser. No. 11/690,361 filed Mar. 23, 2007 (U.S. Pat. No. 7,767,830); which is a continuation of U.S. patent application Ser. No. 10/555,364 filed Oct. 16, 2006 (now abandoned), which is a U.S. National Phase Application of PCT/US2003/034655 filed Oct. 31, 2003, which claims priority to U.S. Provisional Patent Application No. 60/467,159 filed May 2, 2003, U.S. Provisional Patent Application No. 60/476,083 filed Jun. 4, 2003, U.S. Provisional Patent Application No. 60/475,884 filed Jun. 5, 2003, U.S. Provisional Patent Application No. 60/475,912 filed Jun. 5, 2003, U.S. Provisional Patent Application No. 60/476,447 filed Jun. 5, 2003, U.S. Provisional Patent Application No. 60/489,659 filed Jul. 23, 2003, and U.S. Provisional Patent Application No. 60/493,392 filed Aug. 7, 2003. All of these applications are incorporated herein by reference in their entireties.

BACKGROUND

1. Technical Field

The present invention is directed to aminocyclohexyl ether compounds, pharmaceutical compositions, and processes for the synthesis of the aminocyclohexyl ether compounds, and therapeutic uses thereof.

2. Description of the Related Art

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

For example, cardiac ion channels are proteins that reside in the cell membrane and control the electrical activity of cardiac tissue. In response to external stimuli, such as changes in potential across the cell membrane, these ion channels can form a pore through the cell membrane, and allow movement of specific ions into or out of the cell. The integrated behavior of thousands of ion channels in a single cell results in an ionic current, and the integrated behavior of many of these ionic currents makes up the characteristic cardiac action potential.

Arrhythmia is a variation from the normal rhythm of the heart beat and generally represents the end product of abnormal ion-channel structure, number or function. Both atrial arrhythmias and ventricular arrhythmias are known. The major cause of fatalities due to cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these will be first heart attacks and 450,000 will be recurrent attacks. About one-third of the people experiencing these attacks will die of them. At least 250,000 people a year die of coronary heart disease within 1 hour of the onset of symptoms and before they reach a hospital. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., *N. Engl. J. Med.* 327(14):1031 Oct. 1, 1992, discussion 1031-2; Kannel and Wolf, *Am. Heart J.* 123(1):264-7 Jan. 1992). Its prevalence is likely to increase as the population ages and it is estimated that 3-5% of patients over the age of 60 years have AF (Kannel W. B., Abbot R. D., Savage D. D., McNamara P. M., *N. Engl. J. Med.* 306(17): 1018-22, 1982; Wolf P. A., Abbot R. D., Kannel W. B. *Stroke.* 22(8):983-8, 1991). While AF is rarely fatal, it can impair cardiac function and is a major cause of stroke (Hinton R. C., Kistler J. P., Fallon J. T., Friedlich A. L., Fisher C. M., *American Journal of Cardiology* 40(4):509-13, 1977; Wolf P. A., Abbot R. D., Kannel W. B., *Archives of Internal Medicine* 147(9):1561-4, 1987; Wolf P. A., Abbot R. D., Kannel W. B. *Stroke.* 22(8):983-8, 1991; Cabin H. S., Clubb K. S., Hall C., Perlmutter R. A., Feinstein A. R., *American Journal of Cardiology* 65(16):1112-6, 1990).

WO95/08544 discloses a class of aminocyclohexylester compounds as useful in the treatment of arrhythmias.

WO93/19056 discloses a class of aminocyclohexylamides as useful in the treatment of arrhythmia and in the inducement of local anaesthesia.

WO99/50225 discloses a class of aminocyclohexylether compounds as useful in the treatment of arrhythmias.

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Fuch and Podrid, 1992; Nattel S., Hadjis T., Talajic M., *Drugs* 48(3):345-71, 1994). However, drug therapy is often limited by adverse effects, including the possibility of increased mortality, and inadequate efficacy (Feld G. K., *Circulation.* 83(6):2248-50, 1990; Coplen S. E., Antman E. M., Berlin J. A., Hewitt P., Chalmers T. C., *Circulation* 1991; 83(2):714 and *Circulation* 82(4):1106-16, 1990; Flaker G. C., Blackshear J. L., McBride R., Kronmal R. A., Halperin J. L., Hart R. G., *Journal of the American College of Cardiology* 20(3):527-32, 1992; CAST, *N. Engl. J. Med.* 321:406, 1989; Nattel S., *Cardiovascular Research.* 37(3):567-77, 1998). Conversion rates for Class I antiarrhythmics range between 50-90% (Nattel S., Hadjis T., Talajic M., *Drugs* 48(3):345-71, 1994; Steinbeck G., Remp T., Hoffmann E., *Journal of Cardiovascular Electrophysiology.* 9(8 Suppl):S104-8, 1998). Class III antiarrhythmics appear to be more effective for terminating atrial flutter than for AF and are generally regarded as less effective than Class I drugs for terminating of AF (Nattel S., Hadjis T., Talajic M., *Drugs.* 48(3):345-71, 1994; Capucci A., Aschieri D., Villani G. Q., *Drugs & Aging* 13(1):51-70, 1998). Examples of such drugs include ibutilide, dofetilide and sotalol. Conversion rates for these drugs range between 30-50% for recent onset AF (Capucci A., Aschieri D., Villani G. Q., *Drugs & Aging* 13(1): 51-70, 1998), and they are also associated with a risk of the induction of Torsades de Pointes ventricular tachyarrhythmias. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *American Journal of Cardiology* 78(8A):46-52, 1996). Such events are particularly tragic in the case of AF as this arrhythmia is rarely a fatal in and of itself.

There remains a need in the art to identify new antiarrhythmic treatments, for both ventricular arrhythmias as well as for atrial arrhythmias. The present invention fulfills this need, and further provides other related advantages.

BRIEF SUMMARY

In one embodiment, the present invention provides a compound of formula (IA), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

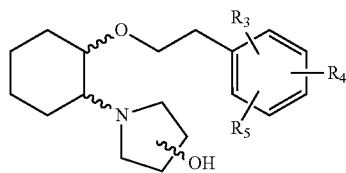
(IA)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In one embodiment, the present invention provides a compound of formula (IB), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

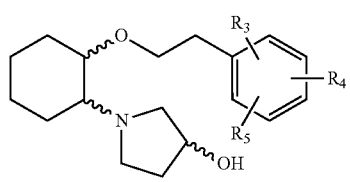
(IB)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In one embodiment, the present invention provides a compound of formula (IC), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

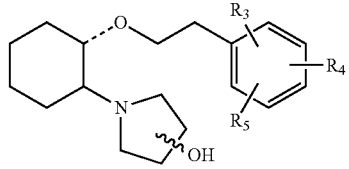
(IC)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In one embodiment, the present invention provides a compound of formula (ID), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

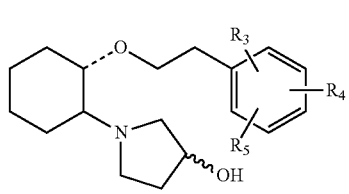
(ID)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In one embodiment, the present invention provides a compound of formula (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

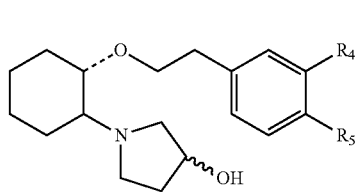
(IE)

wherein, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_4$ and $R_5$ cannot all be hydrogen.

In another embodiment, the present invention provides a compound or any salt thereof, or any solvate thereof, or mixture comprising one or more said compounds or any salt thereof, or any solvate thereof, selected from the group consisting of:

| Structure | Chemical name |
|---|---|
| 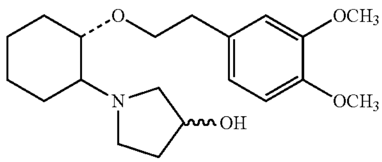 | (1R,2R)/(1S,2S)-2-[(3R)/(3S)-Hydroxypyrrolidinyl]-1-(3,4-dimethoxyphenethoxy)-cyclohexane |
| 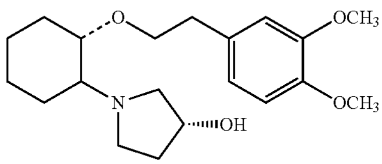 | (1R,2R)/(1S,2S)-2-[(3R)-Hydroxypyrrolidinyl]-1-(3,4-dimethoxyphenethoxy)-cyclohexane |
| 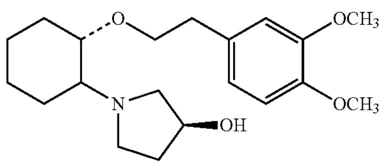 | (1R,2R)/(1S,2S)-2-[(3S)-Hydroxypyrrolidinyl]-1-(3,4-dimethoxyphenethoxy)-cyclohexane |
| 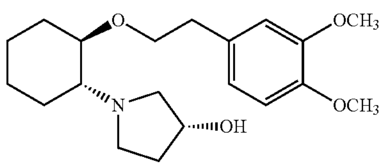 | (1R,2R)-2-[(3R)-Hydroxypyrrolidinyl]-1-(3,4-dimethoxyphenethoxy)-cyclohexane |
| 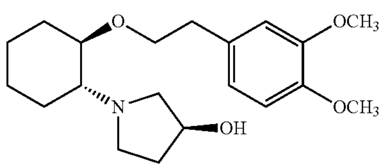 | (1R,2R)-2-[(3S)-Hydroxypyrrolidinyl]-1-(3,4-dimethoxyphenethoxy)-cyclohexane |
| 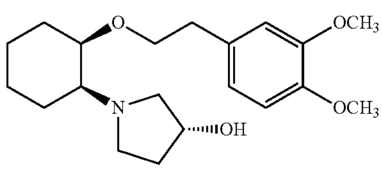 | (1R,2S)-2-[(3R)-Hydroxypyrrolidinyl]-1-(3,4-dimethoxyphenethoxy)-cyclohexane |
| 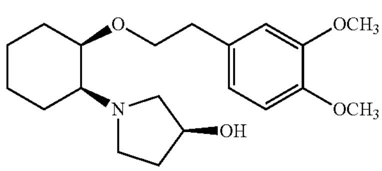 | (1R,2S)-2-[(3S)-Hydroxypyrrolidinyl]-1-(3,4-dimethoxyphenethoxy)-cyclohexane |
| 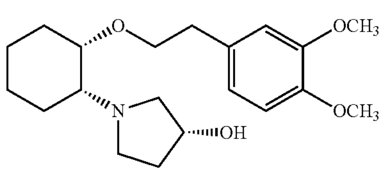 | (1S,2R)-2-[(3R)-Hydroxypyrrolidinyl]-1-(3,4-dimethoxyphenethoxy)-cyclohexane |
| 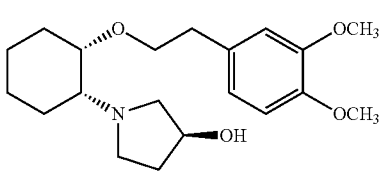 | (1S,2R)-2-[(3S)-Hydroxypyrrolidinyl]-1-(3,4-dimethoxyphenethoxy)-cyclohexane |

-continued

| Structure | Chemical name |
|---|---|
| [structure] | (1S,2S)-2-[(3R)-Hydroxypyrrolidinyl]-1-(3,4-dimethoxyphenethoxy)-cyclohexane |
| [structure] | (1S,2S)-2-[(3S)-Hydroxypyrrolidinyl]-1-(3,4-dimethoxyphenethoxy)-cyclohexane |
| [structure] | (1R,2S)/(1S,2R)-2-[(3R)/(3S)-Hydroxypyrrolidinyl]-1-(3,4-dimethoxyphenethoxy)-cyclohexane |

In another embodiment, the present invention provides a composition that includes one or more of the compounds listed in the above table, or includes a solvate or a pharmaceutically acceptable salt of one or more of the compounds listed in the above table. The composition may or may not include additional components as is described elsewhere in detail in this patent.

In one embodiment, the present invention provides a compound, or mixture comprising compounds, or any solvate thereof, selected from the group consisting of:

| Cpd. # | Structure | Chemical name |
|---|---|---|
| 1 | [structure] •HCl | (1R,2R)-2-[(3R)-Hydroxypyrrolidinyl]-1-(3,4-dimethoxyphenethoxy)-cyclohexane monohydrochloride |
| 2 | [structure] •HCl | (1S,2S)-2-[(3R)-Hydroxypyrrolidinyl]-1-(3,4-dimethoxyphenethoxy)-cyclohexane monohydrochloride |
| 3 | [structure] •HCl | (1R,2R)/(1S,2S)-2-[(3R)/(3S)-Hydroxypyrrolidinyl]-1-(3,4-dimethoxyphenethoxy)-cyclohexane monohydrochloride |
| 4 | [structure] •HCl | (1R,2R)/(1S,2S)-2-[(3R)-Hydroxypyrrolidinyl]-1-(3,4-dimethoxyphenethoxy)-cyclohexane monohydrochloride |

| Cpd. # | Structure | Chemical name |
|---|---|---|
| 5 | 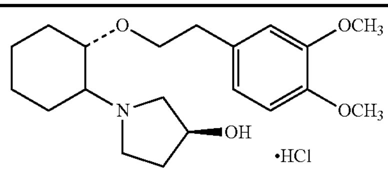 | (1R,2R)/(1S,2S)-2-[(3S)-Hydroxypyrrolidinyl]-1-(3,4-dimethoxyphenethoxy)-cyclohexane monohydrochloride |
| 6 | 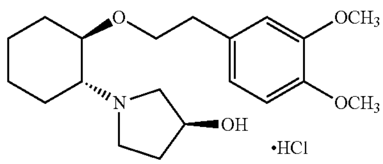 | (1R,2R)-2-[(3S)-Hydroxypyrrolidinyl]-1-(3,4-dimethoxyphenethoxy)-cyclohexane monohydrochloride |
| 7 | 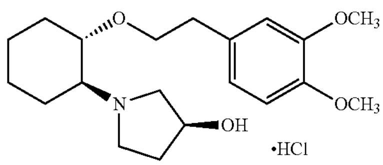 | (1S,2S)-2-[(3S)-Hydroxypyrrolidinyl]-1-(3,4-dimethoxyphenethoxy)-cyclohexane monohydrochloride |

In another embodiment, the present invention provides a composition that includes one or more of the compounds listed in the above table, or includes a solvate of one or more of the compounds listed in the above table. The composition may or may not include additional components as is described elsewhere in detail in this patent.

In one embodiment, the present invention provides a compound which is (1R,2R)-2-[(3R)-Hydroxypyrrolidinyl]-1-(3,4-dimethoxyphenethoxy)-cyclohexane free base or any salt thereof, or any solvate thereof.

In one embodiment, the present invention provides a compound which is (1R,2R)-2-[(3S)-Hydroxypyrrolidinyl]-1-(3,4-dimethoxyphenethoxy)-cyclohexane free base or any salt thereof, or any solvate thereof.

In one embodiment, the present invention provides a compound which is. (1S,2S)-2-[(3R)-Hydroxypyrrolidinyl]-1-(3,4-dimethoxyphenethoxy)-cyclohexane free base or any salt thereof, or any solvate thereof.

In one embodiment, the present invention provides a compound which is (1S,2S)-2-[(3S)-Hydroxypyrrolidinyl]-1-(3,4-dimethoxyphenethoxy)-cyclohexane free base or any salt thereof, or any solvate thereof.

In one embodiment, the present invention provides a compound which is (1R,2R)-2-[(3R)-Hydroxypyrrolidinyl]-1-(3,4-dimethoxyphenethoxy)-cyclohexane monohydrochloride, or any solvate thereof.

In one embodiment, the present invention provides a compound which is (1R,2R)-2-[(3S)-Hydroxypyrrolidinyl]-1-(3,4-dimethoxyphenethoxy)-cyclohexane monohydrochloride, or any solvate thereof.

In one embodiment, the present invention provides a compound which is (1S,2S)-2-[(3R)-Hydroxypyrrolidinyl]-1-(3,4-dimethoxyphenethoxy)-cyclohexane monohydrochloride, or any solvate thereof.

In one embodiment, the present invention provides a compound which is (1S,2S)-2-[(3S)-Hydroxypyrrolidinyl]-1-(3,4-dimethoxyphenethoxy)-cyclohexane monohydrochloride, or any solvate thereof.

The present invention also provides protenated versions of all of the compounds described in this patent. That is, for each compound described in this patent, the invention also includes the quaternary protenated amine form of the compound. These quaternary protenated amine forms of the compounds may be present in the solid phase, for example in crystalline or amorphous form, and may be present in solution. These quaternary protenated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

In other embodiments, the present invention provides a composition or medicament that includes one or more compounds, selected from any of the compounds described in this patent or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

In other embodiments, the present invention provides a composition or medicament that includes one or more compounds according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

In other embodiments, the present invention provides a composition or medicament that includes one or more compounds according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with a pharmaceutically acceptable carrier, diluent or excipient, and further provides a method for the manufacture of such a composition or medicament.

In other embodiments, the present invention provides one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above, for use in methods for modulating ion channel activity in a warm-blooded animal or for modulating ion channel activity in vitro. In one version of this embodiment, the warm-blooded animal in which the ion channel activity is modulated is a mammal; in one version, the warm-blooded animal is a human; in one version, the warm-blooded animal is a farm animal.

As disclosed within the present invention, a variety of cardiac pathological conditions may be treated and/or prevented by the use of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above. Without being bound by theory, the inventors believe that the compounds of the present invention are ion channel modulating compounds that either singly or together with one or more additional compounds are able to selectively modulate certain ionic currents. The ion currents referred to herein are generally cardiac currents and more specifically, are the sodium currents and early repolarising currents.

Throughout this patent the inventors describe various means by which they believe the compounds described in this patent may act. Such descriptions are not intended to be limiting but represent the inventors' belief as to how the compounds may act.

The pathological conditions that may be treated and/or prevented by the present invention may include, but are not limited to, various cardiovascular diseases.

The cardiac pathological conditions that may be treated and/or prevented by the present invention may include, but are not limited to, arrhythmias such as the various types of atrial and ventricular arrhythmias, e.g., atrial fibrillation, atrial flutter, ventricular fibrillation, ventricular flutter.

In another embodiment, the present invention provides ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation.

In other embodiments, the present invention provides a method for modulating ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating ion channel activity in an in vitro setting comprising administering in vitro an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the activity/conductance of ion channel in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating potassium ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating cardiac sodium currents activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating cardiac early repolarising currents and cardiac sodium currents ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing arrhythmia in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing arrhythmia in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2 S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In other embodiments, the present invention provides a composition or medicament that contain one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof as described above, in an amount effective to treat a disease or condition in a warm-blooded animal suffering from or having the disease or condition, and/or prevent a disease or condition in a warm-blooded animal that would otherwise occur, and further contains a pharmaceutically acceptable carrier, diluent or excipient.

The invention further provides for methods of treating a disease or condition in a warm-blooded animal suffering from or having the disease or condition, and/or preventing a disease or condition from arising in a warm-blooded animal, wherein a therapeutically effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above, is administered to a warm-blooded animal in need thereof. By way of illustration and not by way of limitation, examples of some of the diseases, disorders and conditions to which the compounds, compositions, medicaments and methods of the present invention have applicability are as follows: arrhythmia, atrial arrhythmia, ventricular arrhythmia, atrial fibrillation, ventricular fibrillation, atrial flutter, ventricular flutter, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

In one version, the compounds of the present invention may be used to treat and/or prevent arrhythmia, atrial arrhythmia, ventricular arrhythmia, atrial fibrillation, ventricular fibrillation, atrial flutter, or ventricular flutter; in another version the compounds may be used to treat arrhythmia, atrial arrhythmia, ventricular arrhythmia, atrial fibrillation, ventricular fibrillation, atrial flutter, or ventricular flutter; in another version the compounds may be used to prevent arrhythmia, atrial arrhythmia, ventricular arrhythmia, atrial fibrillation, ventricular fibrillation, atrial flutter, or ventricular flutter.

In other embodiments, the present invention provides a composition or medicament containing an amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof as described above, effective to produce analgesia or local anesthesia in a warm-blooded animal in need thereof, and a pharmaceutically acceptable carrier, diluent, or excipient.

The invention further provides a method for producing, analgesia or local anesthesia in a warm-blooded animal which includes administering to a warm-blooded animal in need thereof an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, or a composition or medicament that includes said compound or mixture comprising compounds as described above. These compositions, medicaments and methods may be used to relieve or forestall the sensation of pain in a warm-blooded animal.

In other embodiments, the present invention provides a composition or medicament containing an amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof as described above, effective to enhance the libido in a warm-blooded animal in need thereof, and a pharmaceutically acceptable carrier, diluent, or excipient.

The invention further provides a method for enhancing libido in a warm-blooded animal which includes administering to a warm-blooded animal in need thereof an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, or a composition or medicament that includes said compound or mixture comprising compounds as described above. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

The compounds of the present invention are effective antiarrhythmic agents. The compounds according to the present invention have been found to exhibit advantageously low Central Nervous System (CNS) toxicity whilst retaining high antiarrhythmic activity.

In another embodiment the present invention provides methods for the synthesis of compounds of the present invention such as those according to formula (IA), (IB), (IC), (ID), or (IE), and in particular methods for the synthesis of the compounds;

(1R,2R)-2-[(3R)-Hydroxypyrrolidinyl]-1-(3,4-dimethoxyphenethoxy)-cyclohexane free base and the corresponding monohydrochloride;

(1S,2S)-2-[(3R)-Hydroxypyrrolidinyl]-1-(3,4-dimethoxyphenethoxy)-cyclohexane free base and the corresponding monohydrochloride;

(1R,2R)/(1S,2S)-2-[(3R)/(3S)-Hydroxypyrrolidinyl]-1-(3,4-dimethoxyphenethoxy)-cyclohexane free base and the corresponding monohydrochloride;

(1R,2R)/(1S,2S)-2-[(3R)-Hydroxypyrrolidinyl]-1-(3,4-dimethoxyphenethoxy)-cyclohexane free base and the corresponding monohydrochloride;

(1R,2R)/(1S,2S)-2-[(3S)-Hydroxypyrrolidinyl]-1-(3,4-dimethoxyphenethoxy)-cyclohexane free base and the corresponding monohydrochloride;

(1R,2R)-2-[(3S)-Hydroxypyrrolidinyl]-1-(3,4-dimethoxyphenethoxy)-cyclohexane free base and the corresponding monohydrochloride;

(1S,2S)-2-[(3S)-Hydroxypyrrolidinyl]-1-(3,4-dimethoxyphenethoxy)-cyclohexane free base and the corresponding monohydrochloride;

Some general synthetic processes for aminocyclohexyl ethers have been described in WO 99/50225 and references cited therein.

These and other embodiments of the present invention will become evident upon reference to the following description, drawings and examples.

Figure 2:
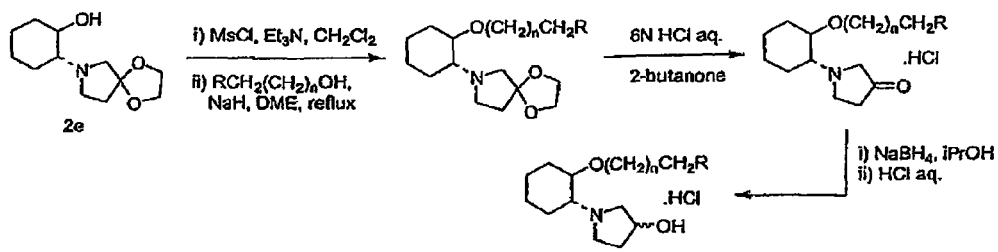

(1R,2R)-2-[(3R)-Hydroxypyrrolidinyl]-1-(3,4-dimethoxyphenethoxy)-cyclohexane free base;

(1R,2R)-2-[(3R)-Hydroxypyrrolidinyl]-1-(3,4-dimethoxyphenethoxy)-cyclohexane monohydrochloride (Compound 1);

(1S,2S)-2-[(3R)-Hydroxypyrrolidinyl]-1-(3,4-dimethoxyphenethoxy)-cyclohexane free base;

(1S,2S)-2-[(3R)-Hydroxypyrrolidinyl]-1-(3,4-dimethoxyphenethoxy)-cyclohexane monohydrochloride (Compound 2);

(1R,2R)/(1S,2S)-2-[(3R)/(3S)-Hydroxypyrrolidinyl]-1-(3,4-dimethoxyphenethoxy)-cyclohexane free base;

(1R,2R)/(1S,2S)-2-[(3R)/(3S)-Hydroxypyrrolidinyl]-1-(3,4-dimethoxyphenethoxy)-cyclohexane monohydrochloride (Compound 3);

(1R,2R)/(1S,2S)-2-[(3R)-Hydroxypyrrolidinyl]-1-(3,4-dimethoxyphenethoxy)-cyclohexane free base;

(1R,2R)/(1S,2S)-2-[(3R)-Hydroxypyrrolidinyl]-1-(3,4-dimethoxyphenethoxy)-cyclohexane monohydrochloride (Compound 4);

(1R,2R)/(1S,2S)-2-[(3S)-Hydroxypyrrolidinyl]-1-(3,4-dimethoxyphenethoxy)-cyclohexane free base;

(1R,2R)/(1S,2S)-2-[(3s)-Hydroxypyrrolidinyl]-1-(3,4-dimethoxyphenethoxy)-cyclohexane monohydrochloride (Compound 5);

(1R,2R)-2-[(3S)-Hydroxypyrrolidinyl]-1-(3,4-dimethoxyphenethoxy)-cyclohexane free base;

(1R,2R)-2-[(3S)-Hydroxypyrrolidinyl]-1-(3,4-dimethoxyphenethoxy)-cyclohexane monohydrochloride (Compound 6);

(1S,2S)-2-[(3R)-Hydroxypyrrolidinyl]-1-(3,4-dimethoxyphenethoxy)-cyclohexane free base;

(1S,2S)-2-[(3S)-Hydroxypyrrolidinyl]-1-(3,4-dimethoxyphenethoxy)-cyclohexane monohydrochloride (Compound 7);

FIG. 2 illustrates a synthetic methodology that may be employed to prepare a trans-aminocyclohexyl ether compound of the present invention.

Figure 3:
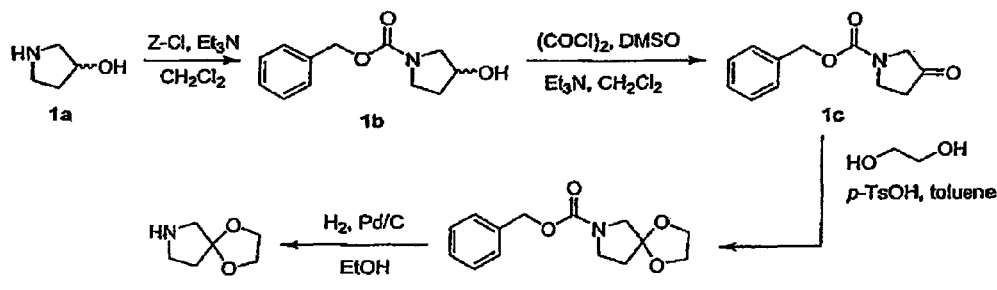

FIG. 3 illustrates a synthetic methodology for preparing amine 1e required for the formation of amino alcohol 2e (as shown in FIG. 2).

Figure 4:
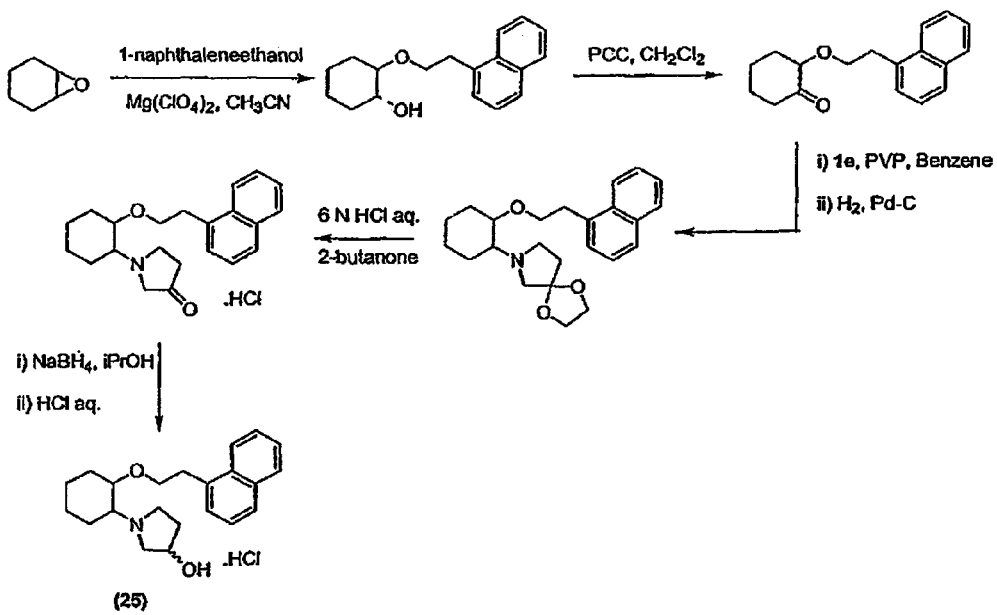

FIG. 4 illustrates a synthetic sequence that may be used to prepare a cis-aminocyclohexyl ether compound of the present invention such as compound 25.

Figure 5:
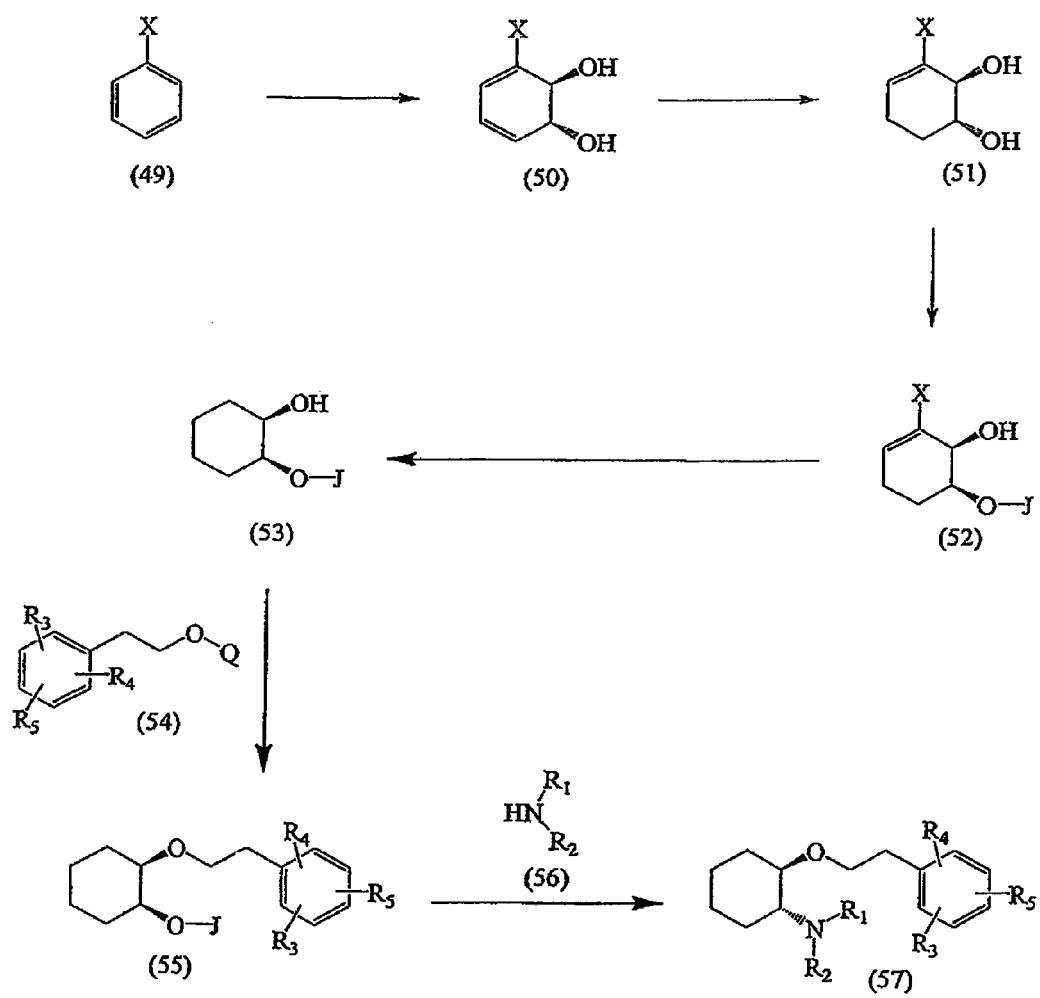

FIG. 5 illustrates a general reaction scheme that may be used as a process for preparing a stereoisomerically substantially pure trans-(1R,2R)-aminocyclohexyl ether compound of formula (57).

Figure 6:
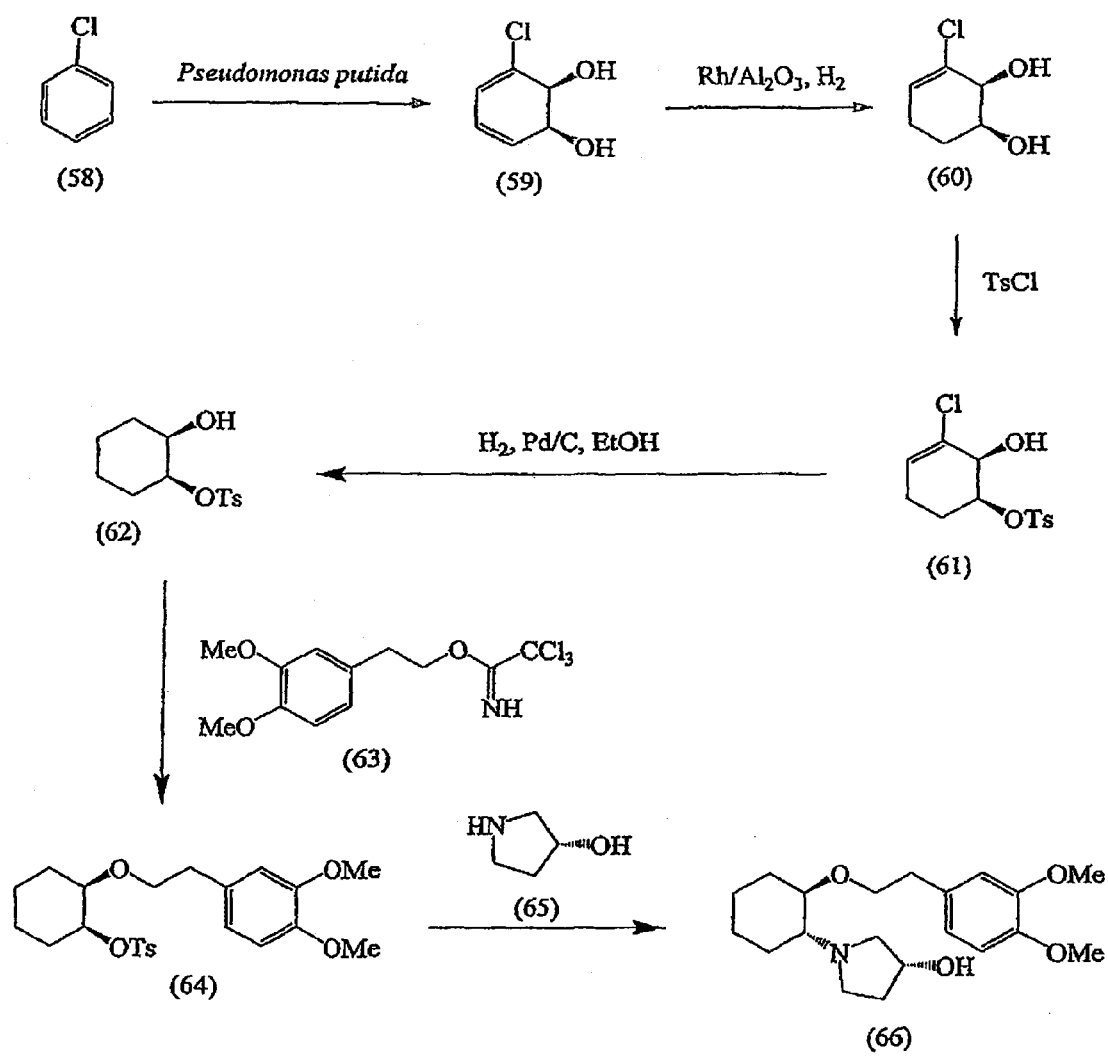

FIG. 6 illustrates a reaction scheme that may be used as a process for preparing a stereoisomerically substantially pure trans-(1R,2R)-aminocyclohexyl ether compound of formula (66).

Figure 7:
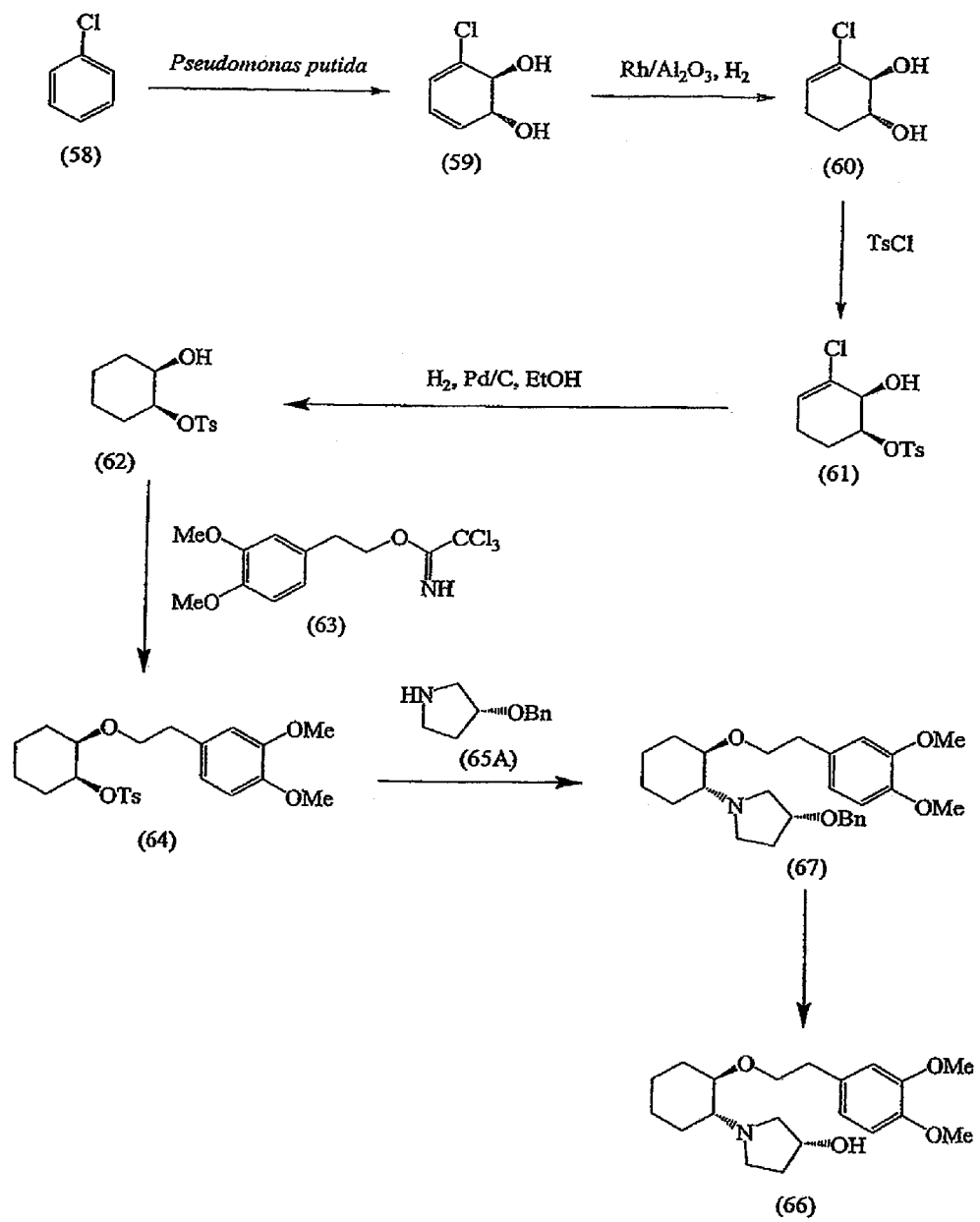

FIG. 7 illustrates a reaction scheme that may be used as a process for preparing a stereoisomerically substantially pure trans-(1R,2R)-aminocyclohexyl ether compound of formula (66).

Figure 8:
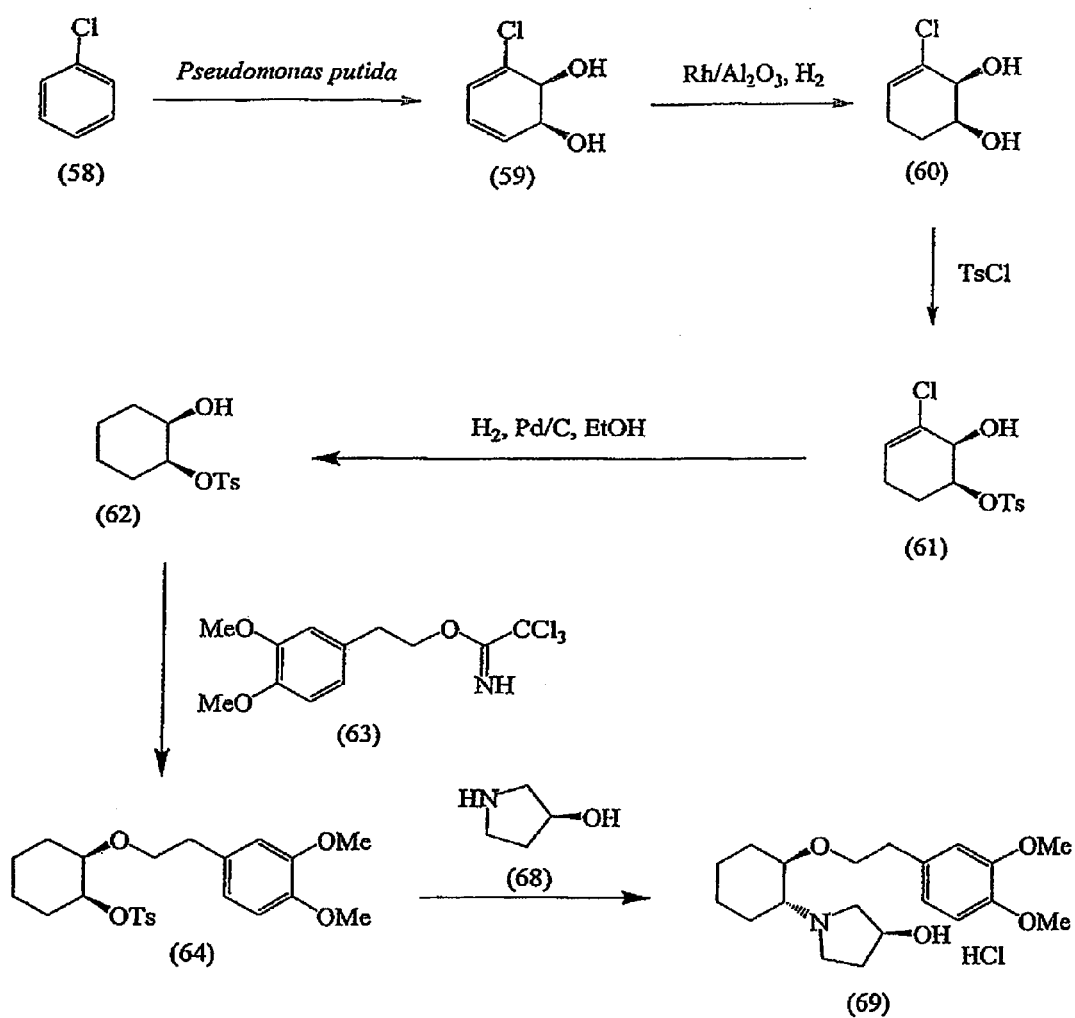

FIG. 8 illustrates a reaction scheme that may be used as a process for preparing a stereoisomerically substantially pure trans-(1R,2R)-aminocyclohexyl ether compound of formula (69).

Figure 9:
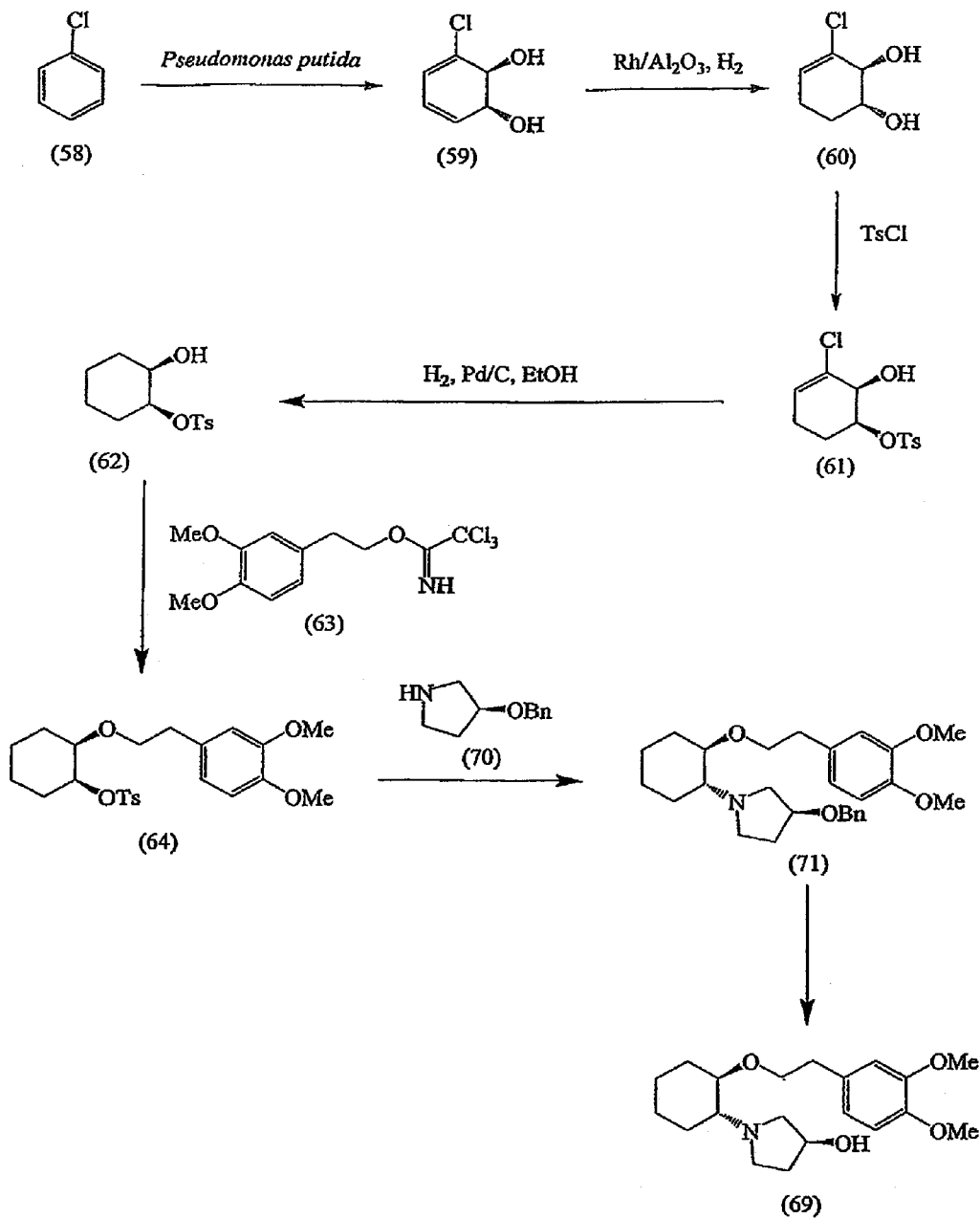

FIG. 9 illustrates a reaction scheme that may be used as a process for preparing a stereoisomerically substantially pure trans-(1R,2R)-aminocyclohexyl ether compound of formula (69).

Figure 10:
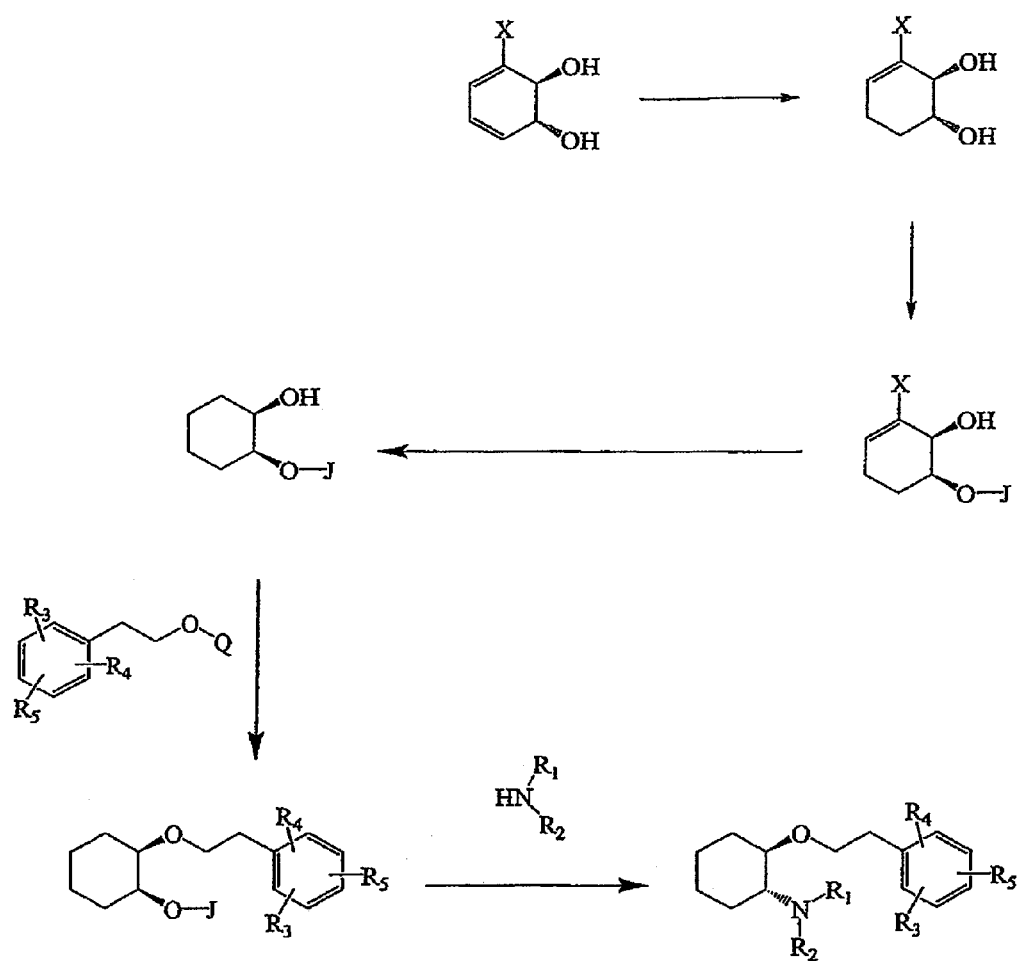

FIG. 10 illustrates a general reaction scheme that may be used as a process for preparing a stereoisomerically substantially pure trans-(1R,2R)-aminocyclohexyl ether compound of formula (57).

Figure 11:
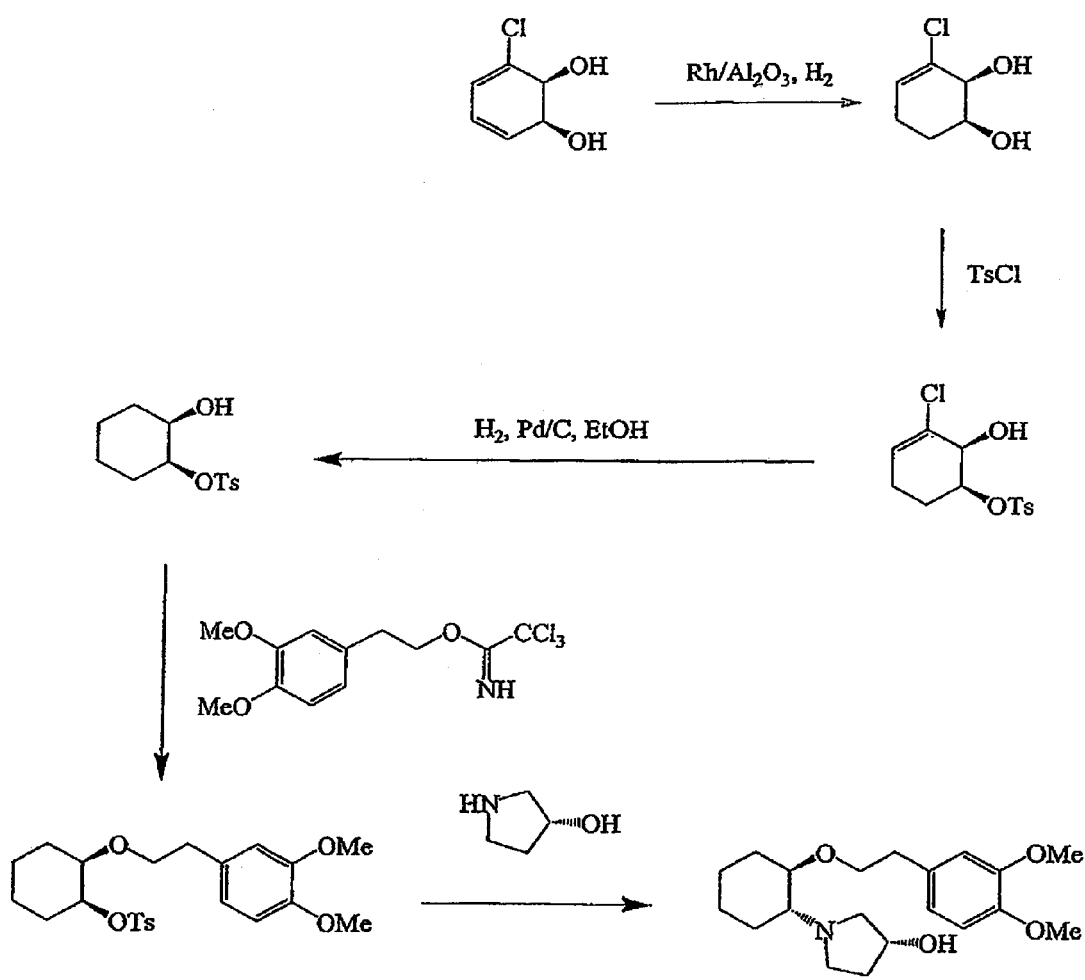

FIG. 11 illustrates a reaction scheme that may be used as a process for preparing a stereoisomerically substantially pure trans-(1R,2R)-aminocyclohexyl ether compound of formula (66).

Figure 12:
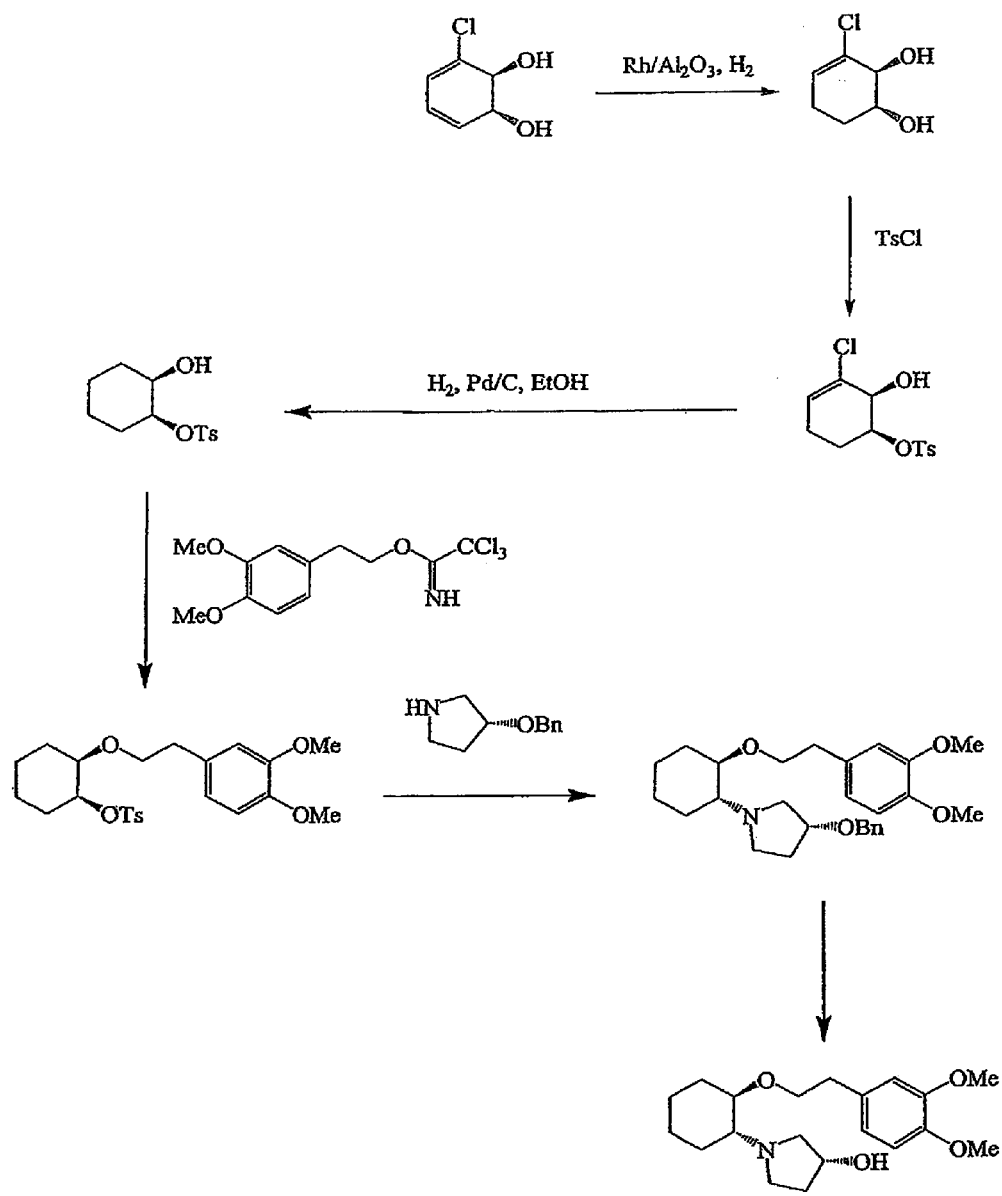

FIG. 12 illustrates a reaction scheme that may be used as a process for preparing a stereoisomerically substantially pure trans-(1R,2R)-aminocyclohexyl ether compound of formula (66).

Figure 13:
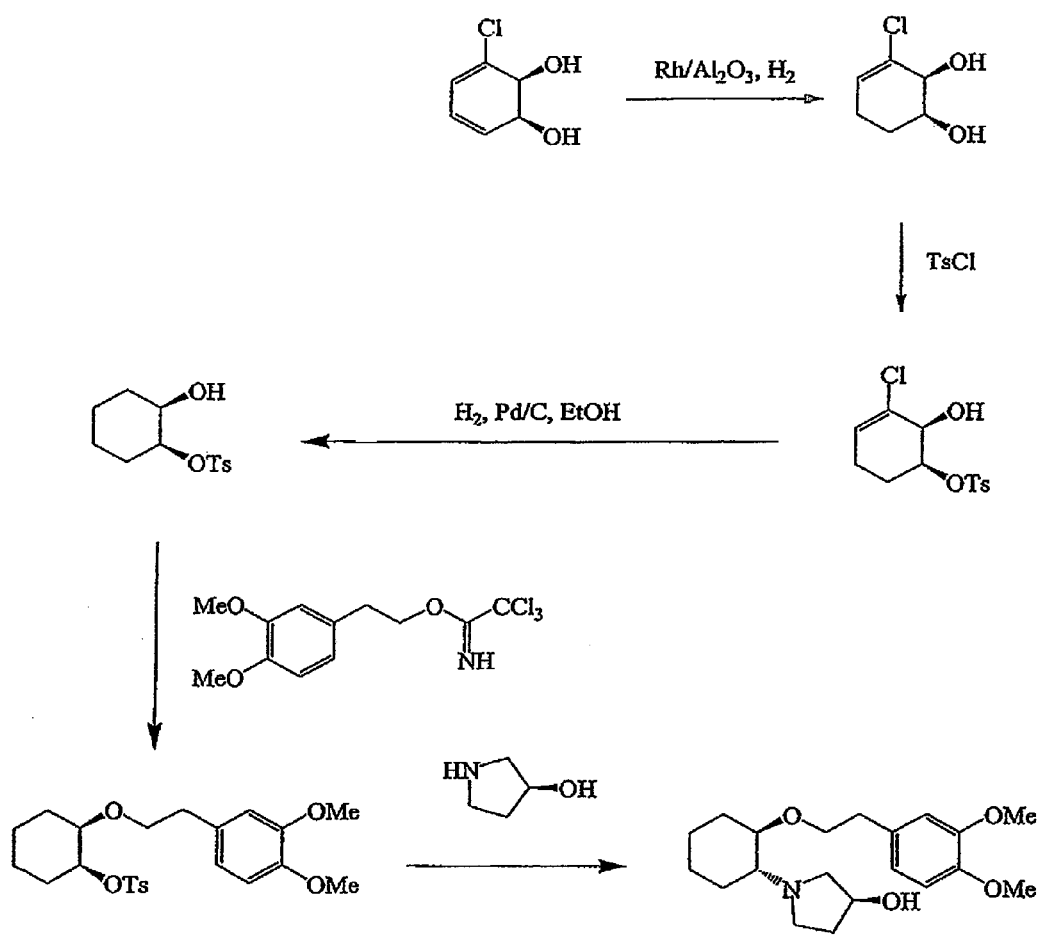

FIG. 13 illustrates a reaction scheme that may be used as a process for preparing a stereoisomerically substantially pure trans-(1R,2R)-aminocyclohexyl ether compound of formula (69).

Figure 14:
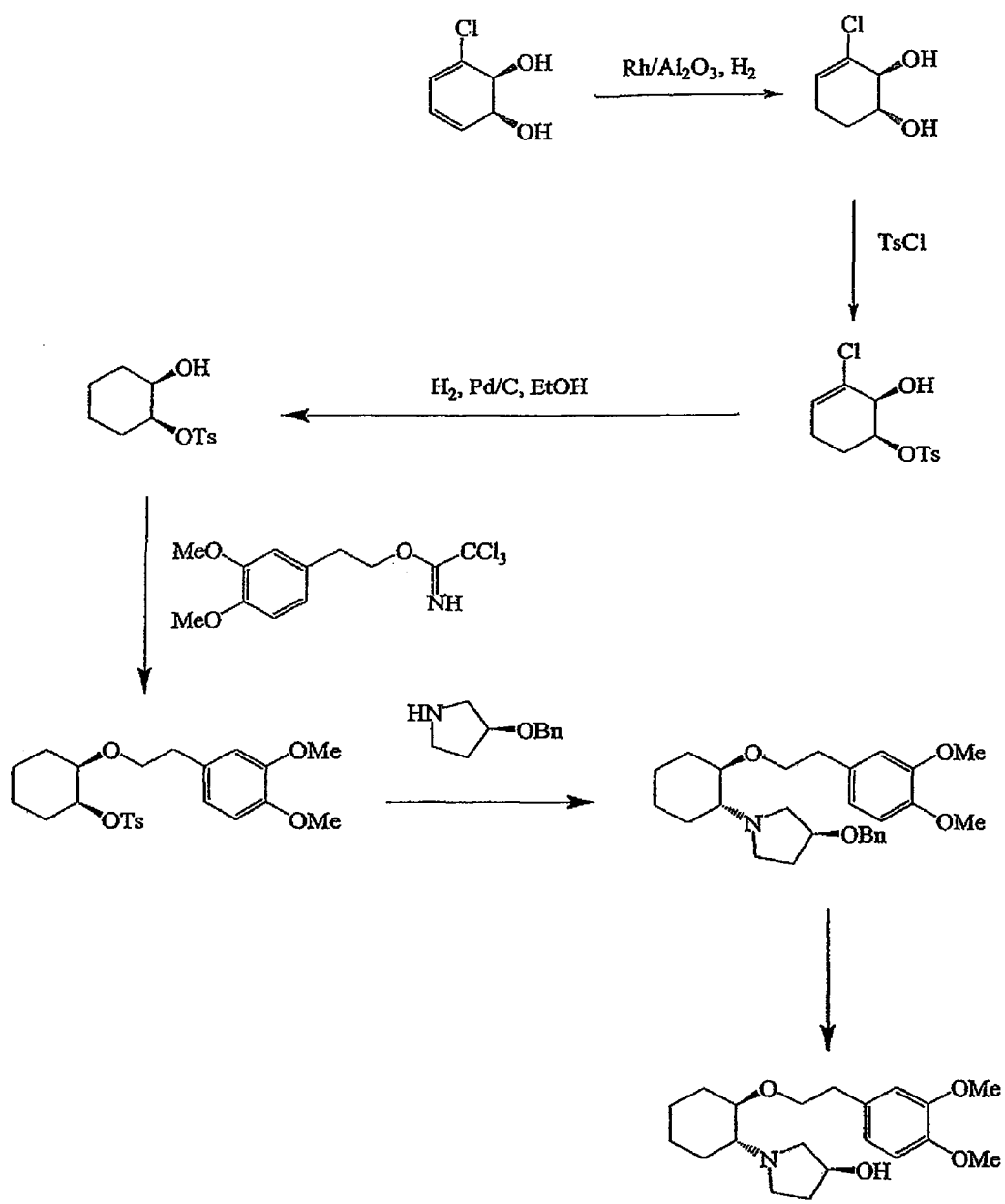

FIG. 14 illustrates a reaction scheme that may be used as a process for preparing a stereoisomerically substantially pure trans-(1R,2R)-aminocyclohexyl ether compound of formula (69).

Figure 15:
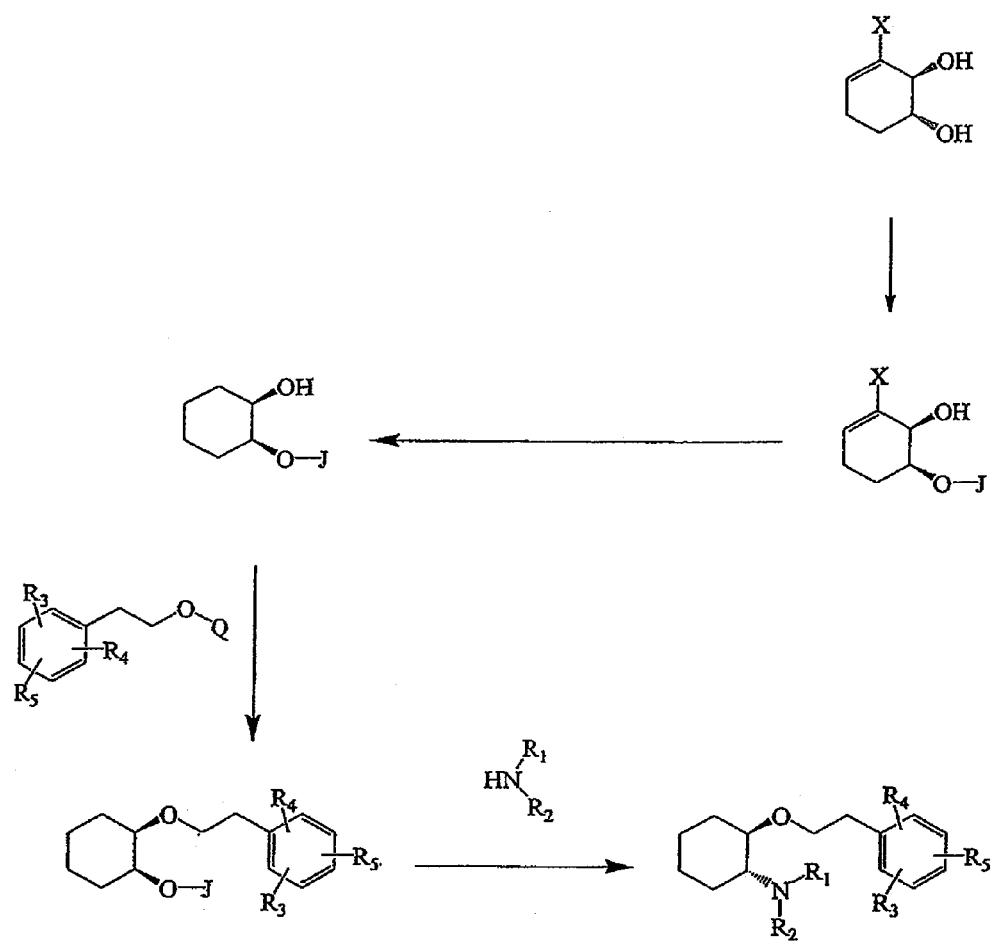

FIG. 15 illustrates a general reaction scheme that may be used as a process for preparing a stereoisomerically substantially pure trans-(1R,2R)-aminocyclohexyl ether compound of formula (57).

Figure 16:
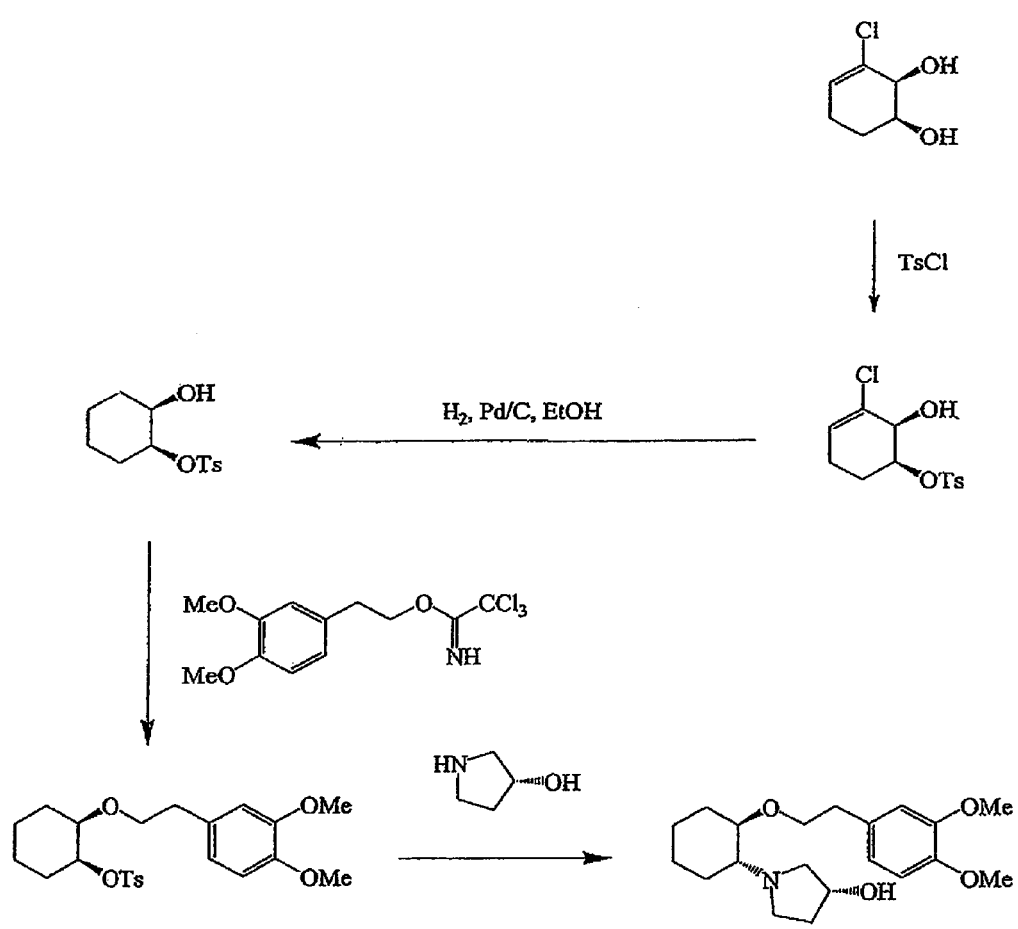

FIG. 16 illustrates a reaction scheme that may be used as a process for preparing a stereoisomerically substantially pure trans-(1R,2R)-aminocyclohexyl ether compound of formula (66).

Figure 17:
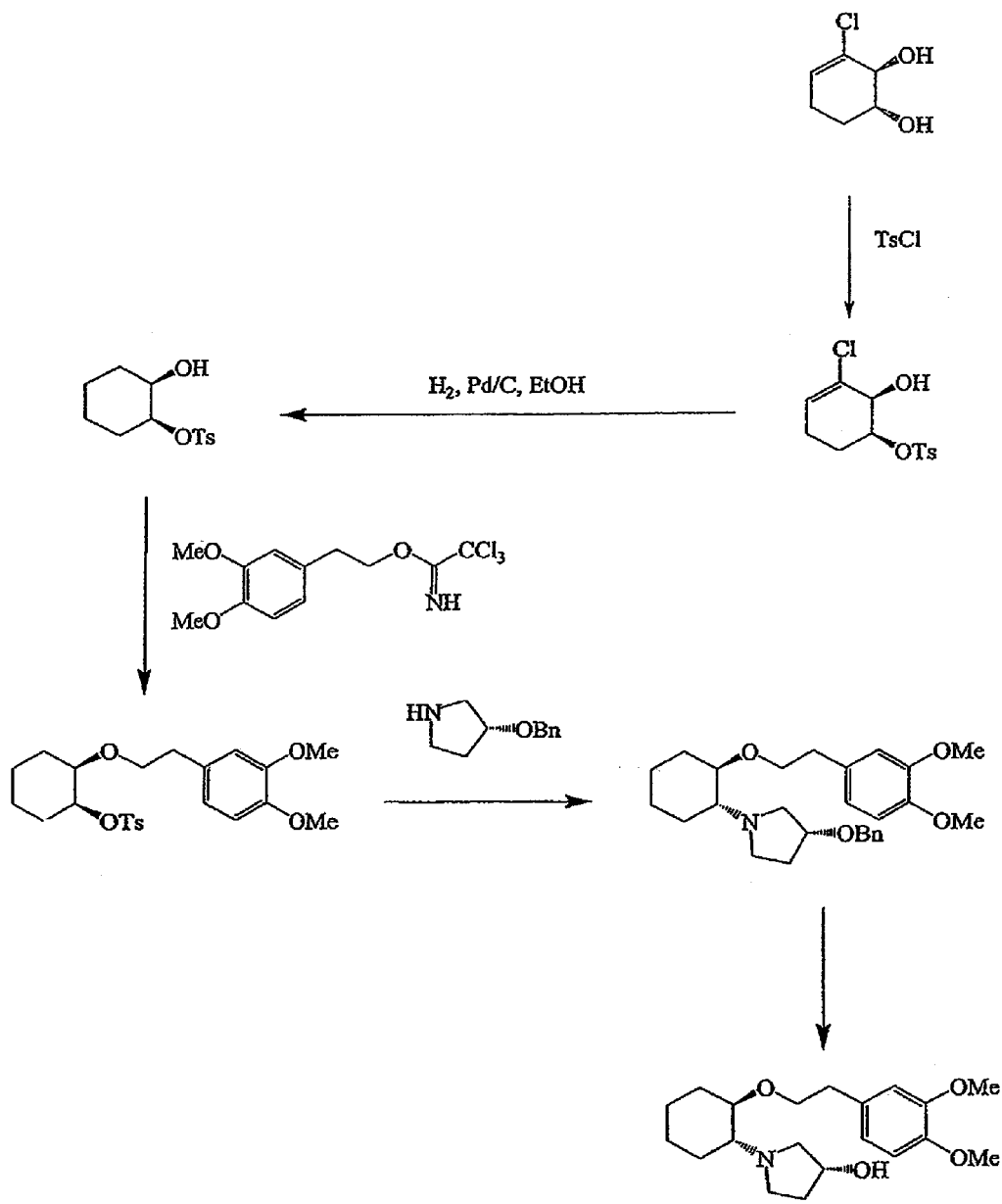

FIG. 17 illustrates a reaction scheme that may be used as a process for preparing a stereoisomerically substantially pure trans-(1R,2R)-aminocyclohexyl ether compound of formula (66).

Figure 18:
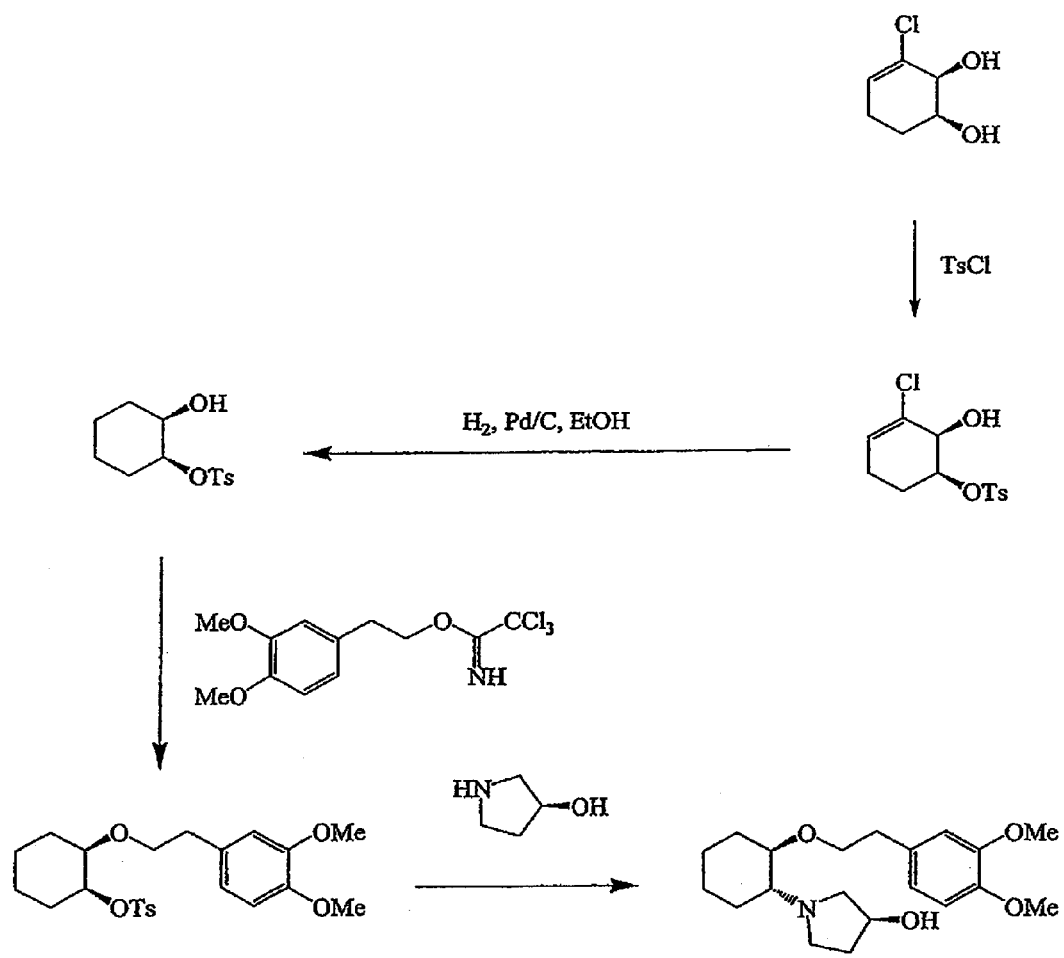

FIG. 18 illustrates a reaction scheme that may be used as a process for preparing a stereoisomerically substantially pure trans-(1R,2R)-aminocyclohexyl ether compound of formula (69).

Figure 19:
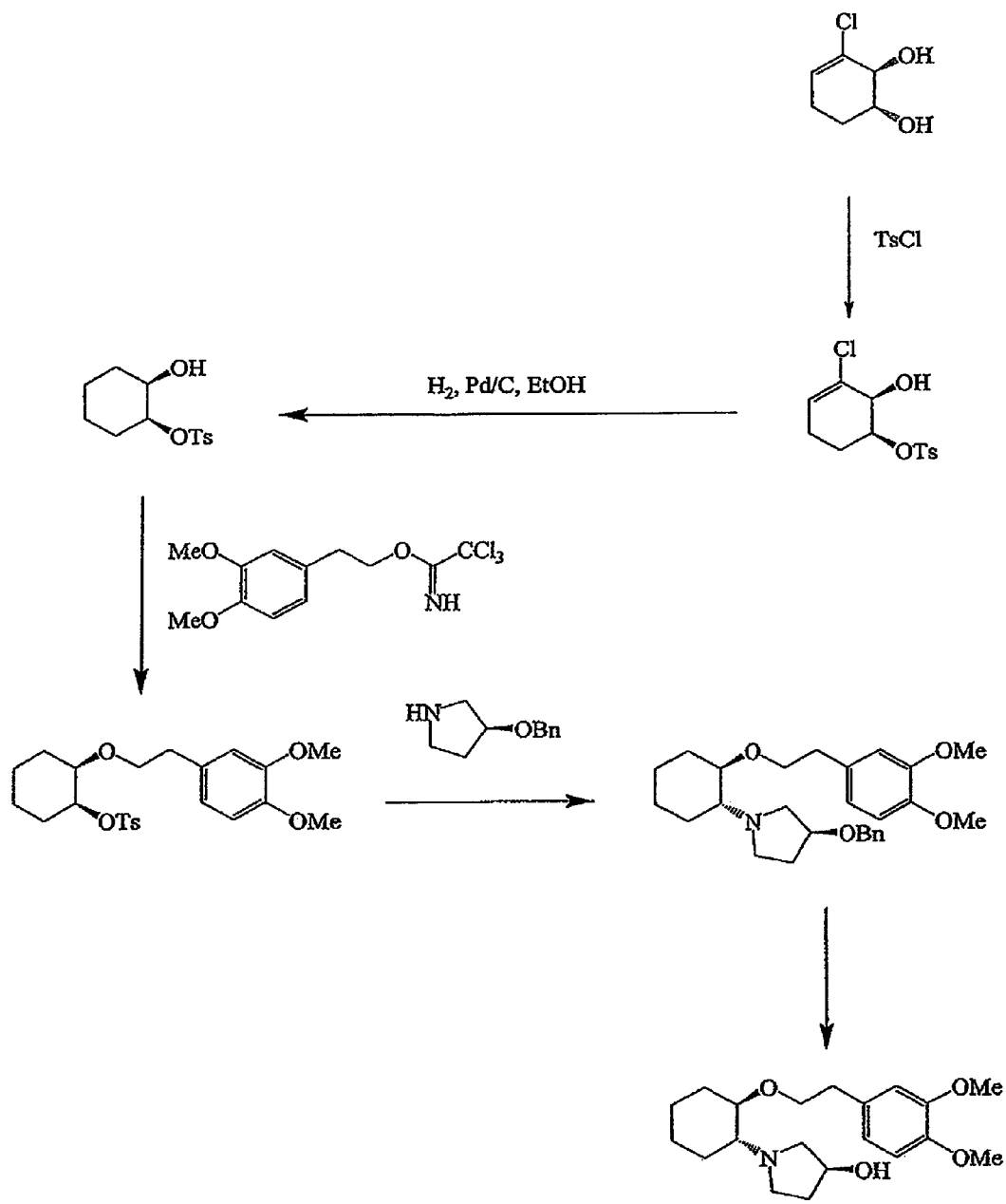

FIG. 19 illustrates a reaction scheme that may be used as a process for preparing a stereoisomerically substantially pure trans-(1R,2R)-aminocyclohexyl ether compound of formula (69).

Figure 20:
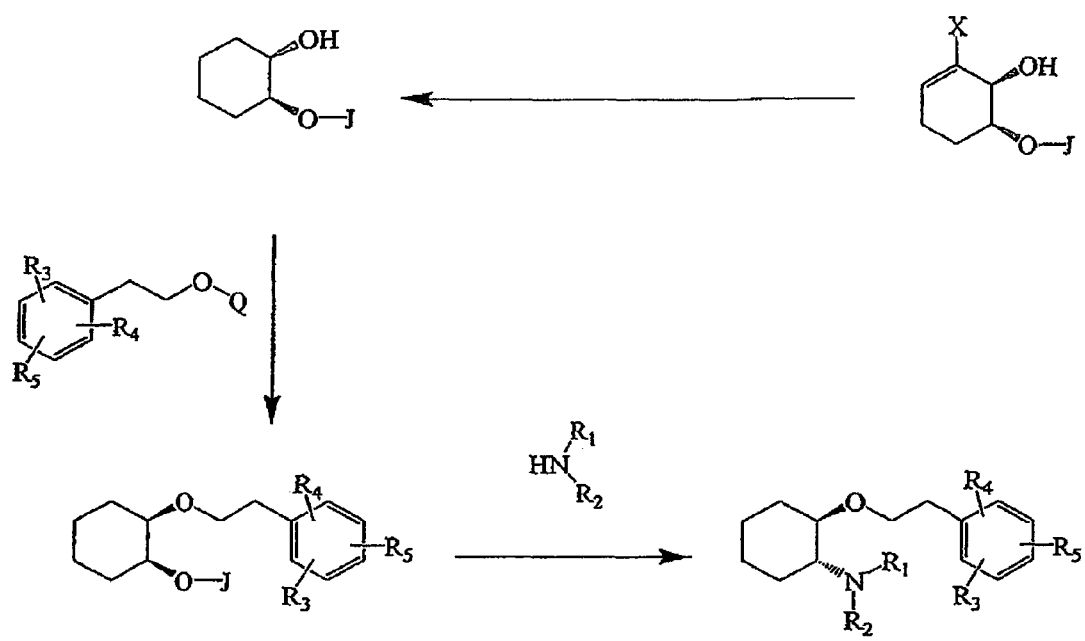

FIG. 20 illustrates a general reaction scheme that may be used as a process for preparing a stereoisomerically substantially pure trans-(1R,2R)-aminocyclohexyl ether compound of formula (57).

Figure 21:
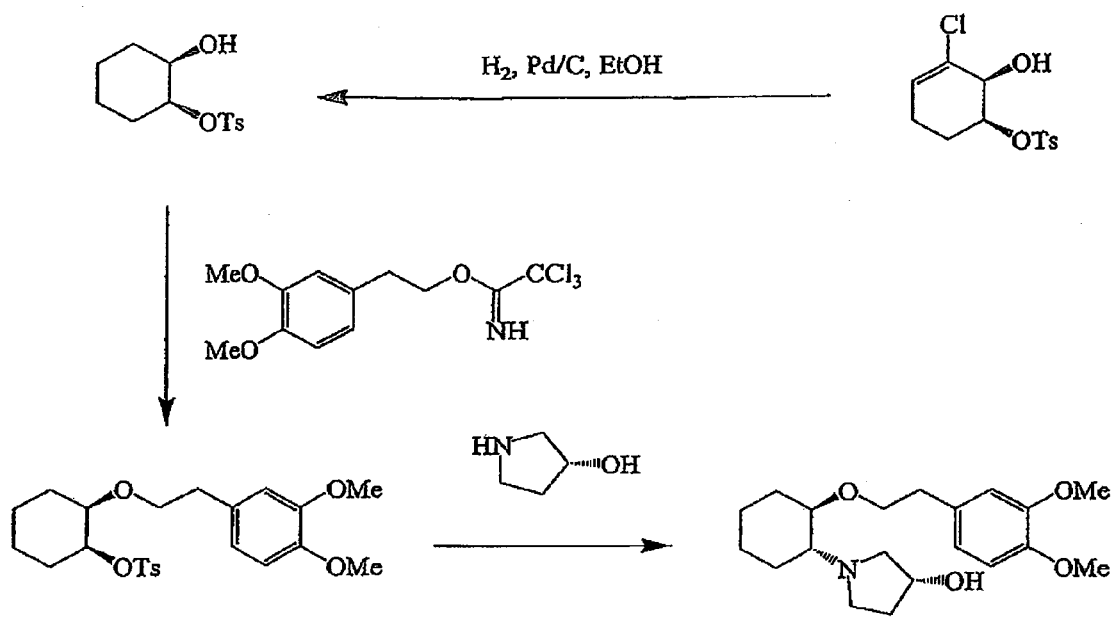

FIG. 21 illustrates a reaction scheme that may be used as a process for preparing a stereoisomerically substantially pure trans-(1R,2R)-aminocyclohexyl ether compound of formula (66).

Figure 22:
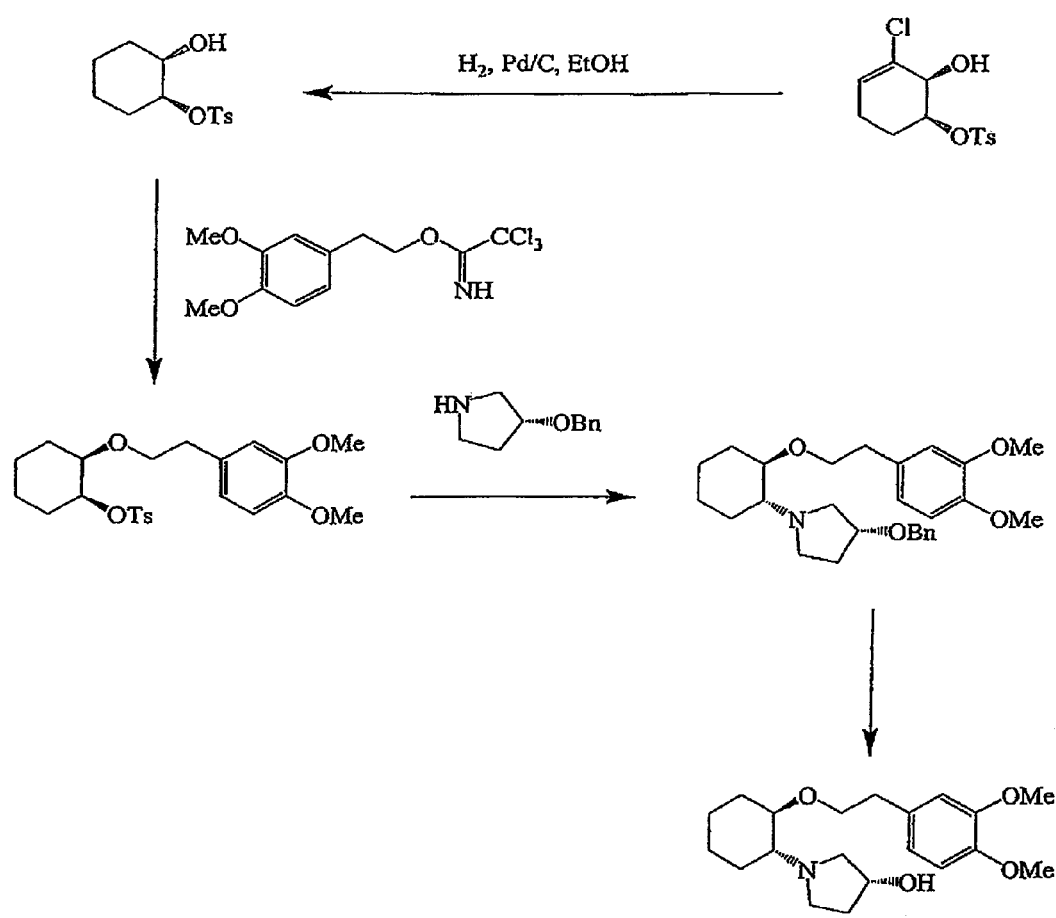

FIG. 22 illustrates a reaction scheme that may be used as a process for preparing a stereoisomerically substantially pure trans-(1R,2R)-aminocyclohexyl ether compound of formula (66).

Figure 23:
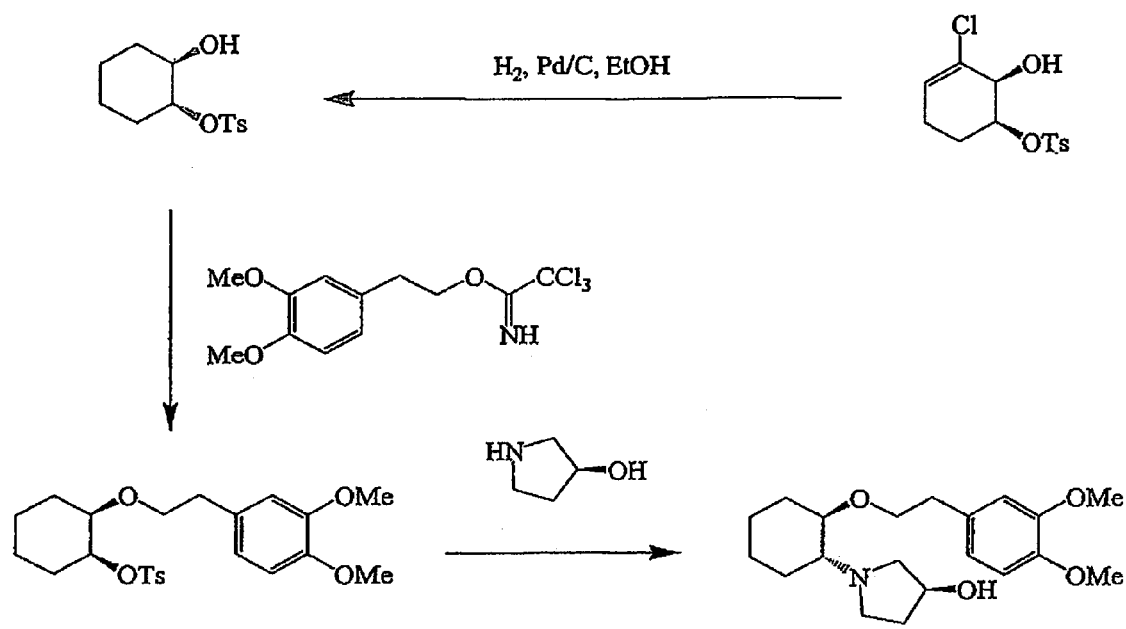

FIG. 23 illustrates a reaction scheme that may be used as a process for preparing a stereoisomerically substantially pure trans-(1R,2R)-aminocyclohexyl ether compound of formula (69).

Figure 24:
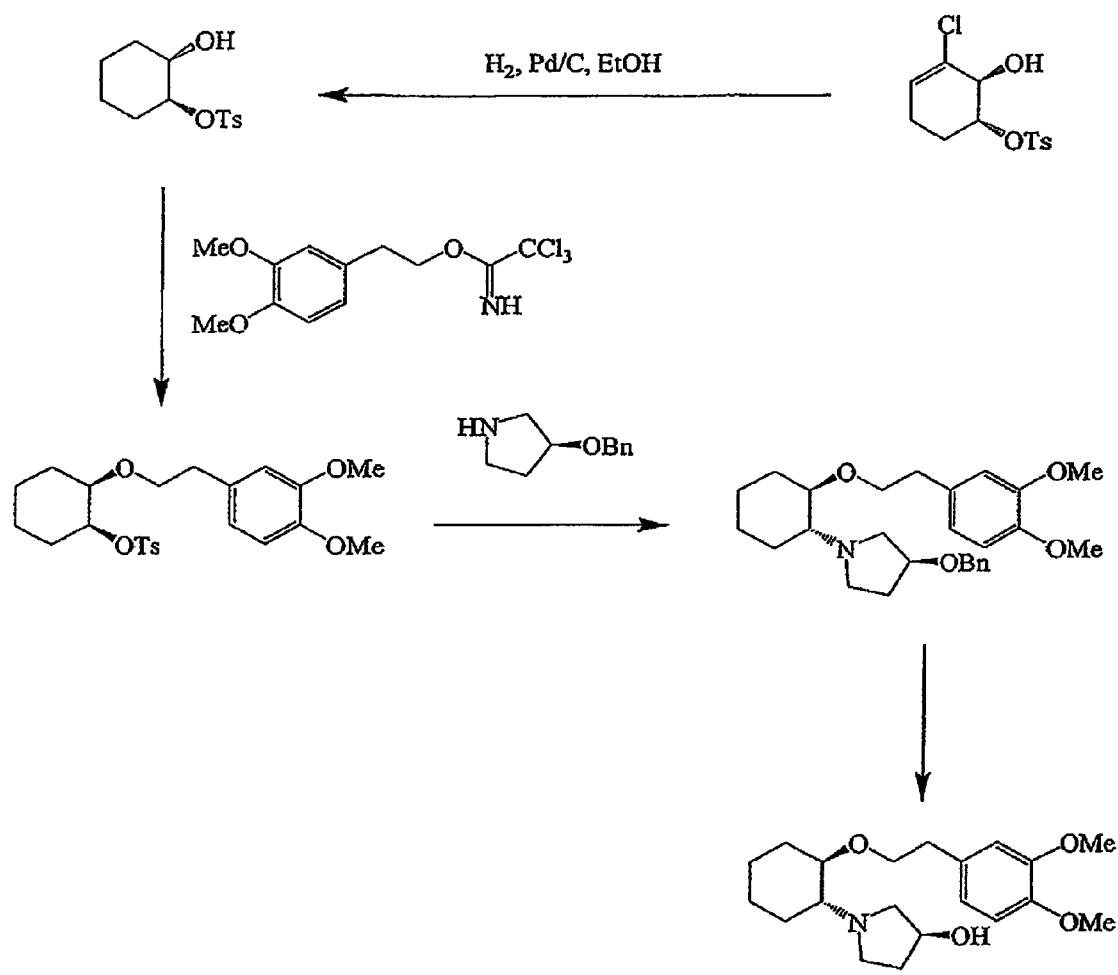

FIG. 24 illustrates a reaction scheme that may be used as a process for preparing a stereoisomerically substantially pure trans-(1R,2R)-aminocyclohexyl ether compound of formula (69).

Figure 25:
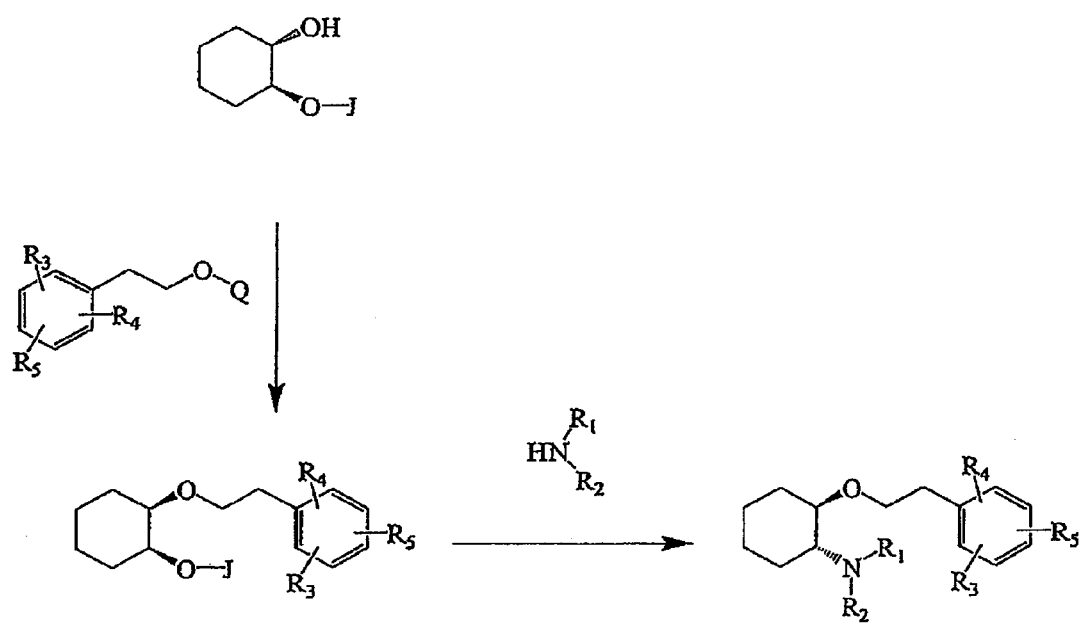

FIG. 25 illustrates a general reaction scheme that may be used as a process for preparing a stereoisomerically substantially pure trans-(1R,2R)-aminocyclohexyl ether compound of formula (57).

Figure 26:
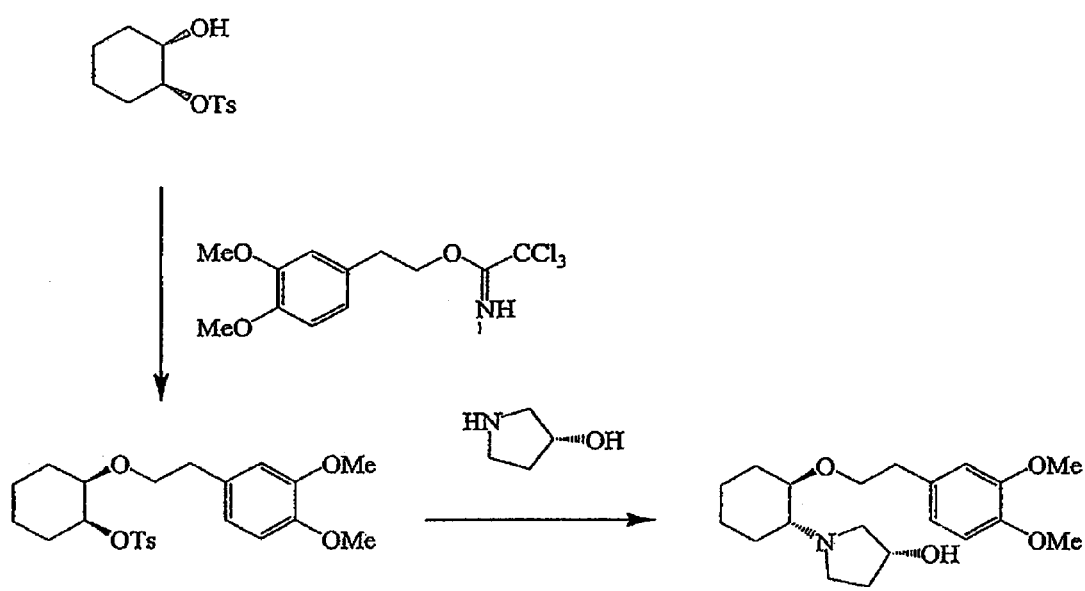

FIG. 26 illustrates a reaction scheme that may be used as a process for preparing a stereoisomerically substantially pure trans-(1R,2R)-aminocyclohexyl ether compound of formula (66).

Figure 27:
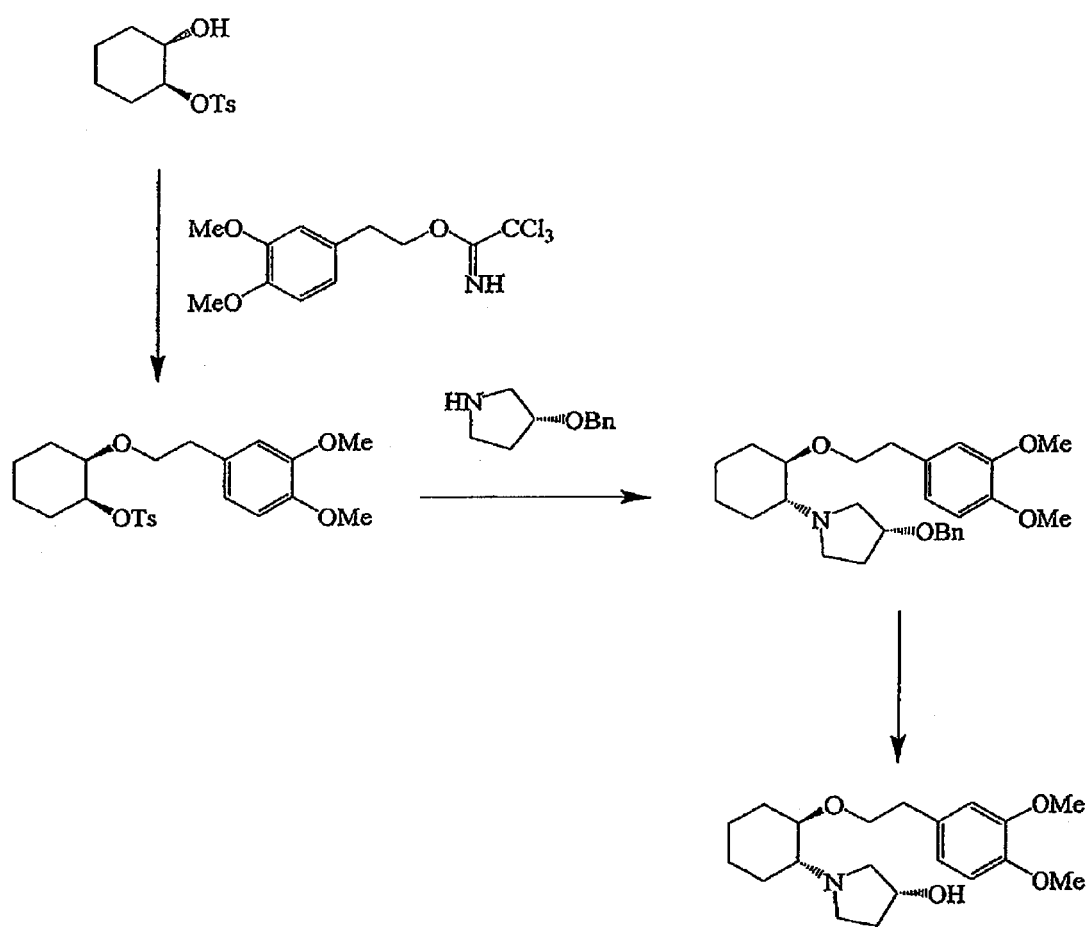

FIG. 27 illustrates a reaction scheme that may be used as a process for preparing a stereoisomerically substantially pure trans-(1R,2R)-aminocyclohexyl ether compound of formula (66).

Figure 28:
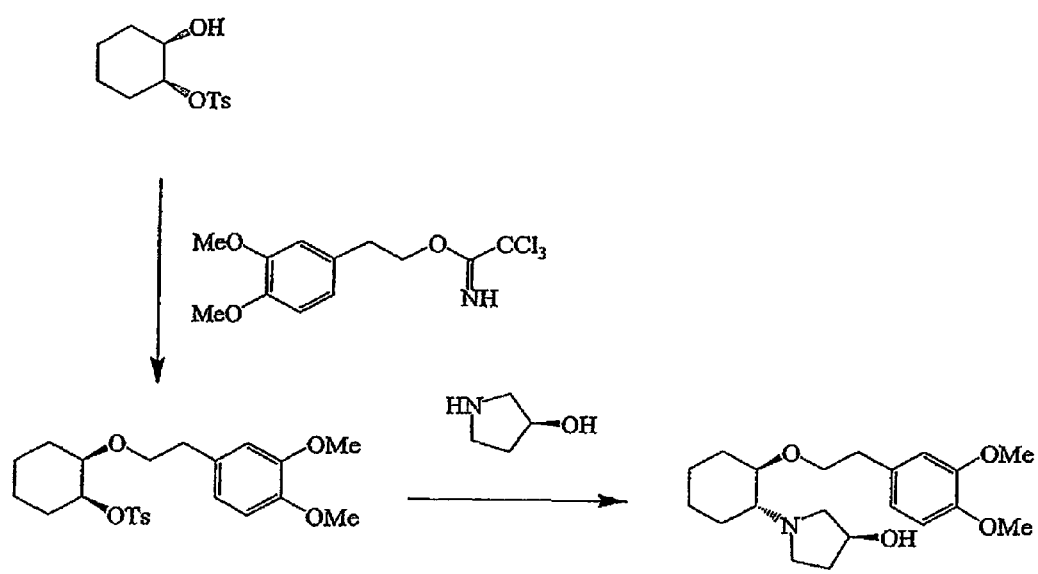

FIG. 28 illustrates a reaction scheme that may be used as a process for preparing a stereoisomerically substantially pure trans-(1R,2R)-aminocyclohexyl ether compound of formula (69).

Figure 29:
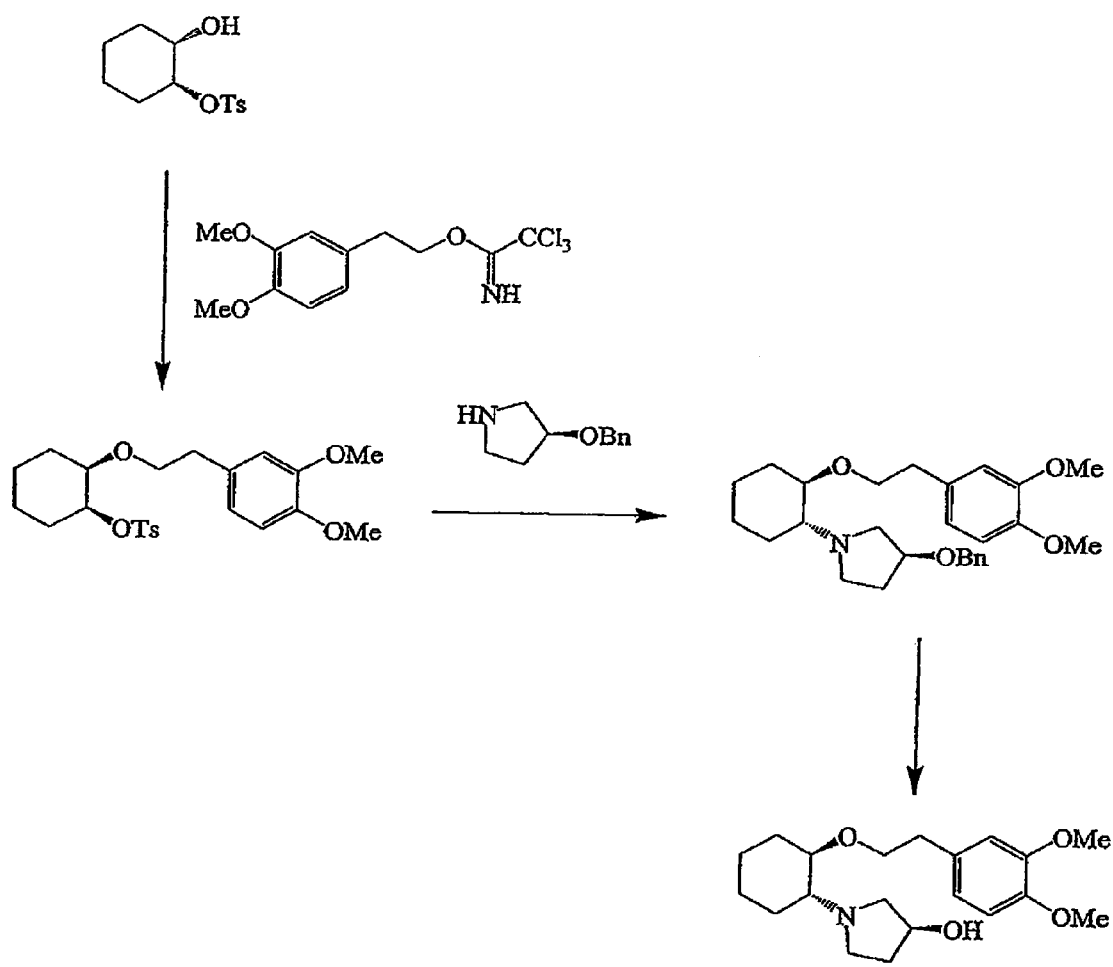

FIG. 29 illustrates a reaction scheme that may be used as a process for preparing a stereoisomerically substantially pure trans-(1R,2R)-aminocyclohexyl ether compound of formula (69).

Figure 30:
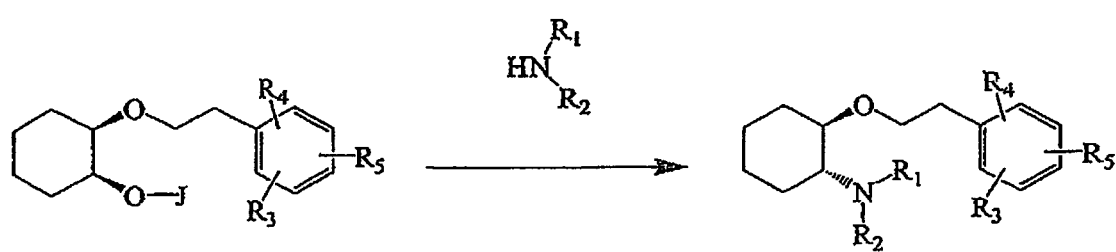

FIG. 30 illustrates a general reaction scheme that may be used as a process for preparing a stereoisomerically substantially pure trans-(1R,2R)-aminocyclohexyl ether compound of formula (57).

Figure 31:
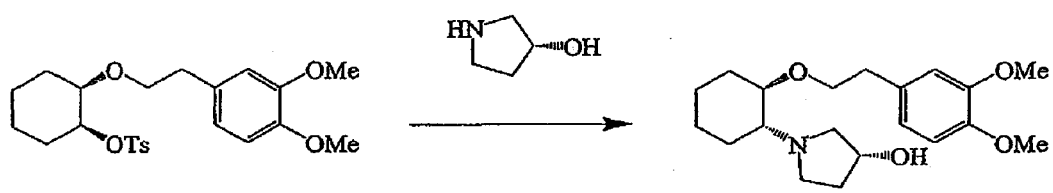

FIG. 31 illustrates a reaction scheme that may be used as a process for preparing a stereoisomerically substantially pure trans-(1R,2R)-aminocyclohexyl ether compound of formula (66).

Figure 32:
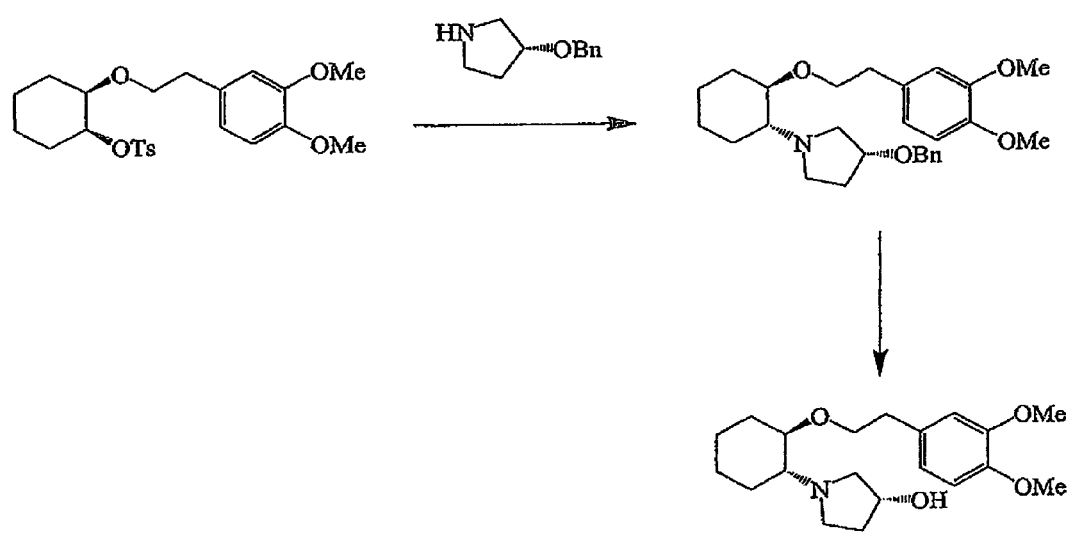

FIG. 32 illustrates a reaction scheme that may be used as a process for preparing a stereoisomerically substantially pure trans-(1R,2R)-aminocyclohexyl ether compound of formula (66).

Figure 33:
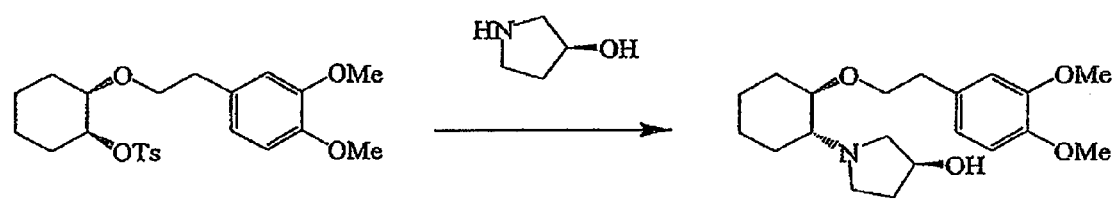

FIG. 33 illustrates a reaction scheme that may be used as a process for preparing a stereoisomerically substantially pure trans-(1R,2R)-aminocyclohexyl ether compound of formula (69).

Figure 34:
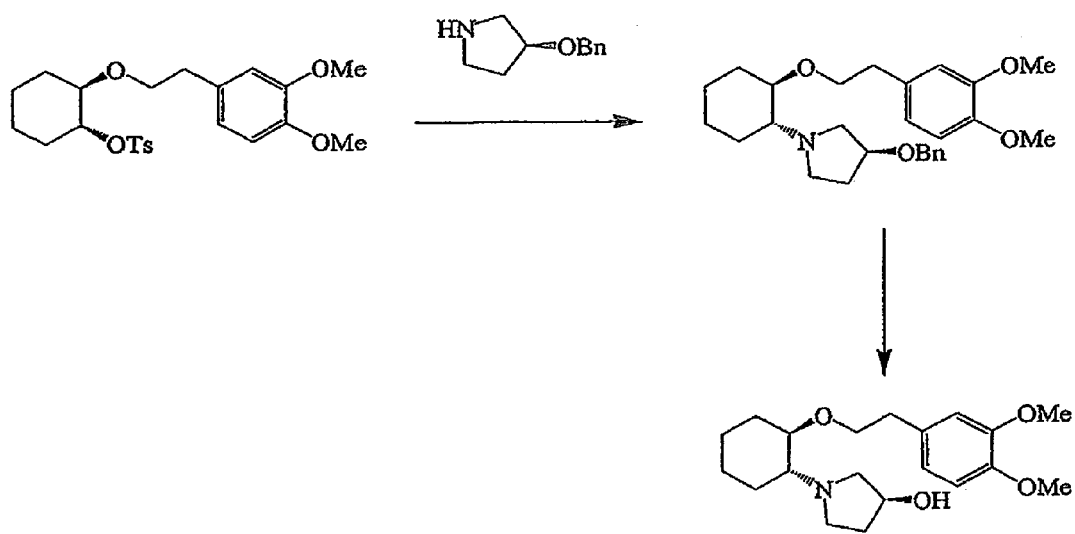

FIG. 34 illustrates a reaction scheme that may be used as a process for preparing a stereoisomerically substantially pure trans-(1R,2R)-aminocyclohexyl ether compound of formula (69).

Figure 35:
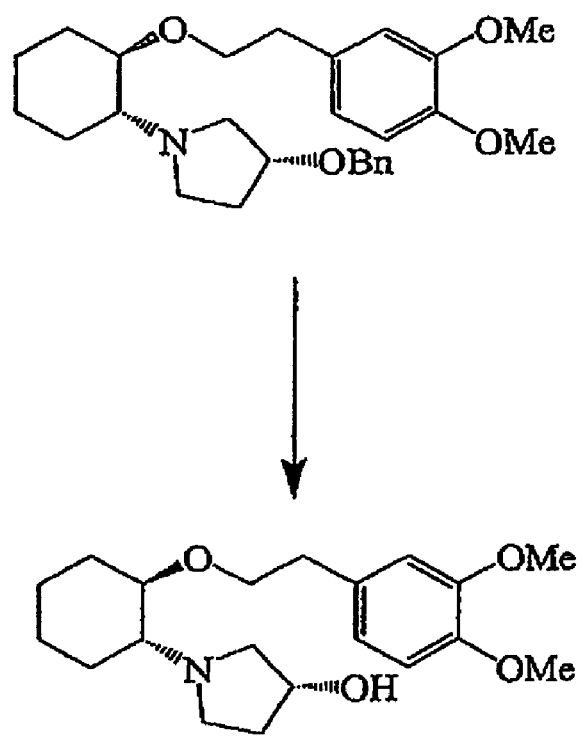

FIG. 35 illustrates a general reaction scheme that may be used as a process for preparing a stereoisomerically substantially pure trans-(1R,2R)-aminocyclohexyl ether compound of formula (66).

Figure 36:
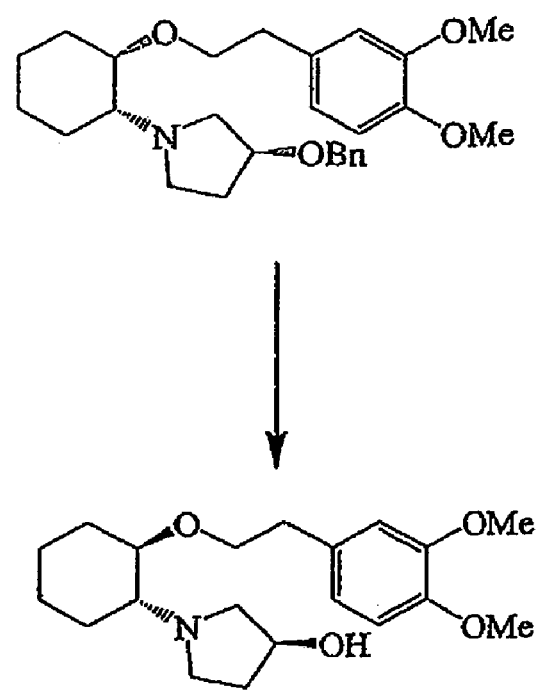

FIG. 36 illustrates a reaction scheme that may be used as a process for preparing a stereoisomerically substantially pure trans-(1R,2R)-aminocyclohexyl ether compound of formula (69).

Figure 37:
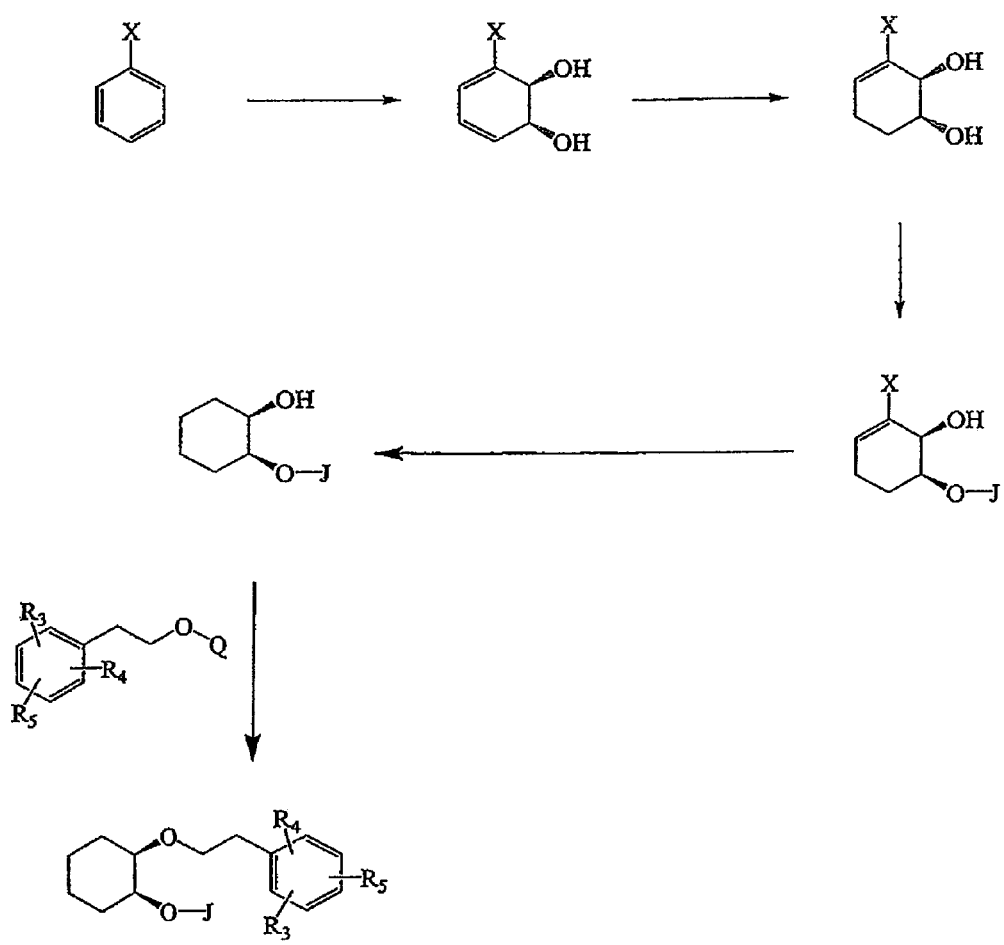

FIG. 37 illustrates a reaction scheme that may be used as a process for preparing a stereoisomerically substantially pure compound of formula (55).

Figure 38:
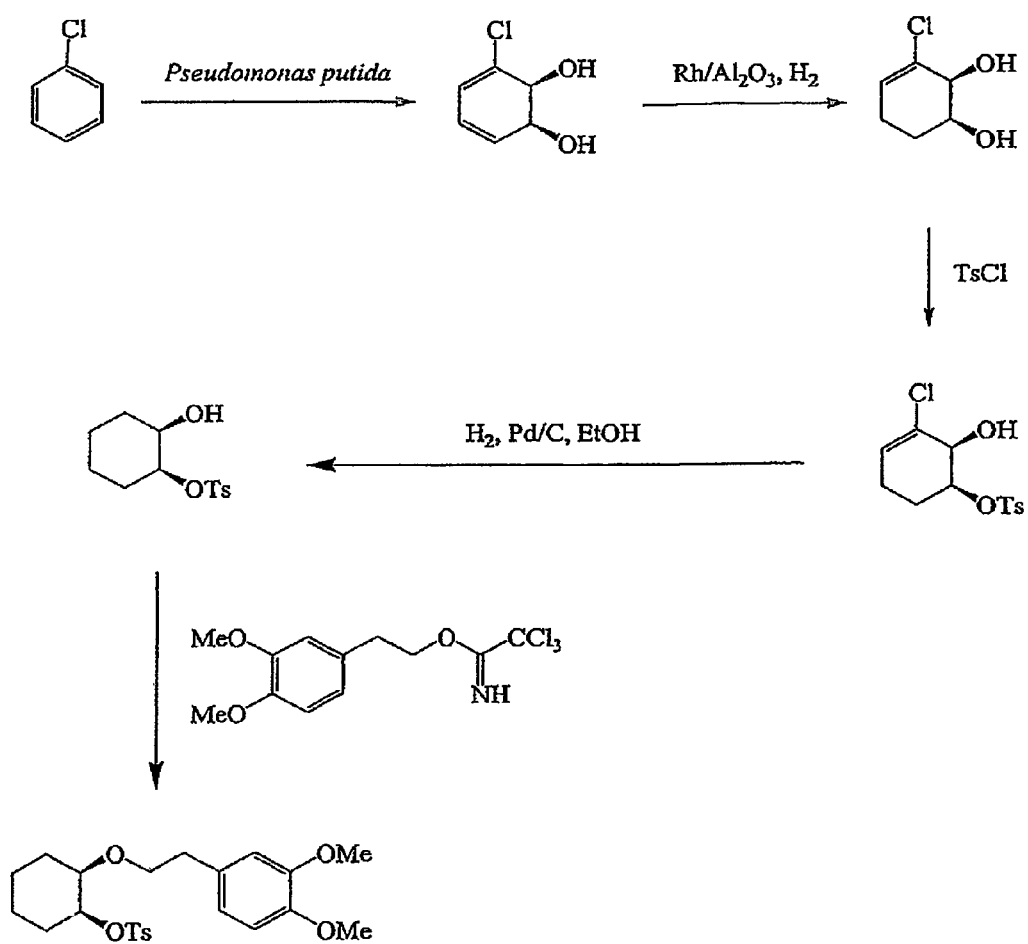

FIG. 38 illustrates a reaction scheme that may be used as a process for preparing a stereoisomerically substantially pure compound of formula (64).

Figure 39:
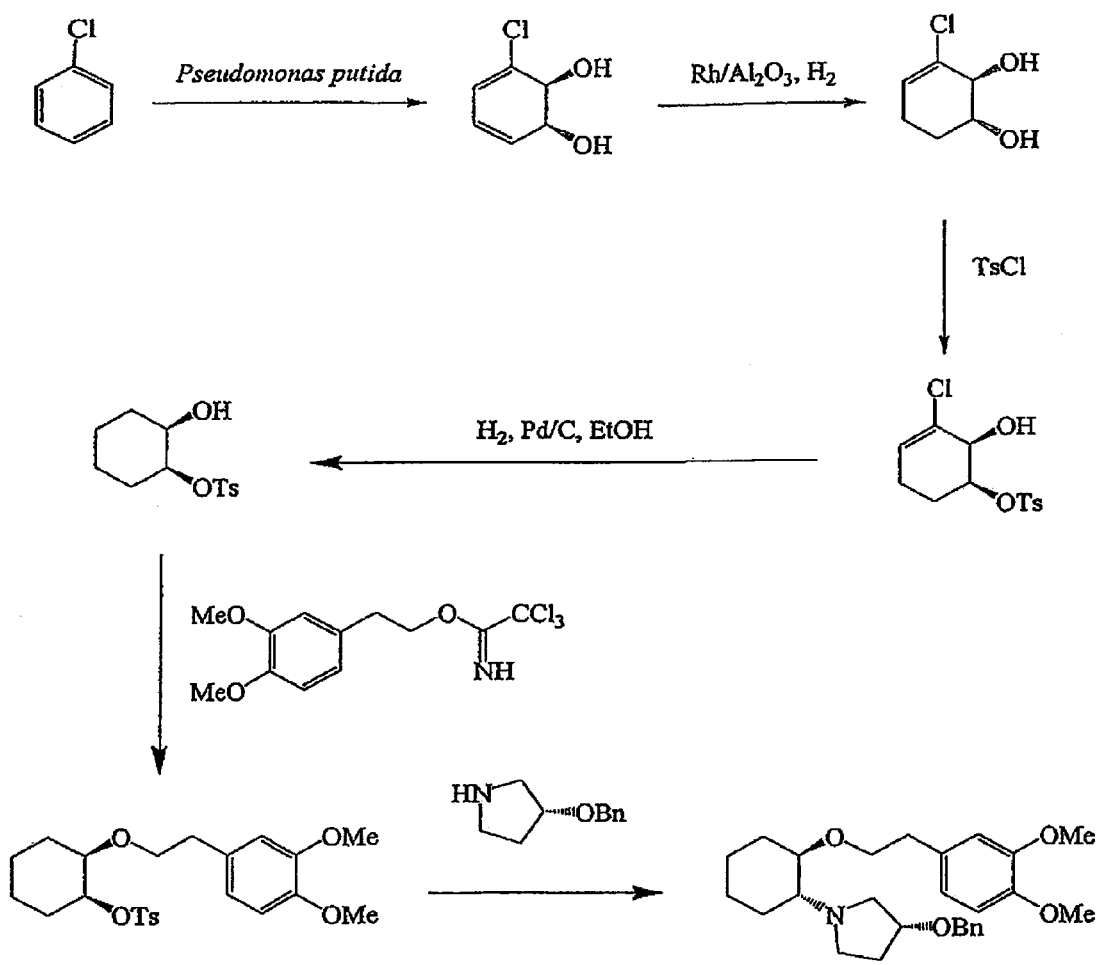

FIG. 39 illustrates a reaction scheme that may be used as a process for preparing a stereoisomerically substantially pure compound of formula (67).

Figure 40:
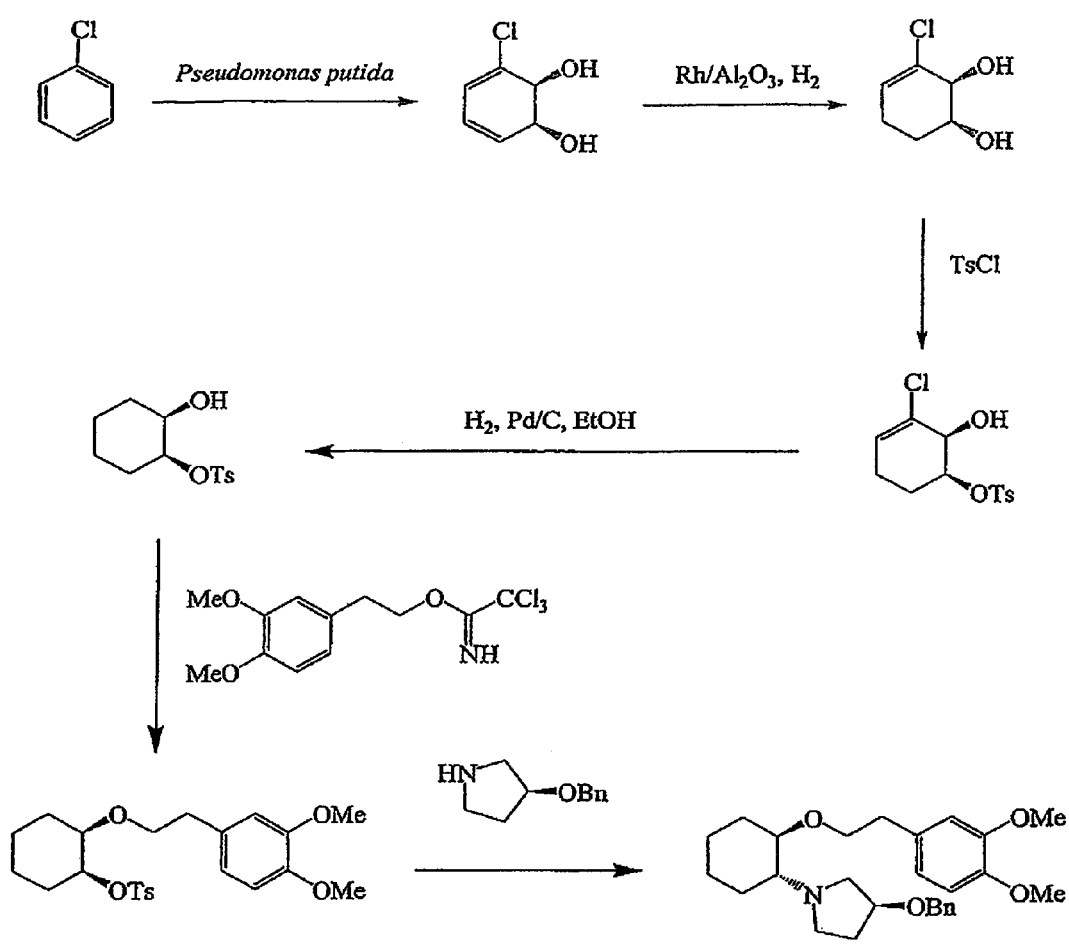

FIG. 40 illustrates a reaction scheme that may be used as a process for preparing a stereoisomerically substantially pure compound of formula (71).

Figure 41:
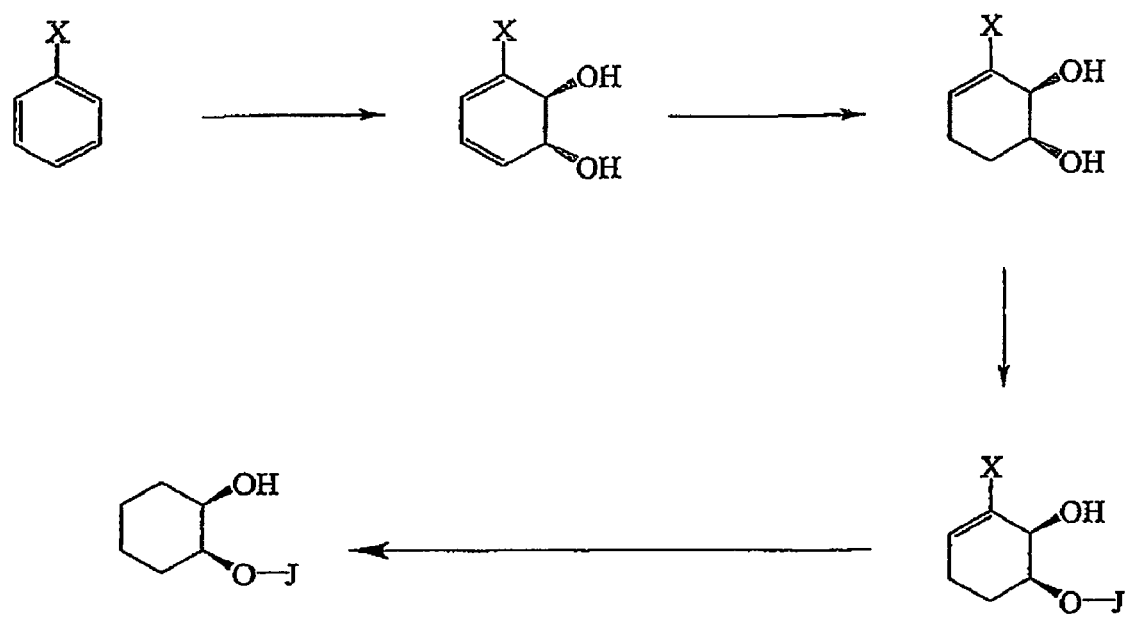

FIG. 41 illustrates a reaction scheme that may be used as a process for preparing a stereoisomerically substantially pure compound of formula (53).

Figure 42:
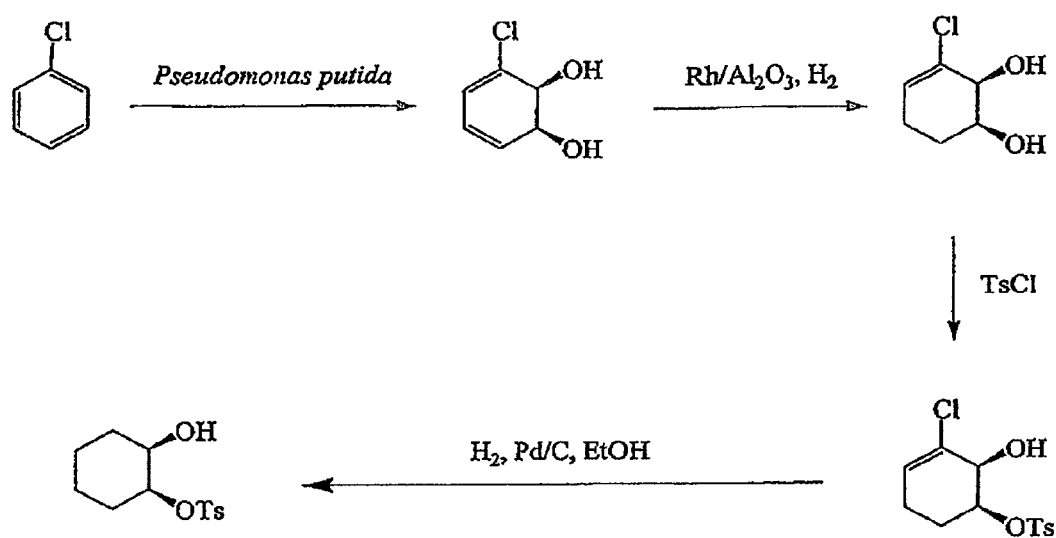

FIG. 42 illustrates a reaction scheme that may be used as a process for preparing a stereoisomerically substantially pure compound of formula (62).

Figure 43:
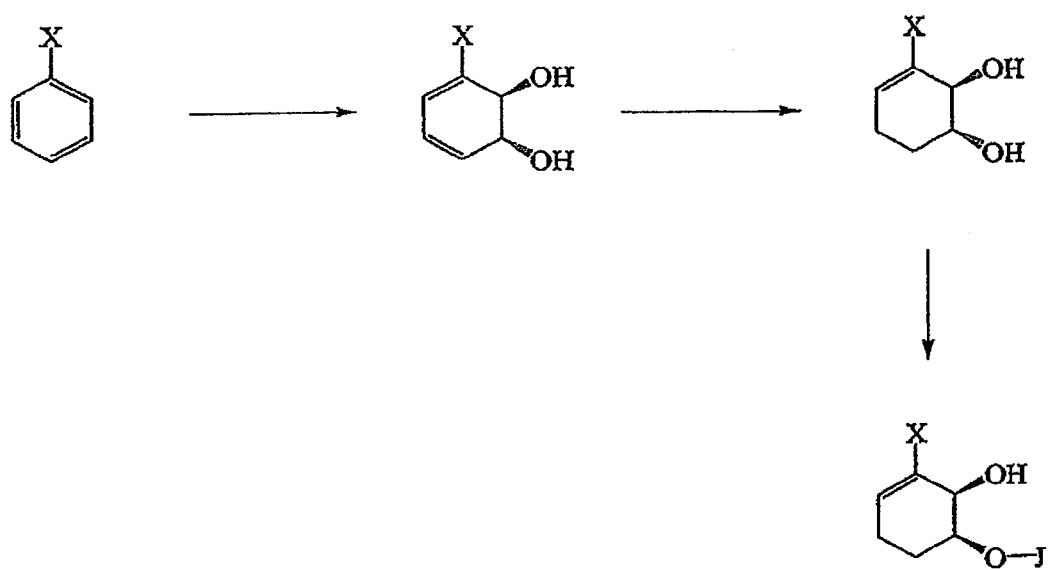

FIG. 43 illustrates a reaction scheme that may be used as a process for preparing a stereoisomerically substantially pure compound of formula (52).

Figure 44:
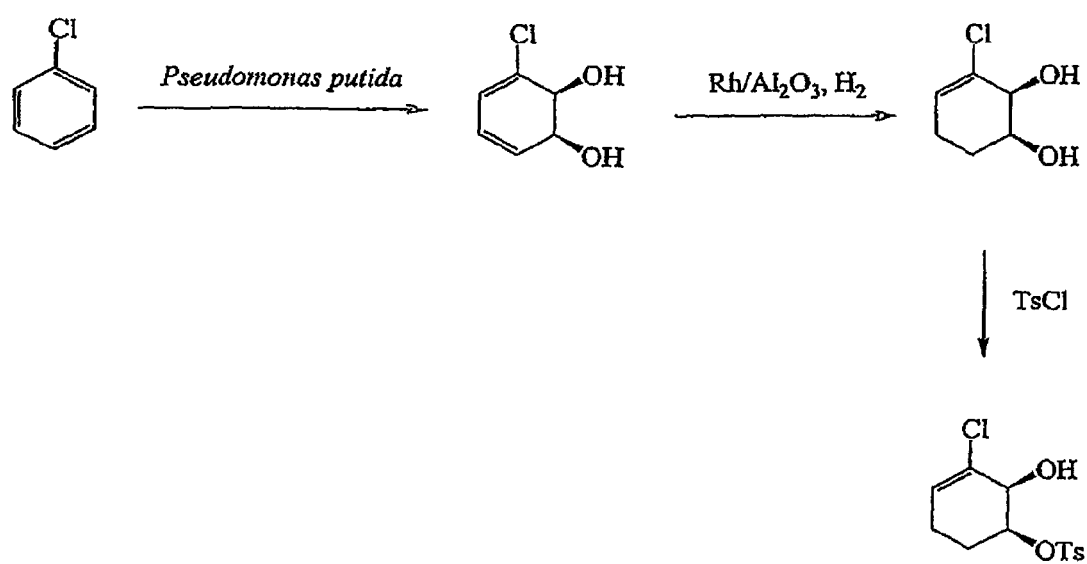

FIG. 44 illustrates a reaction scheme that may be used as a process for preparing a stereoisomerically substantially pure compound of formula (61).

Figure 45:
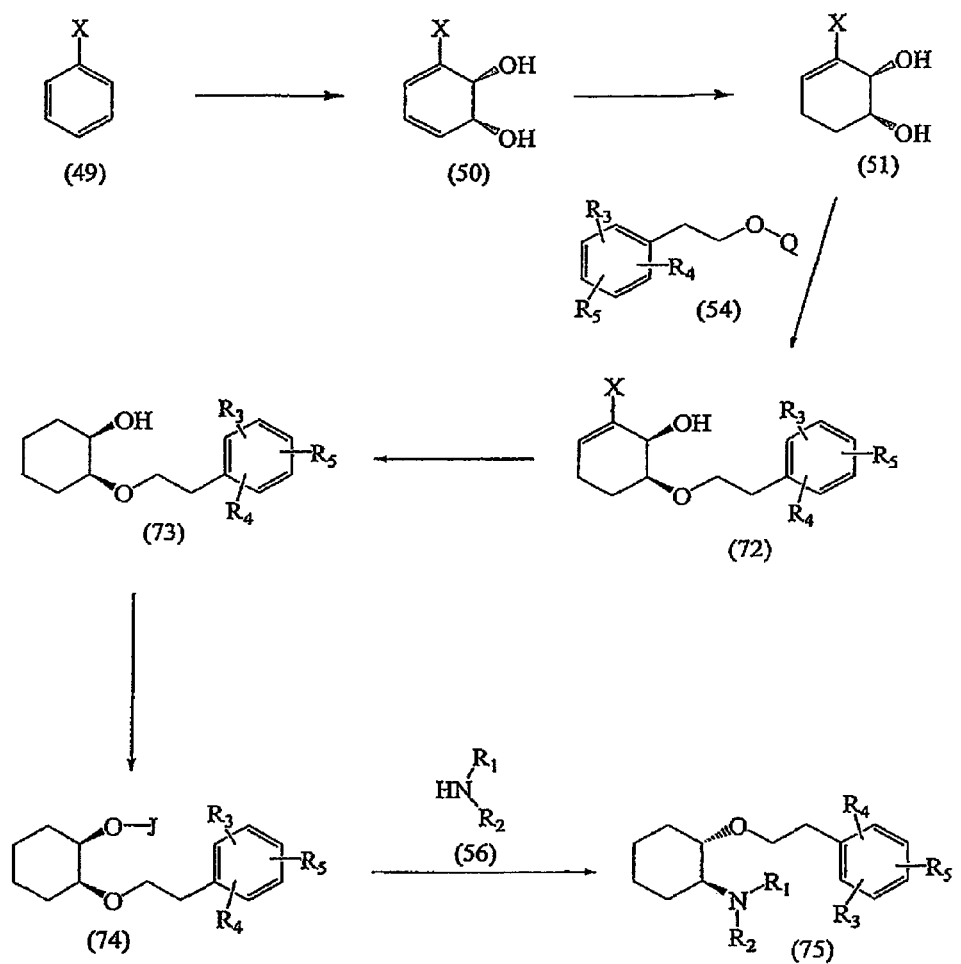

FIG. 45 illustrates a general reaction scheme that may be used as a process for preparing a stereoisomerically substantially pure trans-(1S,2S)-aminocyclohexyl ether compound of formula (75).

Figure 46:
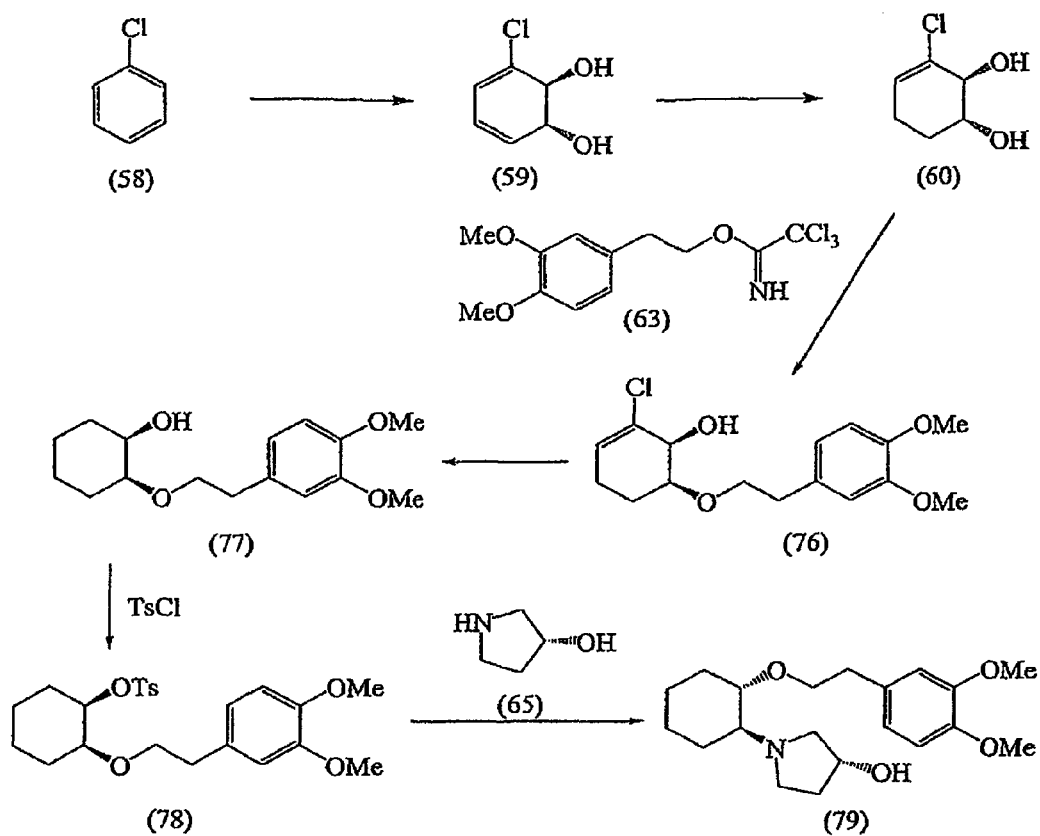

FIG. 46 illustrates a reaction scheme that may be used as a process for preparing a stereoisomerically substantially pure trans-(1S,2S)-aminocyclohexylether compound of formula (79).

Figure 47:
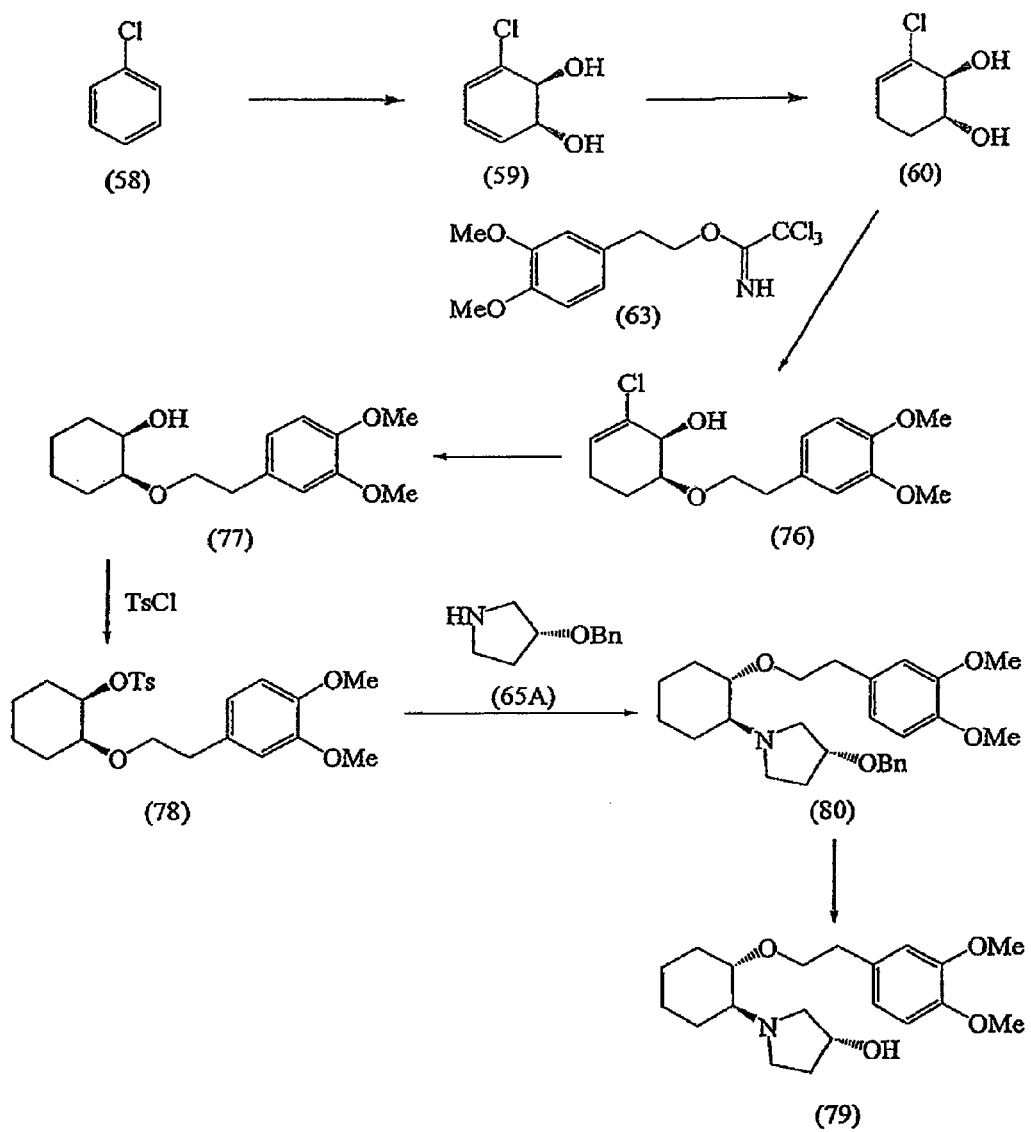

FIG. 47 illustrates a reaction scheme that may be used as a process for preparing a stereoisomerically substantially pure trans-(1S,2S)-aminocyclohexyl ether compound of formula (79).

Figure 48:
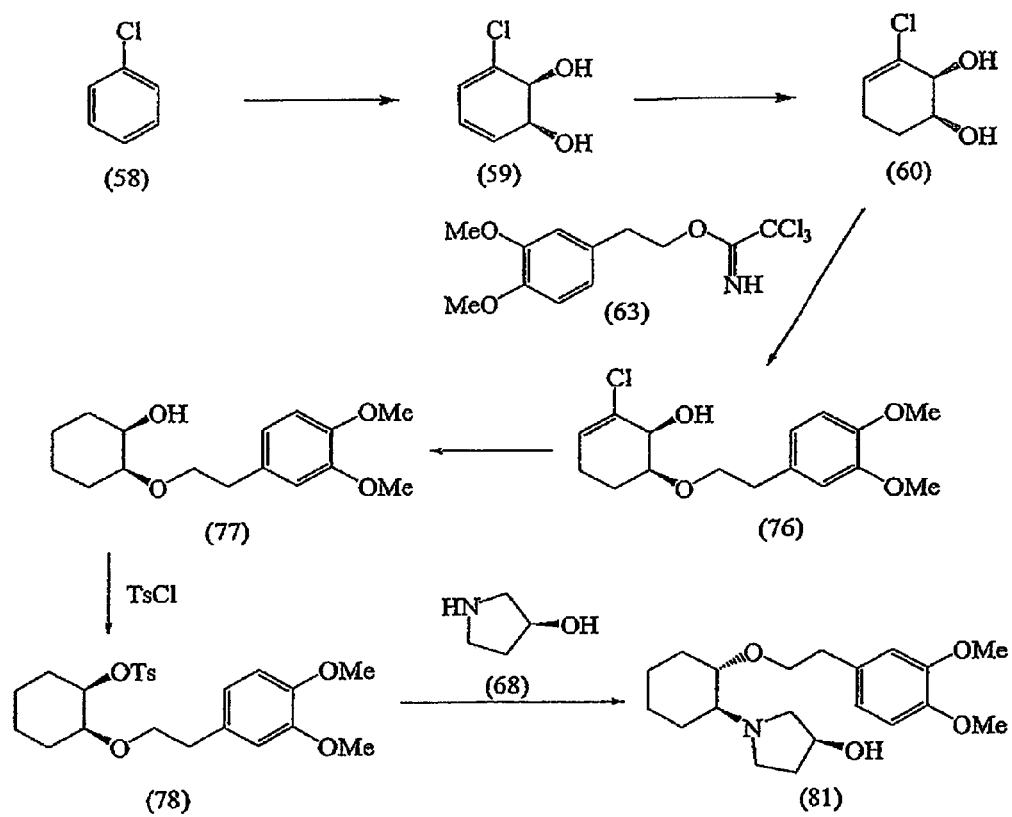

FIG. 48 illustrates a reaction scheme that may be used as a process for preparing a stereoisomerically substantially pure trans-(1S,2S)-aminocyclohexyl ether compound of formula (81).

Figure 49:
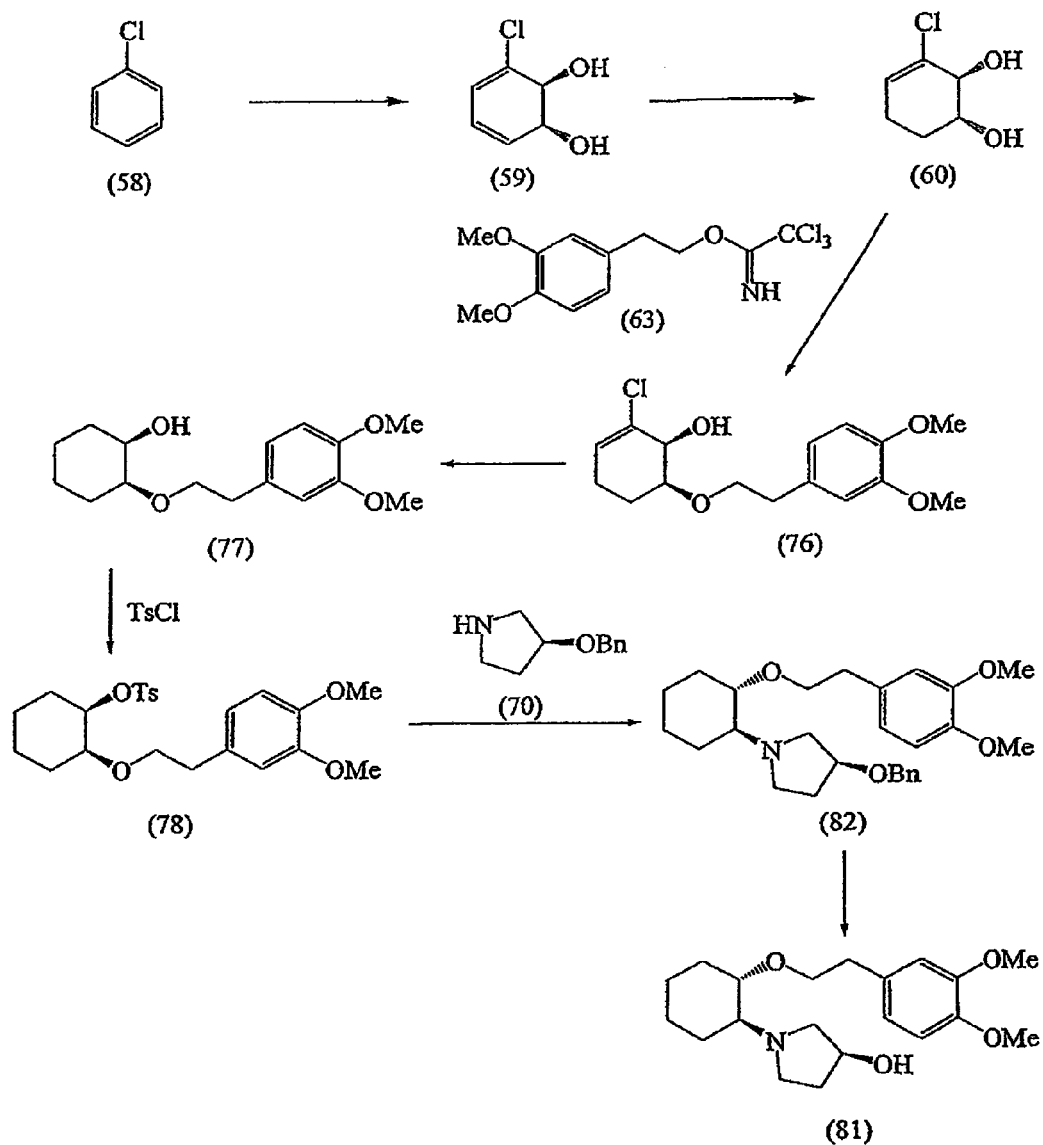

FIG. 49 illustrates a reaction scheme that may be used as a process for preparing a stereoisomerically substantially pure trans-(1S,2S)-aminocyclohexyl ether compound of formula (81).

Figure 50:
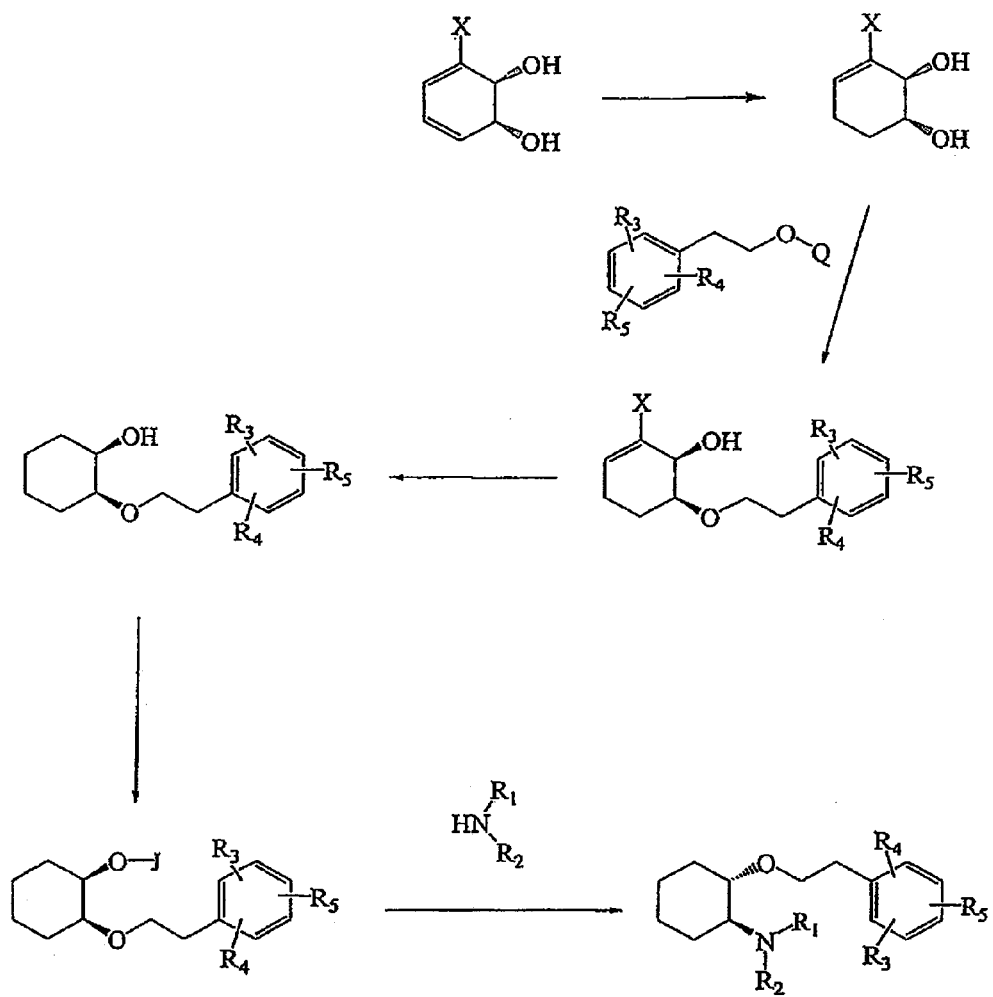

FIG. 50 illustrates a general reaction scheme that may be used as a process for preparing a stereoisomerically substantially pure trans-(1S,2S)-aminocyclohexyl ether compound of formula (75).

Figure 51:
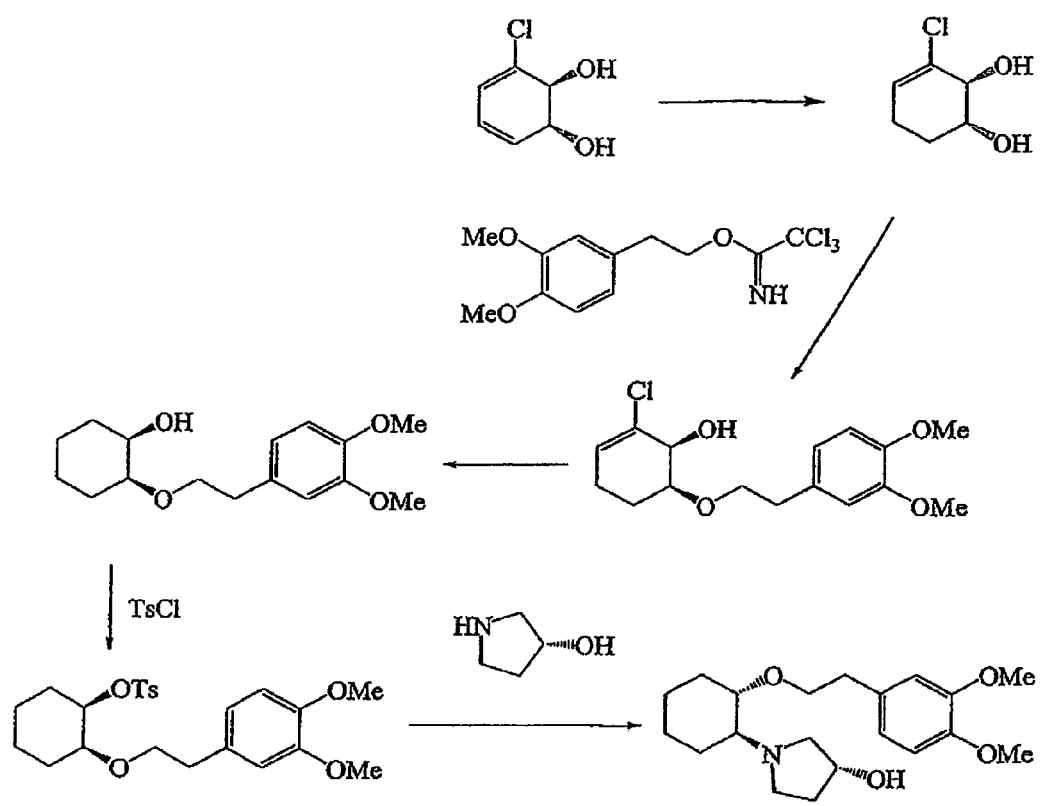

FIG. 51 illustrates a reaction scheme that may be used as a process for preparing a stereoisomerically substantially pure trans-(1S,2S)-aminocyclohexyl ether compound of formula (79).

Figure 52:
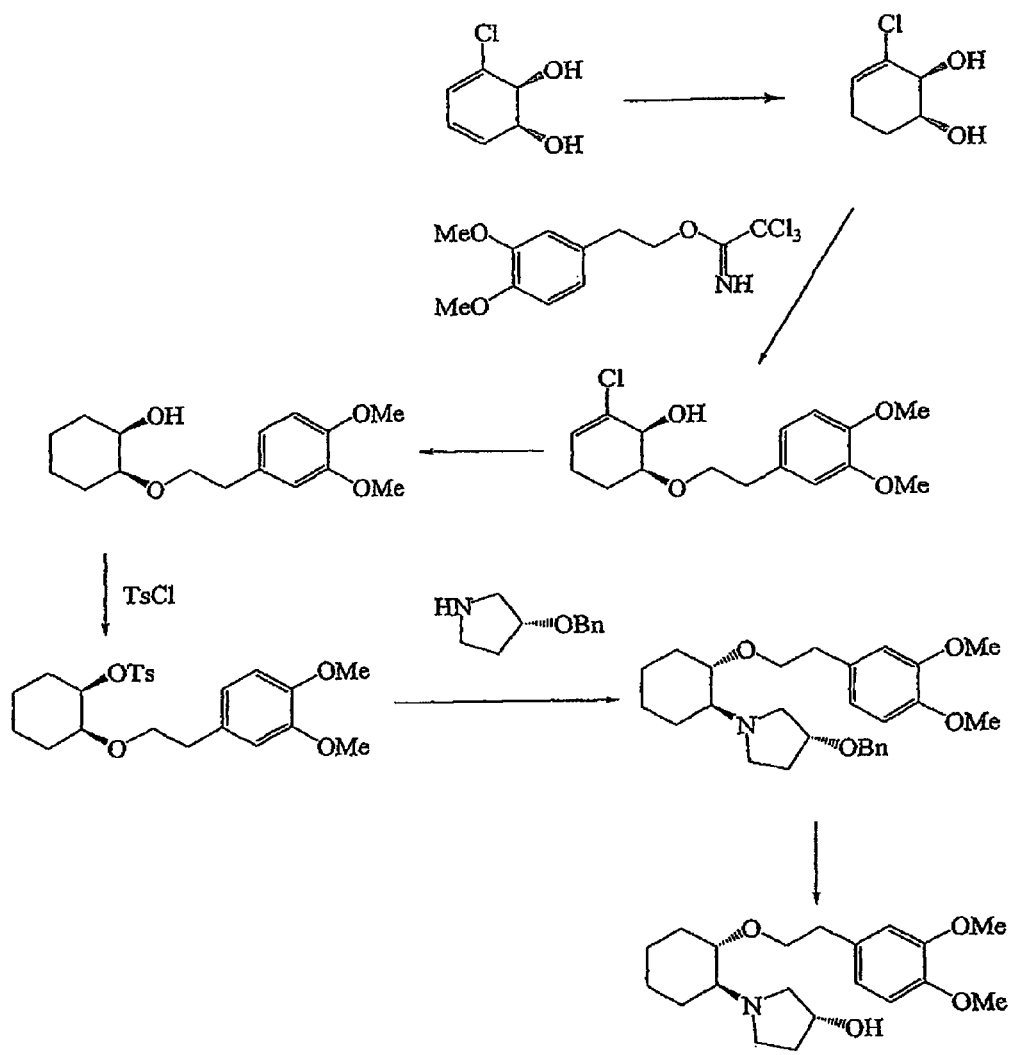

FIG. 52 illustrates a reaction scheme that may be used as a process for preparing a stereoisomerically substantially pure trans-(1S,2S)-aminocyclohexyl ether compound of formula (79).

Figure 53:
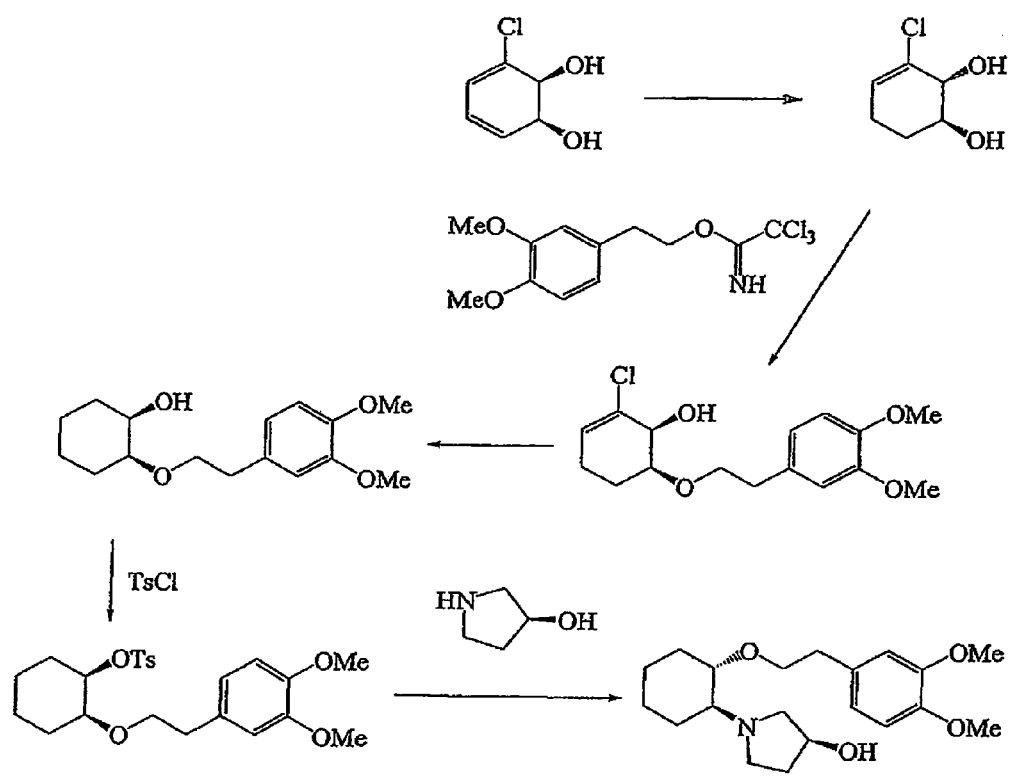

FIG. 53 illustrates a reaction scheme that may be used as a process for preparing a stereoisomerically substantially pure trans-(1S,2S)-aminocyclohexyl ether compound of formula (81).

Figure 54:
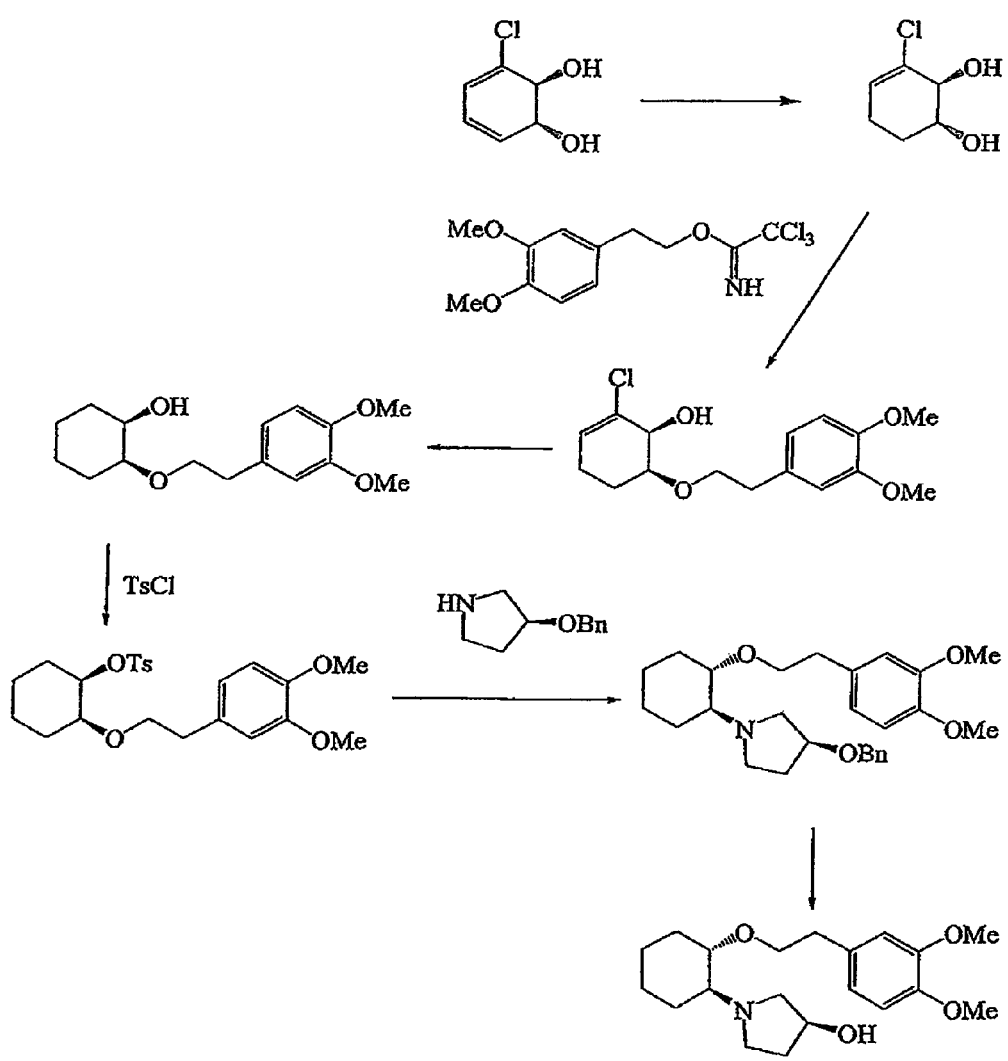

FIG. 54 illustrates a reaction scheme that may be used as a process for preparing a stereoisomerically substantially pure trans-(1S,2S)-aminocyclohexyl ether compound of formula (81).

Figure 55:
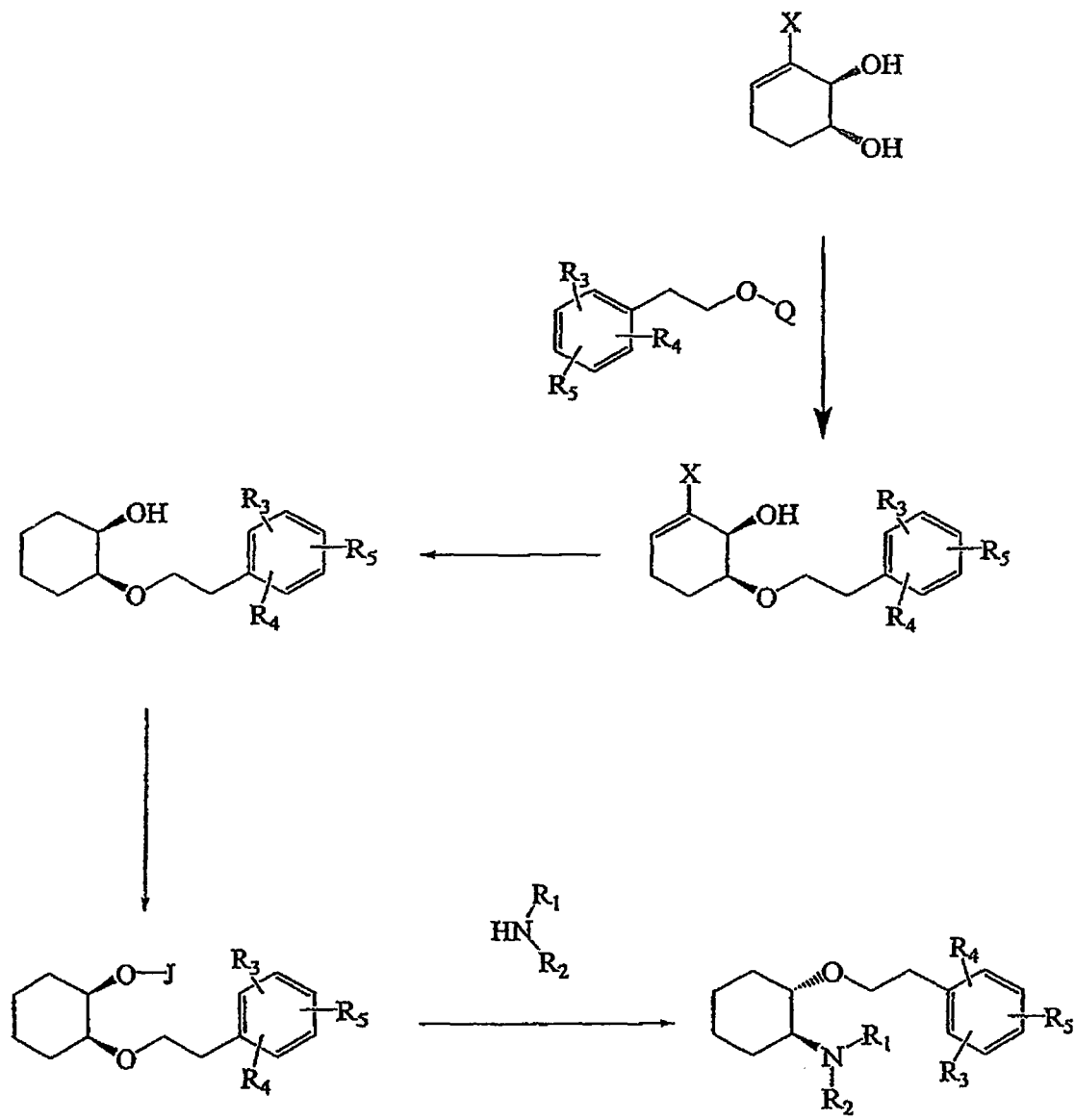

FIG. 55 illustrates a general reaction scheme that may be used as a process for preparing a stereoisomerically substantially pure trans-(1S,2S)-aminocyclohexyl ether compound of formula (75).

Figure 56:
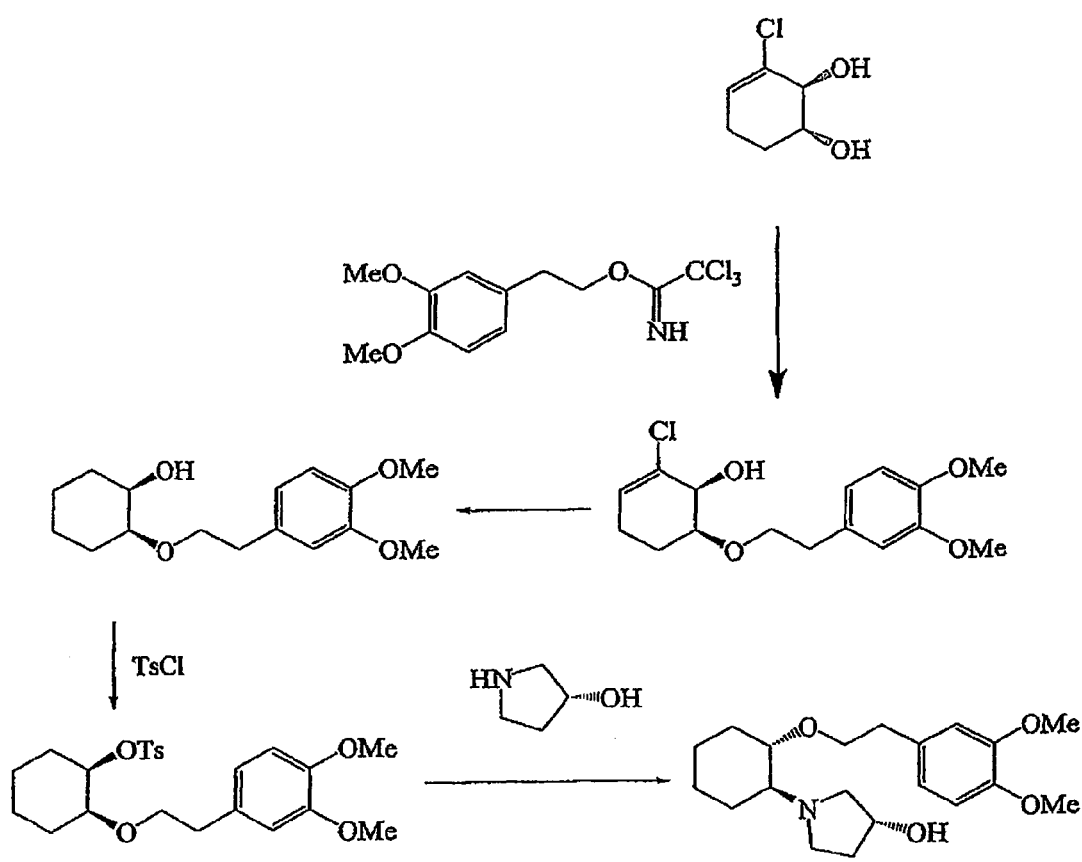

FIG. 56 illustrates a reaction scheme that may be used as a process for preparing a stereoisomerically substantially pure trans-(1S,2S)-aminocyclohexyl ether compound of formula (79).

Figure 57:
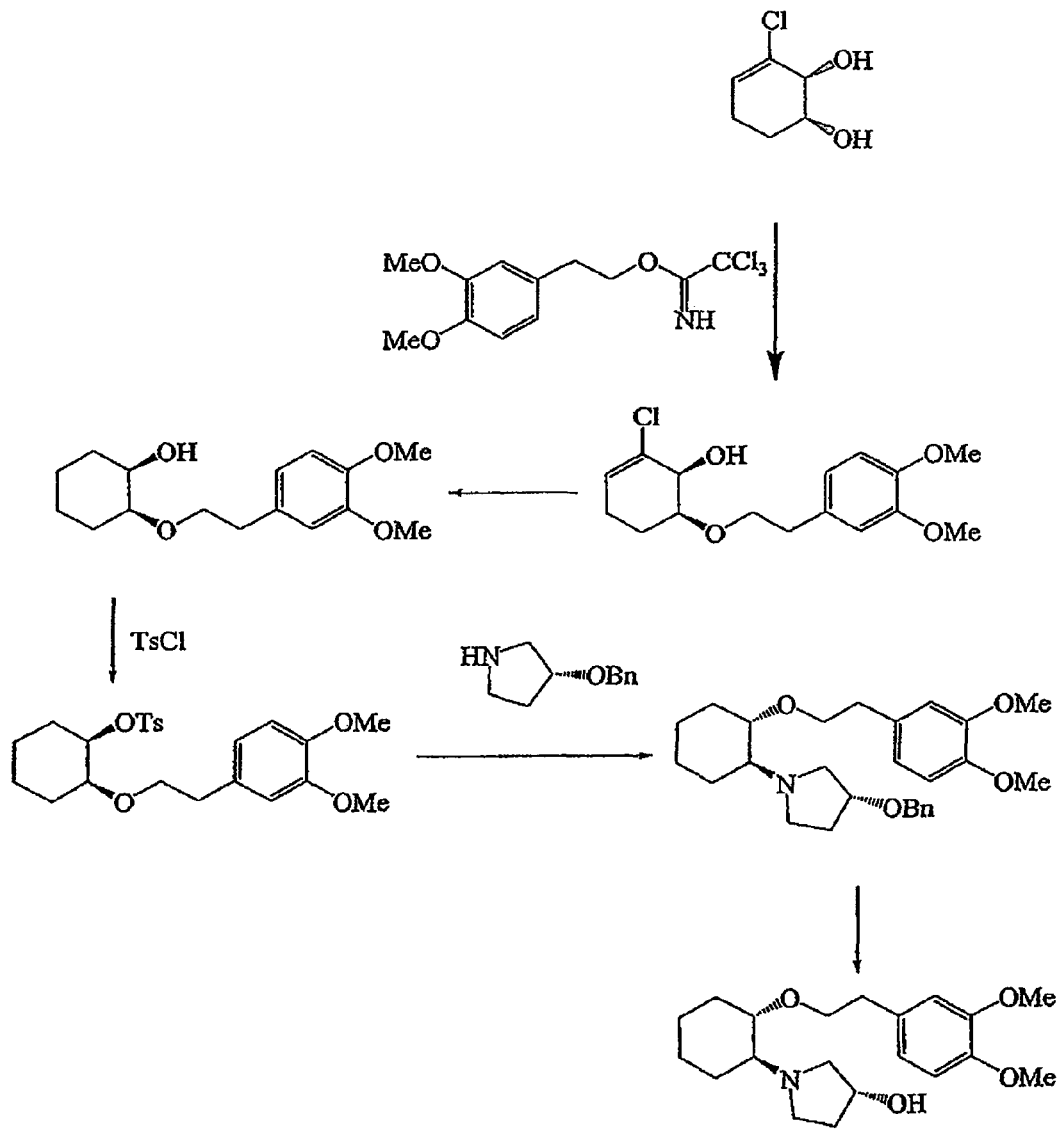

FIG. 57 illustrates a reaction scheme that may be used as a process for preparing a stereoisomerically substantially pure trans-(1S,2S)-aminocyclohexyl ether compound of formula (79).

Figure 58:
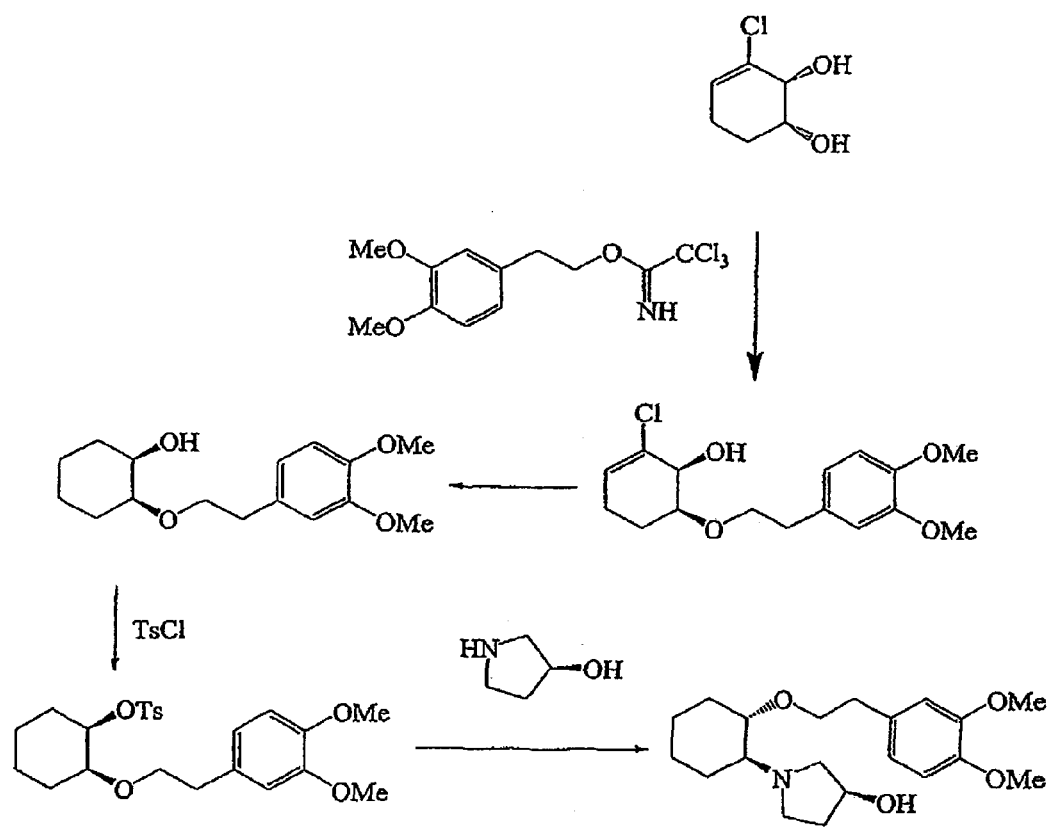

FIG. 58 illustrates a reaction scheme that may be used as a process for preparing a stereoisomerically substantially pure trans-(1S,2S)-aminocyclohexyl ether compound of formula (81).

Figure 59:
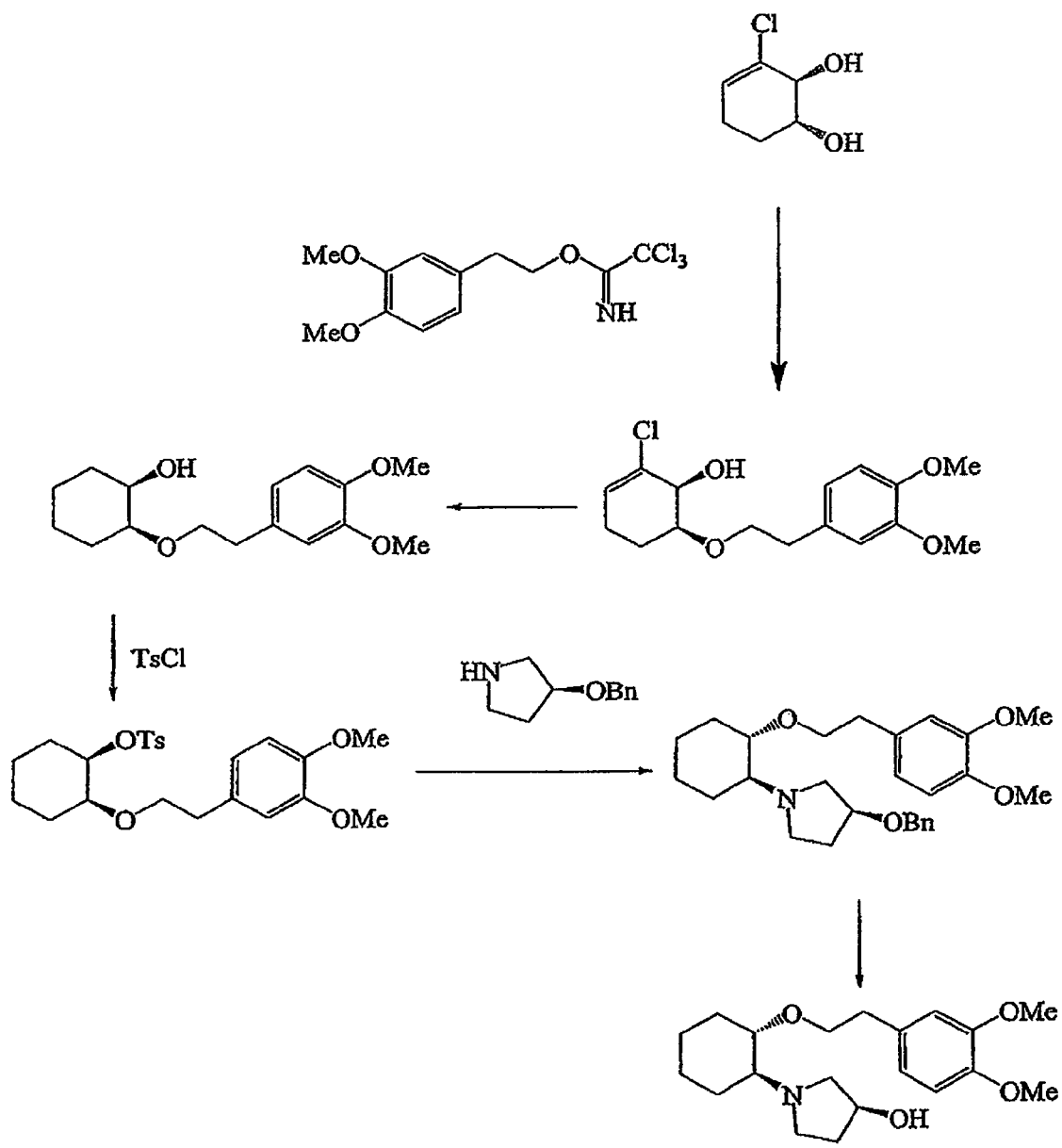

FIG. 59 illustrates a reaction scheme that may be used as a process for preparing a stereoisomerically substantially pure trans-(1S,2S)-aminocyclohexyl ether compound of formula (81).

Figure 60:
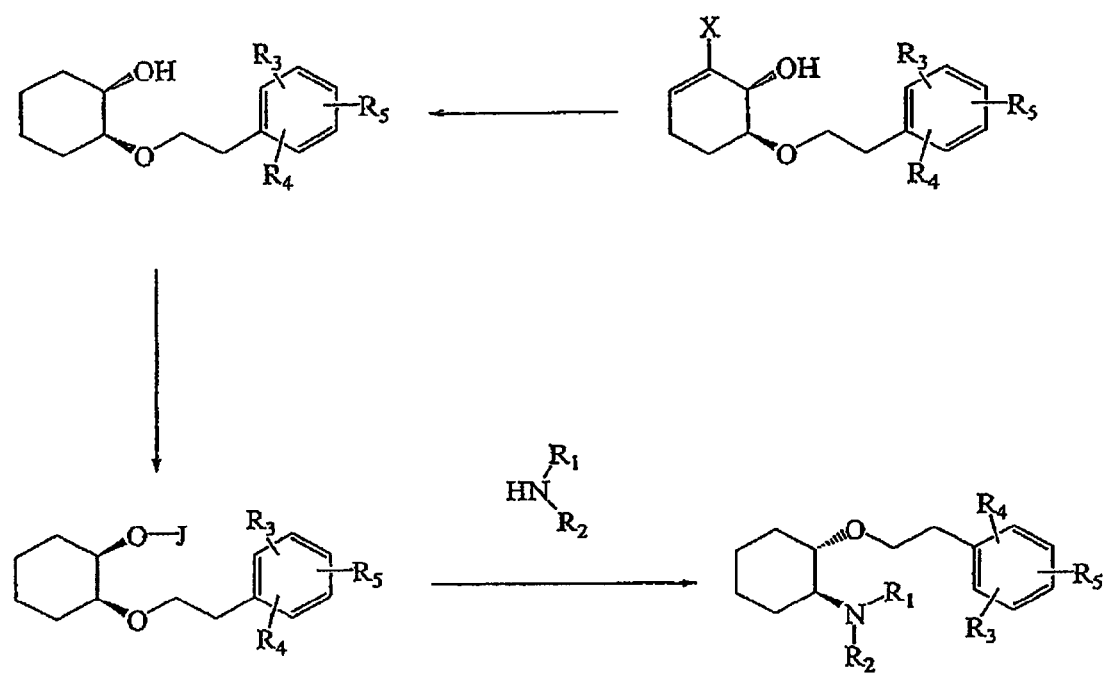

FIG. 60 illustrates a general reaction scheme that may be used as a process for preparing a stereoisomerically substantially pure trans-(1S,2S)-aminocyclohexyl ether compound of formula (75).

Figure 61:
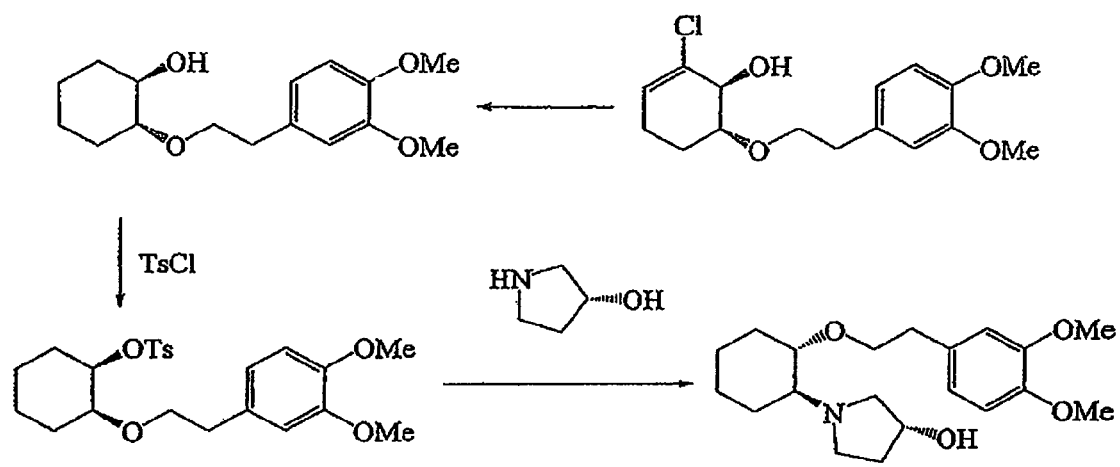

FIG. 61 illustrates a reaction scheme that may be used as a process for preparing a stereoisomerically substantially pure trans-(1S,2S)-aminocyclohexyl ether compound of formula (79).

Figure 62:
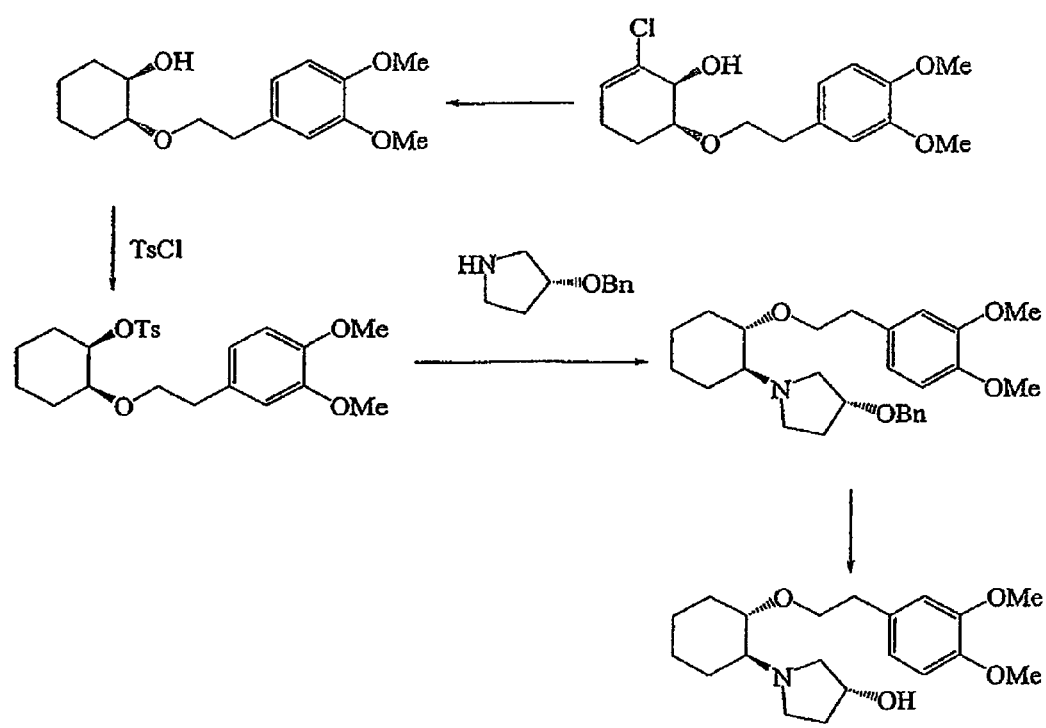

FIG. 62 illustrates a reaction scheme that may be used as a process for preparing a stereoisomerically substantially pure trans-(1S,2S)-aminocyclohexyl ether compound of formula (79).

Figure 63:
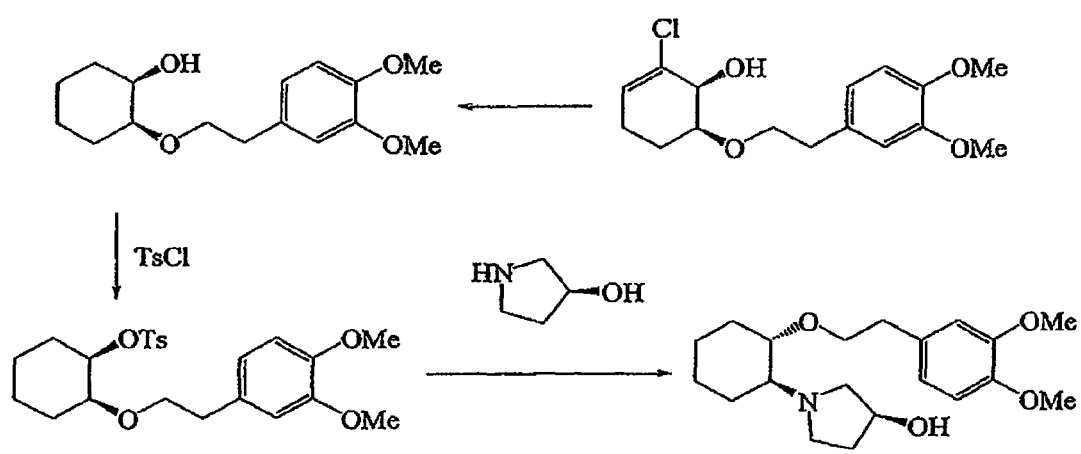

FIG. 63 illustrates a reaction scheme that may be used as a process for preparing a stereoisomerically substantially pure trans-(1S,2S)-aminocyclohexyl ether compound of formula (81).

Figure 64:
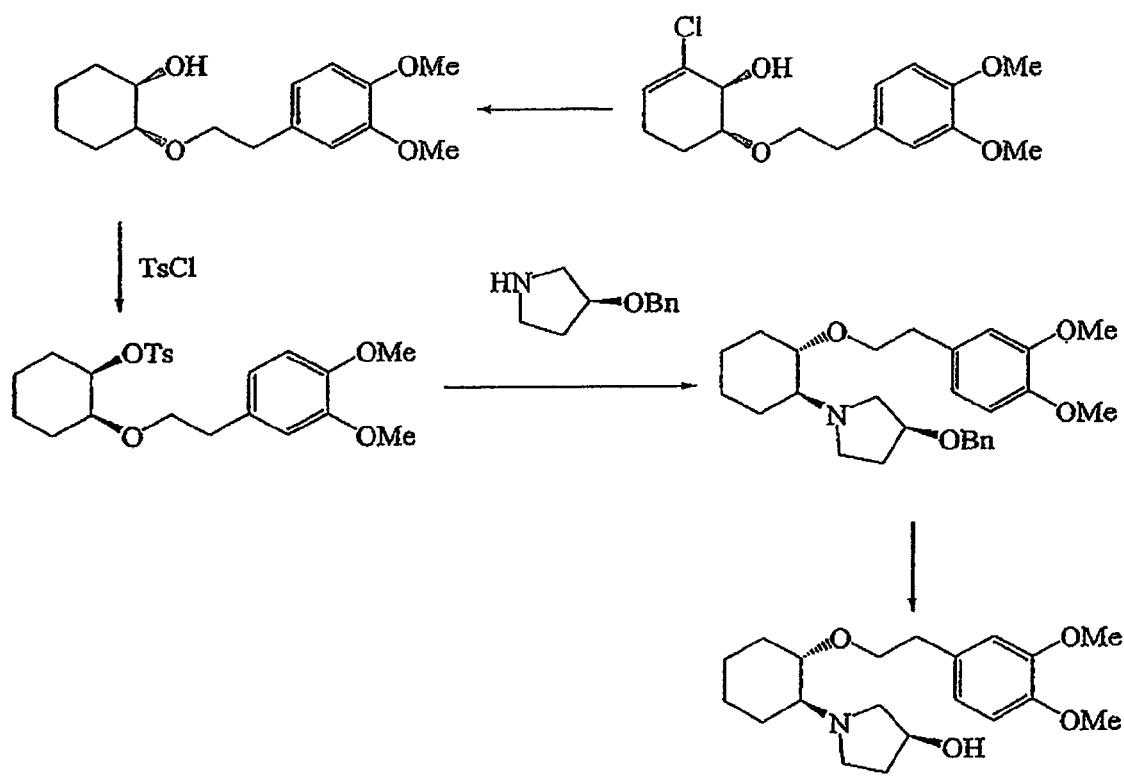

FIG. 64 illustrates a reaction scheme that may be used as a process for preparing a stereoisomerically substantially pure trans-(1S,2S)-aminocyclohexyl ether compound of formula (81).

Figure 65:
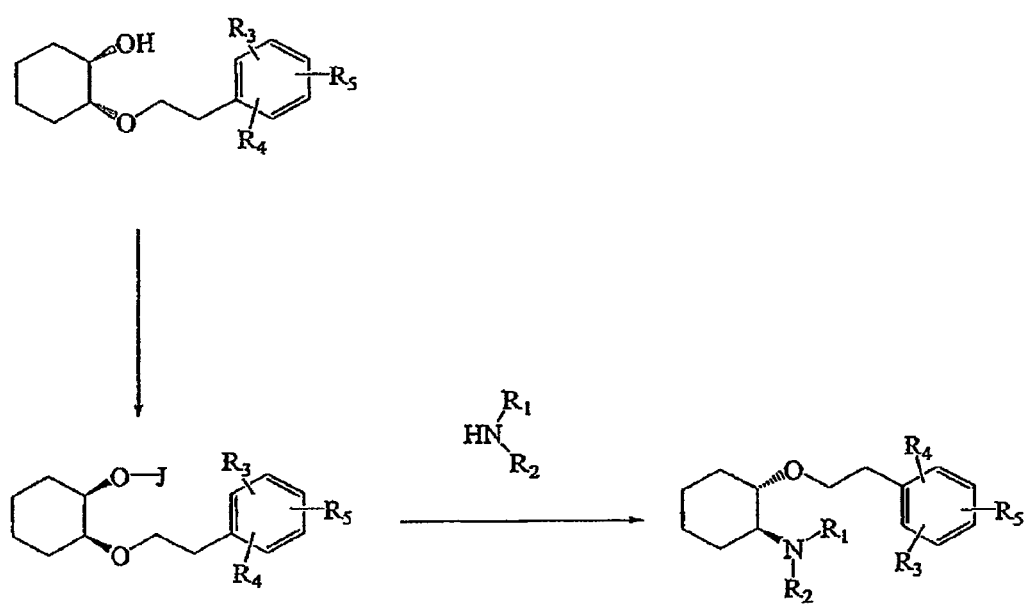

FIG. 65 illustrates a general reaction scheme that may be used as a process for preparing a stereoisomerically substantially pure trans-(1S,2S)-aminocyclohexyl ether compound of formula (75).

Figure 66:
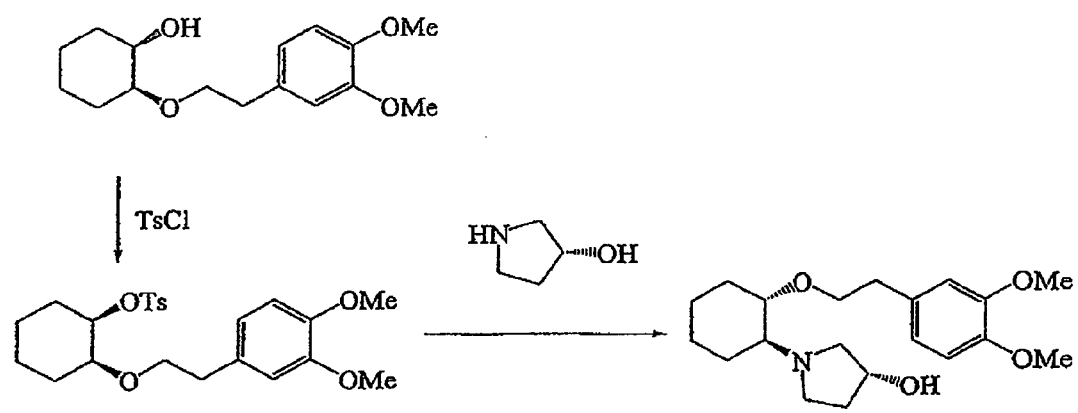

FIG. 66 illustrates a reaction scheme that may be used as a process for preparing a stereoisomerically substantially pure trans-(1S,2S)-aminocyclohexyl ether compound of formula (79).

Figure 67:
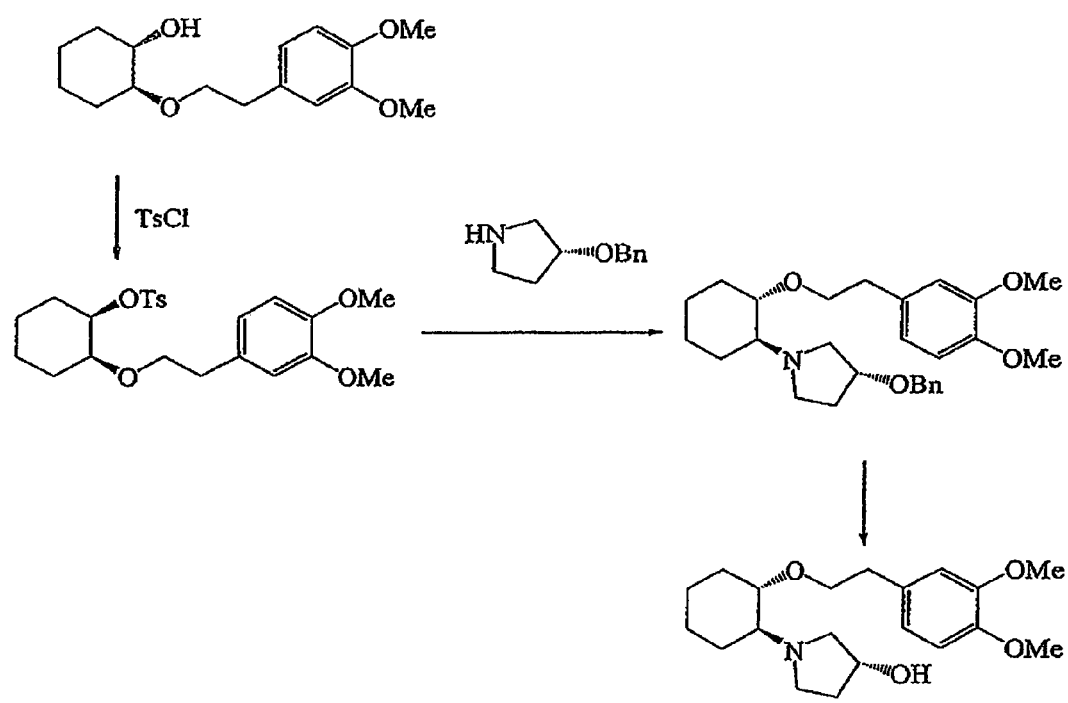

FIG. 67 illustrates a reaction scheme that may be used as a process for preparing a stereoisomerically substantially pure trans-(1S,2S)-aminocyclohexyl ether compound of formula (79).

Figure 68:
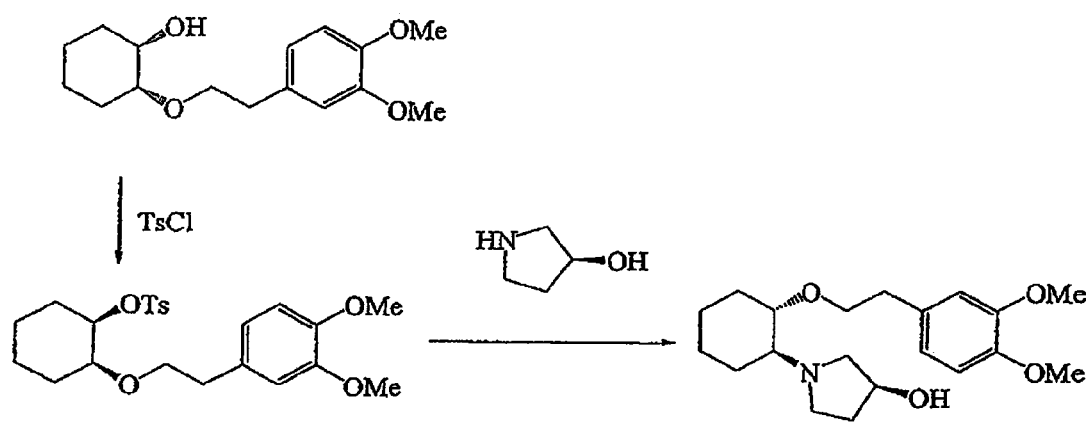

FIG. 68 illustrates a reaction scheme that may be used as a process for preparing a stereoisomerically substantially pure trans-(1S,2S)-aminocyclohexyl ether compound of formula (81).

Figure 69:
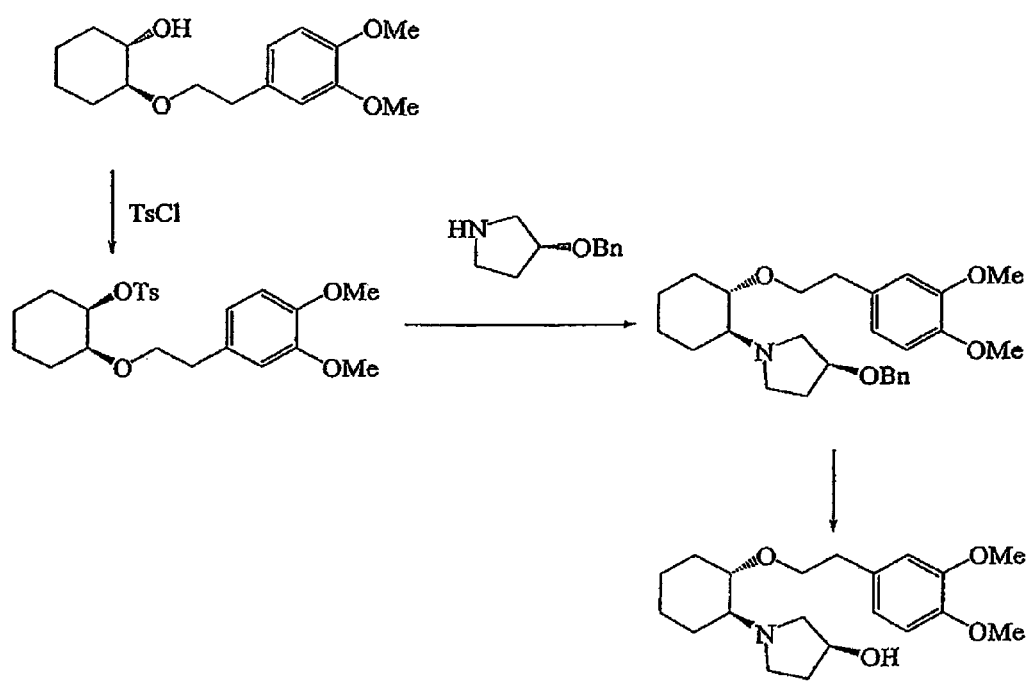

FIG. 69 illustrates a reaction scheme that may be used as a process for preparing a stereoisomerically substantially pure trans-(1S,2S)-aminocyclohexyl ether compound of formula (81).

Figure 70:
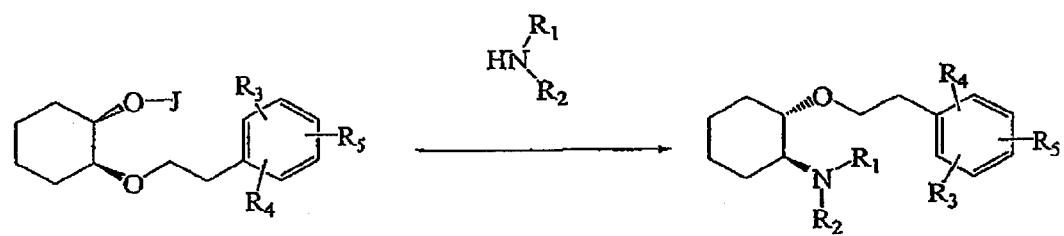

FIG. 70 illustrates a general reaction scheme that may be used as a process for preparing a stereoisomerically substantially pure trans-(1S,2S)-aminocyclohexyl ether compound of formula (75).

Figure 71:
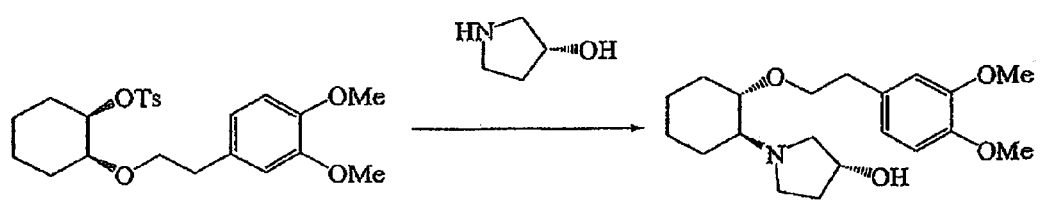

FIG. 71 illustrates a reaction scheme that may be used as a process for preparing a stereoisomerically substantially pure trans-(1S,2S)-aminocyclohexyl ether compound of formula (79).

Figure 72:
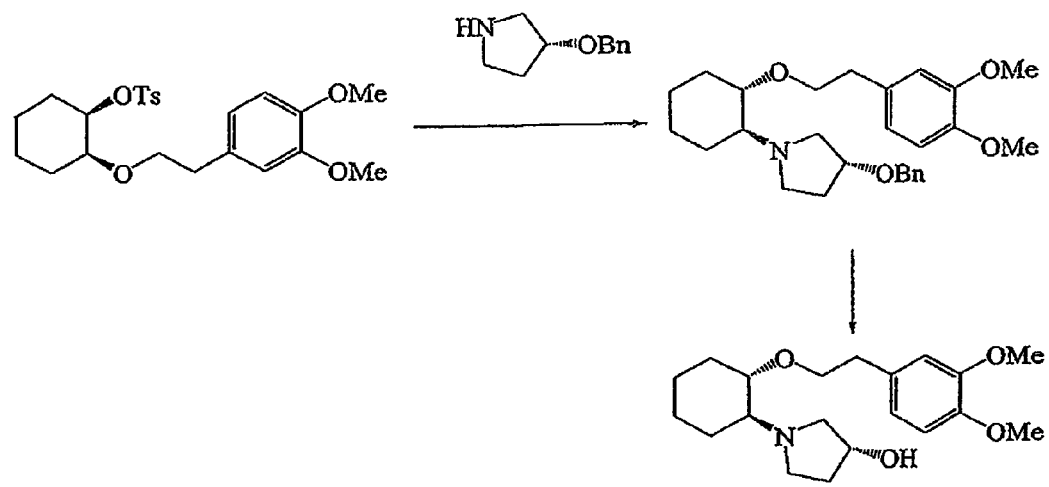

FIG. 72 illustrates a reaction scheme that may be used as a process for preparing a stereoisomerically substantially pure trans-(1S,2S)-aminocyclohexyl ether compound of formula (79).

Figure 73:
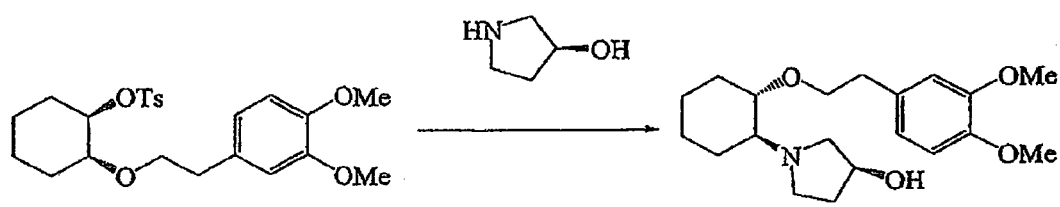

FIG. 73 illustrates a reaction scheme that may be used as a process for preparing a stereoisomerically substantially pure trans-(1S,2S)-aminocyclohexyl ether compound of formula (81).

Figure 74:
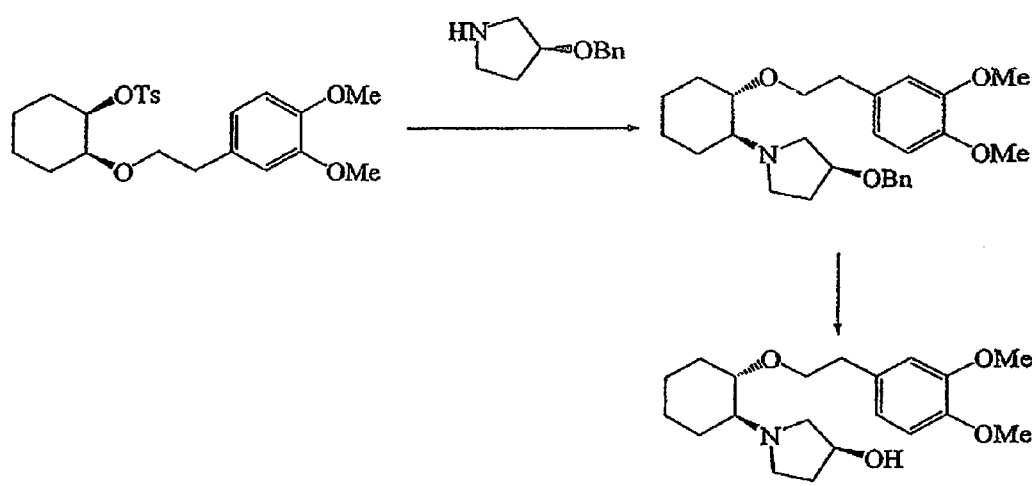

FIG. 74 illustrates a reaction scheme that may be used as a process for preparing a stereoisomerically substantially pure trans-(1S,2S)-aminocyclohexyl ether compound of formula (81).

Figure 75:
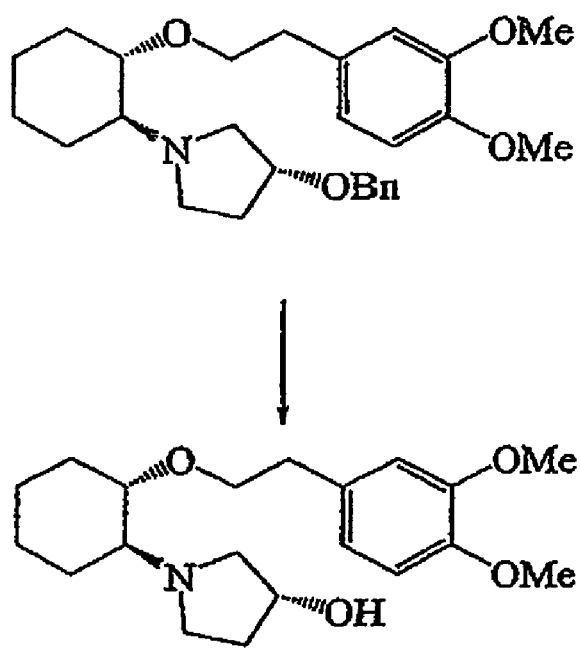

FIG. 75 illustrates a general reaction scheme that may be used as a process for preparing a stereoisomerically substantially pure trans-(1S,2S)-aminocyclohexyl ether compound of formula (79).

Figure 76:
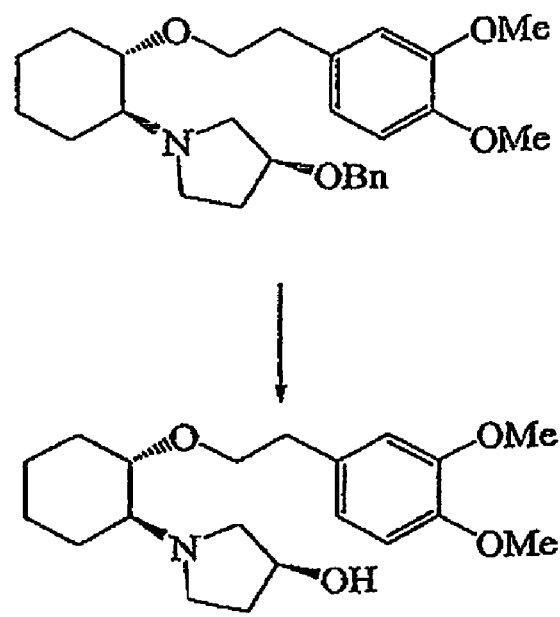

FIG. 76 illustrates a reaction scheme that may be used as a process for preparing a stereoisomerically substantially pure trans-(1S,2S)-aminocyclohexyl ether compound of formula (81).

Figure 77:
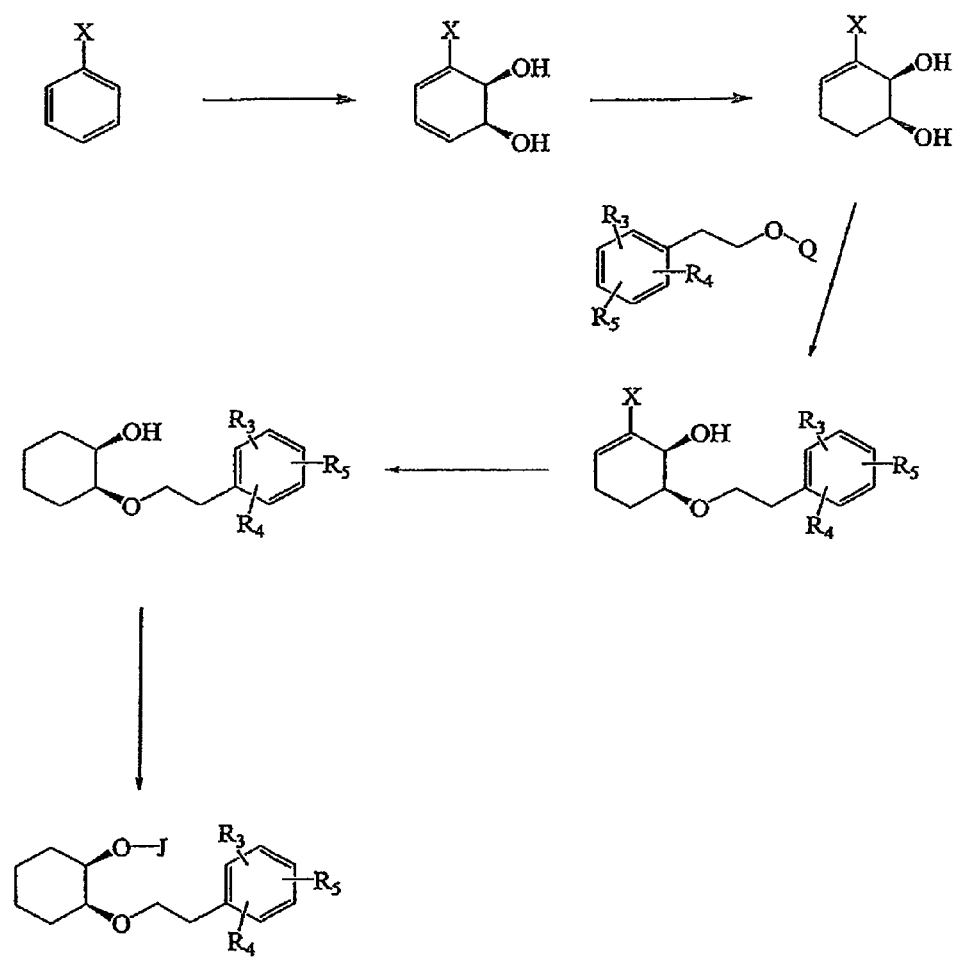

FIG. 77 illustrates a reaction scheme that may be used as a process for preparing a stereoisomerically substantially pure compound of formula (74).

Figure 78:
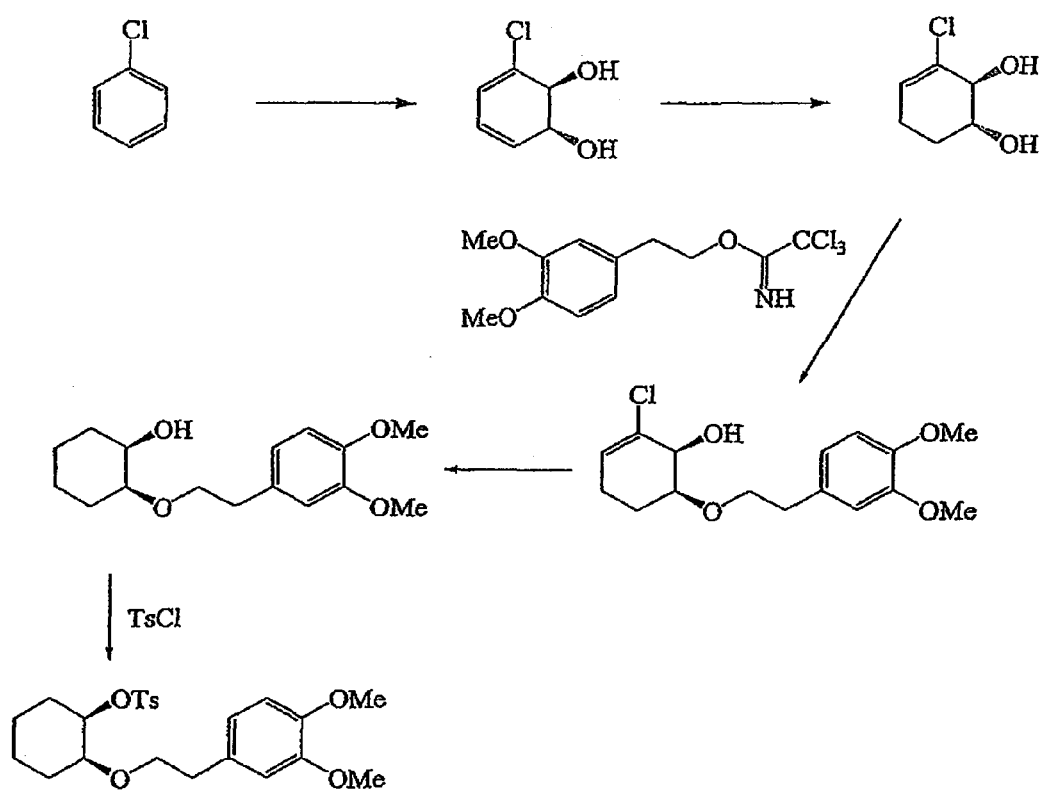

FIG. 78 illustrates a reaction scheme that may be used as a process for preparing a stereoisomerically substantially pure compound of formula (78).

Figure 79:
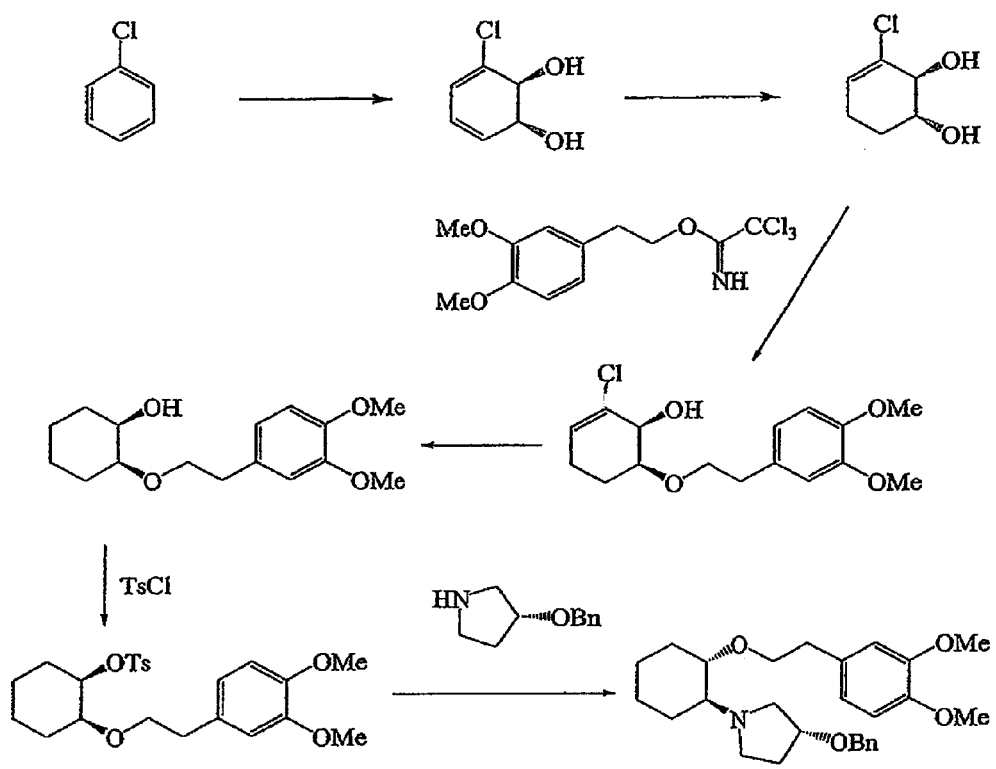

FIG. 79 illustrates a reaction scheme that may be used as a process for preparing a stereoisomerically substantially pure compound of formula (80).

Figure 80:
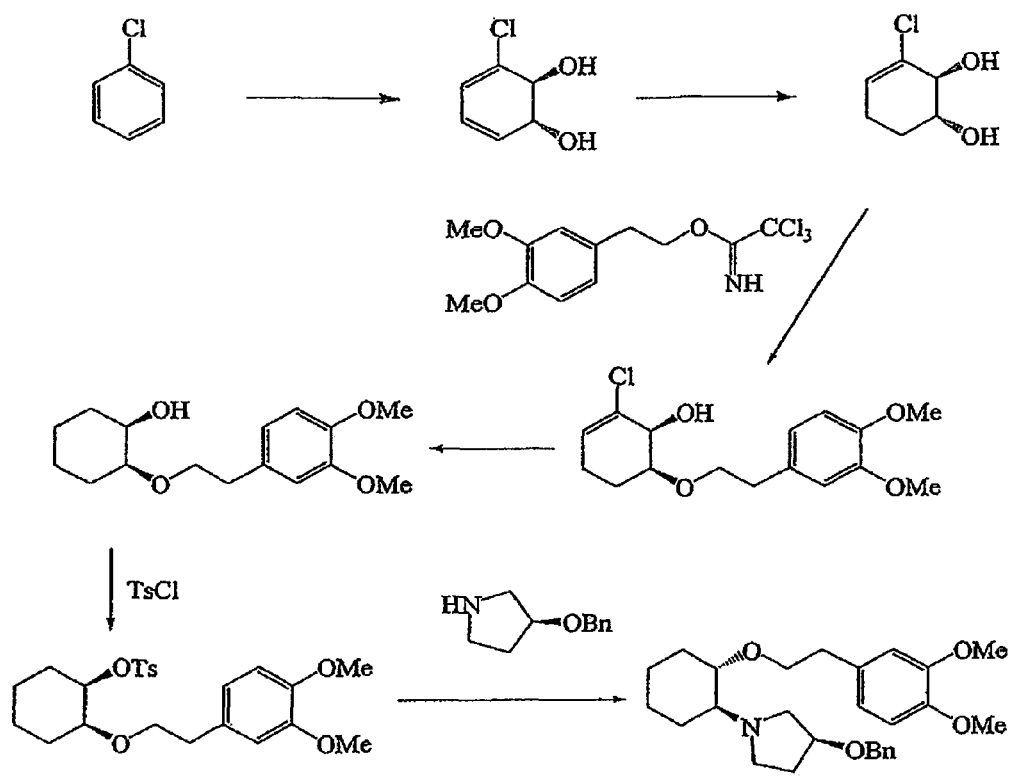

FIG. 80 illustrates a reaction scheme that may be used as a process for preparing a stereoisomerically substantially pure compound of formula (82).

Figure 81:
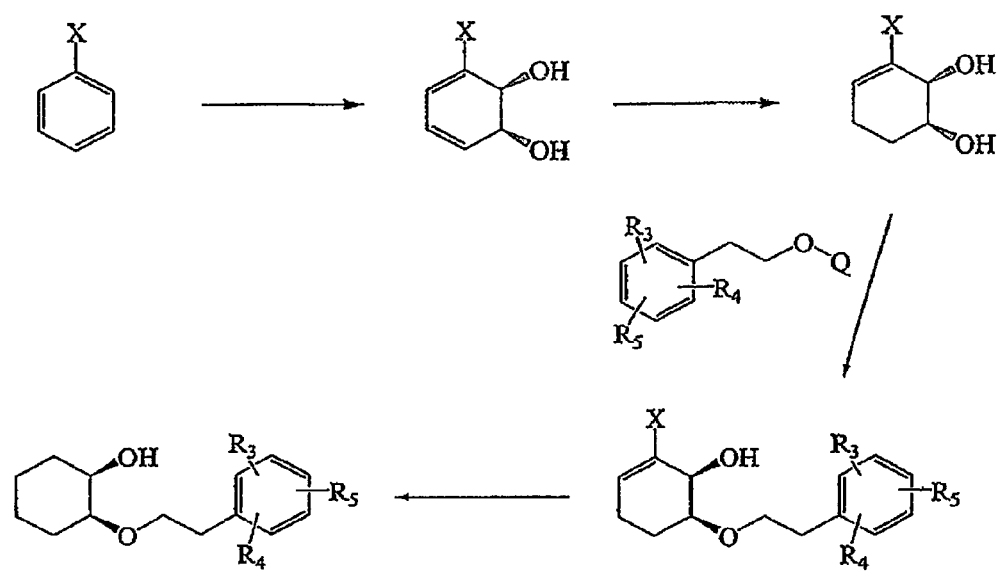

FIG. 81 illustrates a reaction scheme that may be used as a process for preparing a stereoisomerically substantially pure compound of formula (73).

Figure 82:
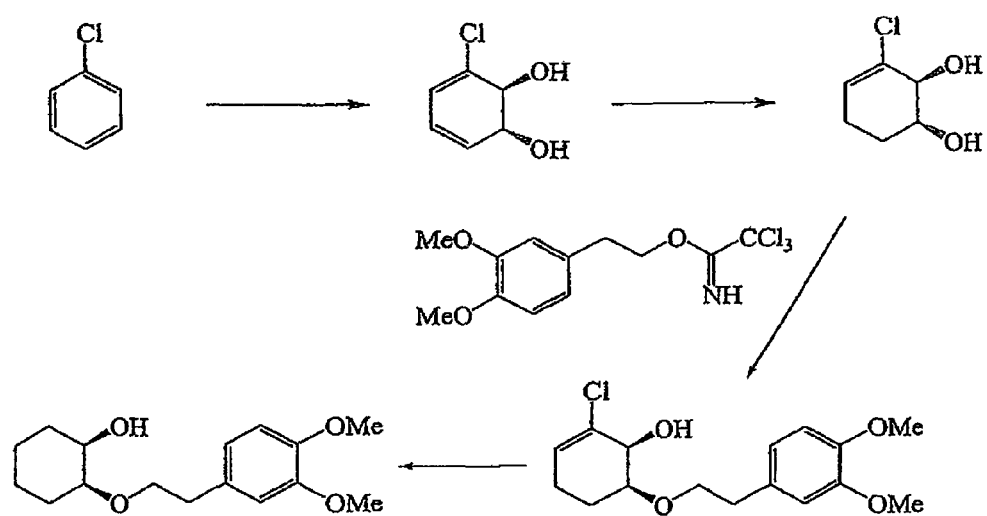

FIG. 82 illustrates a reaction scheme that may be used as a process for preparing a stereoisomerically substantially pure compound of formula (77).

Figure 83:
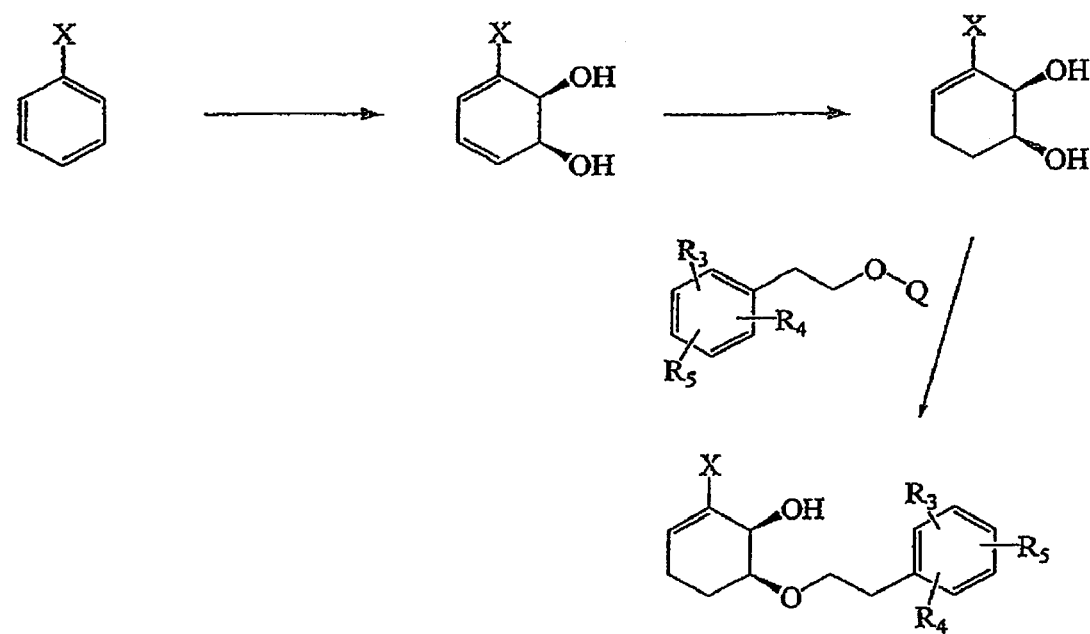

FIG. 83 illustrates a reaction scheme that may be used as a process for preparing a stereoisomerically substantially pure compound of formula (72).

Figure 84:
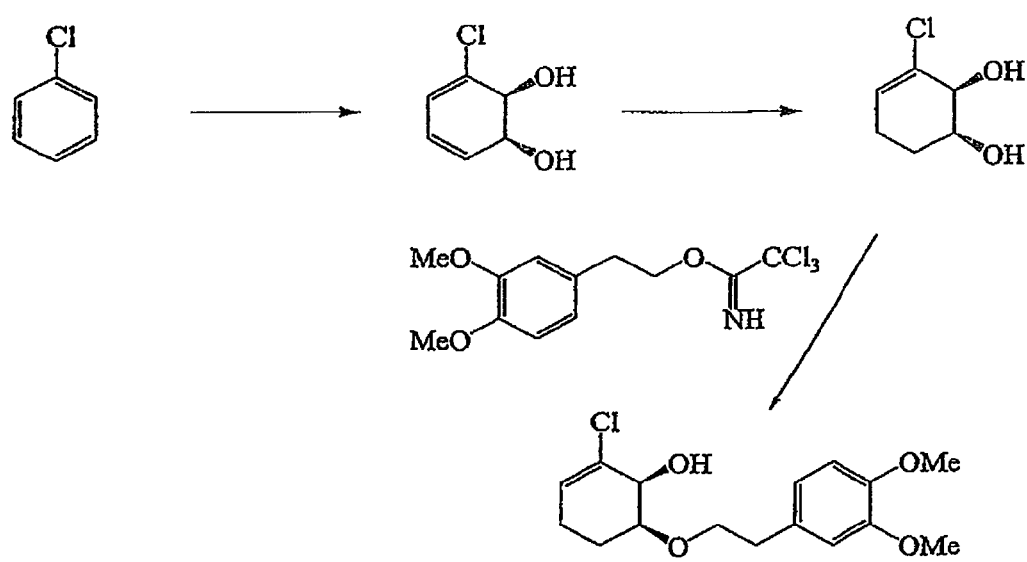

FIG. 84 illustrates a reaction scheme that may be used as a process for preparing a stereoisomerically substantially pure compound of formula (76).

Figure 85:
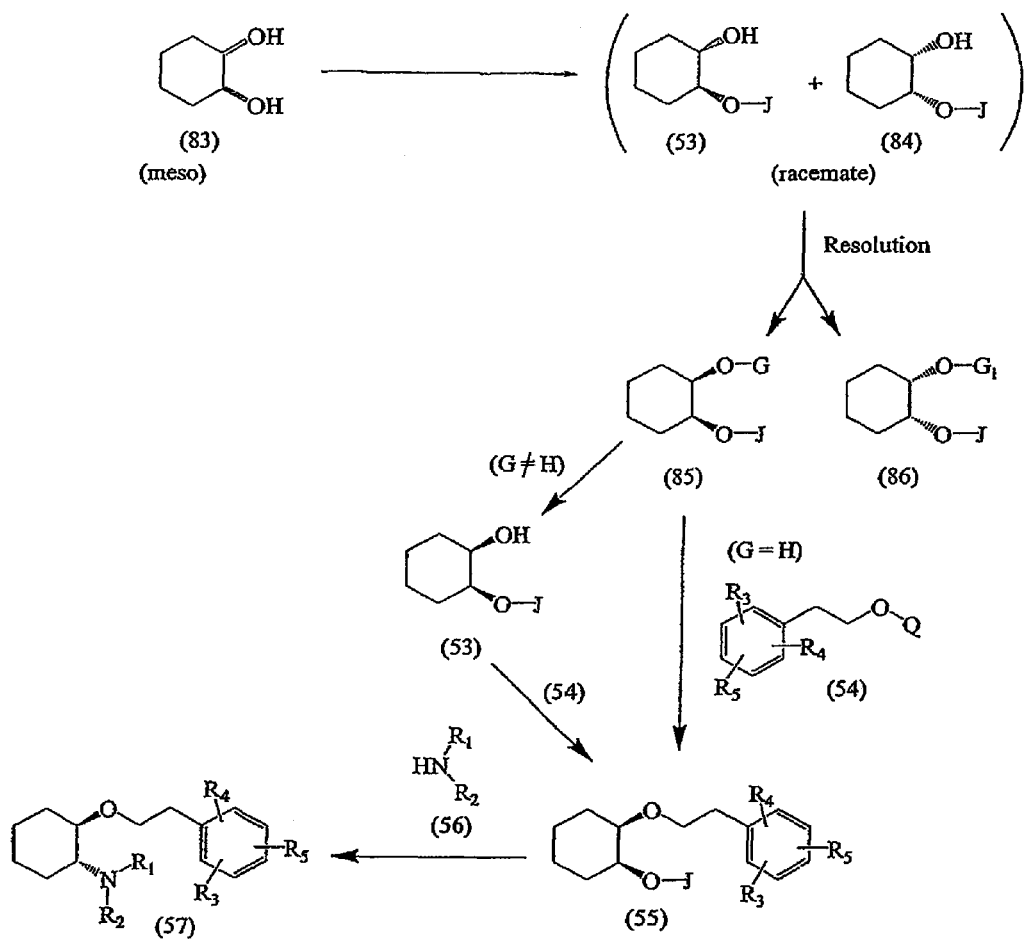

FIG. 85 illustrates a general reaction scheme that may be used as a process for preparing a stereoisomerically substantially pure trans-(1R,2R)-aminocyclohexyl ether compound of formula (57).

Figure 86:
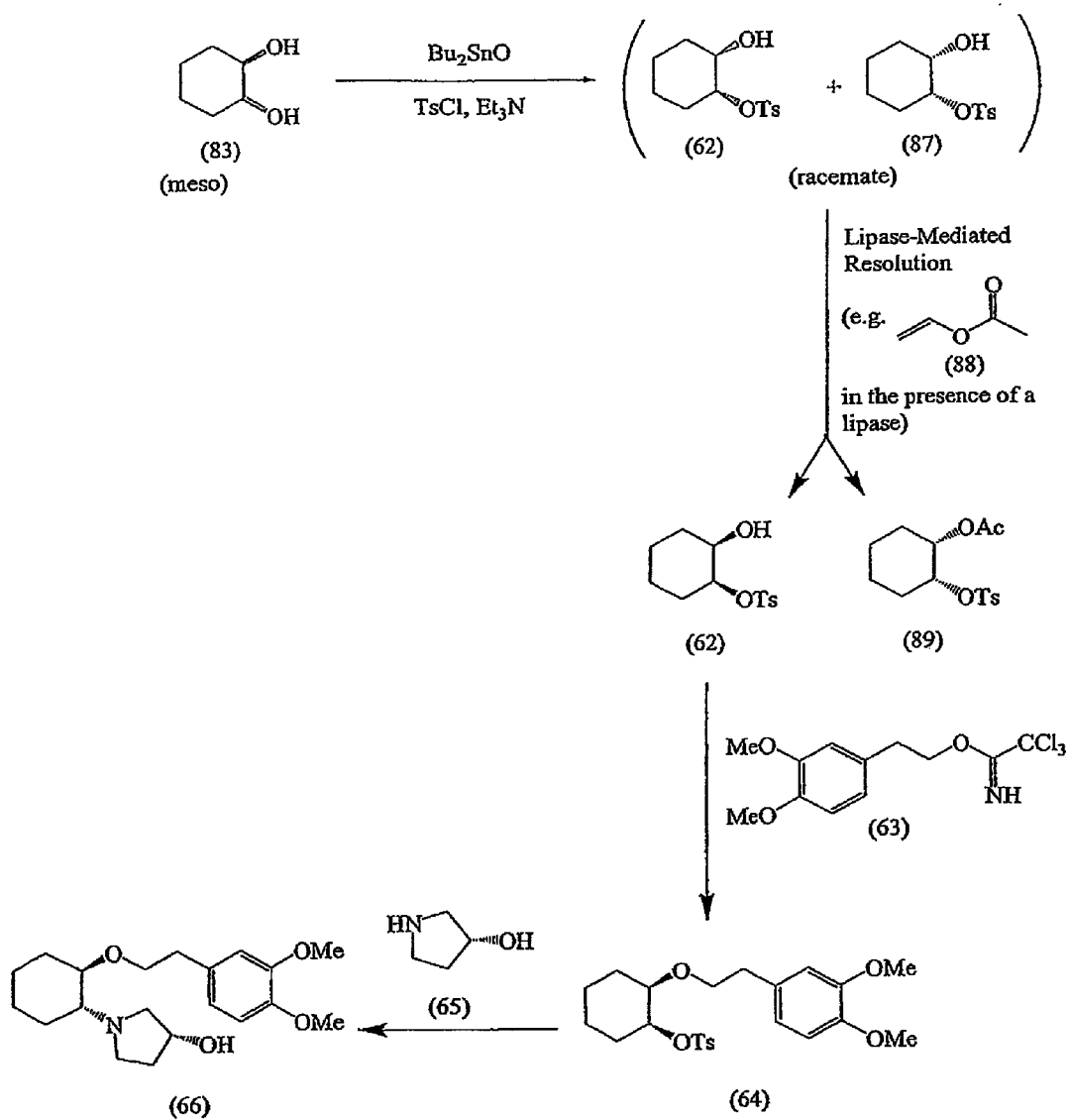

FIG. 86 illustrates a reaction scheme that may be used as a process for preparing a stereoisomerically substantially pure trans-(1R,2R)-aminocyclohexylether compound of formula (66).

Figure 87:
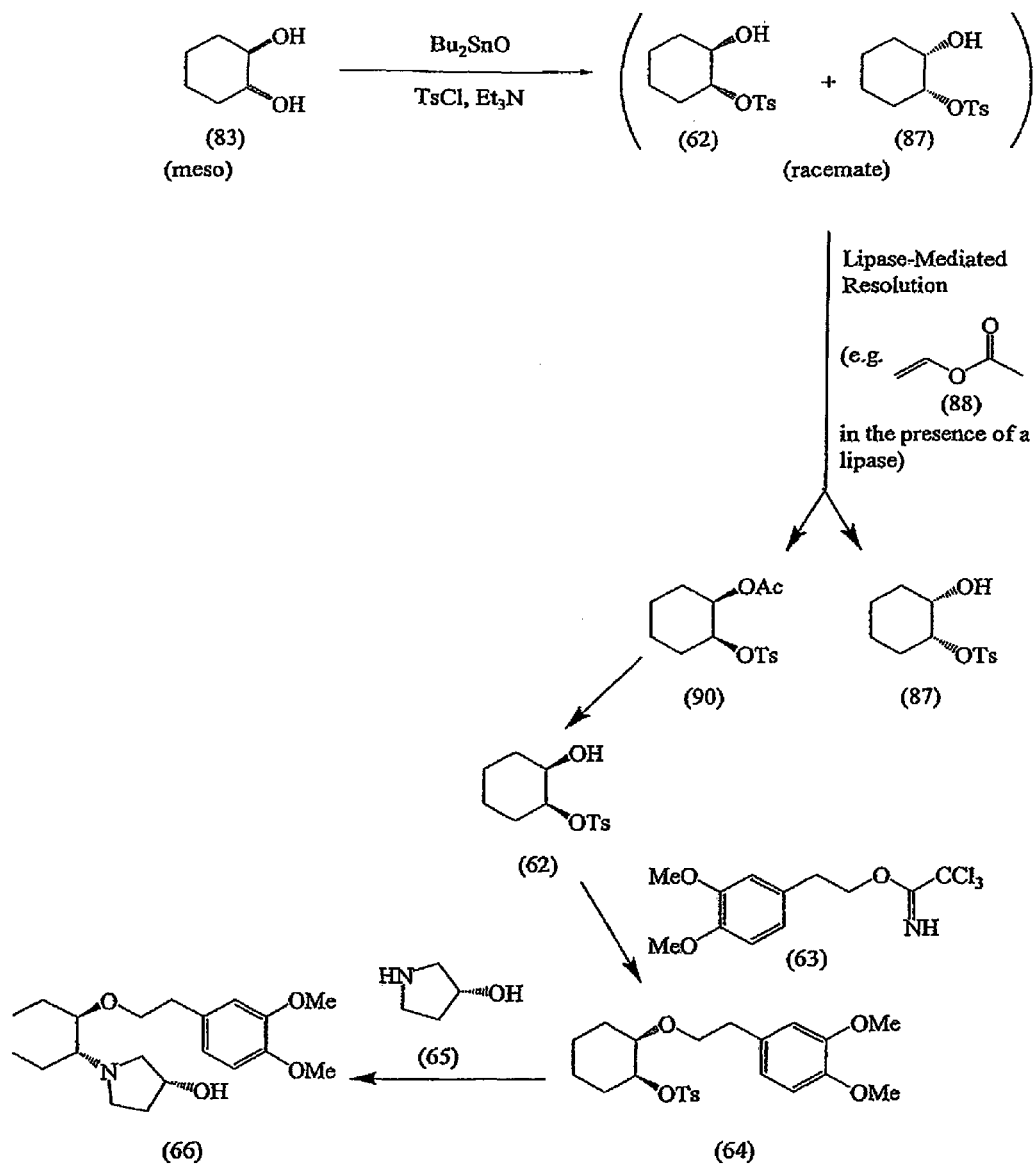

FIG. 87 illustrates a reaction scheme that may be used as a process for preparing a stereoisomerically substantially pure trans-(1R,2R)-aminocyclohexylether compound of formula (66).

Figure 88:
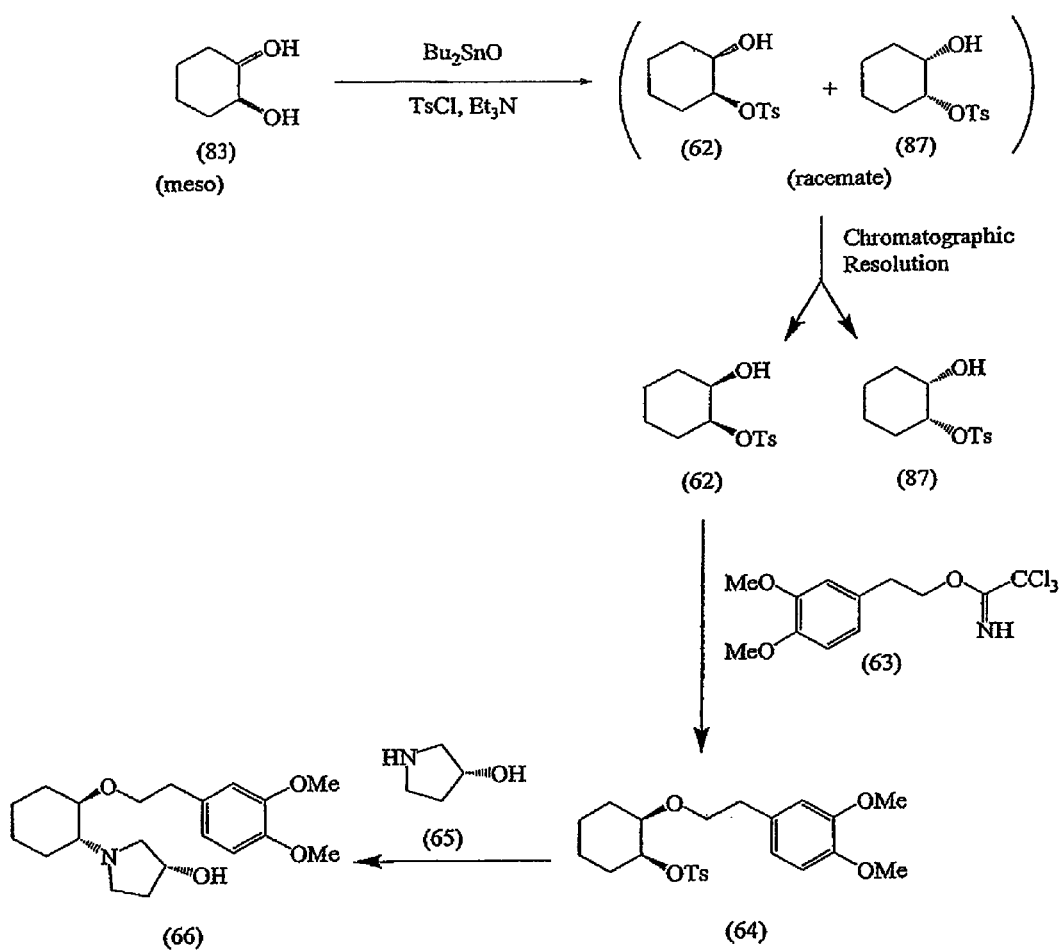

FIG. 88 illustrates a reaction scheme that may be used as a process for preparing a stereoisomerically substantially pure trans-(1R,2R)-aminocyclohexylether compound of formula (66).

Figure 89:
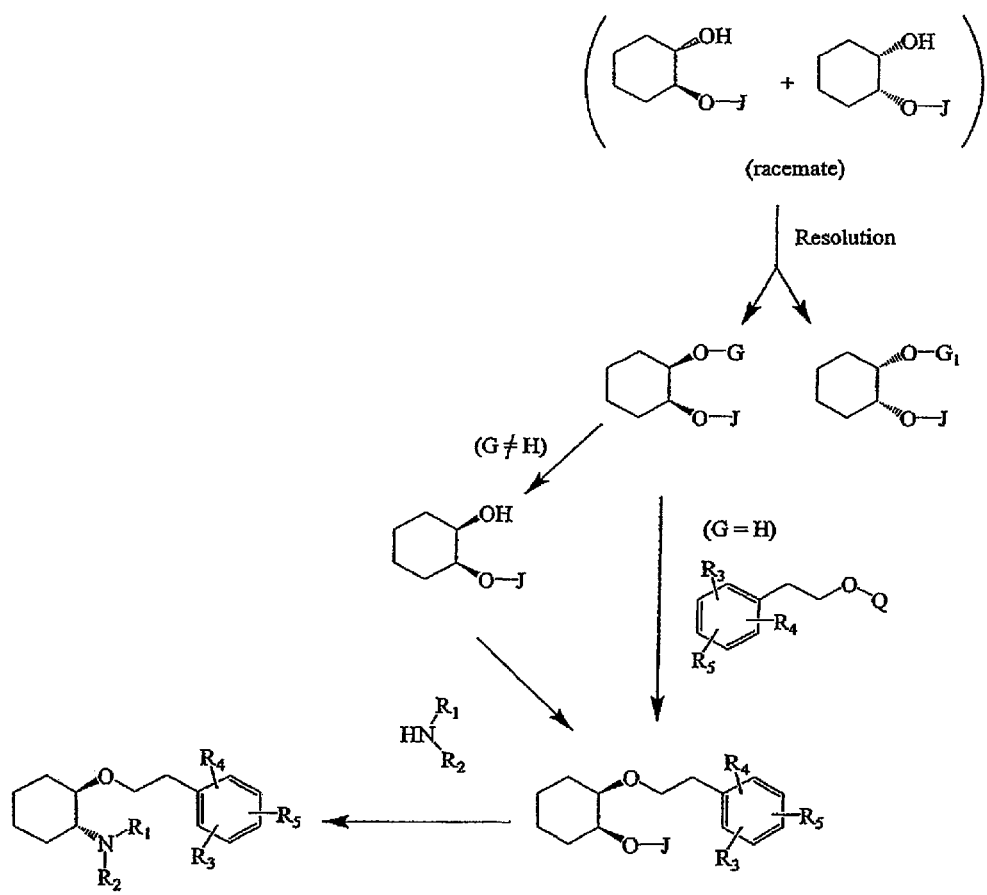

FIG. 89 illustrates a general reaction scheme that may be used as a process for preparing a stereoisomerically substantially pure trans-(1R,2R)-aminocyclohexyl ether compound of formula (57).

Figure 90:
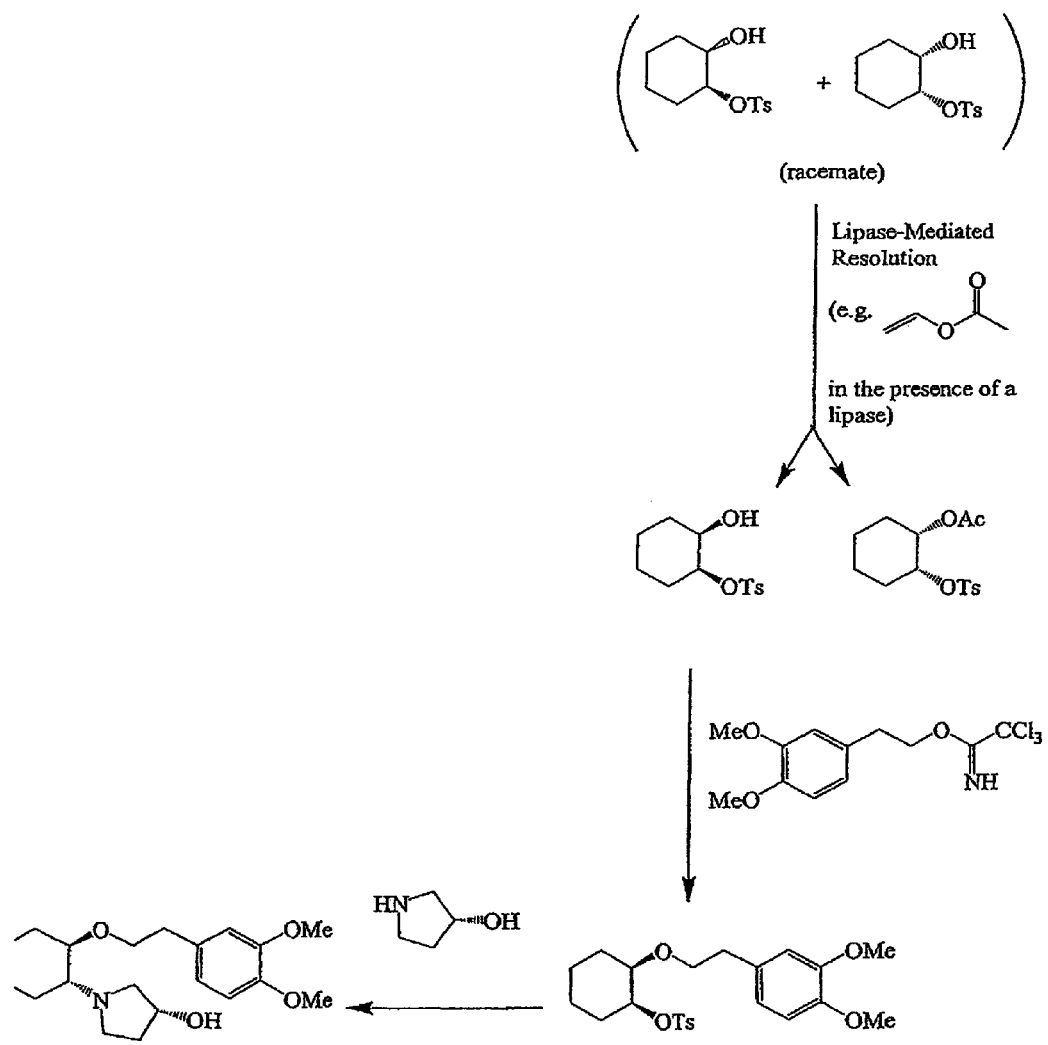

FIG. 90 illustrates a reaction scheme that may be used as a process for preparing a stereoisomerically substantially pure trans-(1R,2R)-aminocyclohexylether compound of formula (66).

Figure 91:
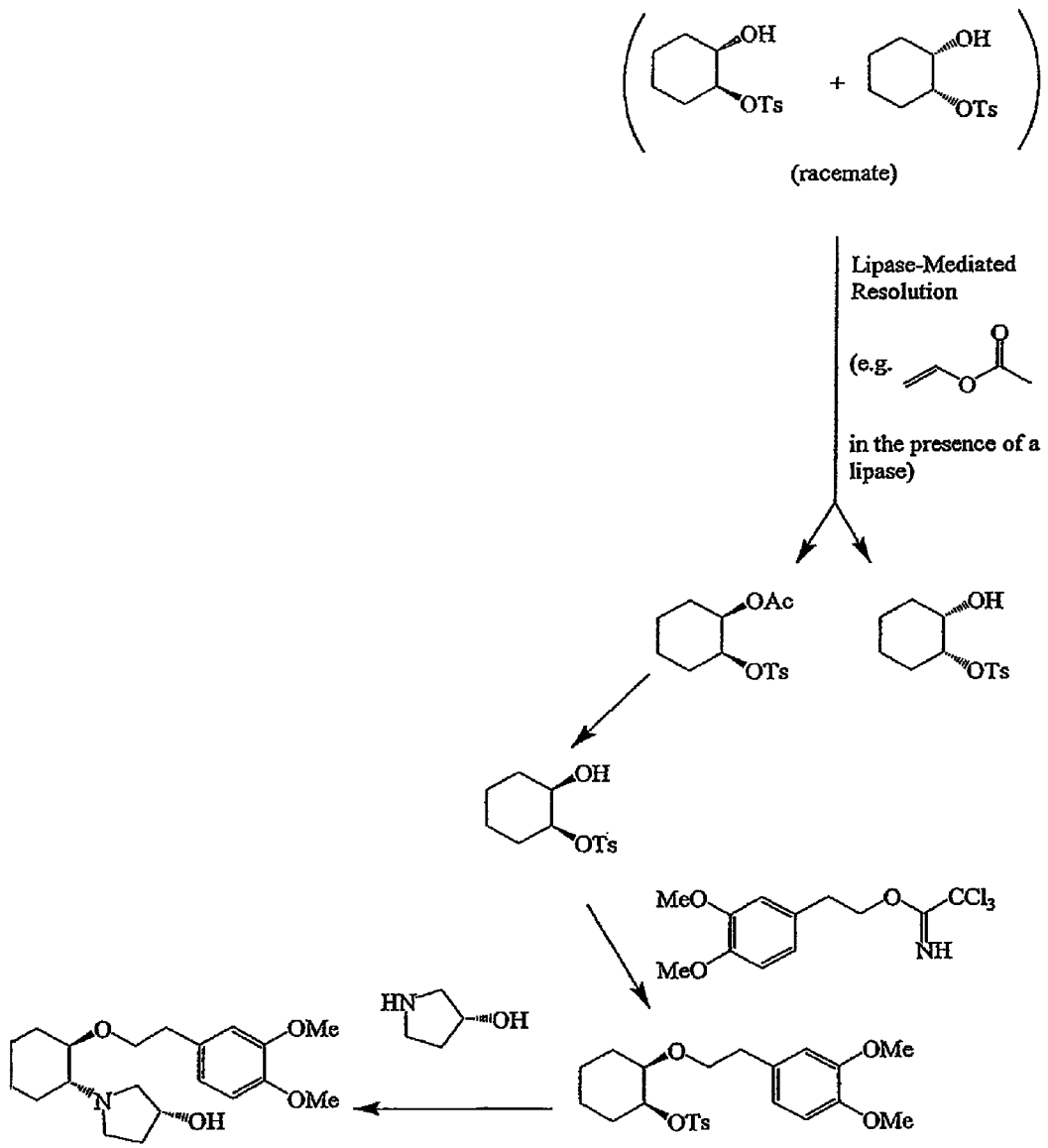

FIG. 91 illustrates a reaction scheme that may be used as a process for preparing a stereoisomerically substantially pure trans-(1R,2R)-aminocyclohexylether compound of formula (66).

Figure 92:
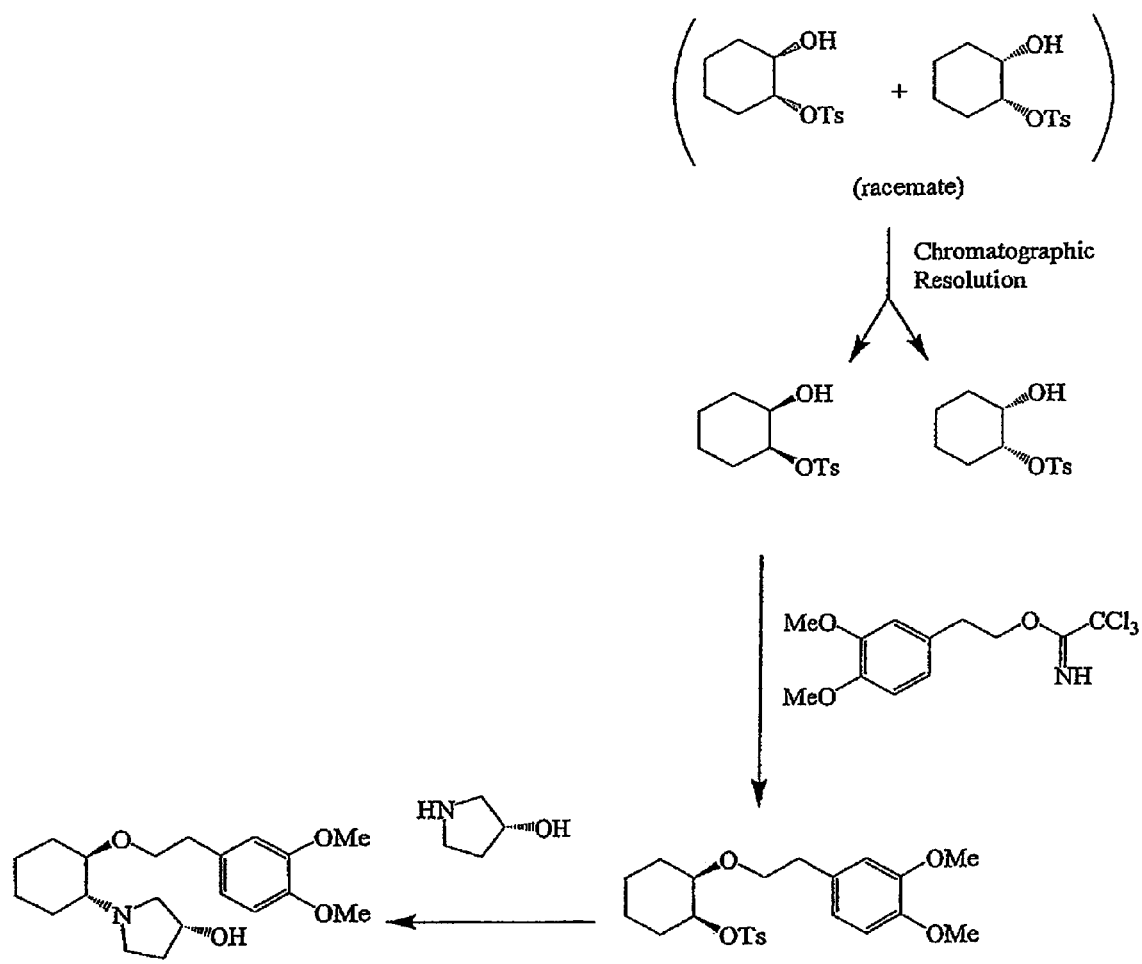

FIG. 92 illustrates a reaction scheme that may be used as a process for preparing a stereoisomerically substantially pure trans-(1R,2R)-aminocyclohexylether compound of formula (66).

Figure 93:
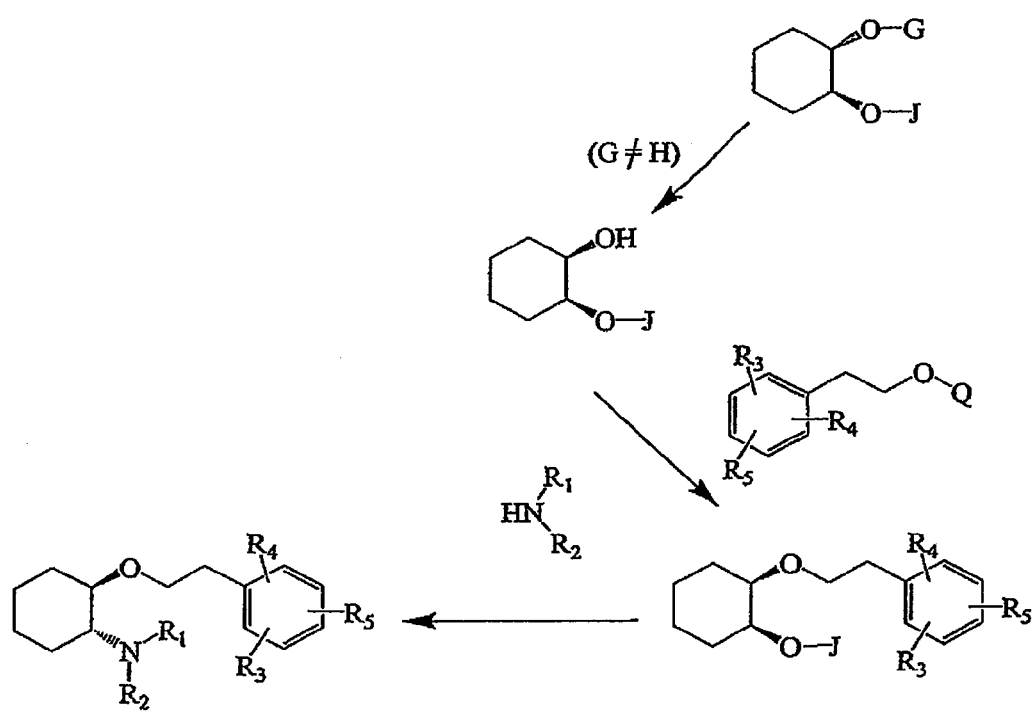

FIG. 93 illustrates a general reaction scheme that may be used as a process for preparing a stereoisomerically substantially pure trans-(1R,2R)-aminocyclohexyl ether compound of formula (57).

Figure 94:
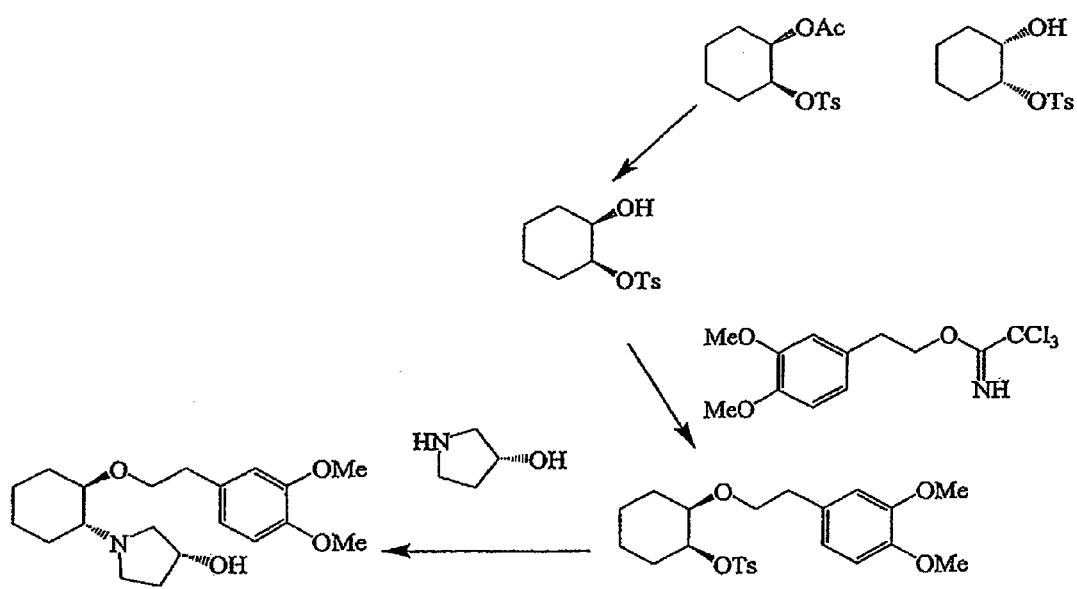

FIG. 94 illustrates a reaction scheme that may be used as a process for preparing a stereoisomerically substantially pure trans-(1R,2R)-aminocyclohexylether compound of formula (66).

Figure 95:
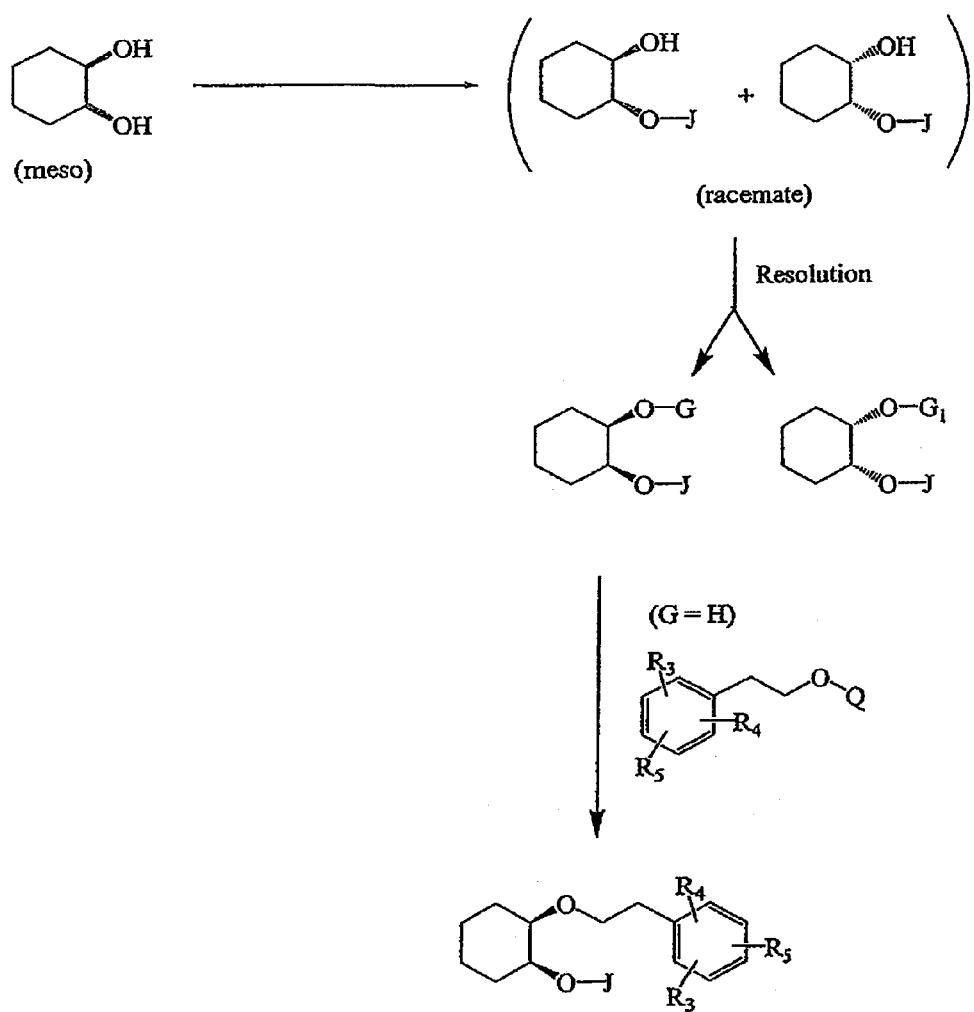

FIG. 95 illustrates a general reaction scheme that may be used as a process for preparing a stereoisomerically substantially pure compound of formula (55).

Figure 96:
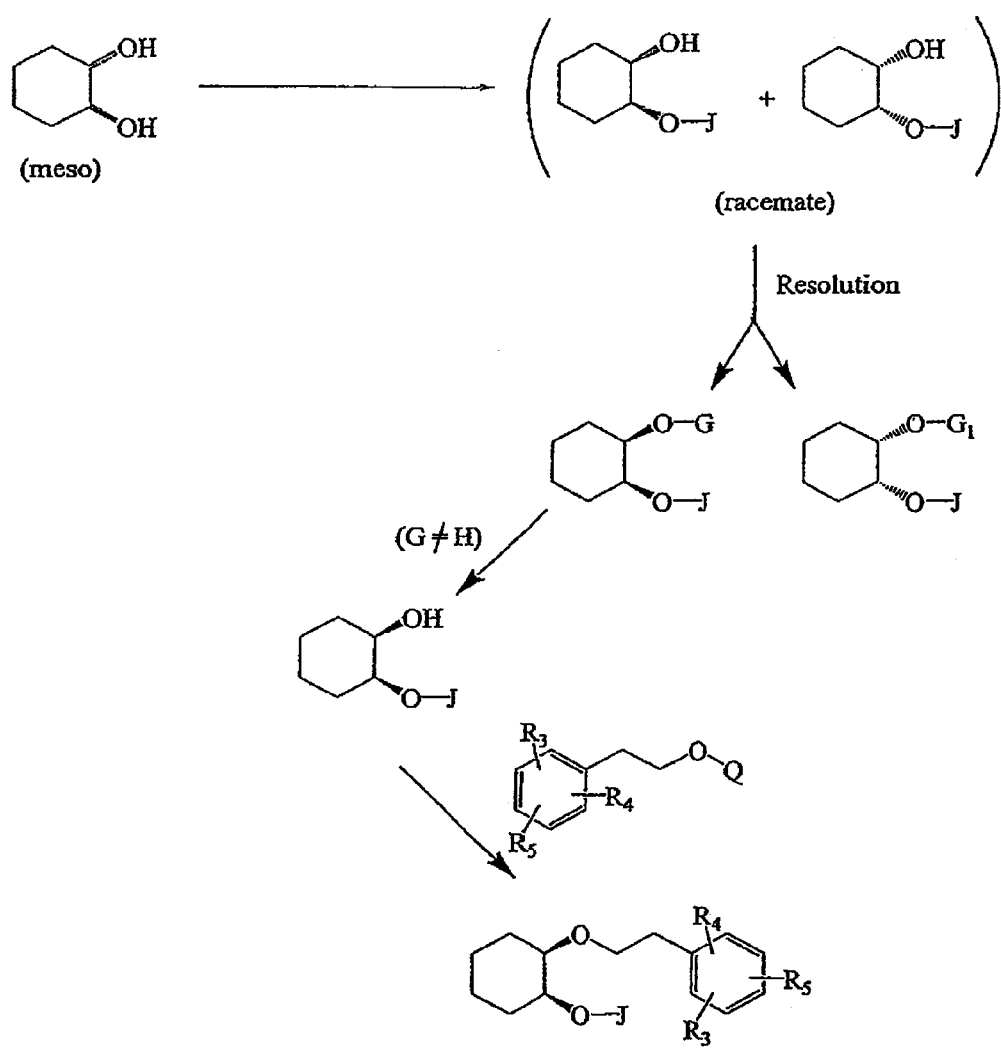

FIG. 96 illustrates general a reaction scheme that may be used as a process for preparing a stereoisomerically substantially pure compound of formula (55).

Figure 97:
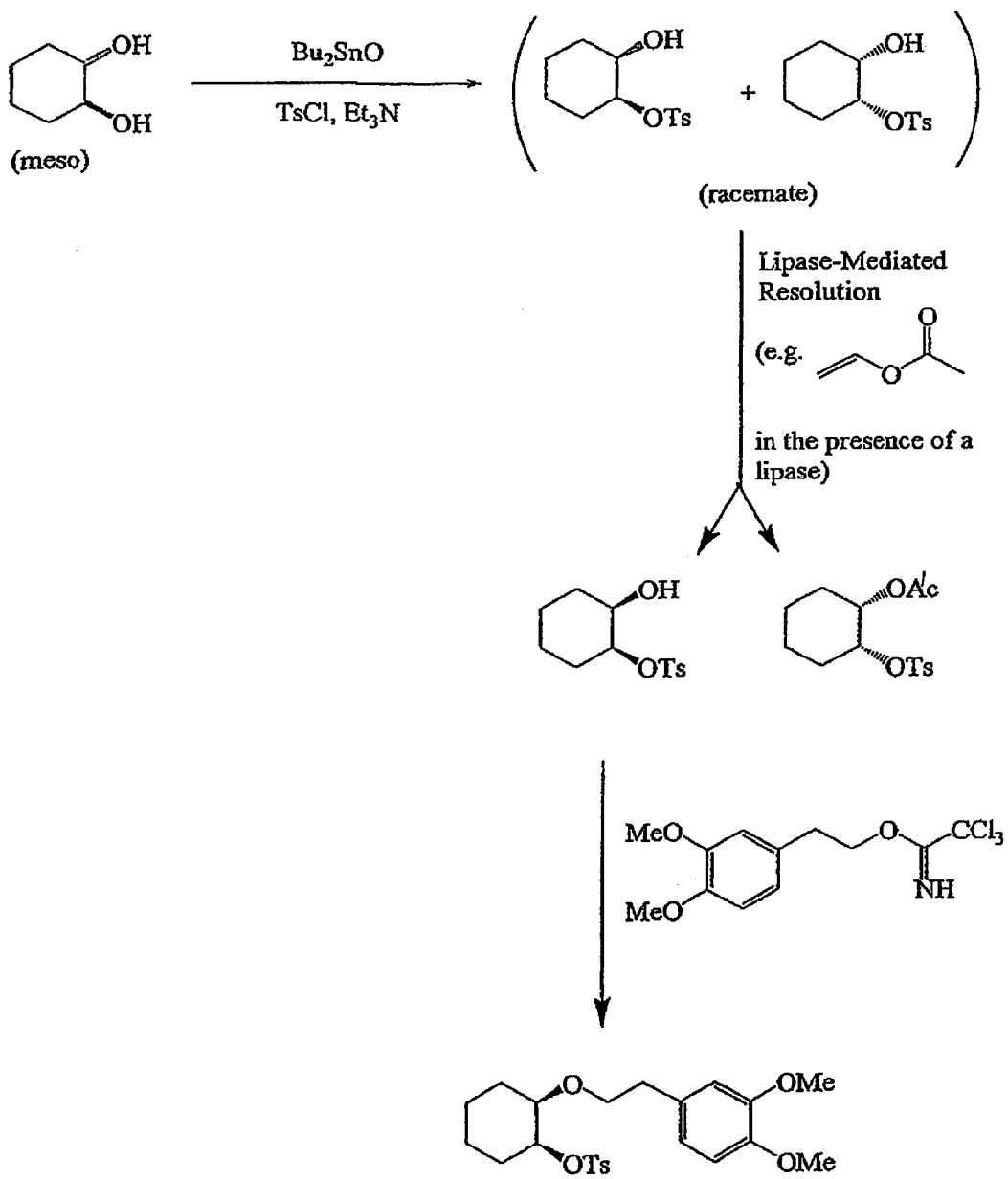

FIG. 97 illustrates a reaction scheme that may be used as a process for preparing a stereoisomerically substantially pure compound of formula (64).

Figure 98:
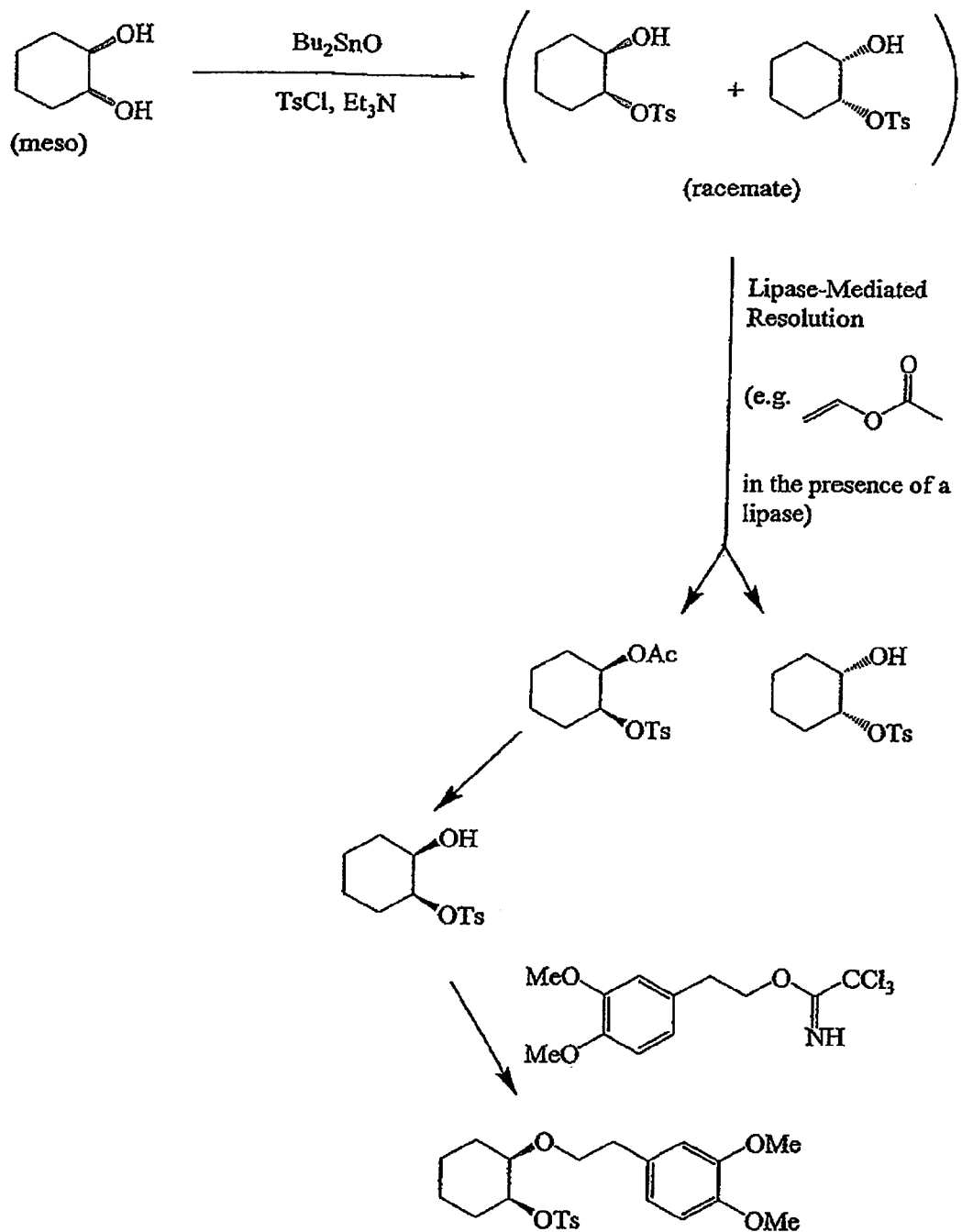

FIG. 98 illustrates a reaction scheme that may be used as a process for preparing a stereoisomerically substantially pure compound of formula (64).

Figure 99:
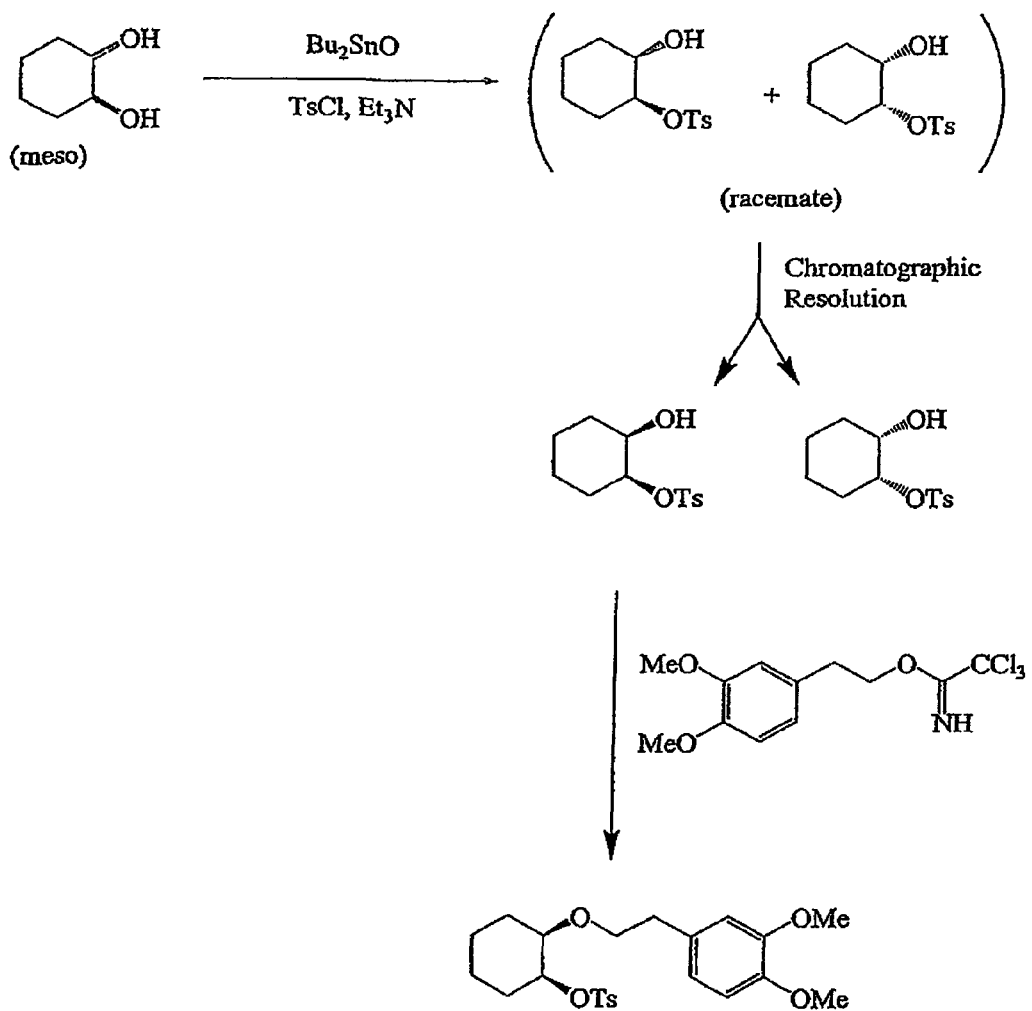

FIG. 99 illustrates a reaction scheme that may be used as a process for preparing a stereoisomerically substantially pure compound of formula (64).

Figure 100:
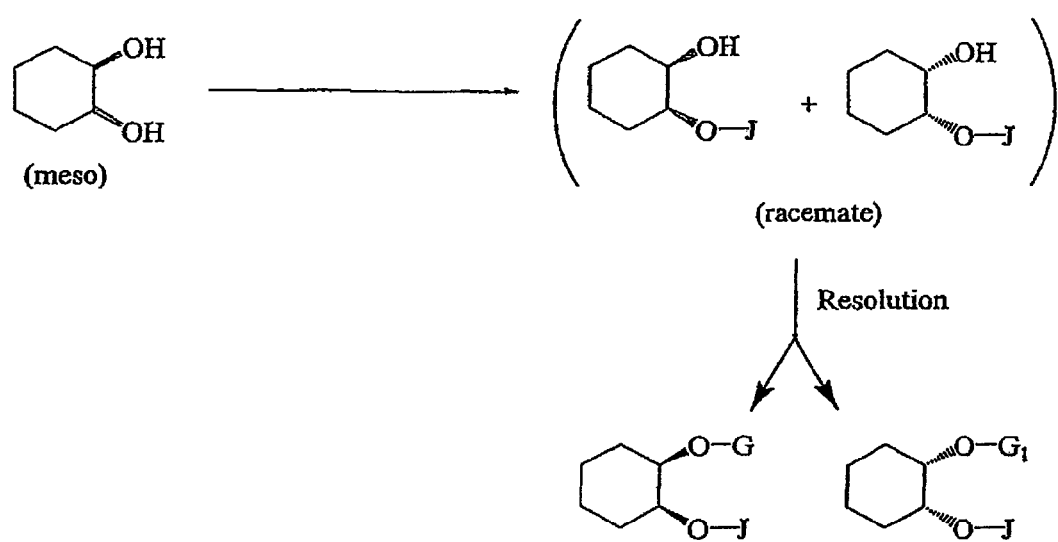

FIG. 100 illustrates a general reaction scheme that may be used as a process for preparing a stereoisomerically substantially pure compound of formula (85) and a stereoisomerically substantially pure compound of formula (86).

Figure 101:
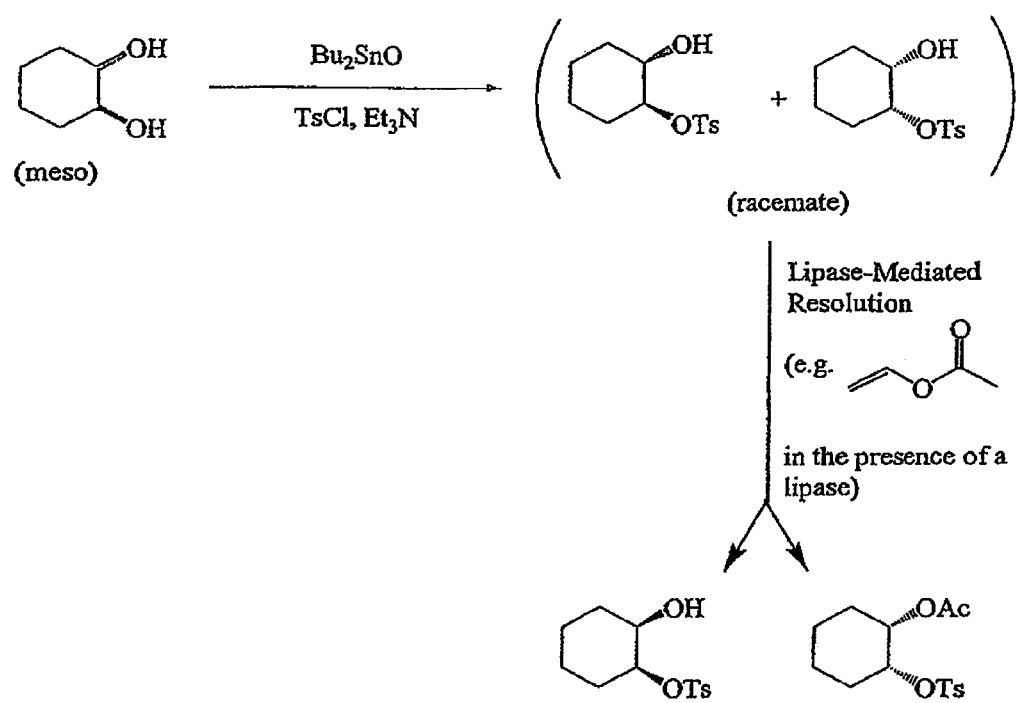

FIG. 101 illustrates a reaction scheme that may be used as a process for preparing a stereoisomerically substantially pure compound of formula (62) and a stereoisomerically substantially pure compound of formula (89).

Figure 102:
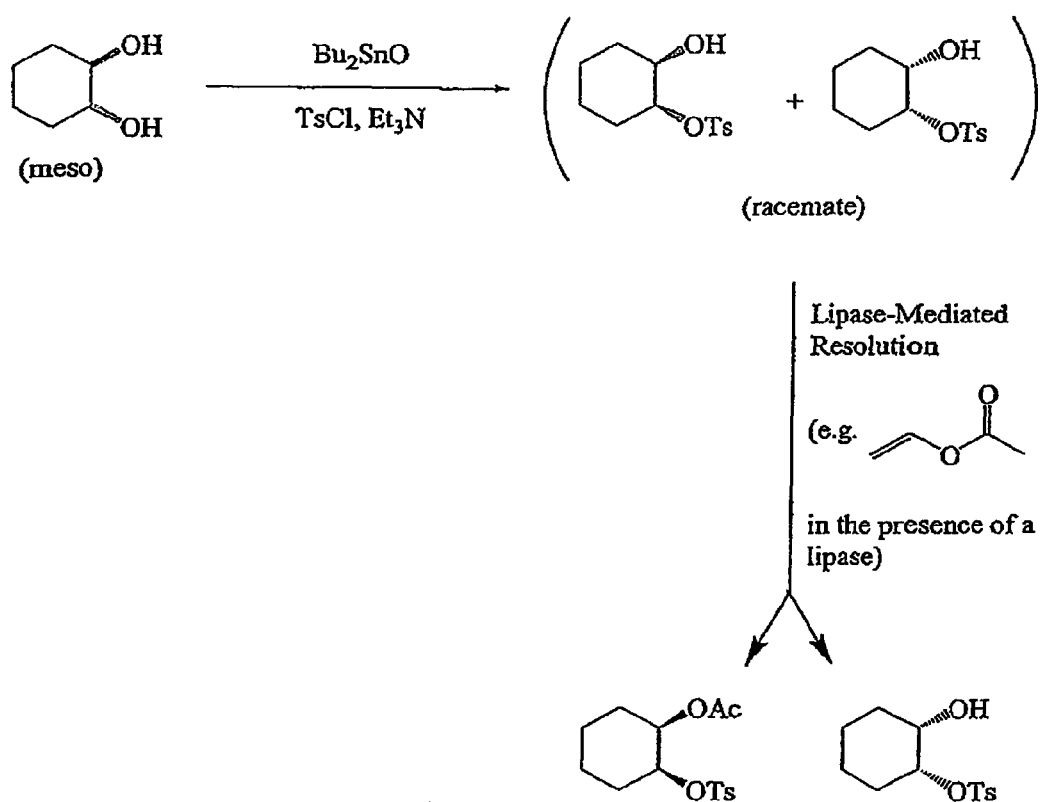

FIG. 102 illustrates a reaction scheme that may be used as a process for preparing a stereoisomerically substantially pure compound of formula (87) and a stereoisomerically substantially pure compound of formula (90).

Figure 103:
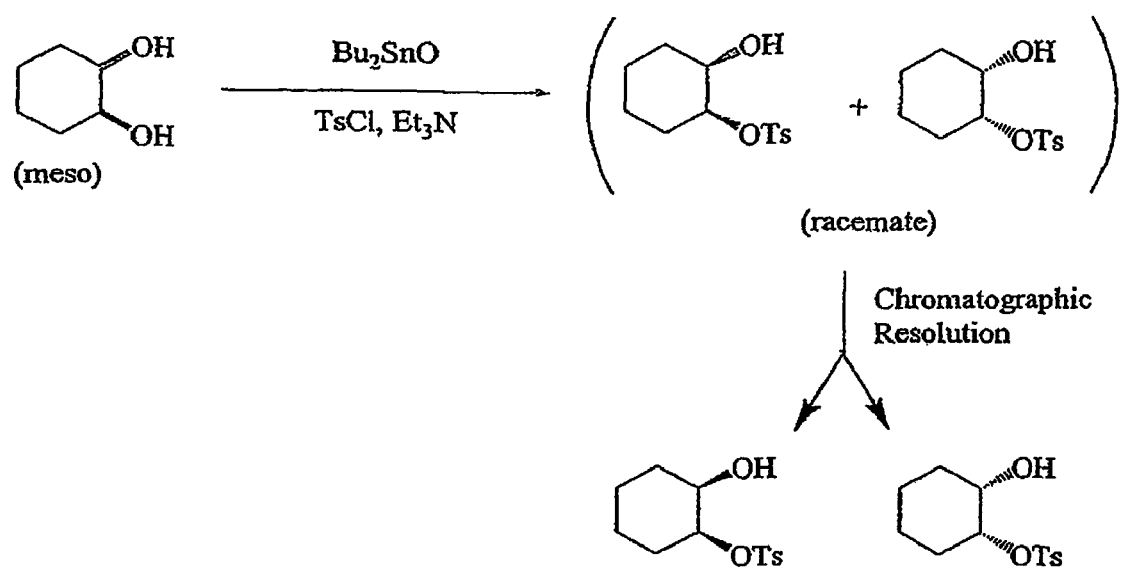

FIG. 103 illustrates a reaction scheme that may be used as a process for preparing a stereoisomerically substantially pure compound of formula (62) and a stereoisomerically substantially pure compound of formula (87).

Figure 104:
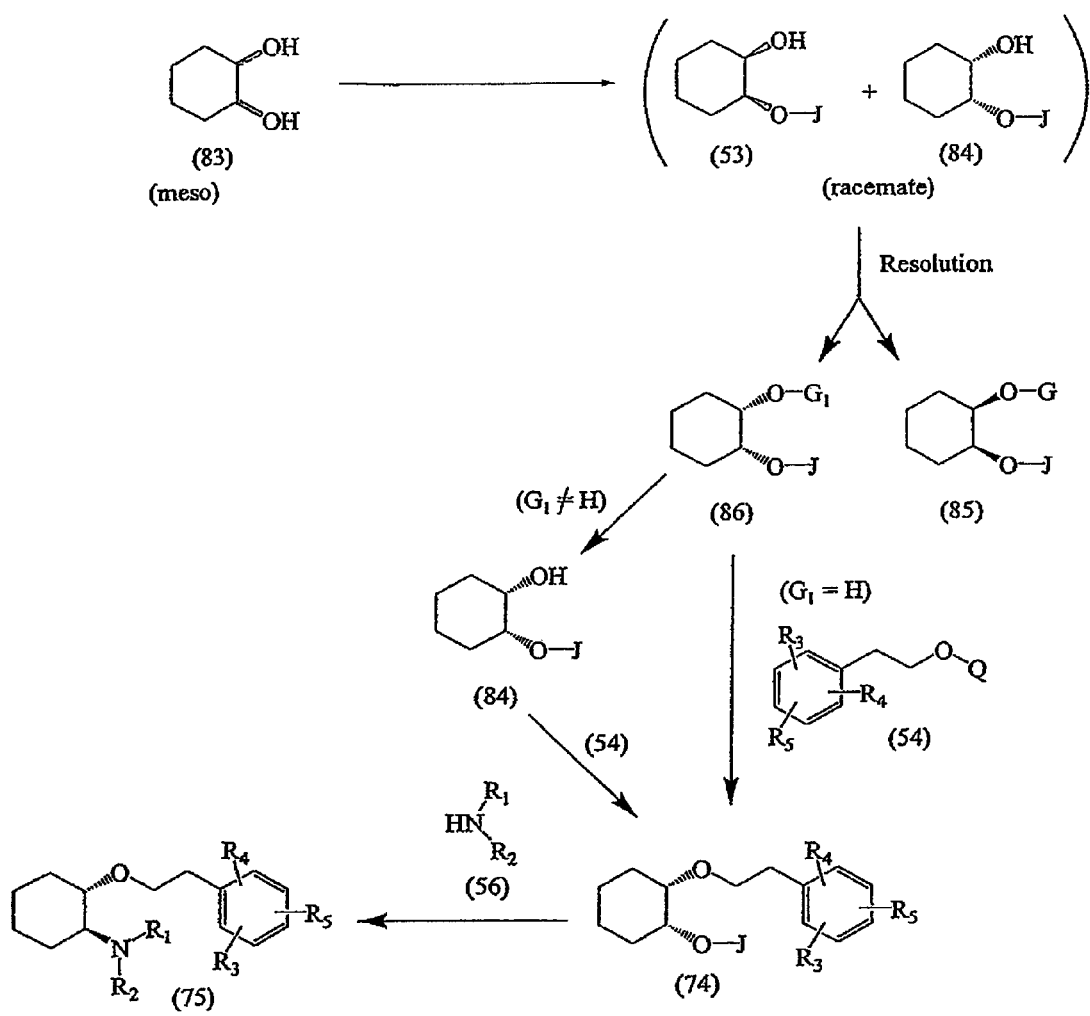

FIG. 104 illustrates a general reaction scheme that may be used as a process for preparing a stereoisomerically substantially pure trans-(1S,2S)-aminocyclohexyl ether compound of formula (75).

Figure 105:
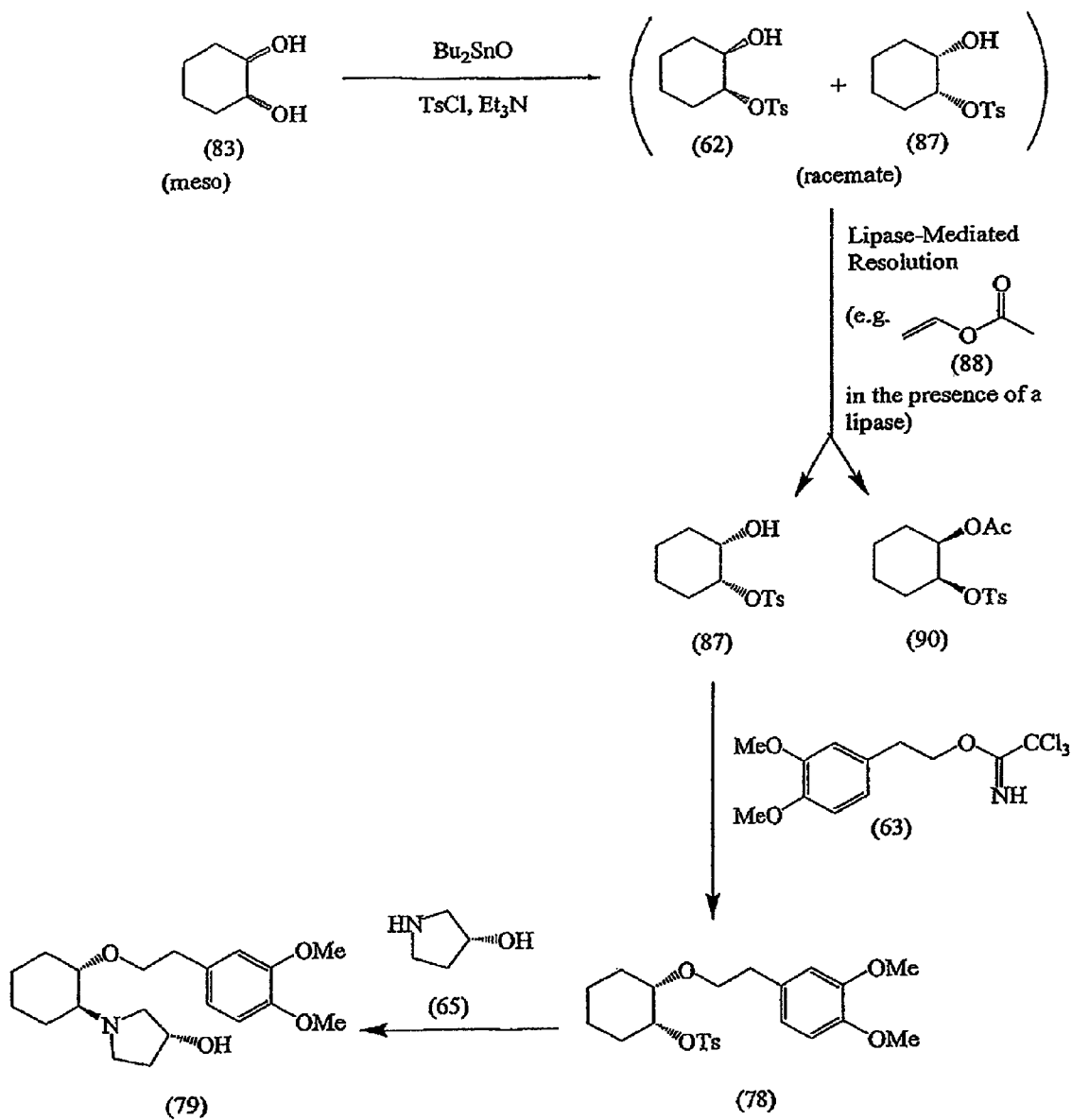

FIG. 105 illustrates a reaction scheme that may be used as a process for preparing a stereoisomerically substantially pure trans-(1S,2S)-aminocyclohexylether compound of formula (79).

Figure 106:
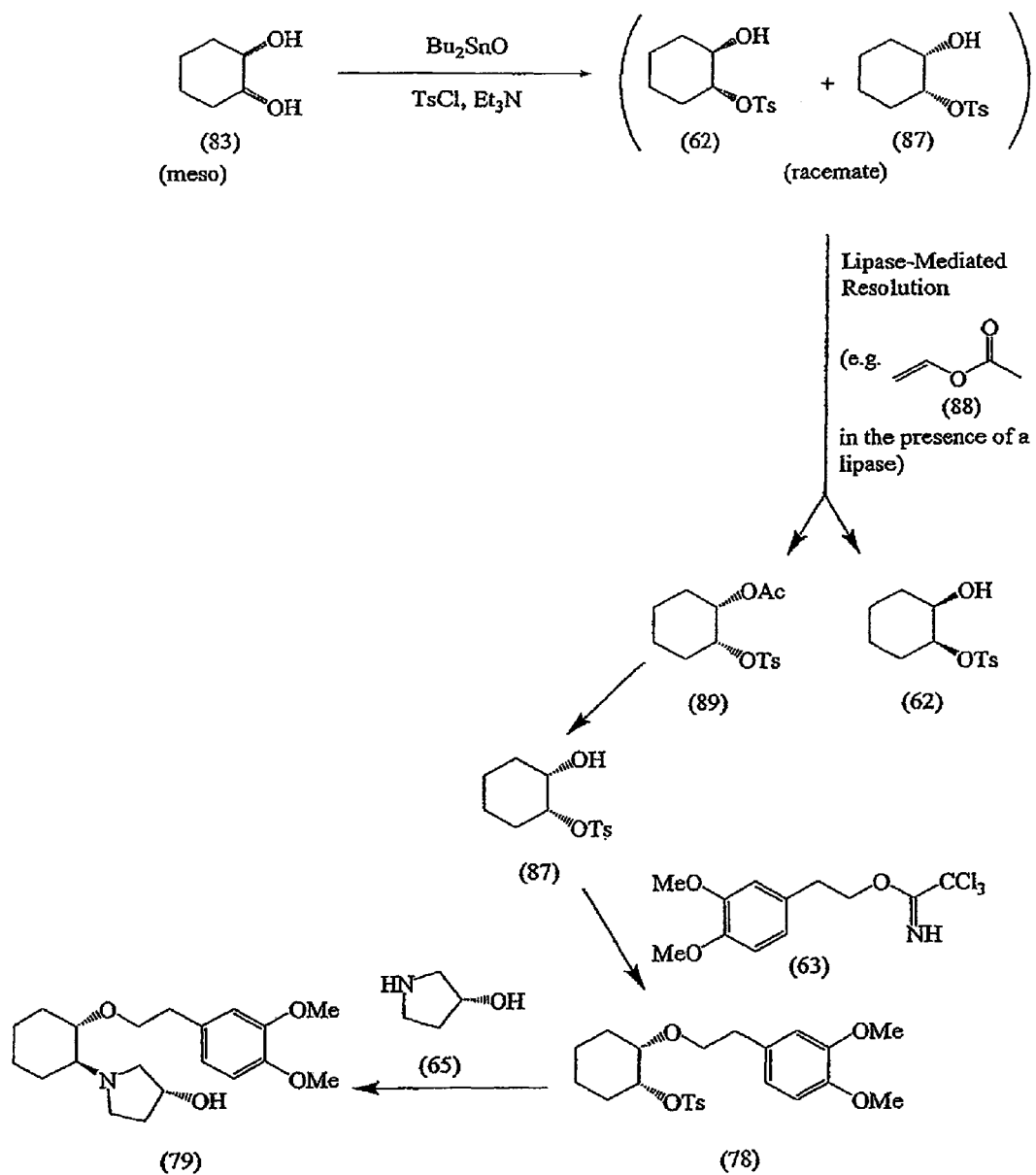

FIG. 106 illustrates a reaction scheme that may be used as a process for preparing a stereoisomerically substantially pure trans-(1S,2S)-aminocyclohexylether compound of formula (79).

Figure 107:
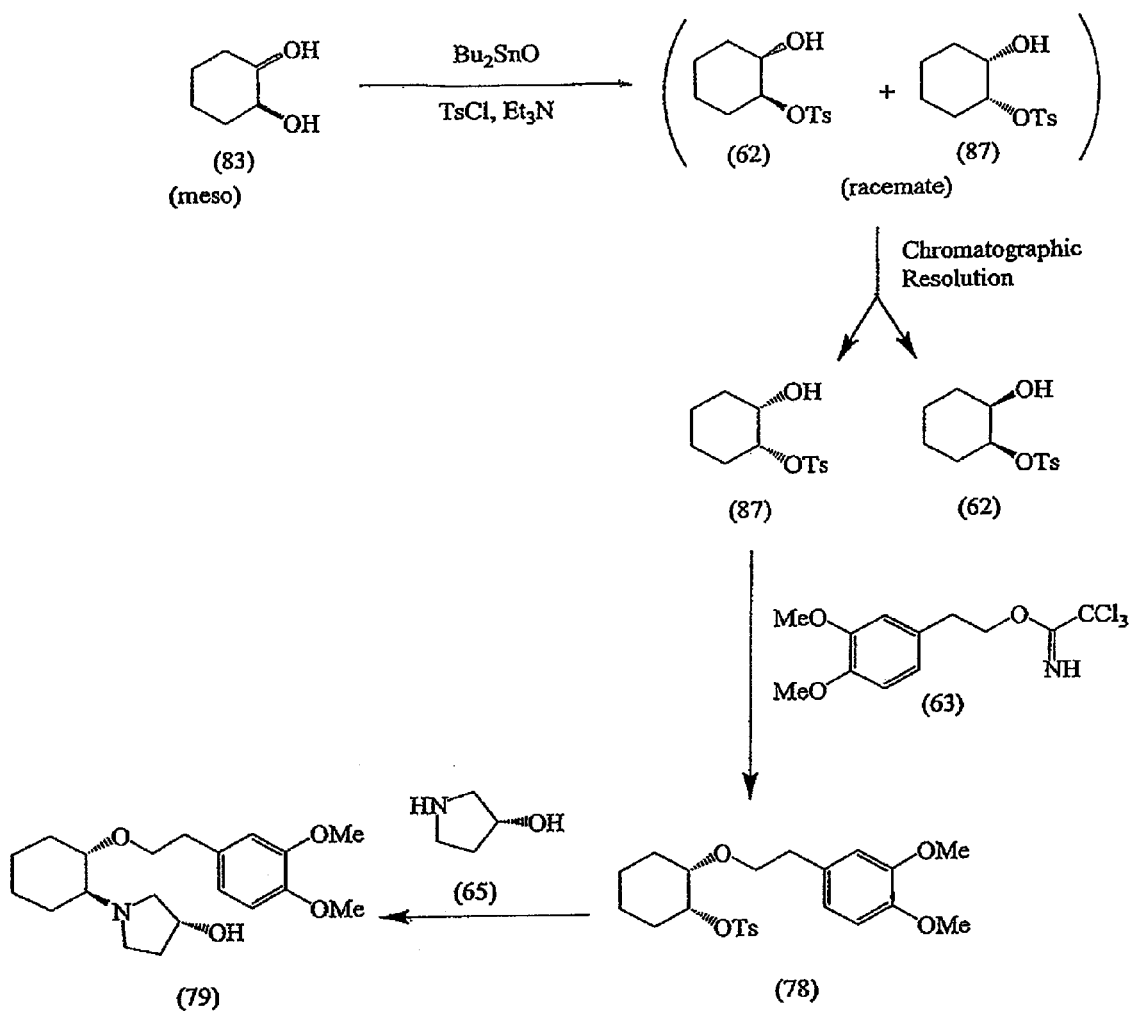

FIG. 107 illustrates a reaction scheme that may be used as a process for preparing a stereoisomerically substantially pure trans-(1S,2S)-aminocyclohexylether compound of formula (79).

Figure 108:
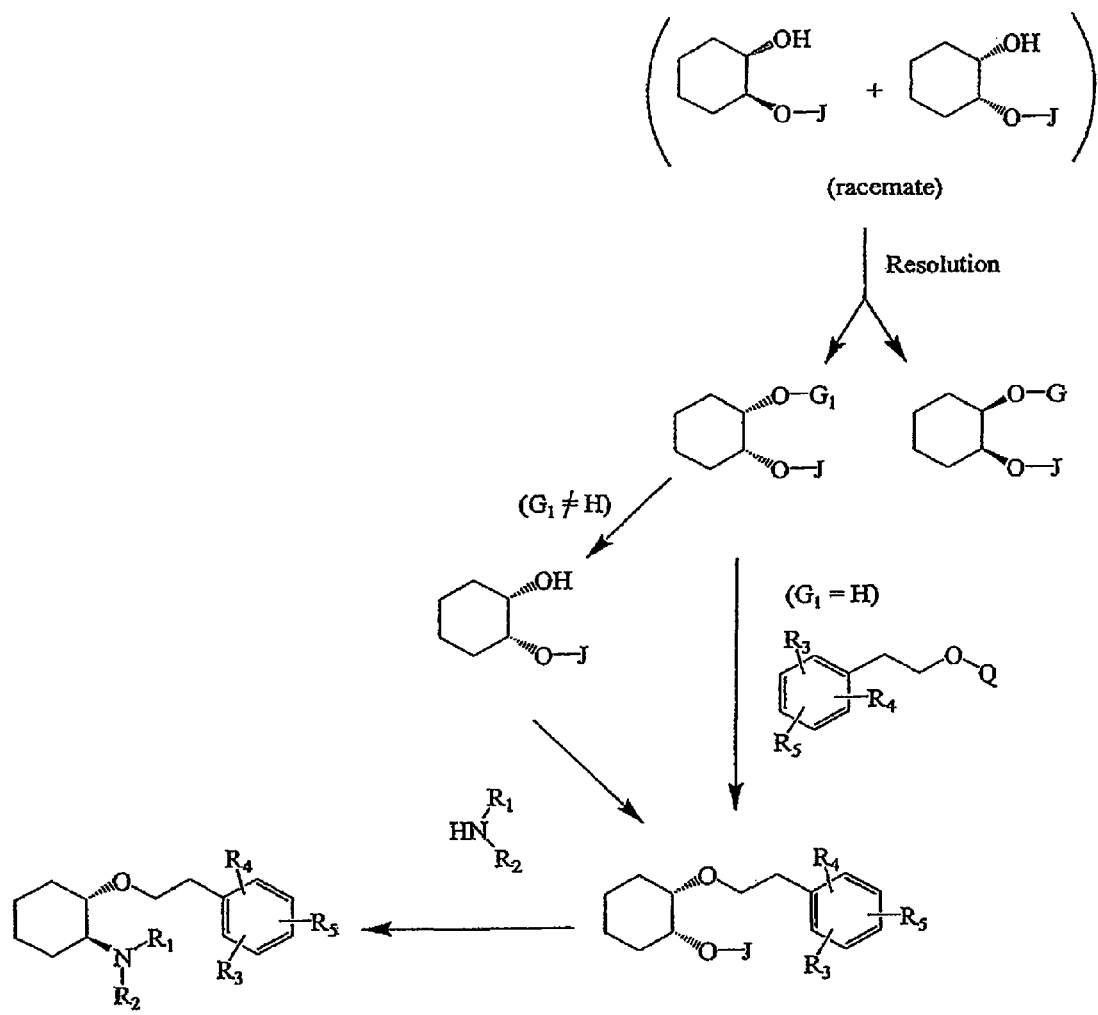

FIG. 108 illustrates a general reaction scheme that may be used as a process for preparing a stereoisomerically substantially pure trans-(1S,2S)-aminocyclohexyl ether compound of formula (75).

Figure 109:
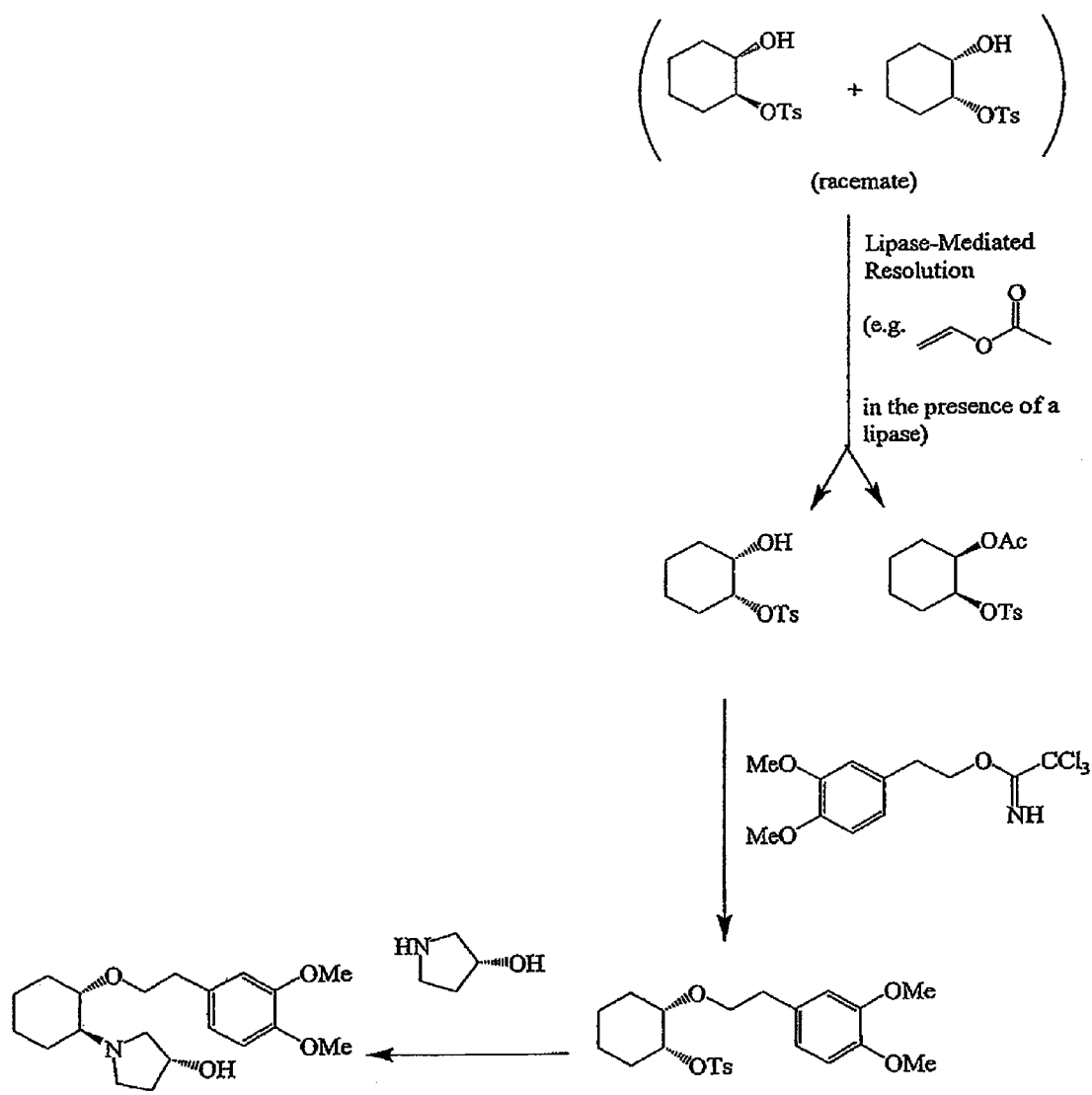

FIG. 109 illustrates a reaction scheme that may be used as a process for preparing a stereoisomerically substantially pure trans-(1S,2S)-aminocyclohexylether compound of formula (79).

Figure 110:
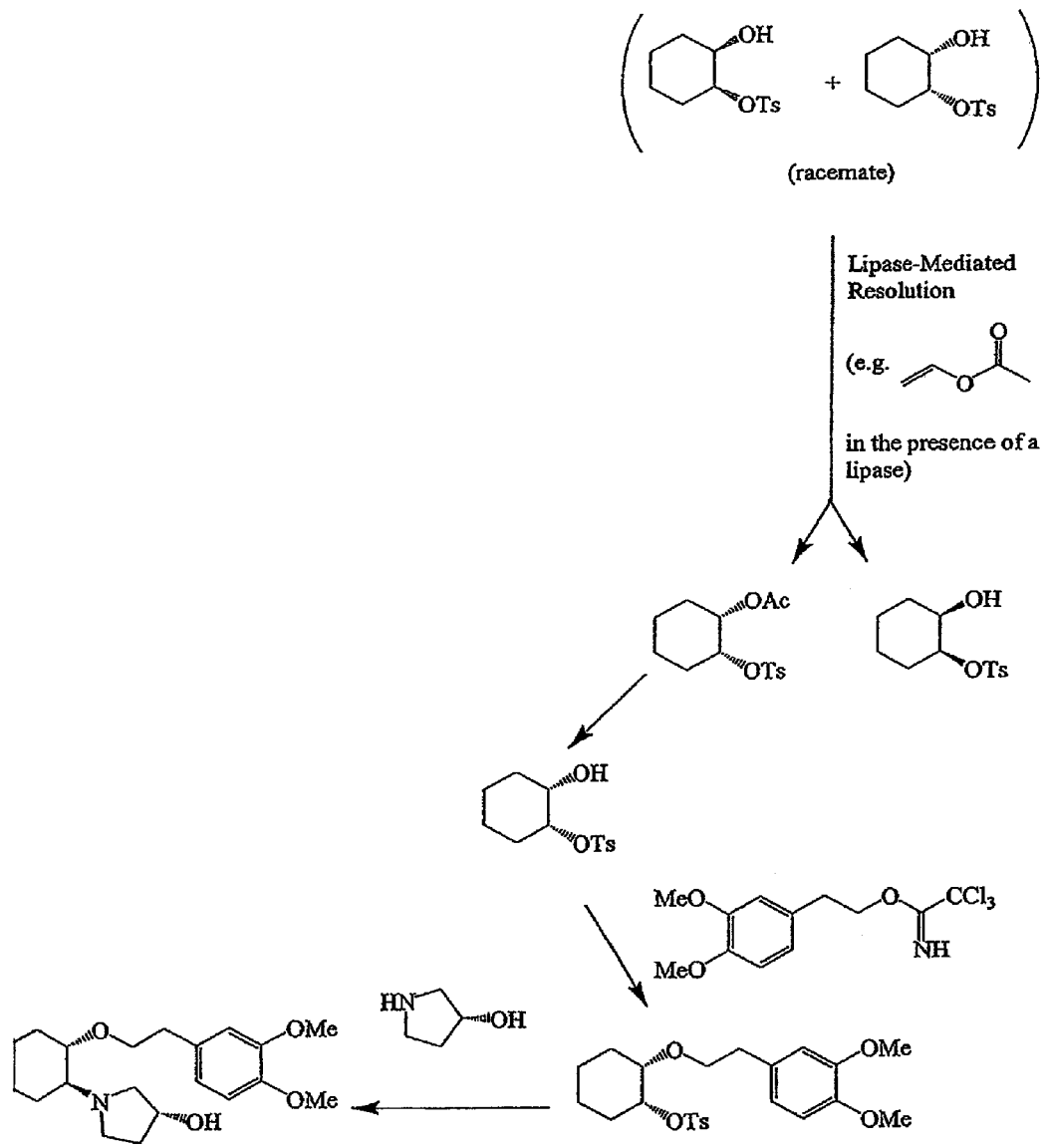

FIG. 110 illustrates a reaction scheme that may be used as a process for preparing a stereoisomerically substantially pure trans-(1S,2S)-aminocyclohexylether compound of formula (79).

Figure 111:
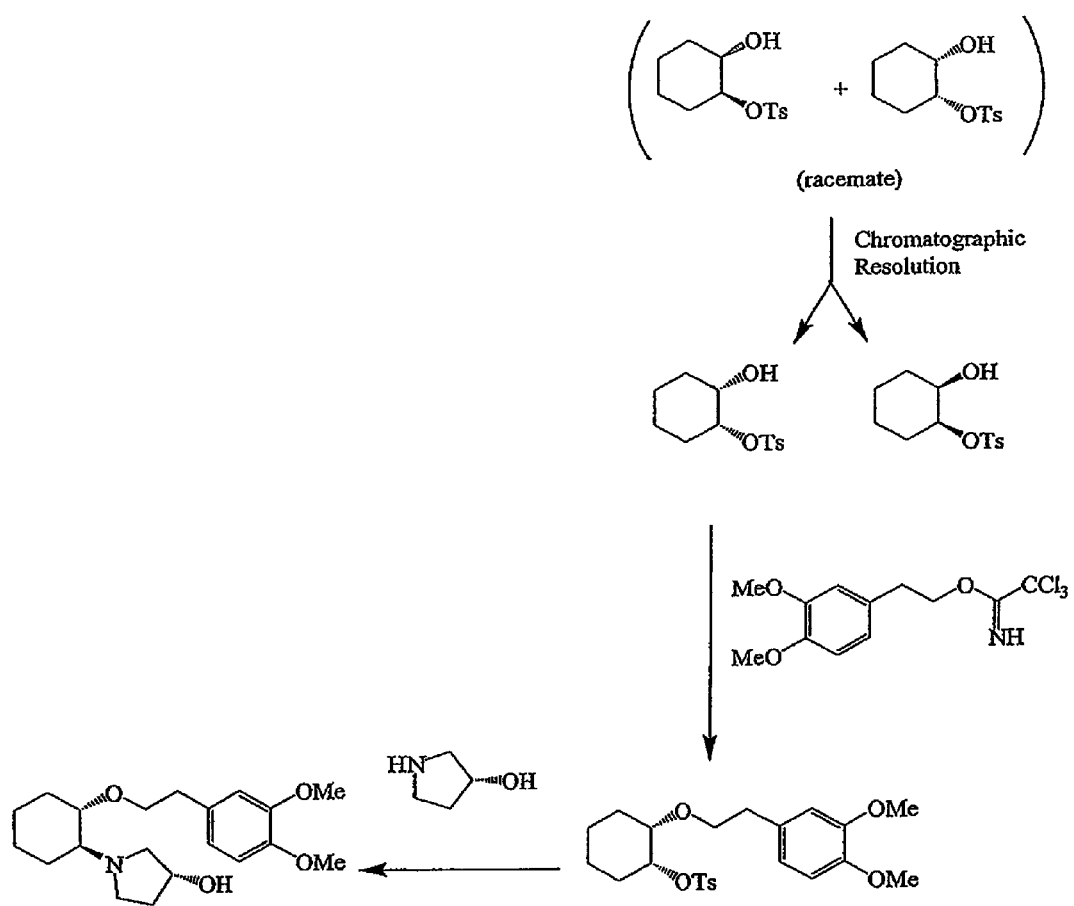

FIG. 111 illustrates a reaction scheme that may be used as a process for preparing a stereoisomerically substantially pure trans-(1S,2S)-aminocyclohexylether compound of formula (79).

Figure 112:
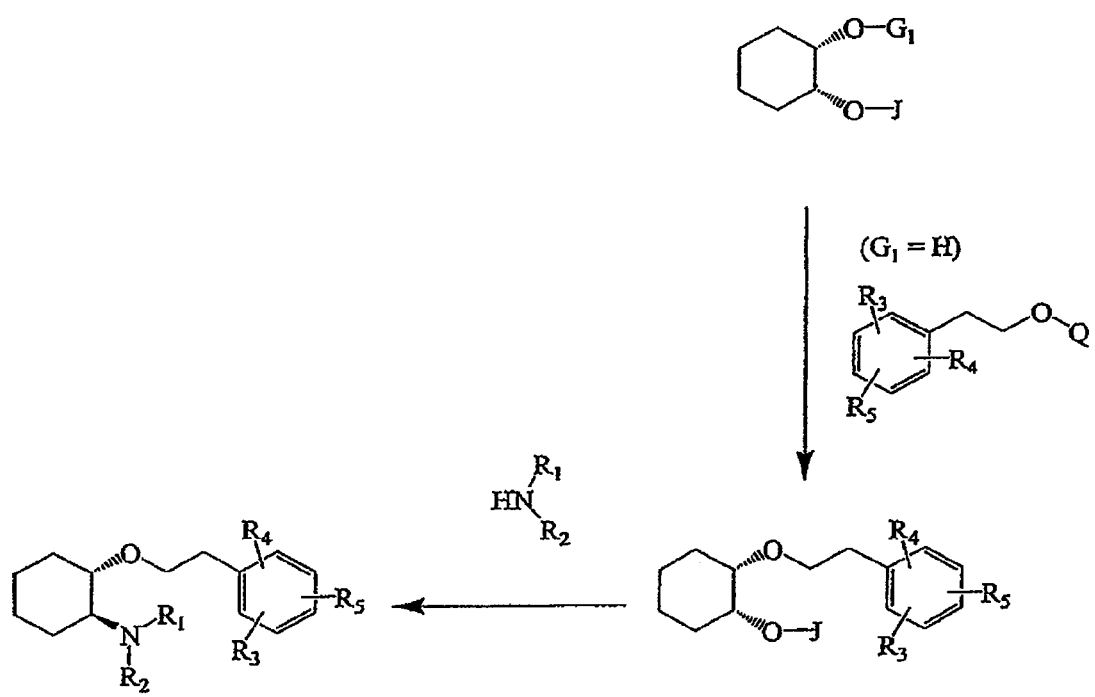

FIG. 112 illustrates a general reaction scheme that may be used as a process for preparing a stereoisomerically substantially pure trans-(1S,2S)-aminocyclohexyl ether compound of formula (75).

Figure 113:
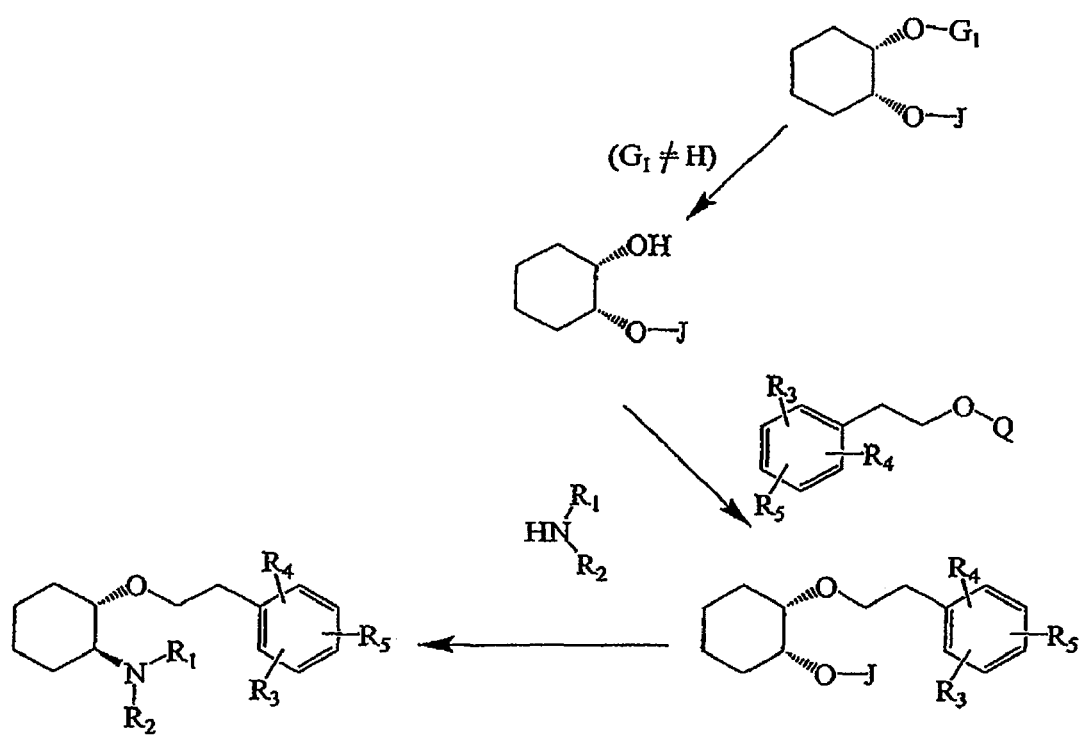

FIG. 113 illustrates a general reaction scheme that may be used as a process for preparing a stereoisomerically substantially pure trans-(1S,2S)-aminocyclohexyl ether compound of formula (75).

Figure 114:
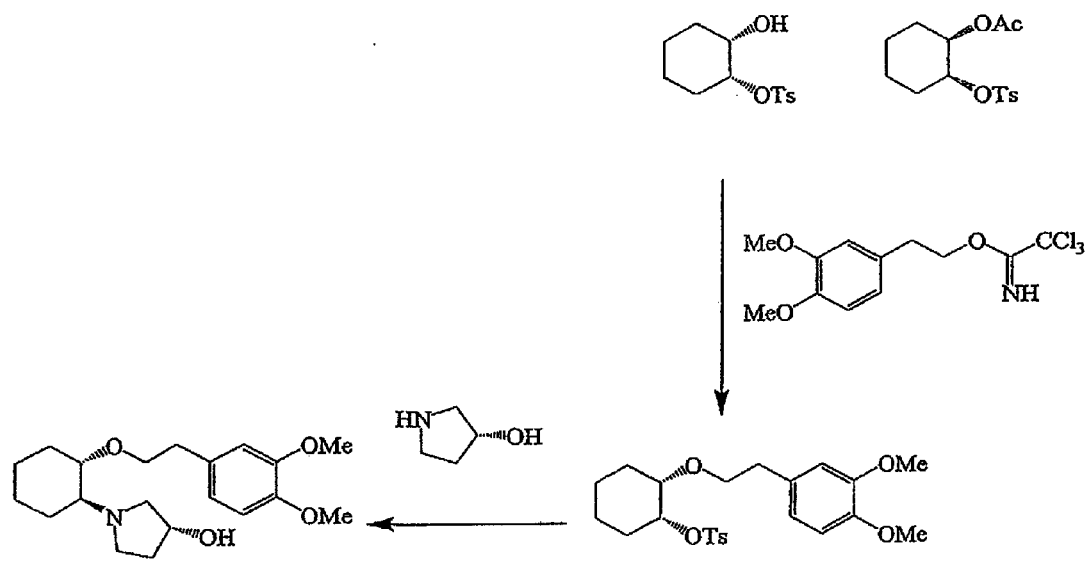

FIG. 114 illustrates a reaction scheme that may be used as a process for preparing a stereoisomerically substantially pure trans-(1S,2S)-aminocyclohexylether compound of formula (79).

Figure 115:
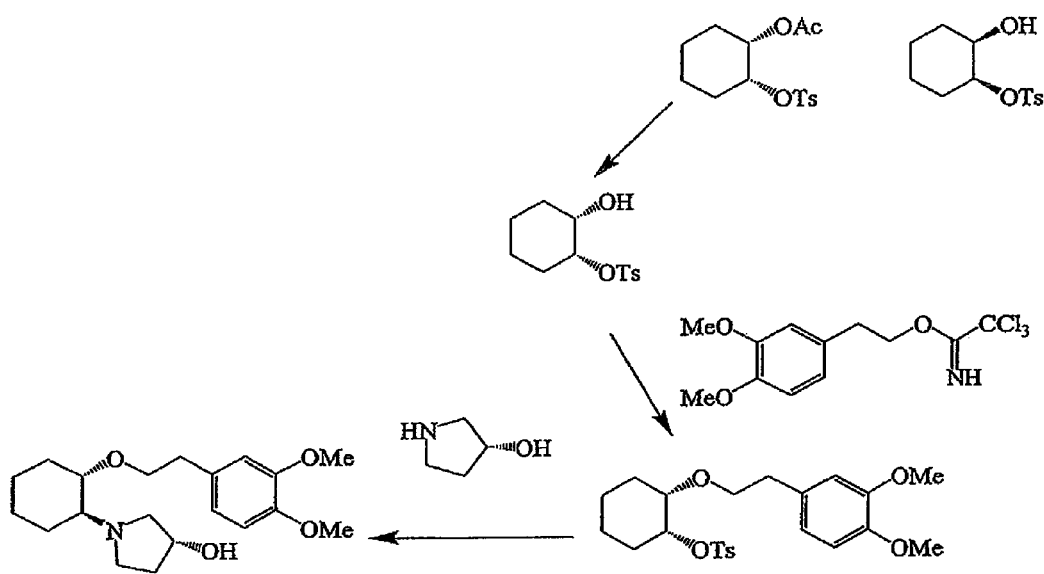

FIG. 115 illustrates a reaction scheme that may be used as a process for preparing a stereoisomerically substantially pure trans-(1S,2S)-aminocyclohexylether compound of formula (79).

Figure 116:
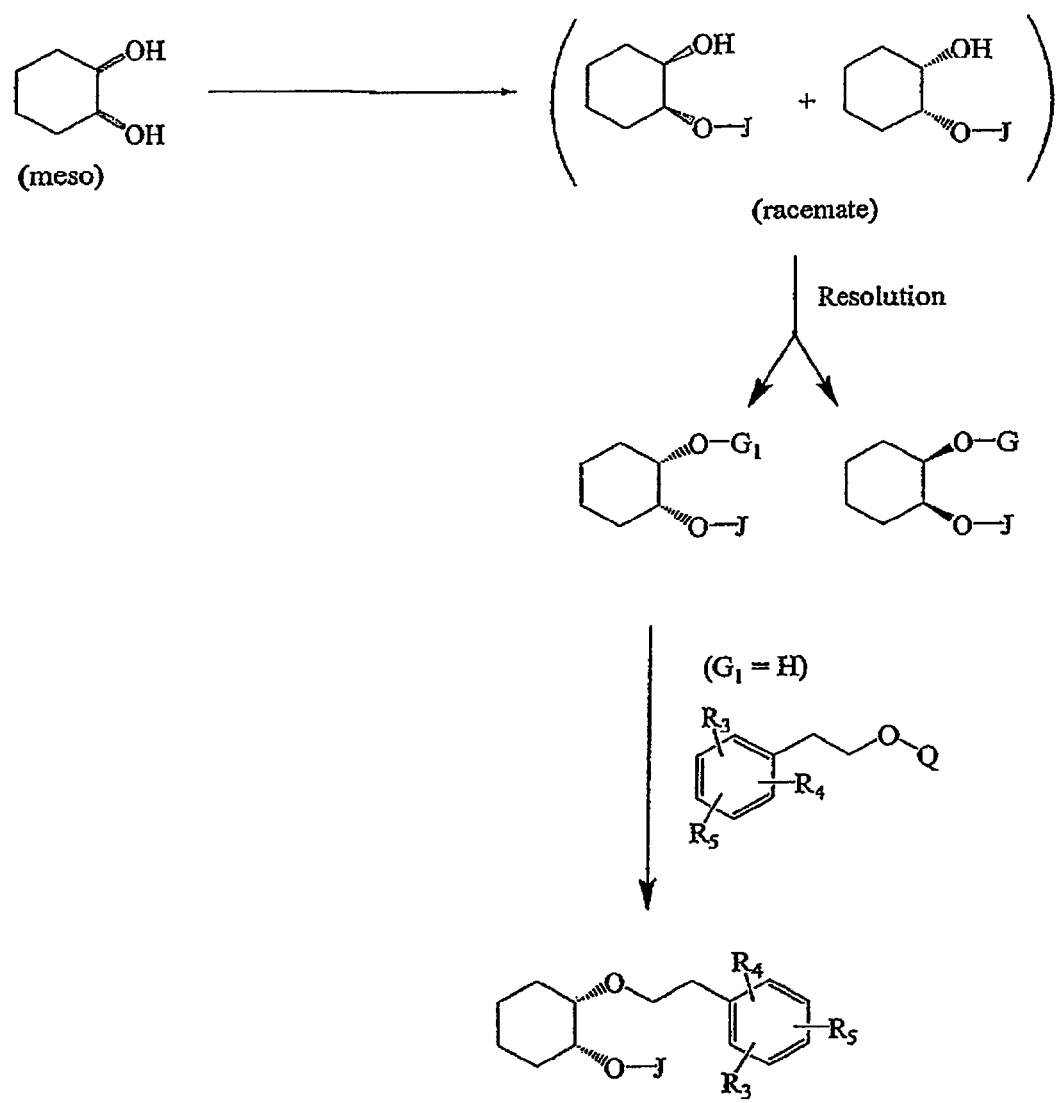

FIG. 116 illustrates a general reaction scheme that may be used as a process for preparing a stereoisomerically substantially pure compound of formula (74).

Figure 117:
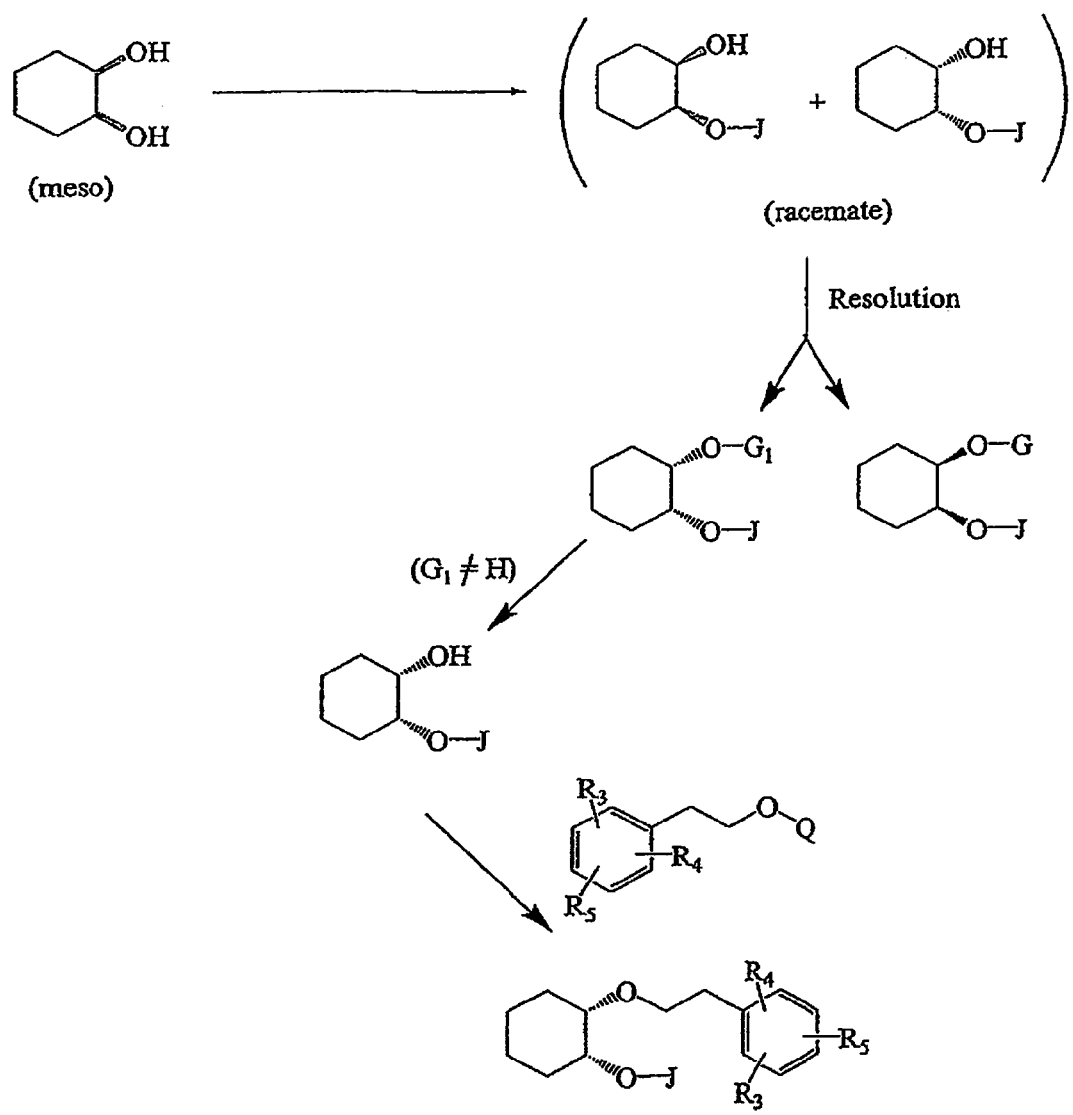

FIG. 117 illustrates general a reaction scheme that may be used as a process for preparing a stereoisomerically substantially pure compound of formula (74).

Figure 118:
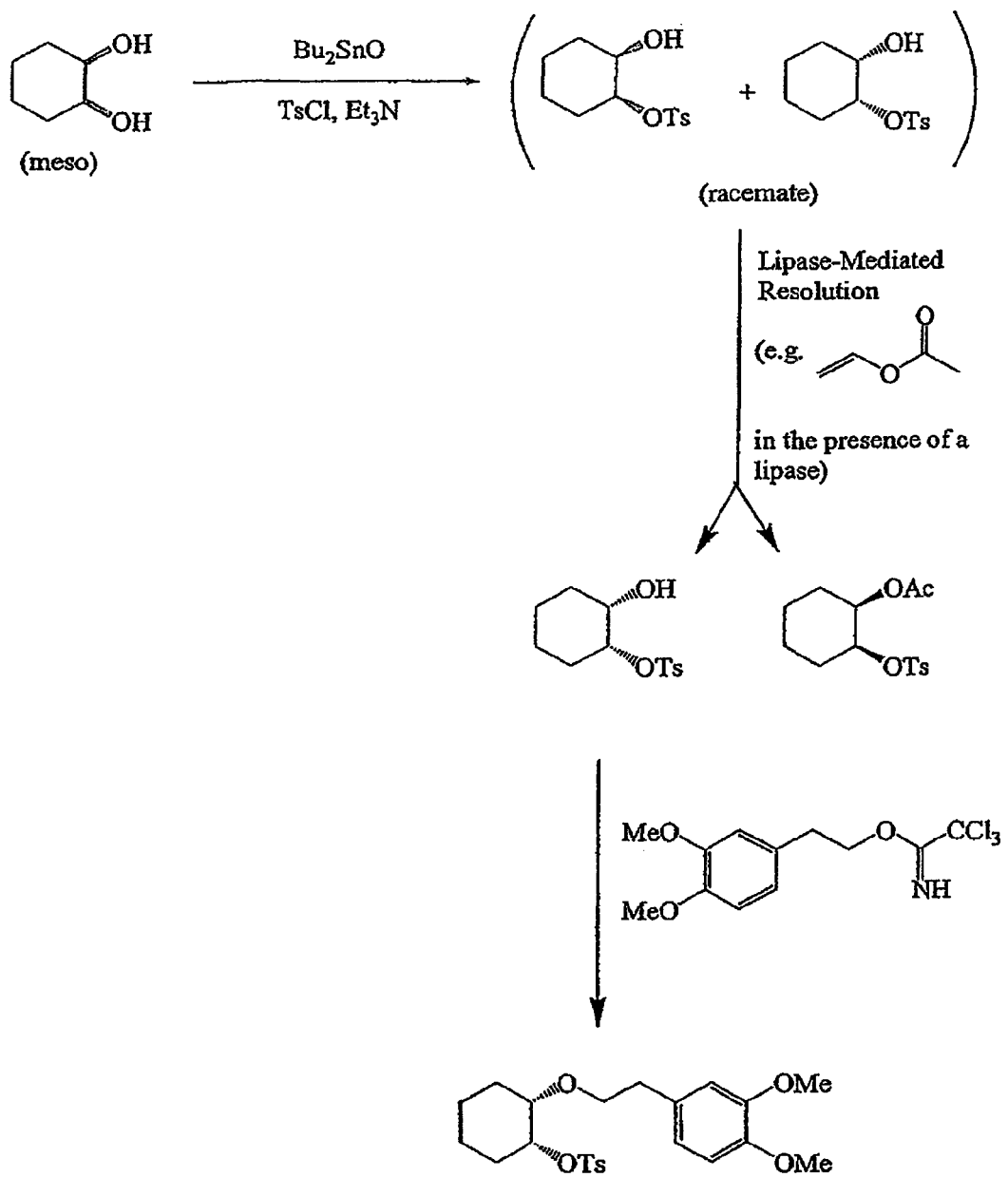

FIG. 118 illustrates a reaction scheme that may be used as a process for preparing a stereoisomerically substantially pure compound of formula (78).

Figure 119:
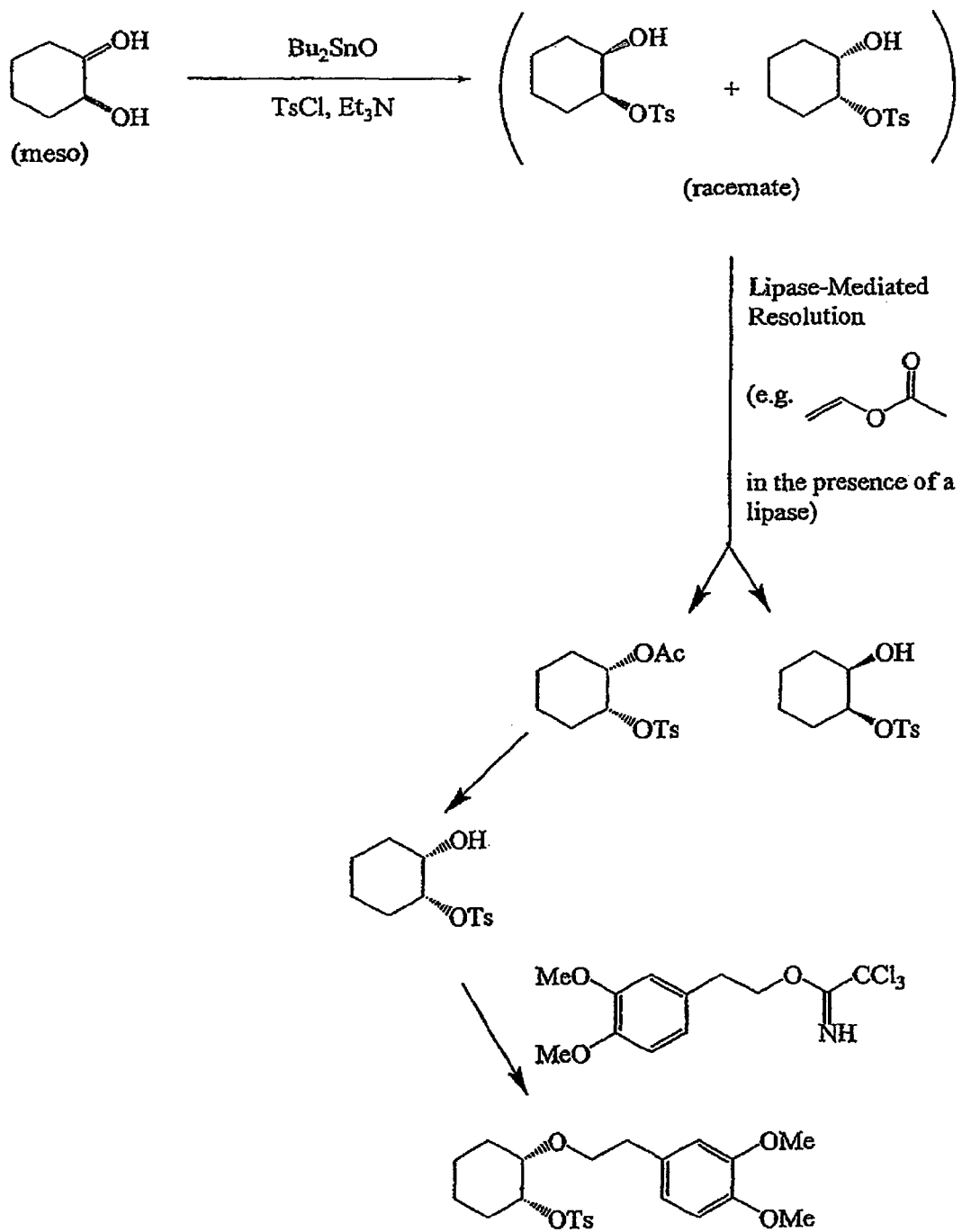

FIG. 119 illustrates a reaction scheme that may be used as a process for preparing a stereoisomerically substantially pure compound of formula (78).

Figure 120:
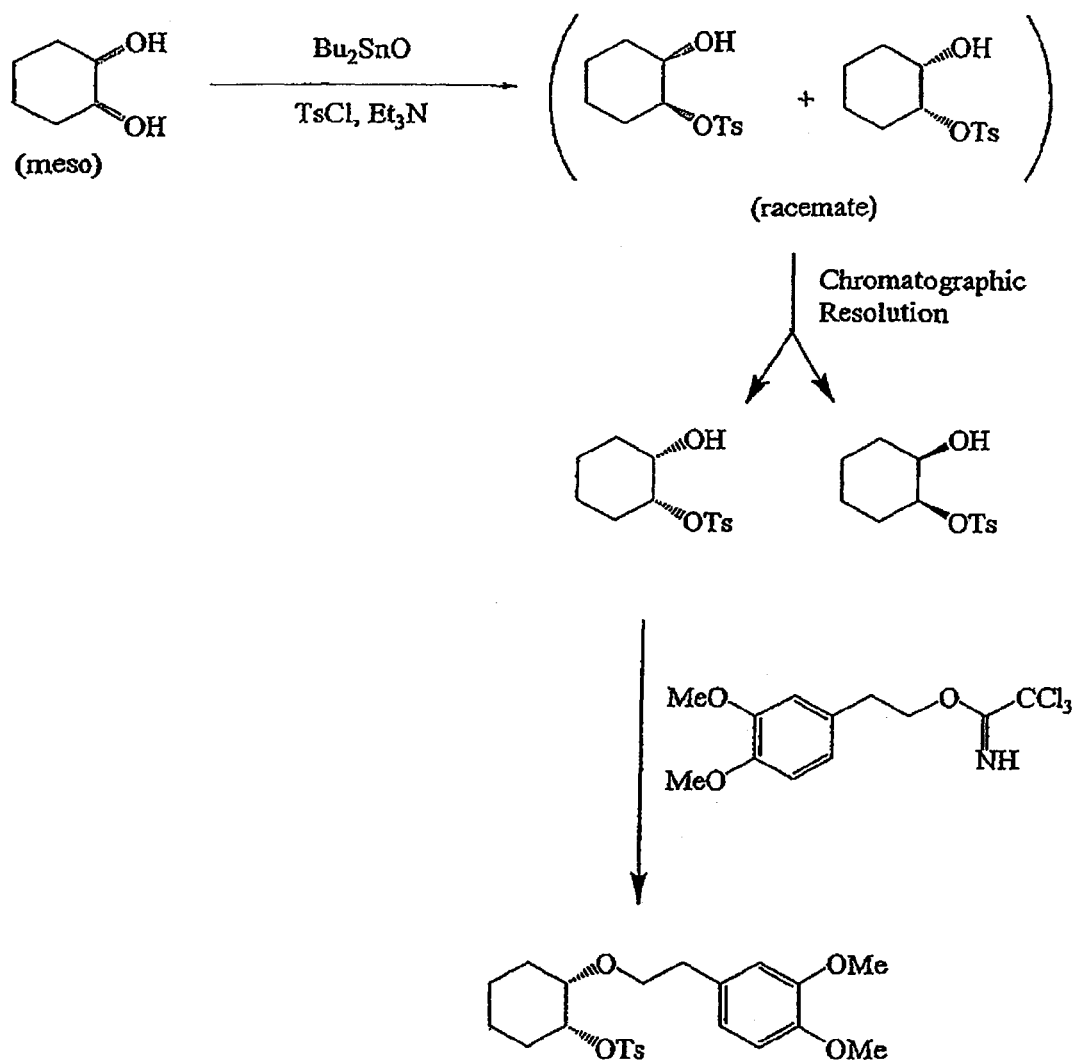

FIG. 120 illustrates a reaction scheme that may be used as a process for preparing a stereoisomerically substantially pure compound of formula (78).

Figure 121:
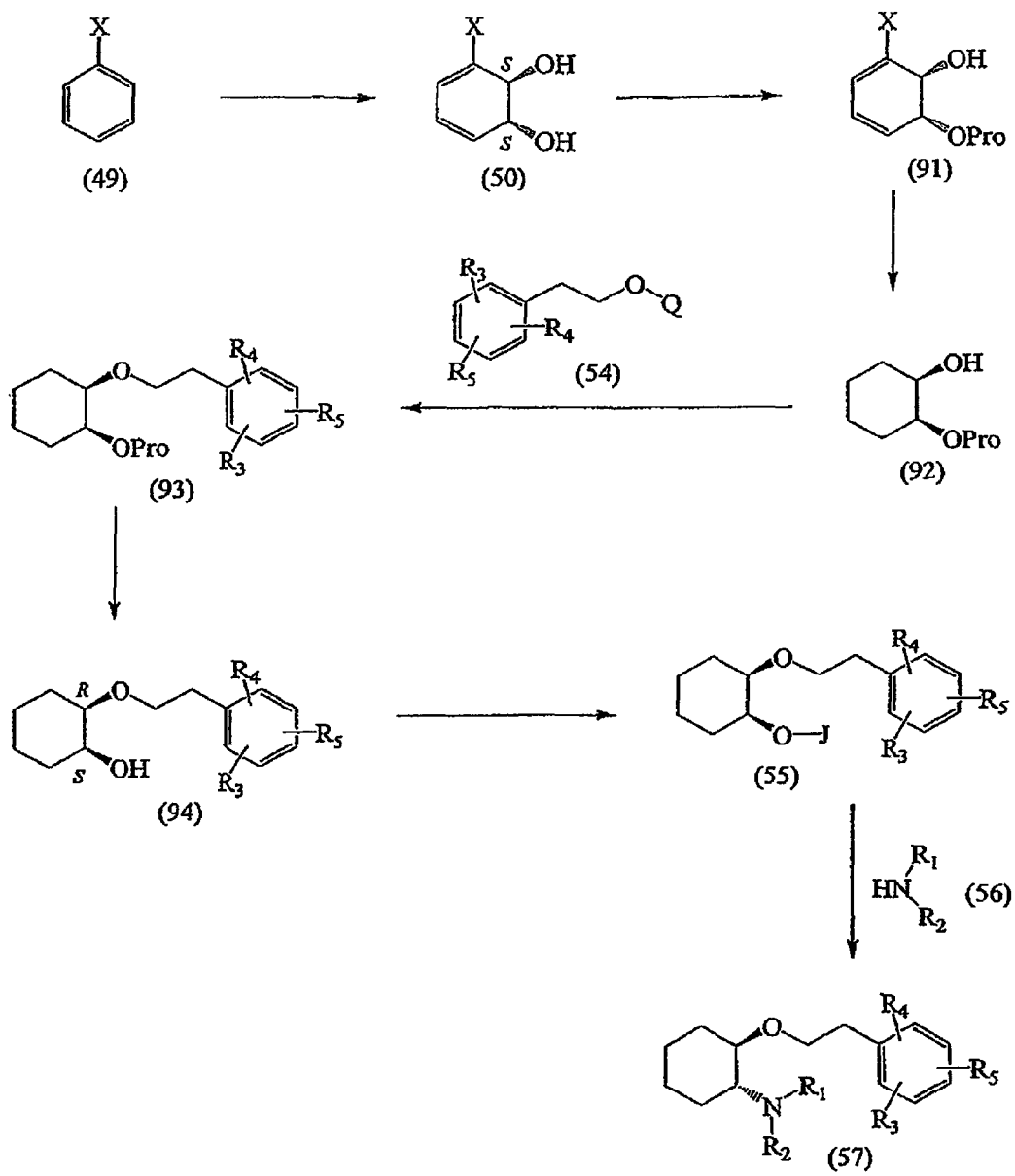

FIG. 121 illustrates a general reaction scheme that may be used as a process for preparing a stereoisomerically substantially pure trans-(1R,2R)-aminocyclohexyl ether compound of formula (57).

Figure 122:
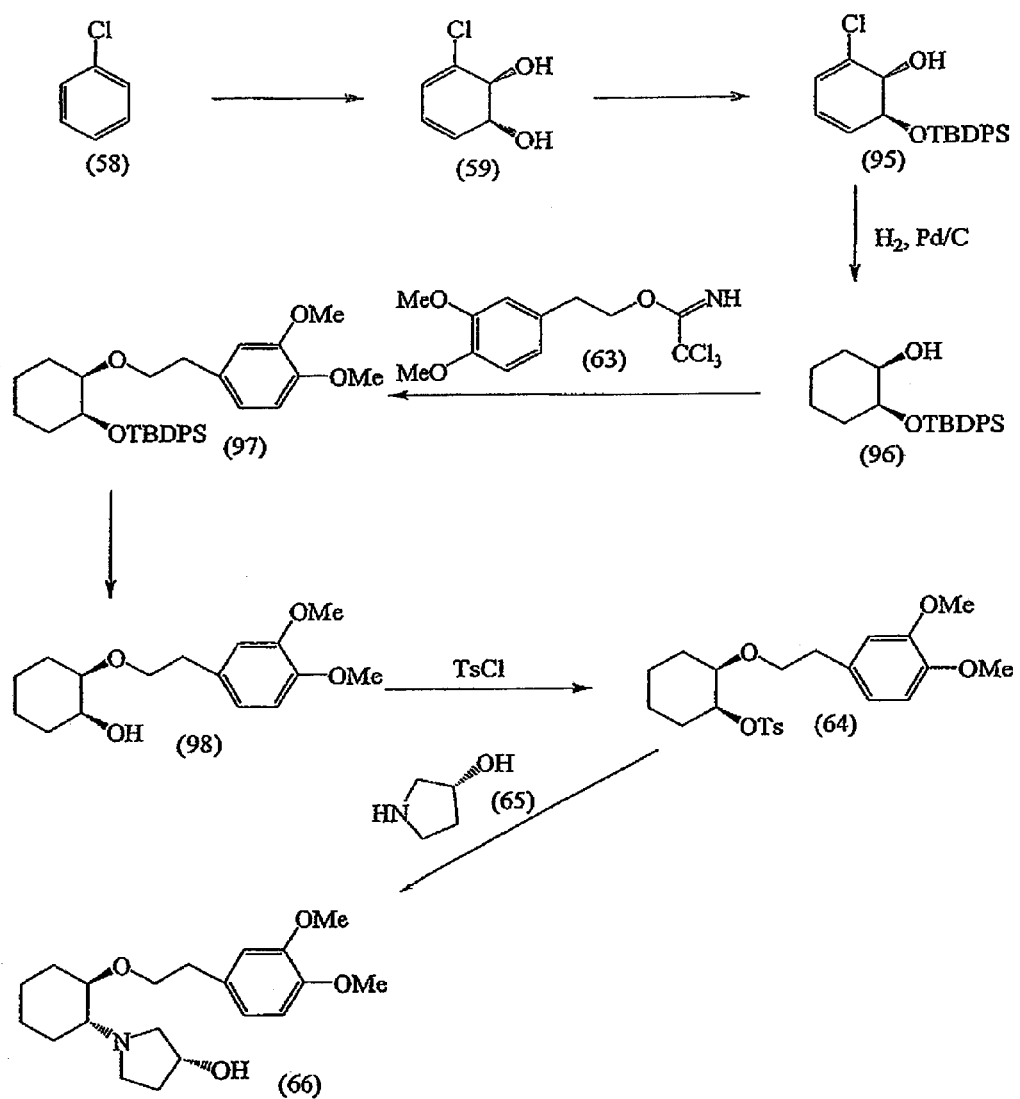

FIG. 122 illustrates a reaction scheme that may be used as a process for preparing a stereoisomerically substantially pure trans-(1R,2R)-aminocyclohexylether compound of formula (66).

Figure 123:
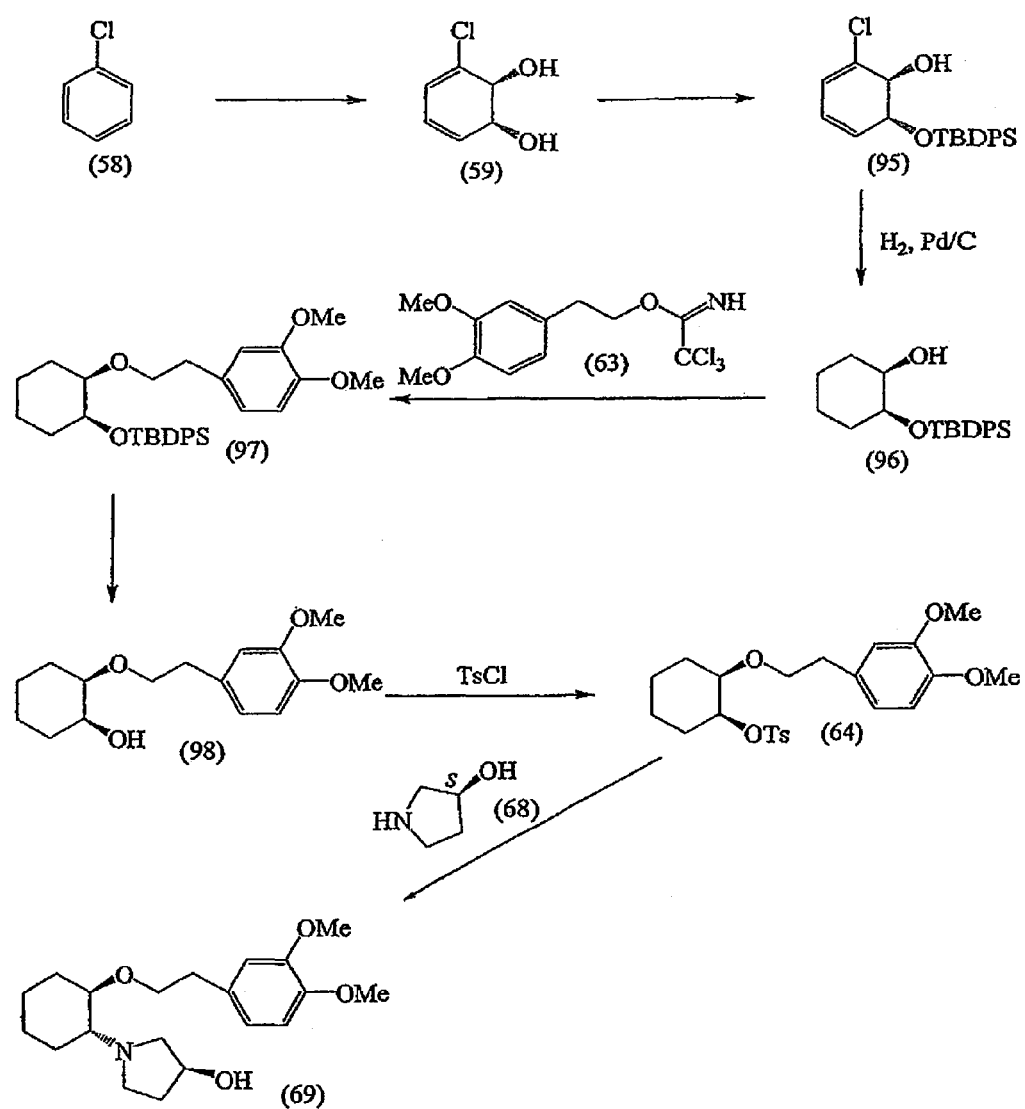

FIG. 123 illustrates a reaction scheme that may be used as a process for preparing a stereoisomerically substantially pure trans-(1R,2R)-aminocyclohexylether compound of formula (69).

Figure 124:
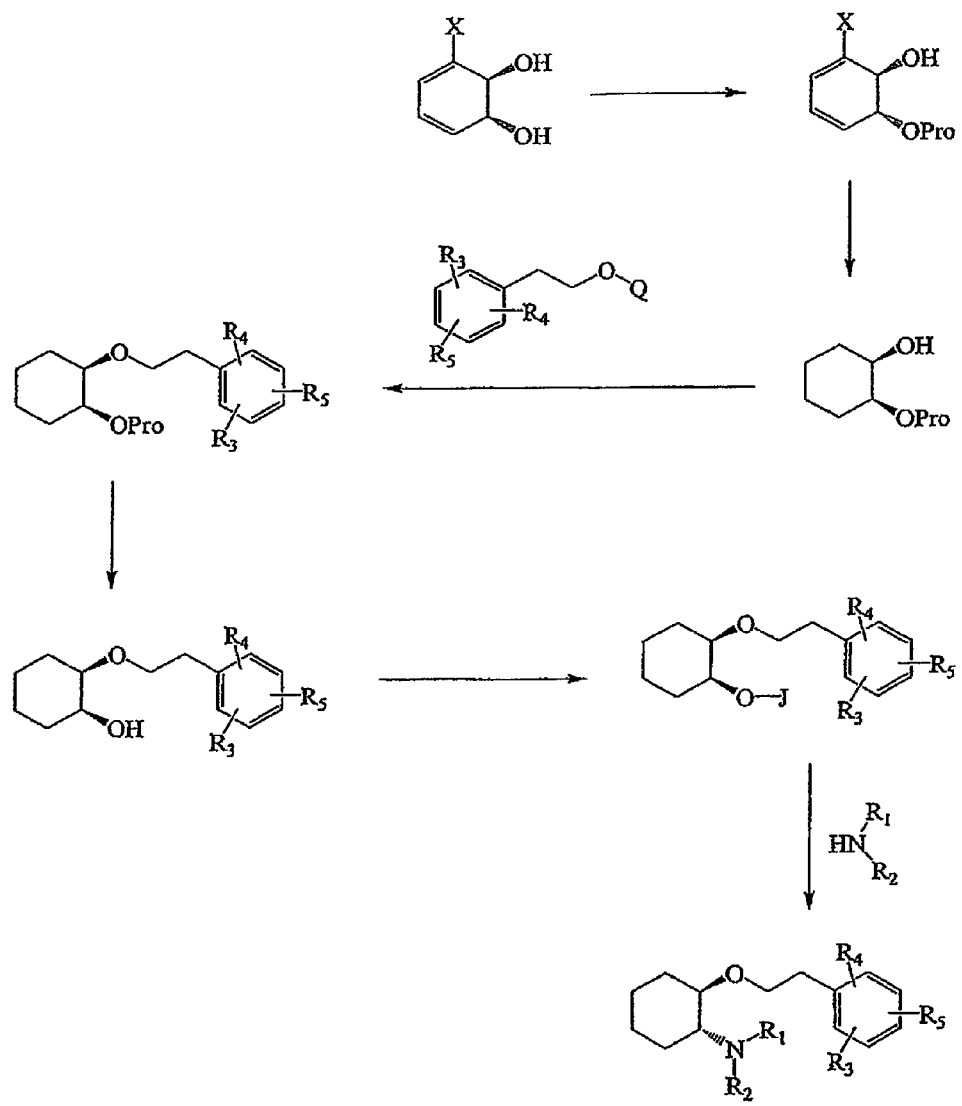

FIG. 124 illustrates a general reaction scheme that may be used as a process for preparing a stereoisomerically substantially pure trans-(1R,2R)-aminocyclohexyl ether compound of formula (57).

Figure 125:
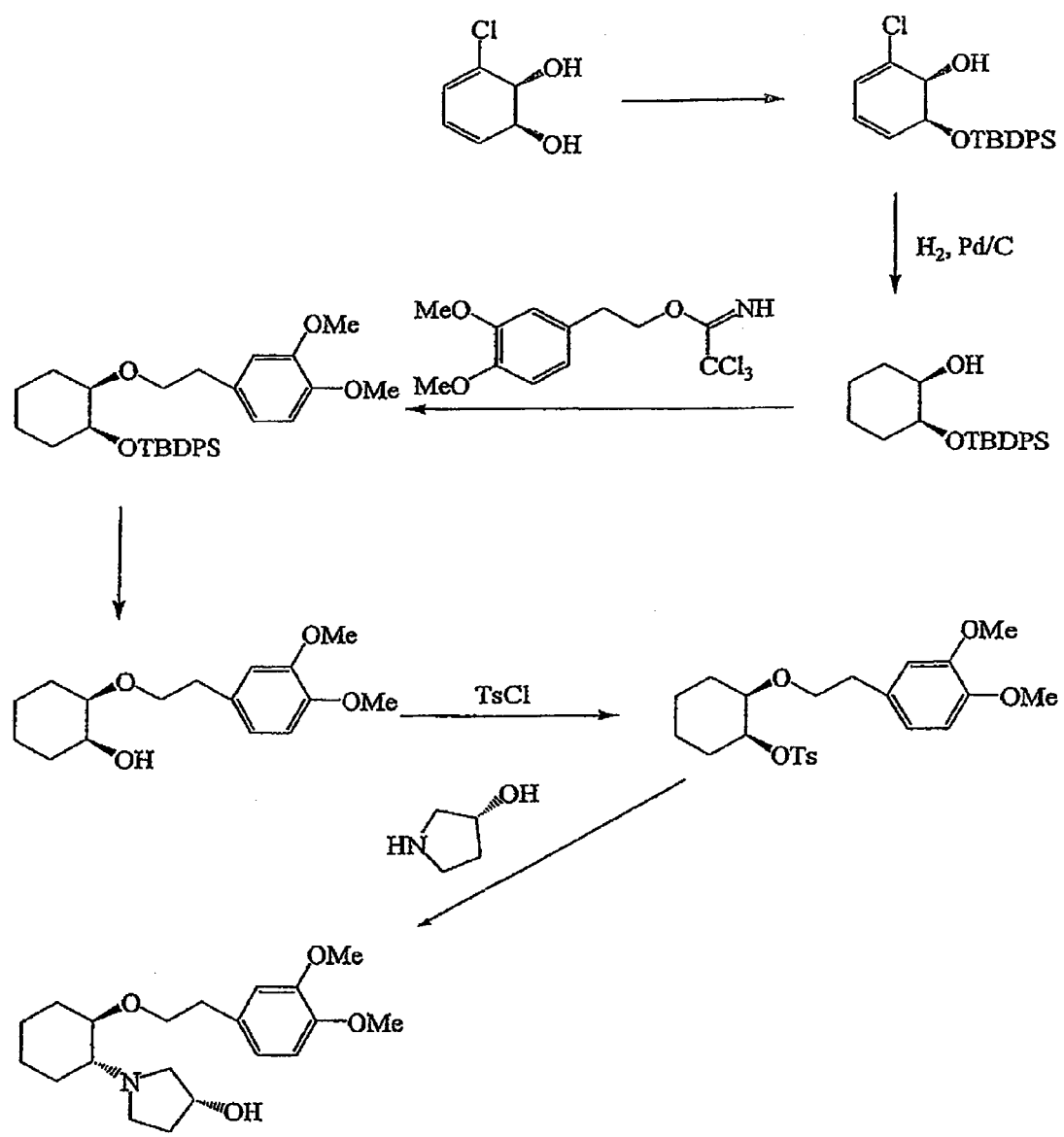

FIG. 125 illustrates a reaction scheme that may be used as a process for preparing a stereoisomerically substantially pure trans-(1R,2R)-aminocyclohexylether compound of formula (66).

Figure 126:
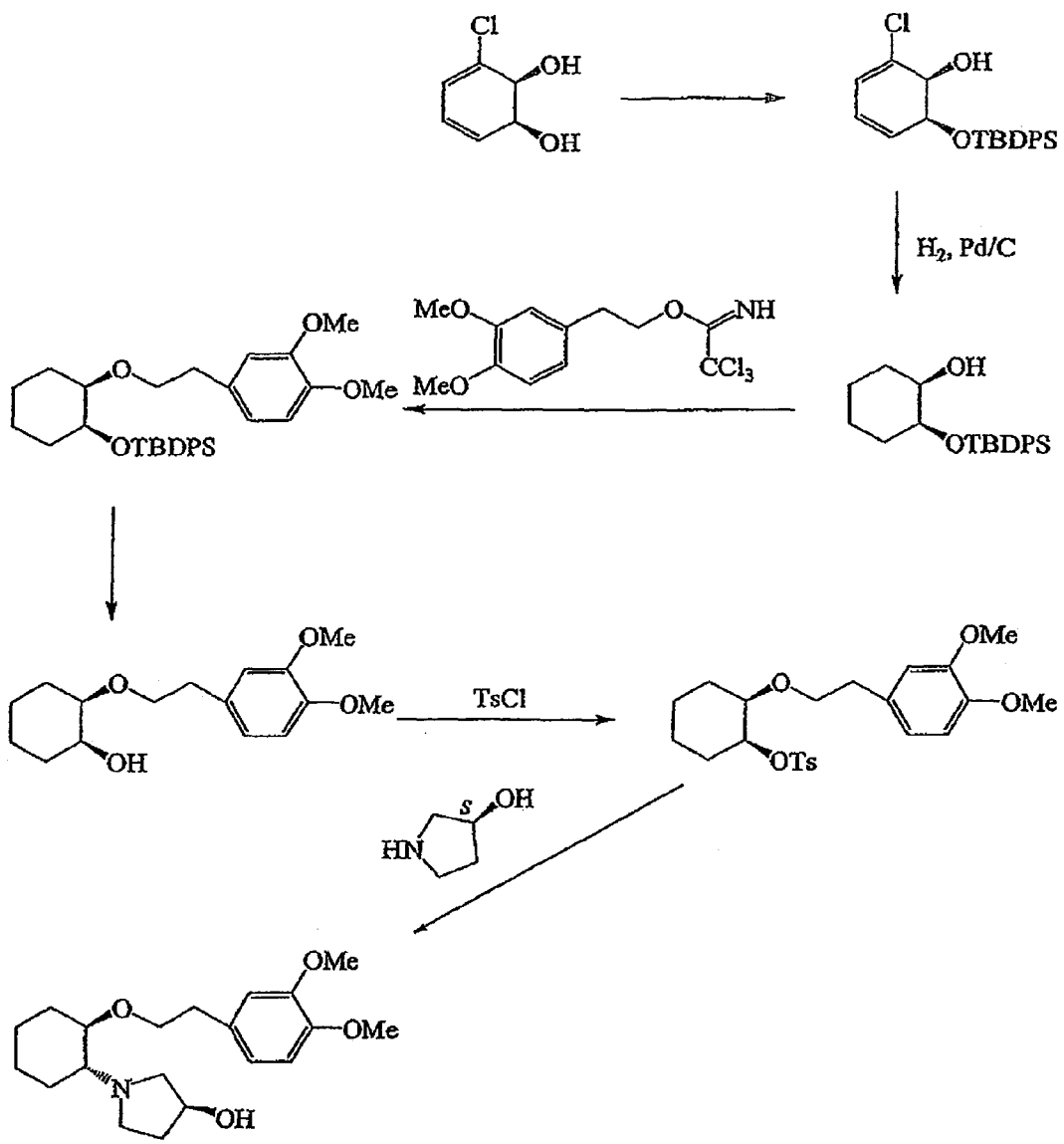

FIG. 126 illustrates a reaction scheme that may be used as a process for preparing a stereoisomerically substantially pure trans-(1R,2R)-aminocyclohexylether compound of formula (69).

Figure 127:
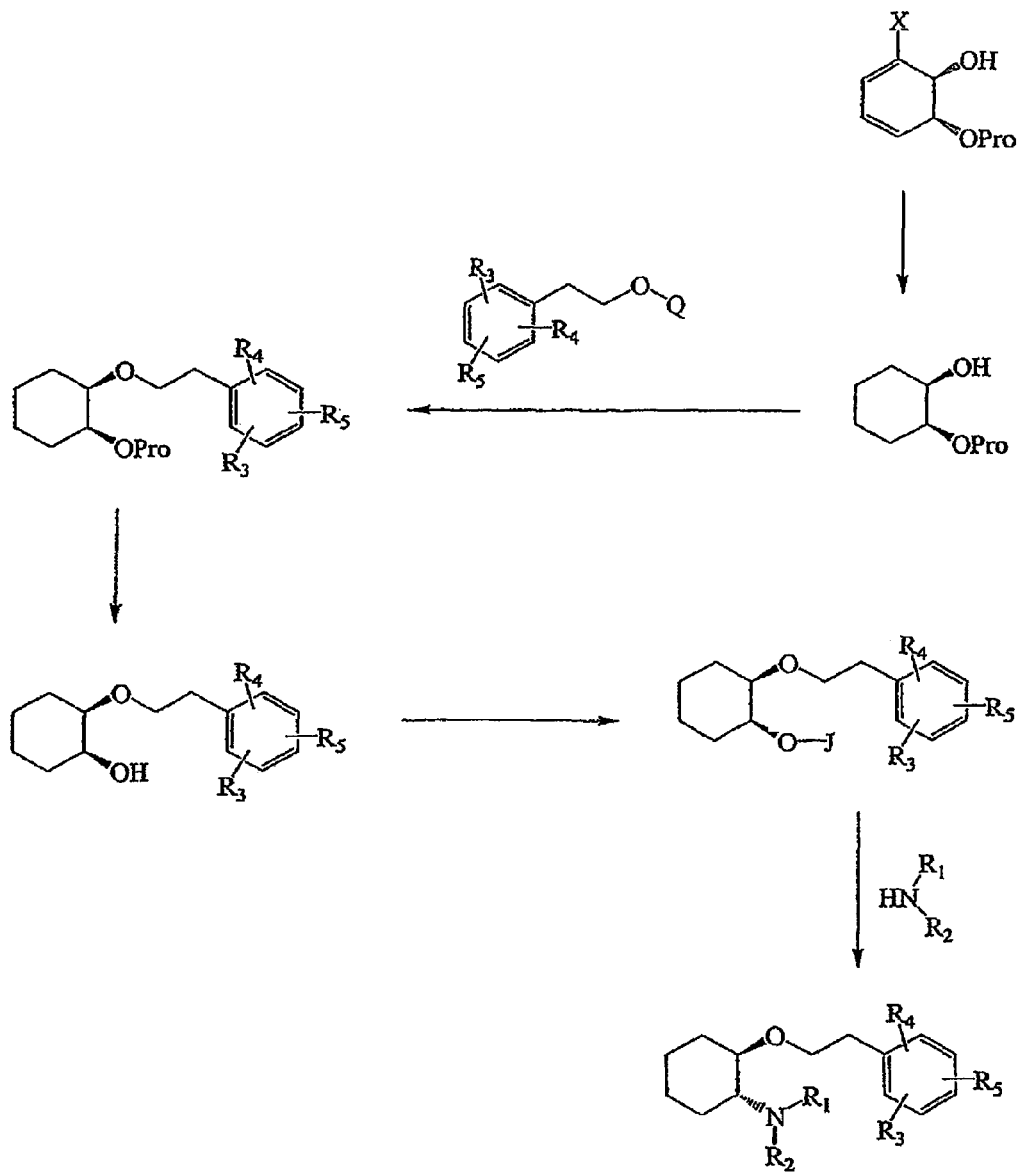

FIG. 127 illustrates a general reaction scheme that may be used as a process for preparing a stereoisomerically substantially pure trans-(1R,2R)-aminocyclohexyl ether compound of formula (57).

Figure 128:
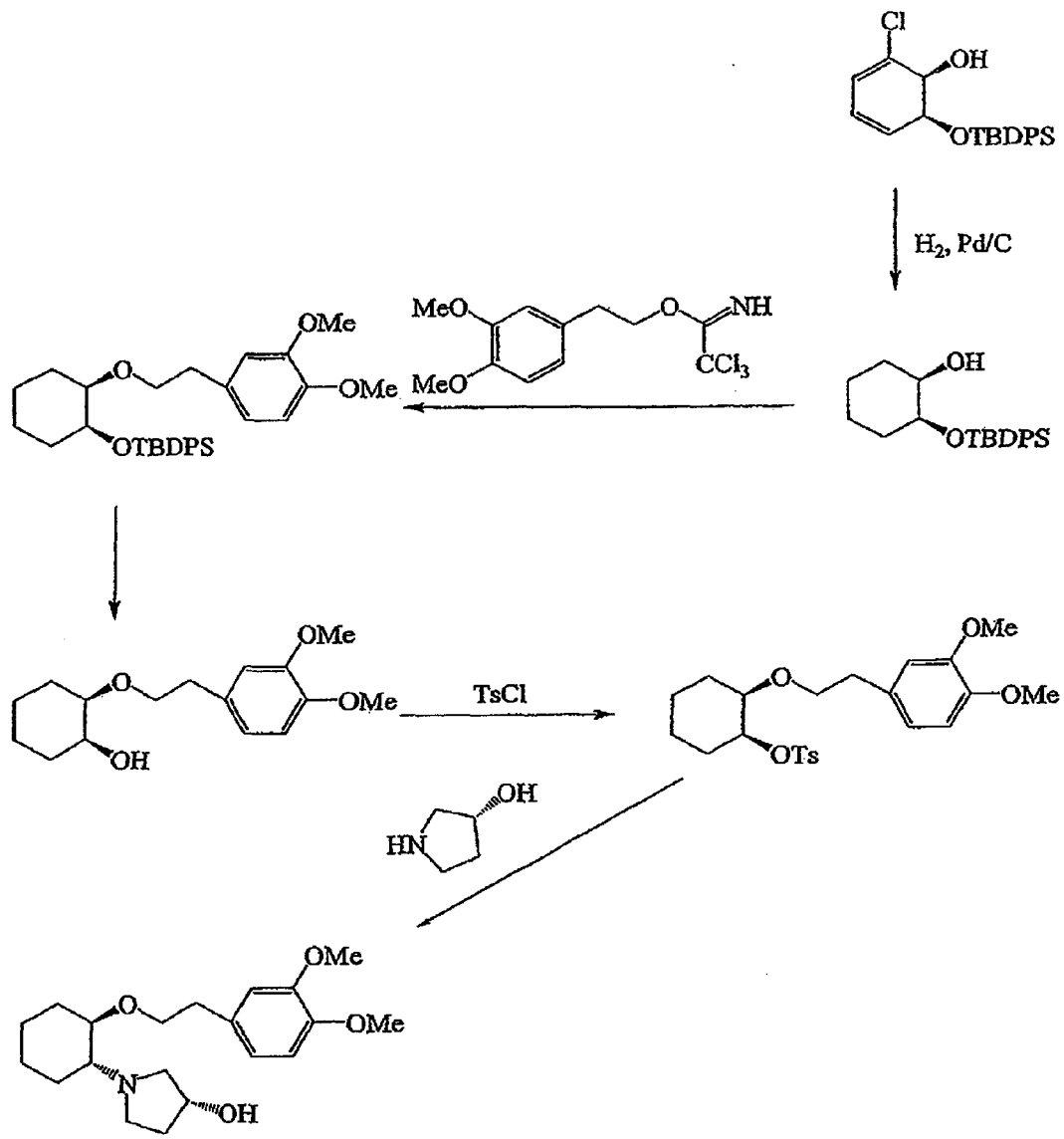

FIG. 128 illustrates a reaction scheme that may be used as a process for preparing a stereoisomerically substantially pure trans-(1R,2R)-aminocyclohexylether compound of formula (66).

Figure 129:
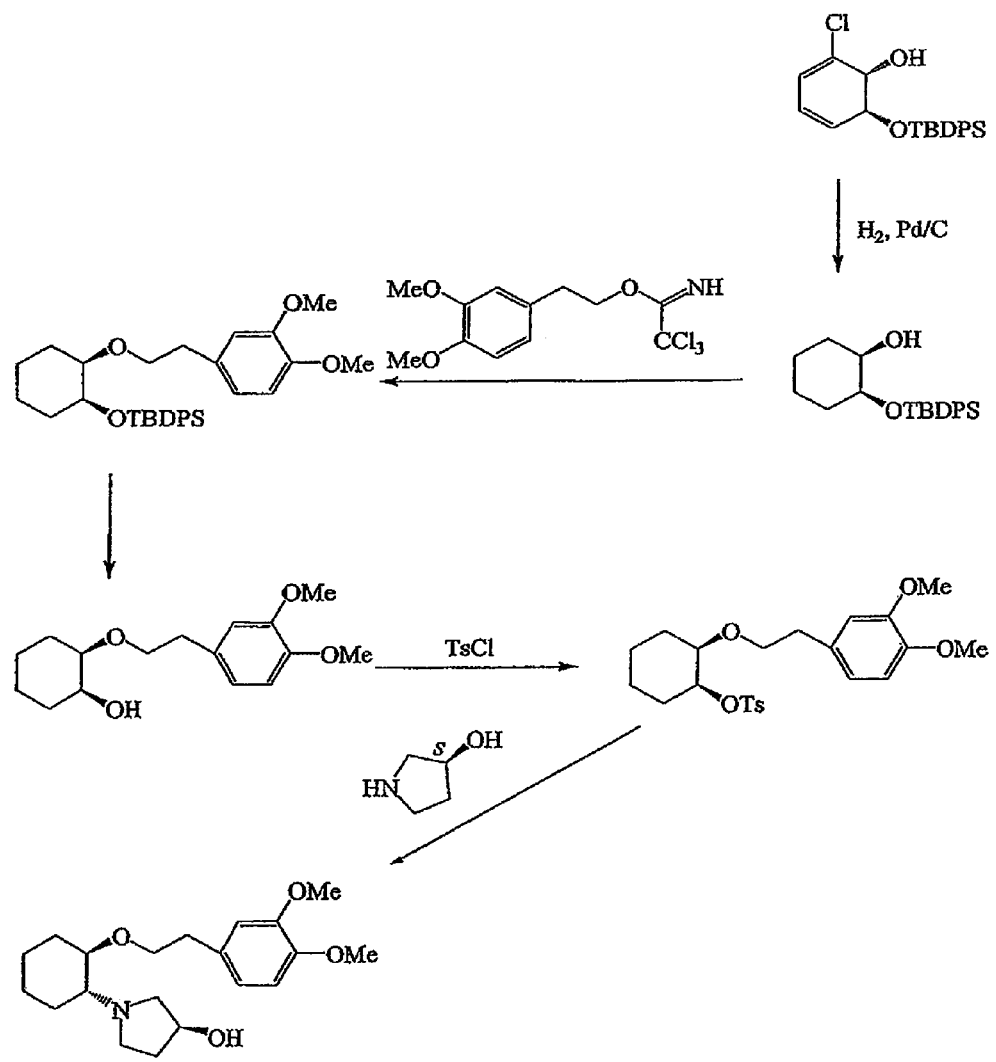

FIG. 129 illustrates a reaction scheme that may be used as a process for preparing a stereoisomerically substantially pure trans-(1R,2R)-aminocyclohexylether compound of formula (69).

Figure 130:
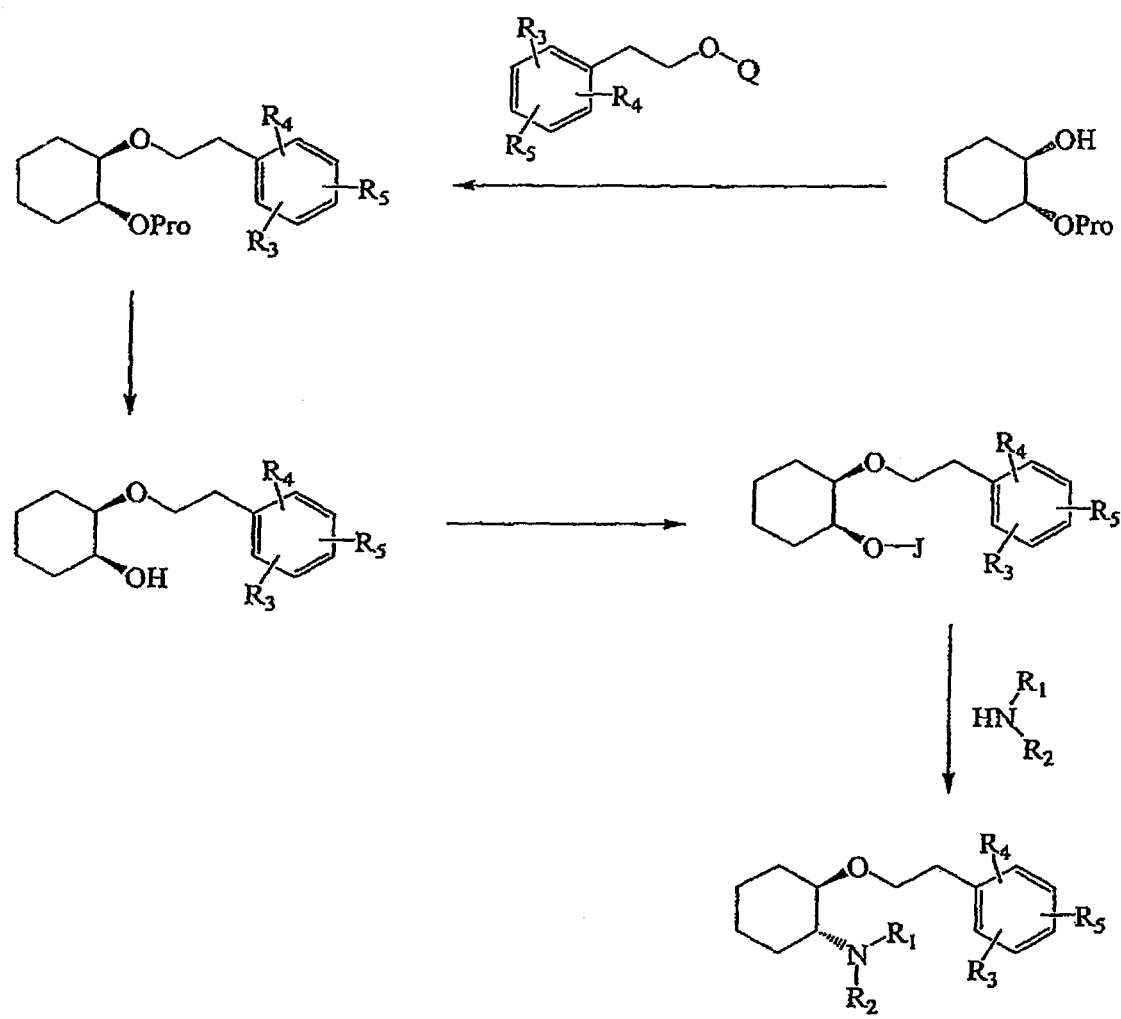

FIG. 130 illustrates a general reaction scheme that may be used as a process for preparing a stereoisomerically substantially pure trans-(1R,2R)-aminocyclohexyl ether compound of formula (57).

Figure 131:
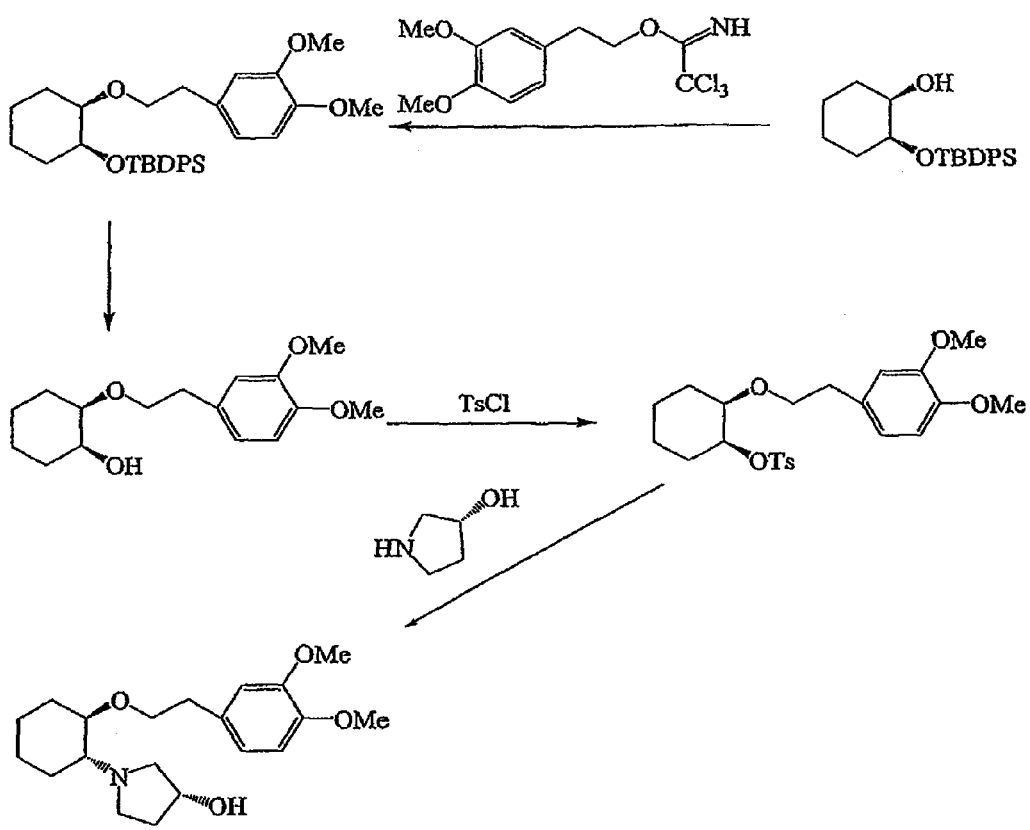

FIG. 131 illustrates a reaction scheme that may be used as a process for preparing a stereoisomerically substantially pure trans-(1R,2R)-aminocyclohexylether compound of formula (66).

Figure 132:
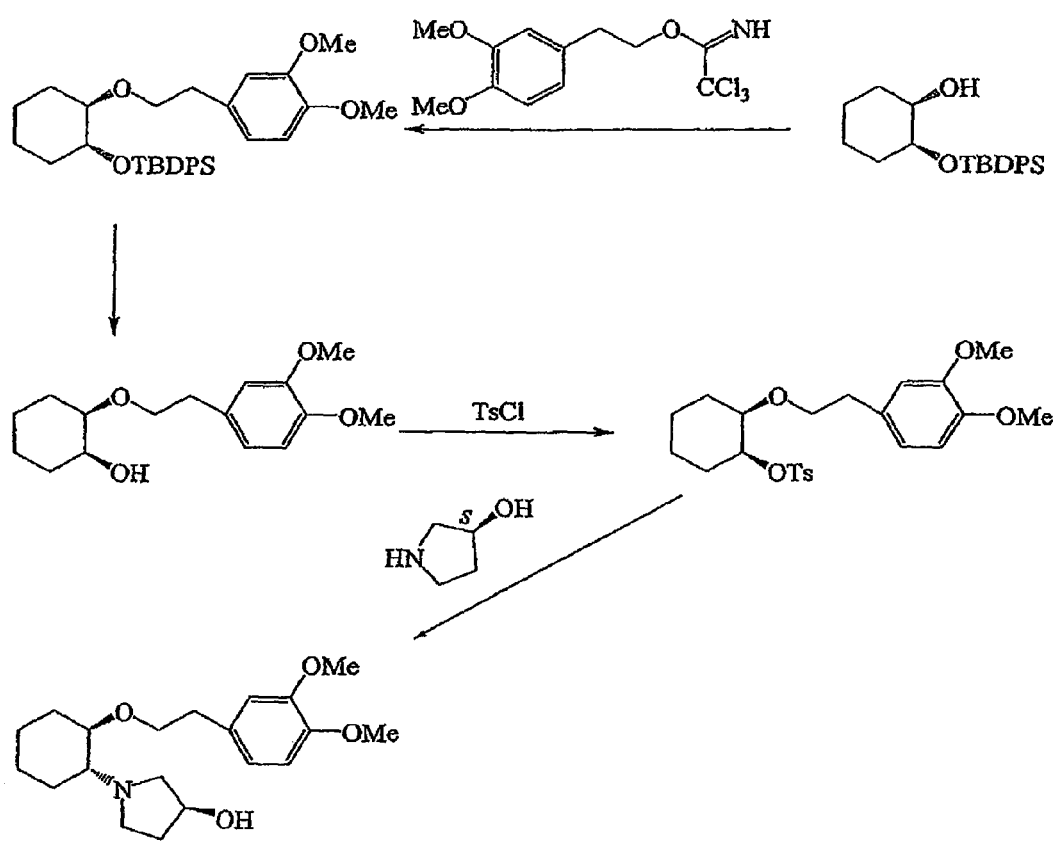

FIG. 132 illustrates a reaction scheme that may be used as a process for preparing a stereoisomerically substantially pure trans-(1R,2R)-aminocyclohexylether compound of formula (69).

Figure 133:
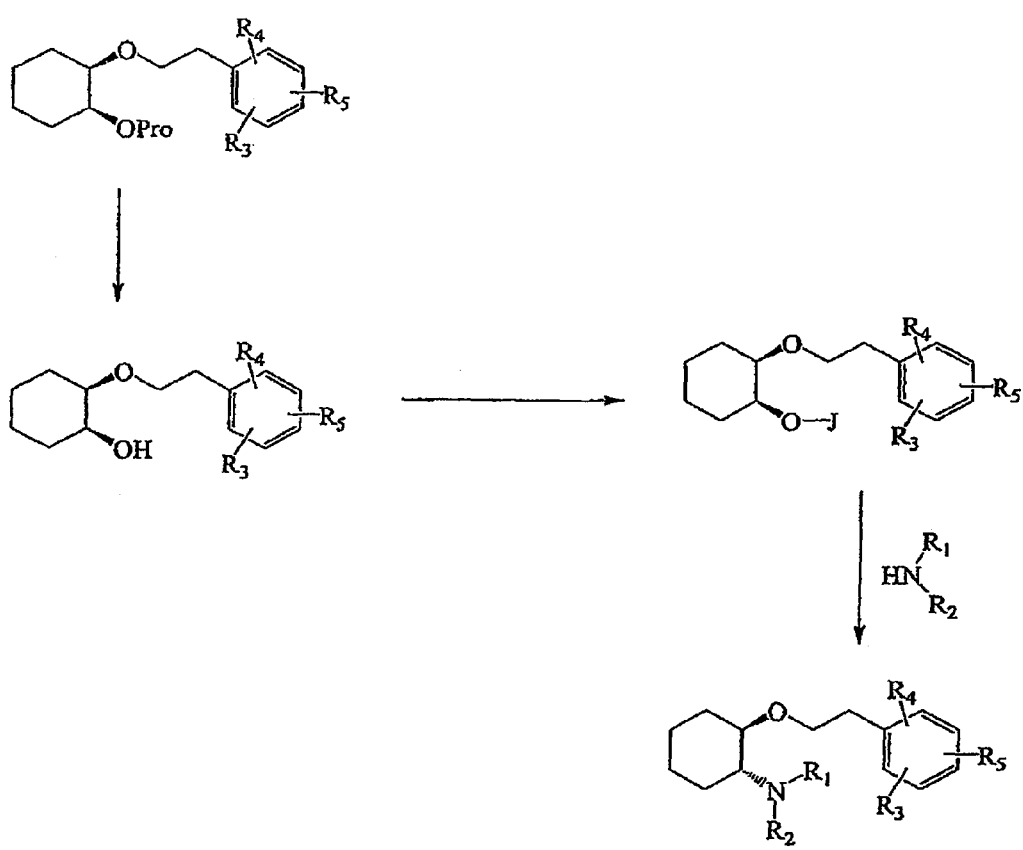

FIG. 133 illustrates a general reaction scheme that may be used as a process for preparing a stereoisomerically substantially pure trans-(1R,2R)-aminocyclohexyl ether compound of formula (57).

Figure 134:
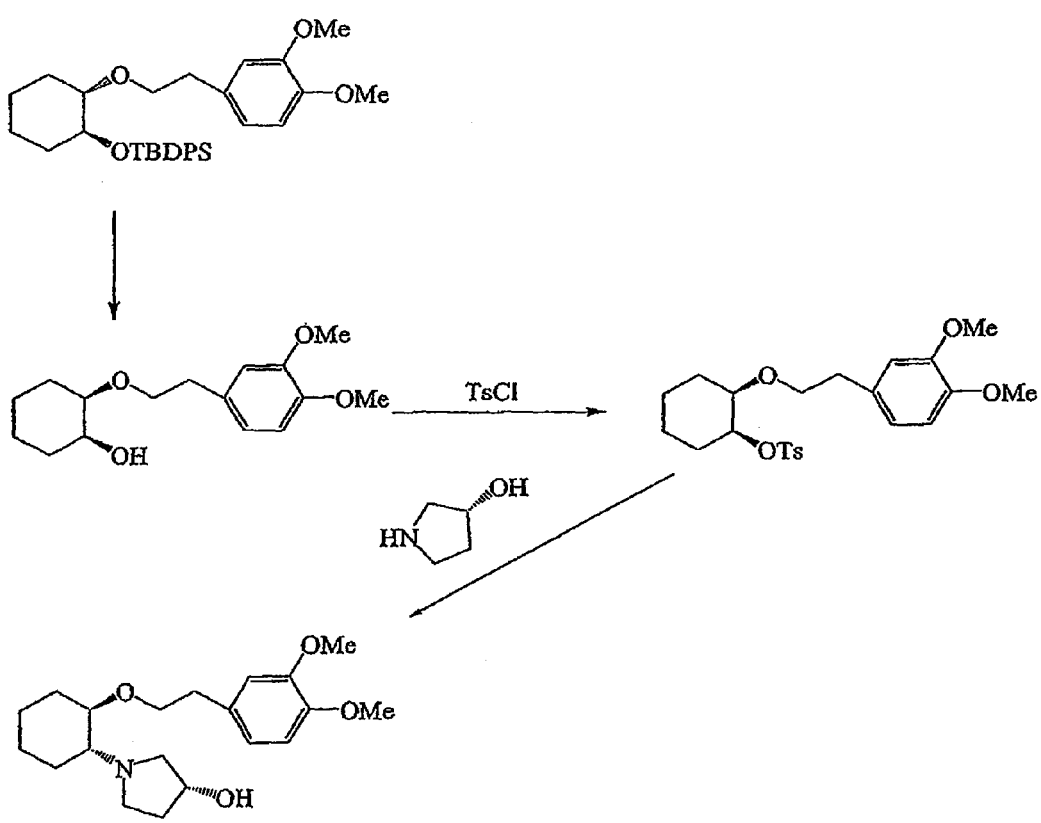

FIG. 134 illustrates a reaction scheme that may be used as a process for preparing a stereoisomerically substantially pure trans-(1R,2R)-aminocyclohexylether compound of formula (66).

Figure 135:
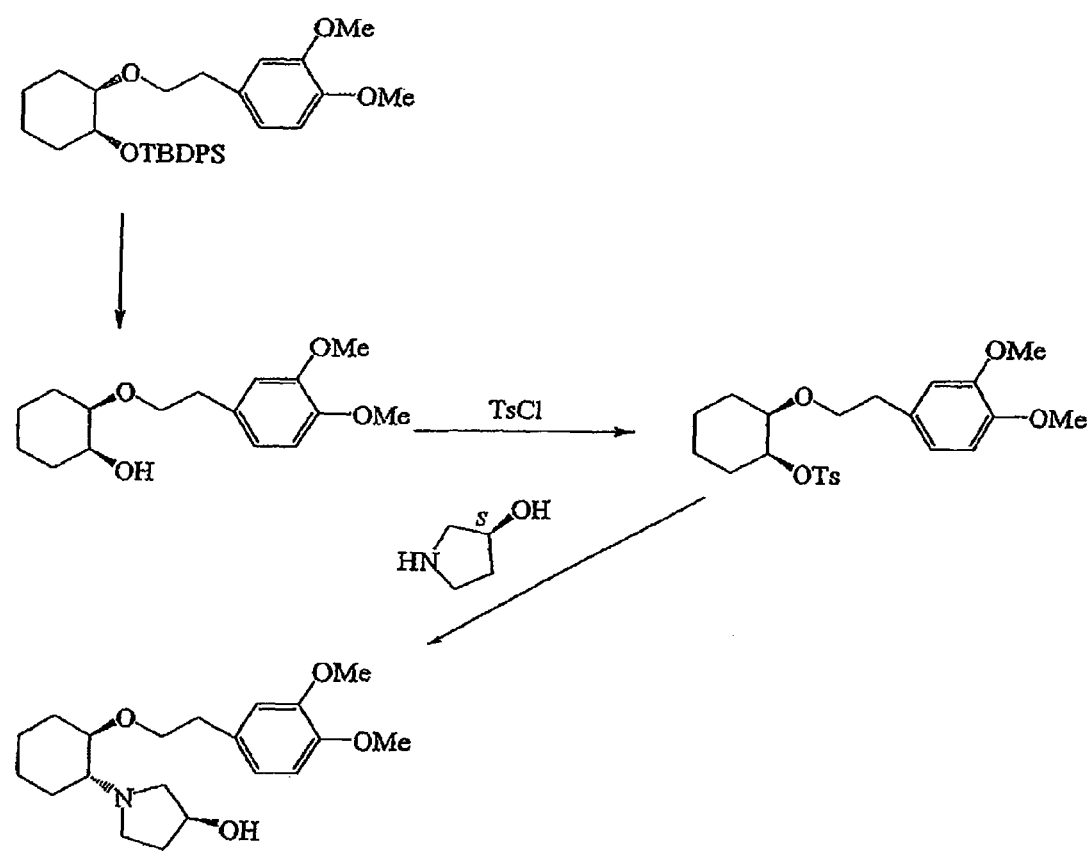

FIG. 135 illustrates a reaction scheme that may be used as a process for preparing a stereoisomerically substantially pure trans-(1R,2R)-aminocyclohexylether compound of formula (69).

Figure 136:
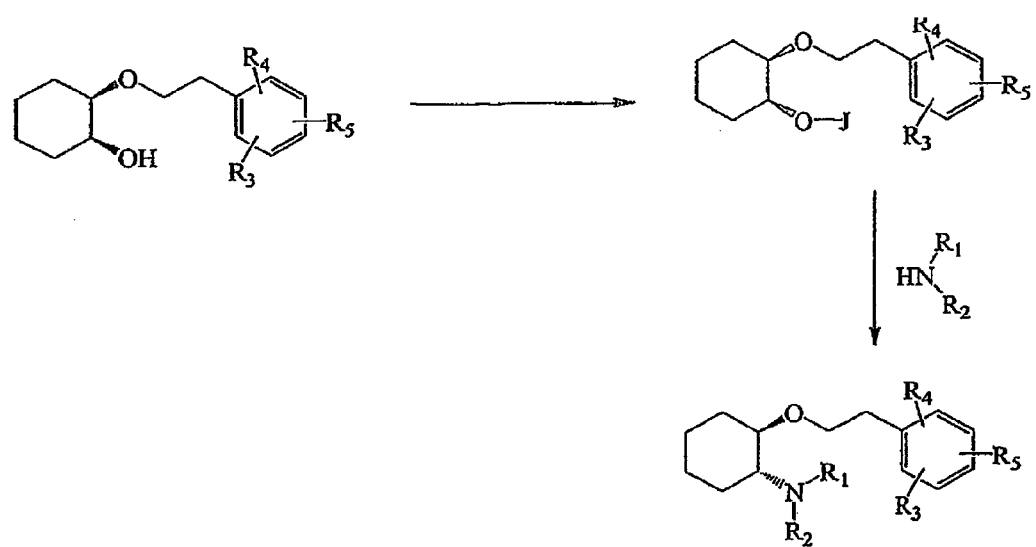

FIG. 136 illustrates a general reaction scheme that may be used as a process for preparing a stereoisomerically substantially pure trans-(1R,2R)-aminocyclohexyl ether compound of formula (57).

Figure 137:
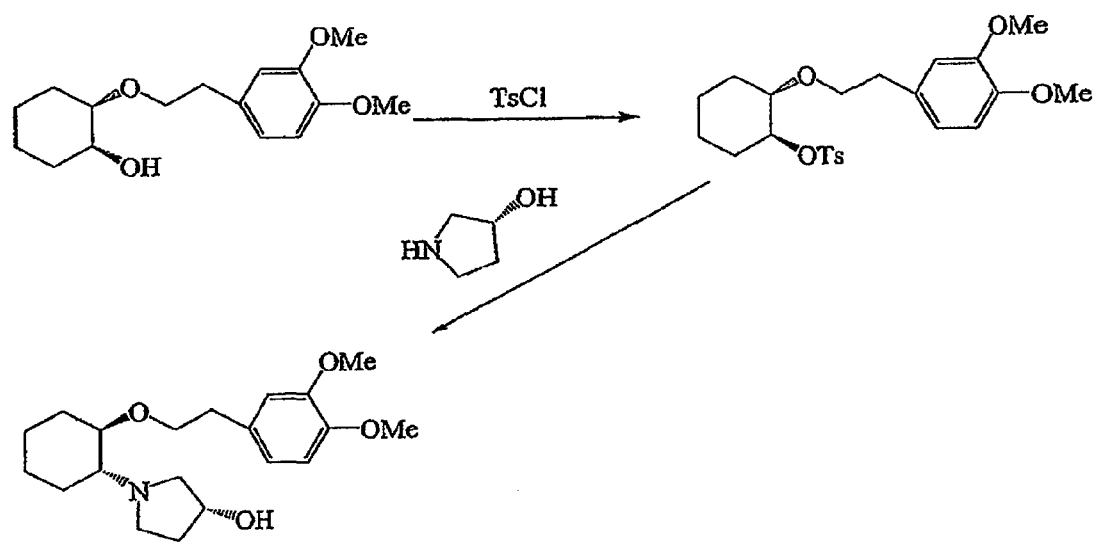

FIG. 137 illustrates a reaction scheme that may be used as a process for preparing a stereoisomerically substantially pure trans-(1R,2R)-aminocyclohexylether compound of formula (66).

Figure 138:
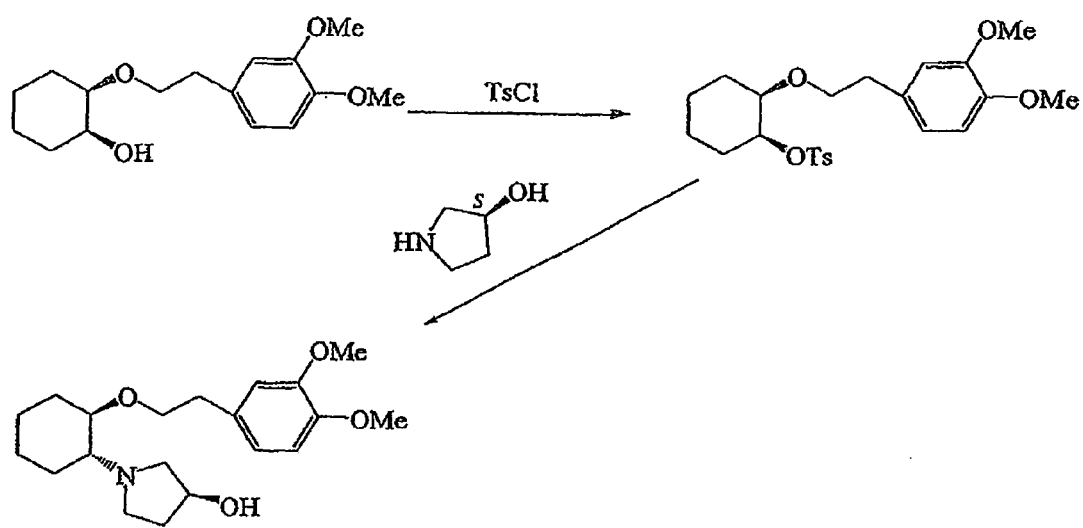

FIG. 138 illustrates a reaction scheme that may be used as a process for preparing a stereoisomerically substantially pure trans-(1R,2R)-aminocyclohexylether compound of formula (69).

Figure 139:
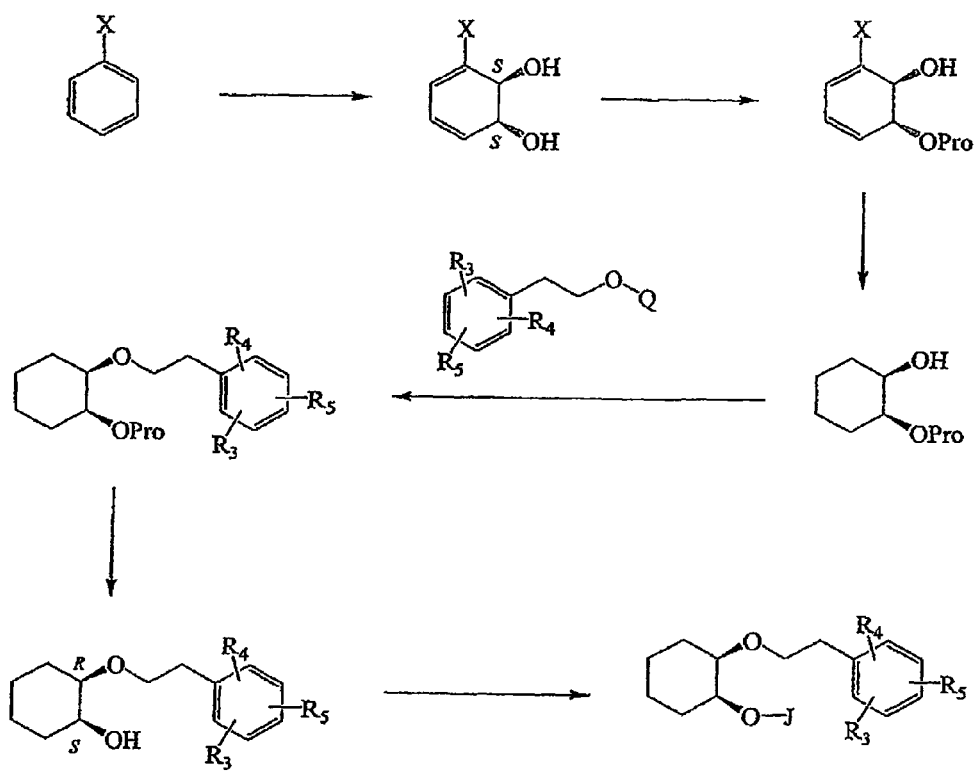

FIG. 139 illustrates a reaction scheme that may be used as a process for preparing a stereoisomerically substantially pure compound of formula (55).

Figure 140:
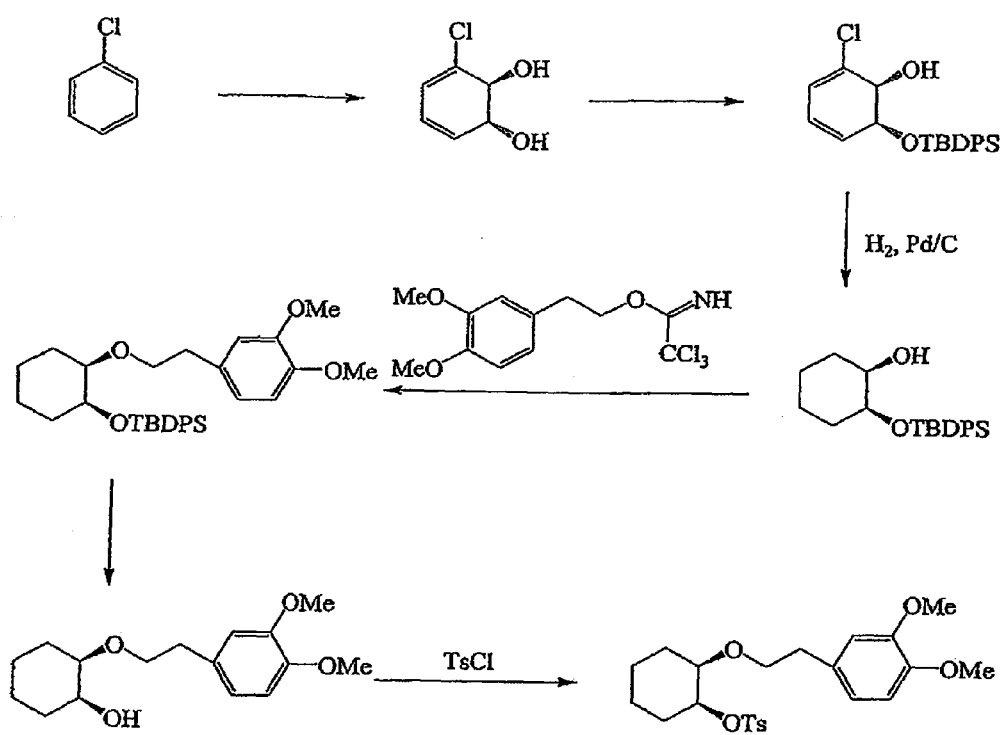

FIG. 140 illustrates a reaction scheme that may be used as a process for preparing a stereoisomerically substantially pure compound of formula (64).

Figure 141:
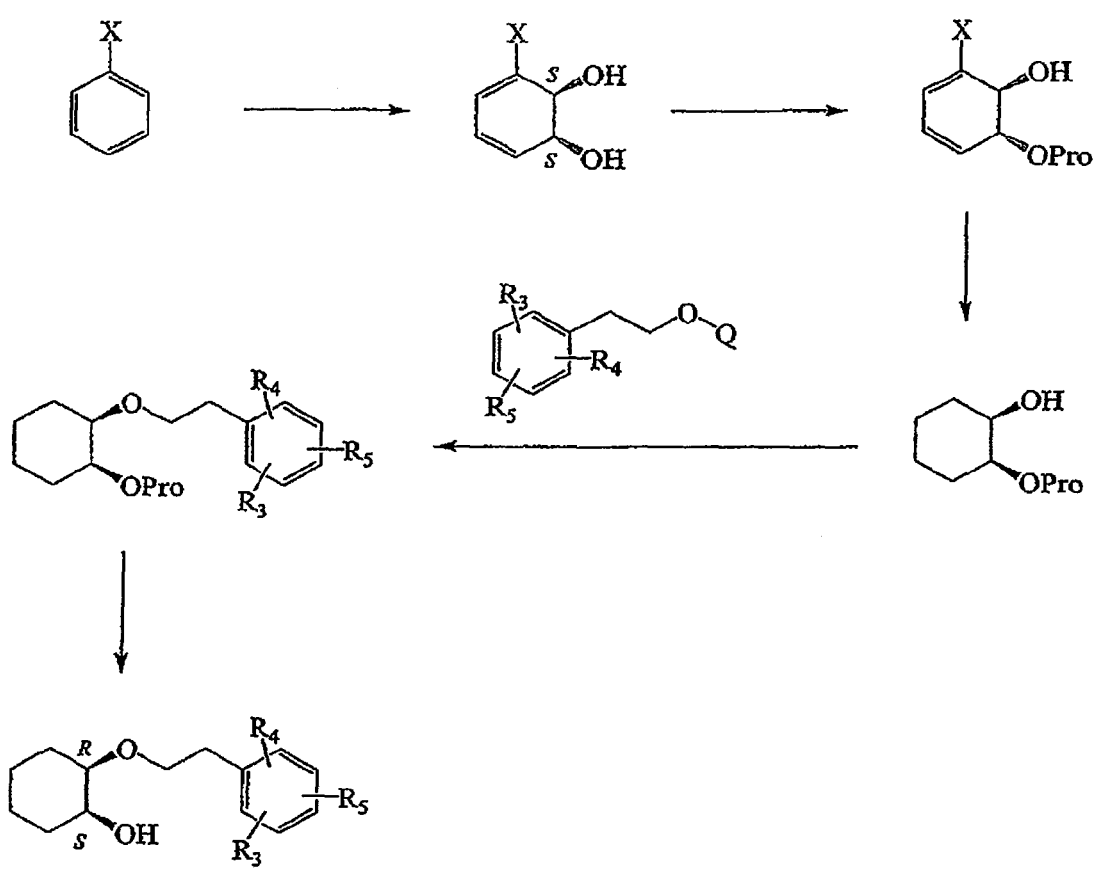

FIG. 141 illustrates a reaction scheme that may be used as a process for preparing a stereoisomerically substantially pure compound of formula (94).

Figure 142:
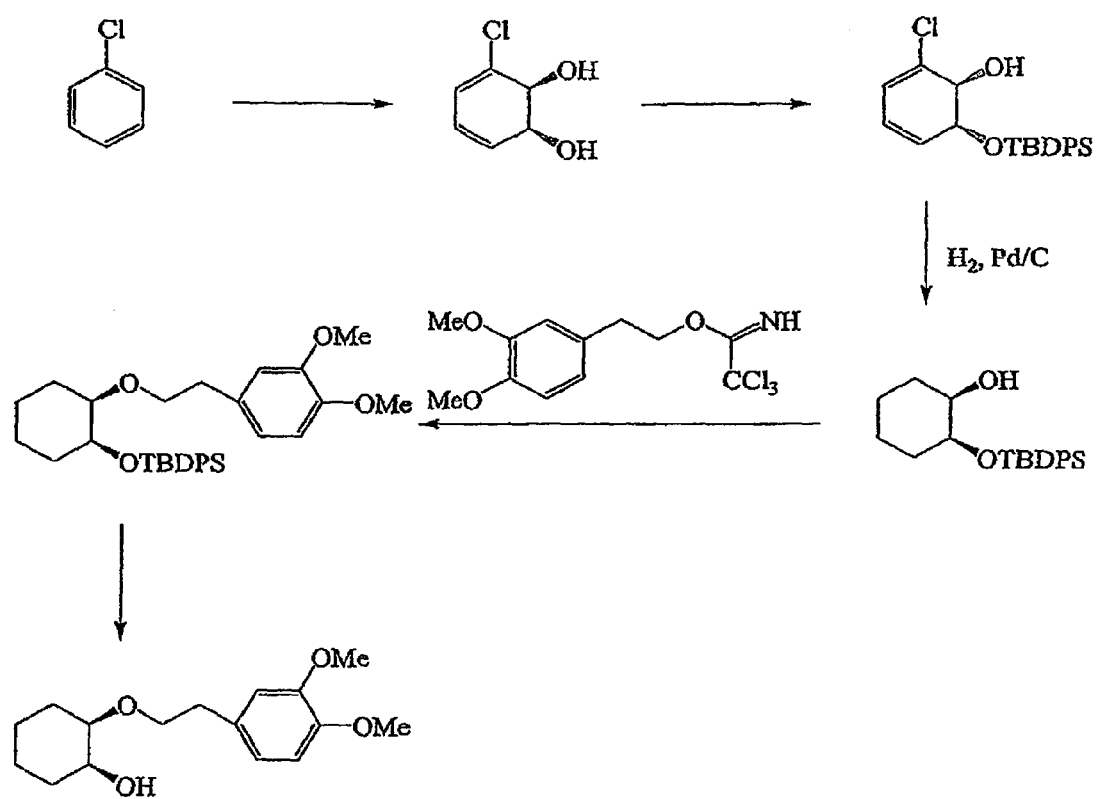

FIG. 142 illustrates a reaction scheme that may be used as a process for preparing a stereoisomerically substantially pure compound of formula (98).

Figure 143:
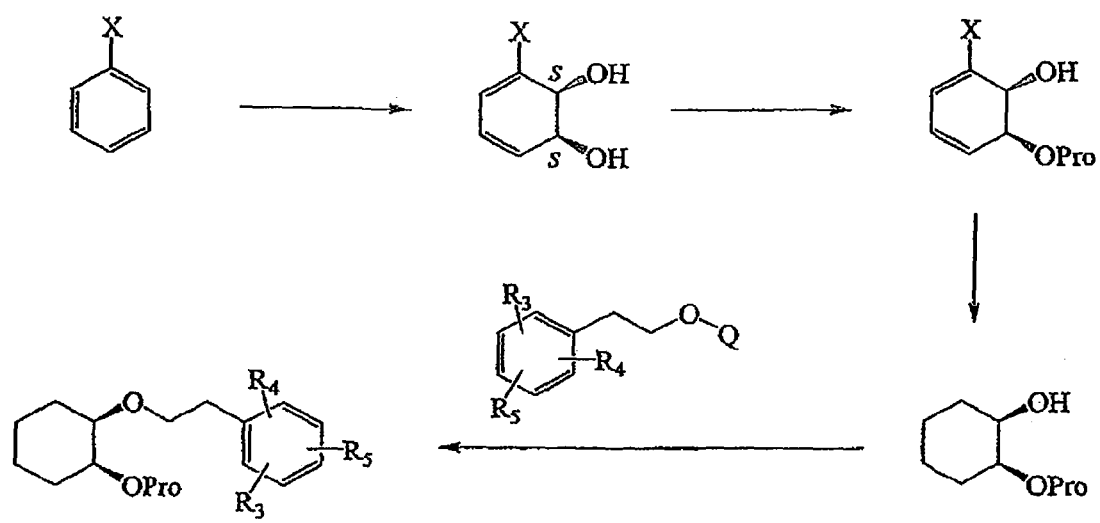

FIG. 143 illustrates a reaction scheme that may be used as a process for preparing a stereoisomerically substantially pure compound of formula (93).

Figure 144:
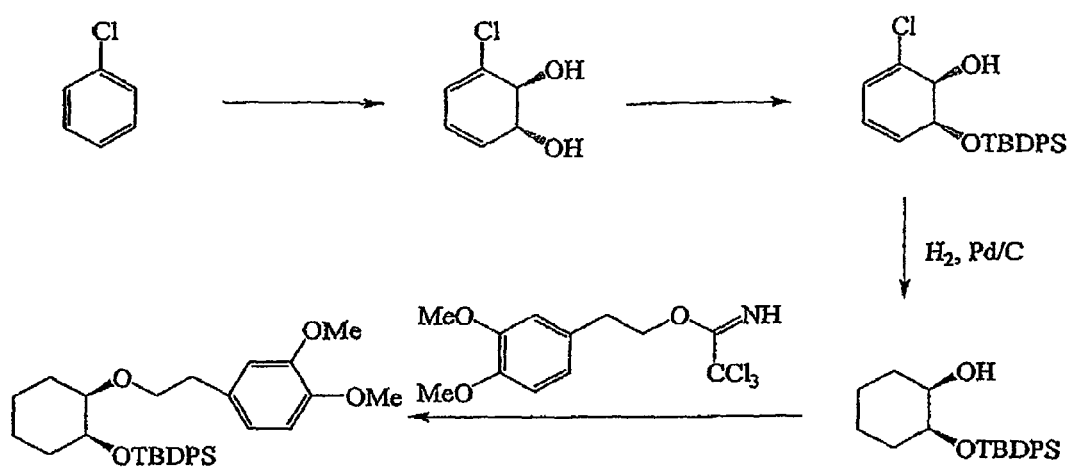

FIG. 144 illustrates a reaction scheme that may be used as a process for preparing a stereoisomerically substantially pure compound of formula (97).

Figure 145:
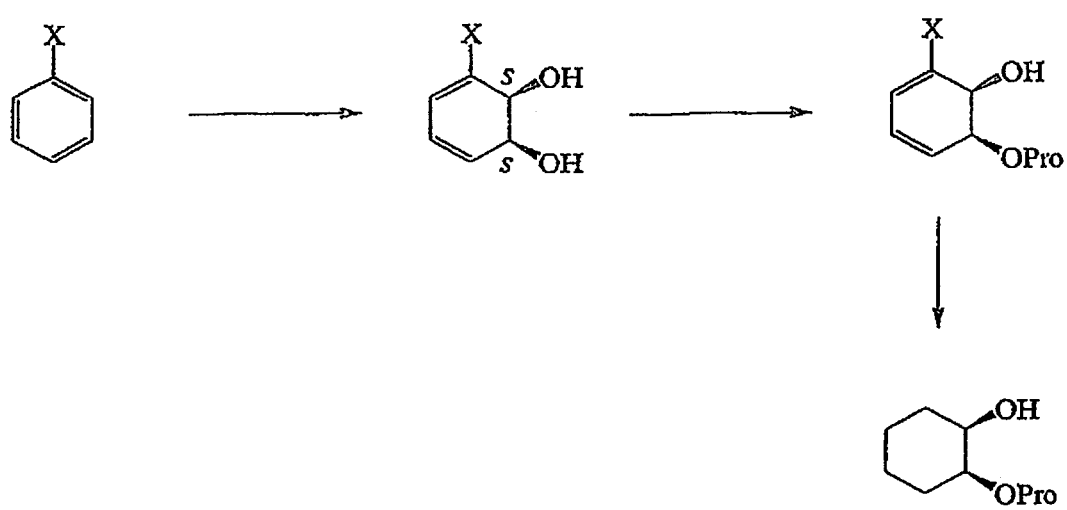

FIG. 145 illustrates a reaction scheme that may be used as a process for preparing a stereoisomerically substantially pure compound of formula (92).

Figure 146:
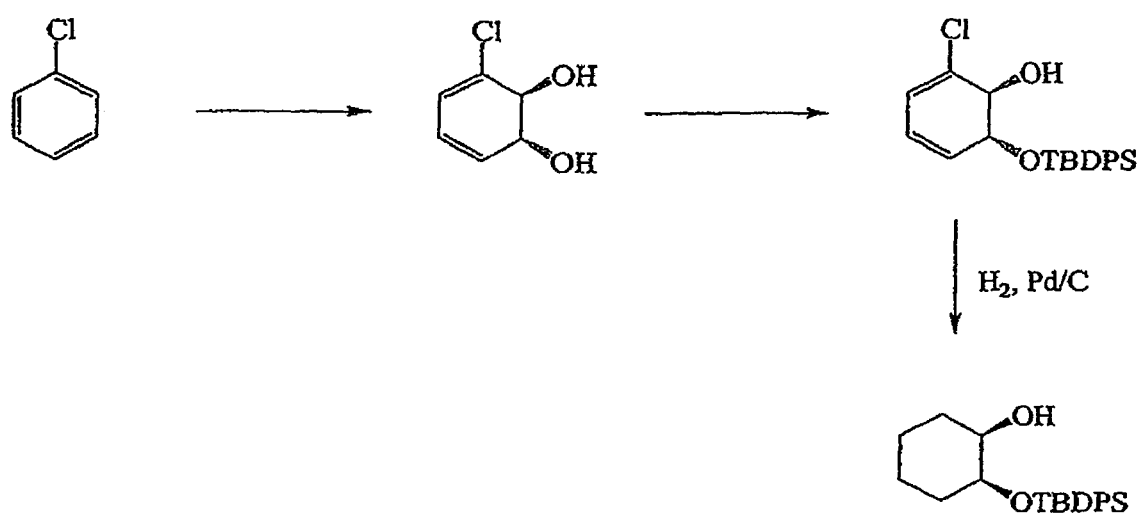

FIG. 146 illustrates a reaction scheme that may be used as a process for preparing a stereoisomerically substantially pure compound of formula (96).

Figure 147:
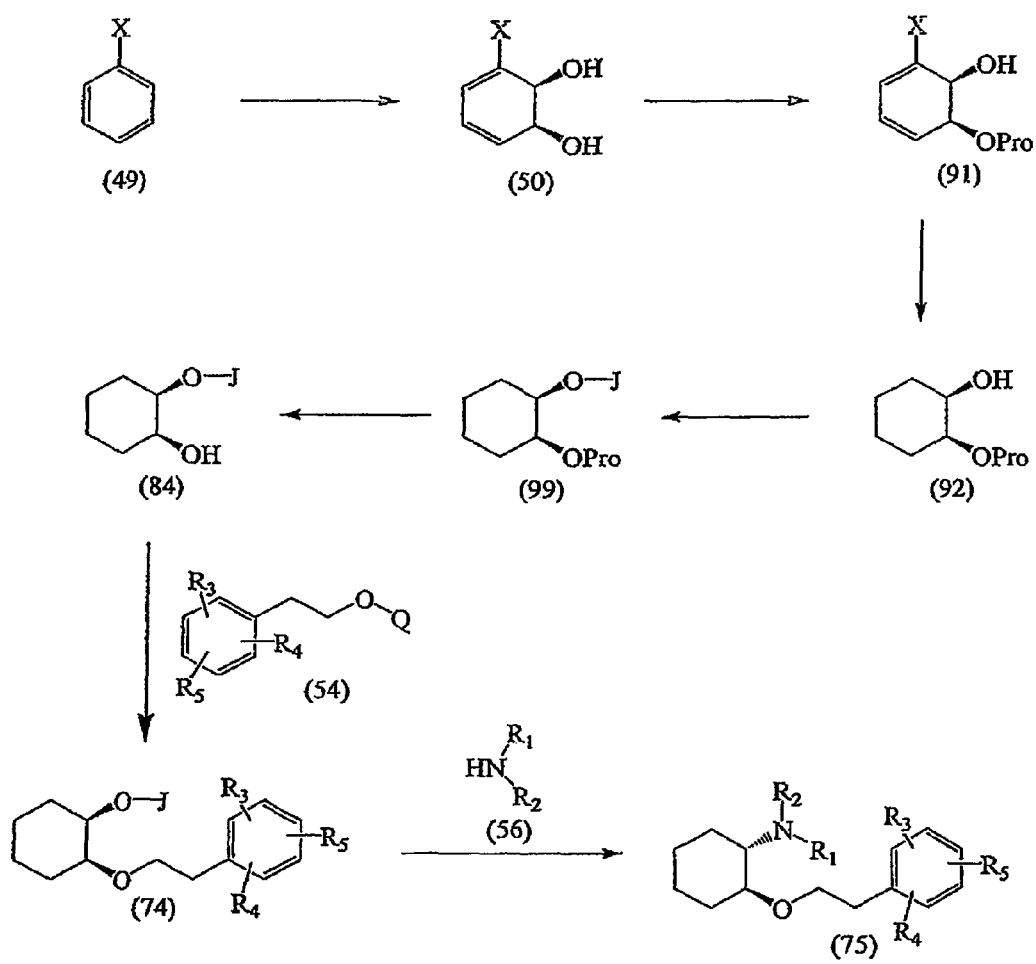

FIG. 147 illustrates a general reaction scheme that may be used as a process for preparing a stereoisomerically substantially pure trans-(1S,2S)-aminocyclohexyl ether compound of formula (75).

Figure 148:
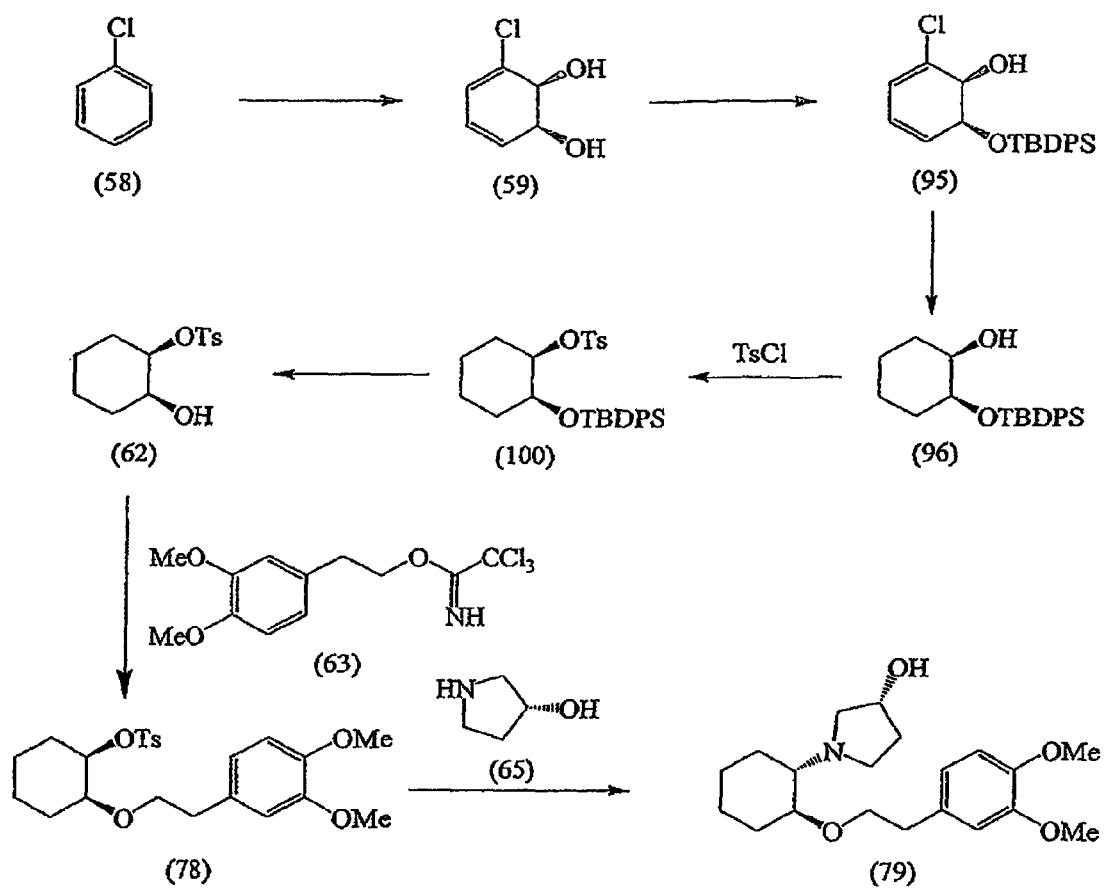

FIG. 148 illustrates a reaction scheme that may be used as a process for preparing a stereoisomerically substantially pure trans-(1S,2S)-aminocyclohexylether compound of formula (79).

Figure 149:
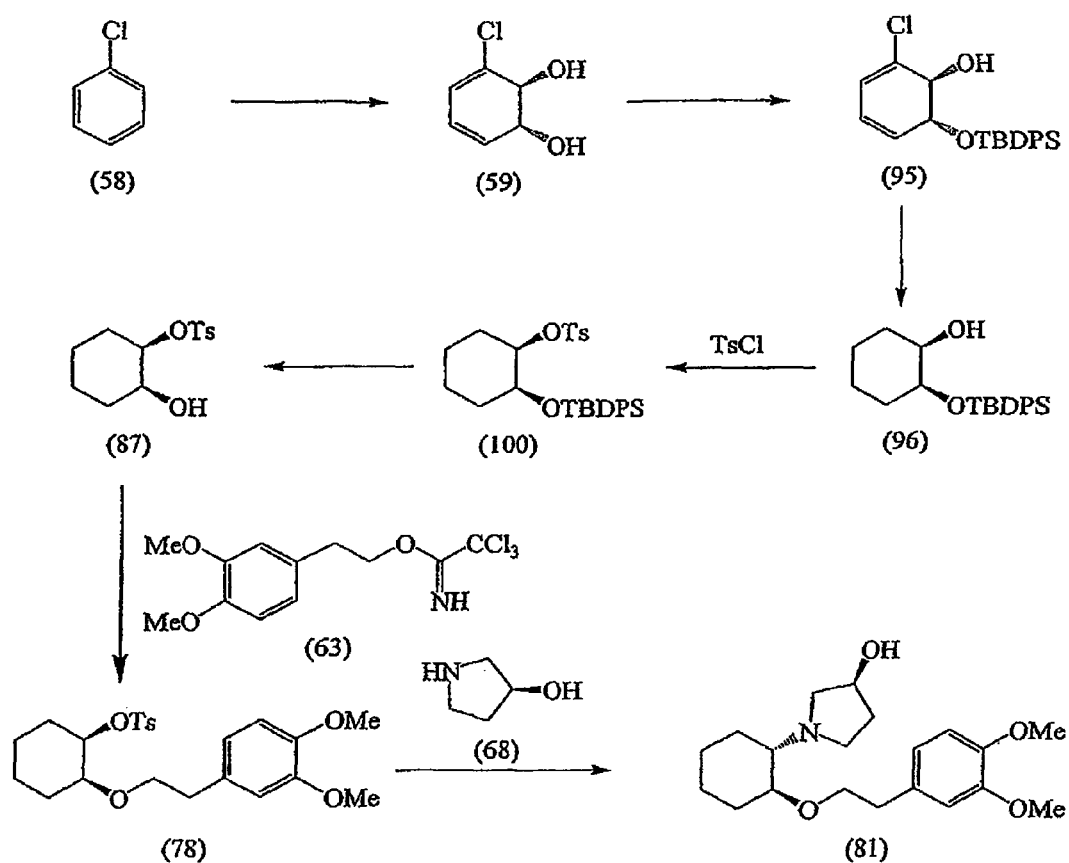

FIG. 149 illustrates a reaction scheme that may be used as a process for preparing a stereoisomerically substantially pure trans-(1S,2S)-aminocyclohexylether compound of formula (81).

Figure 150:
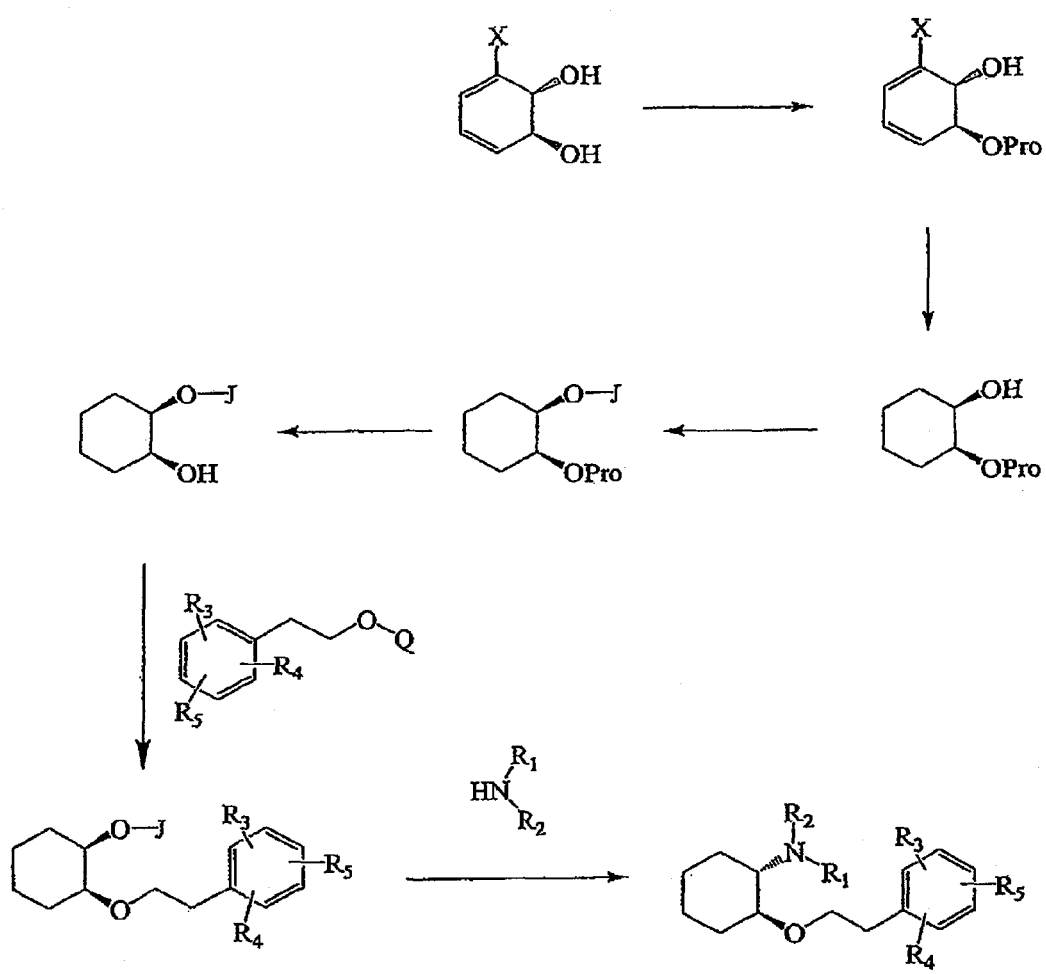

FIG. 150 illustrates a general reaction scheme that may be used as a process for preparing a stereoisomerically substantially pure trans-(1S,2S)-aminocyclohexyl ether compound of formula (75).

Figure 151:
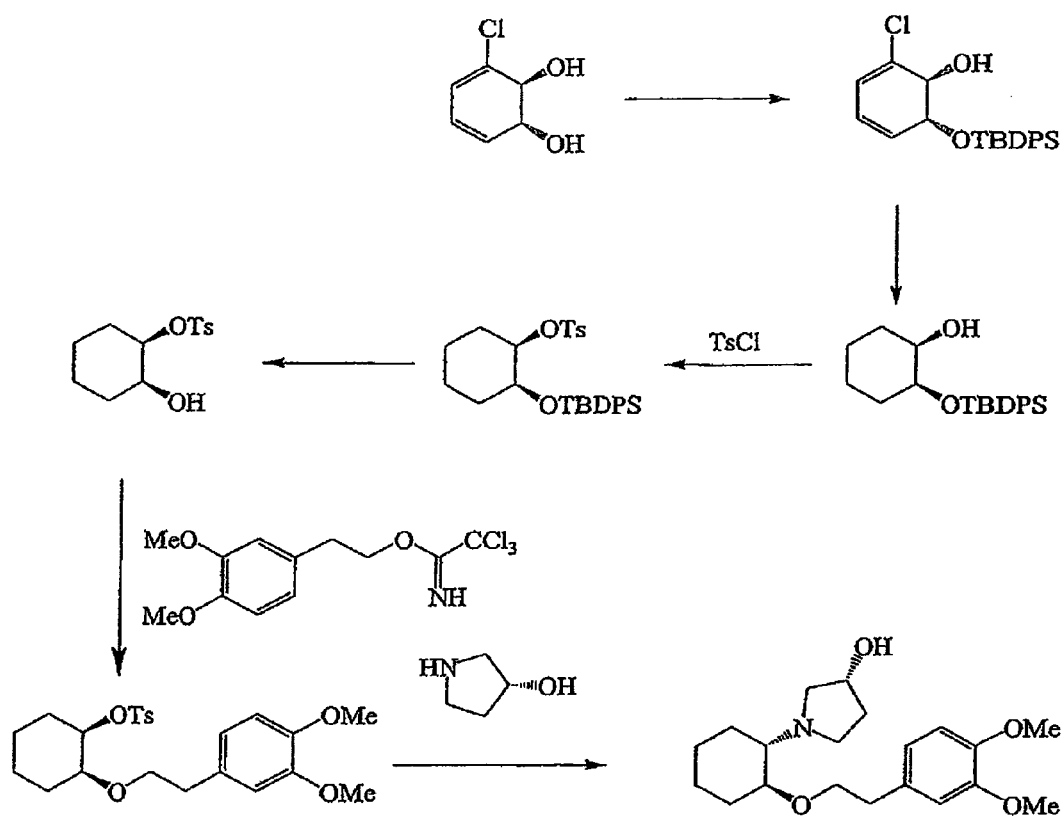

FIG. 151 illustrates a reaction scheme that may be used as a process for preparing a stereoisomerically substantially pure trans-(1S,2S)-aminocyclohexylether compound of formula (79).

Figure 152:
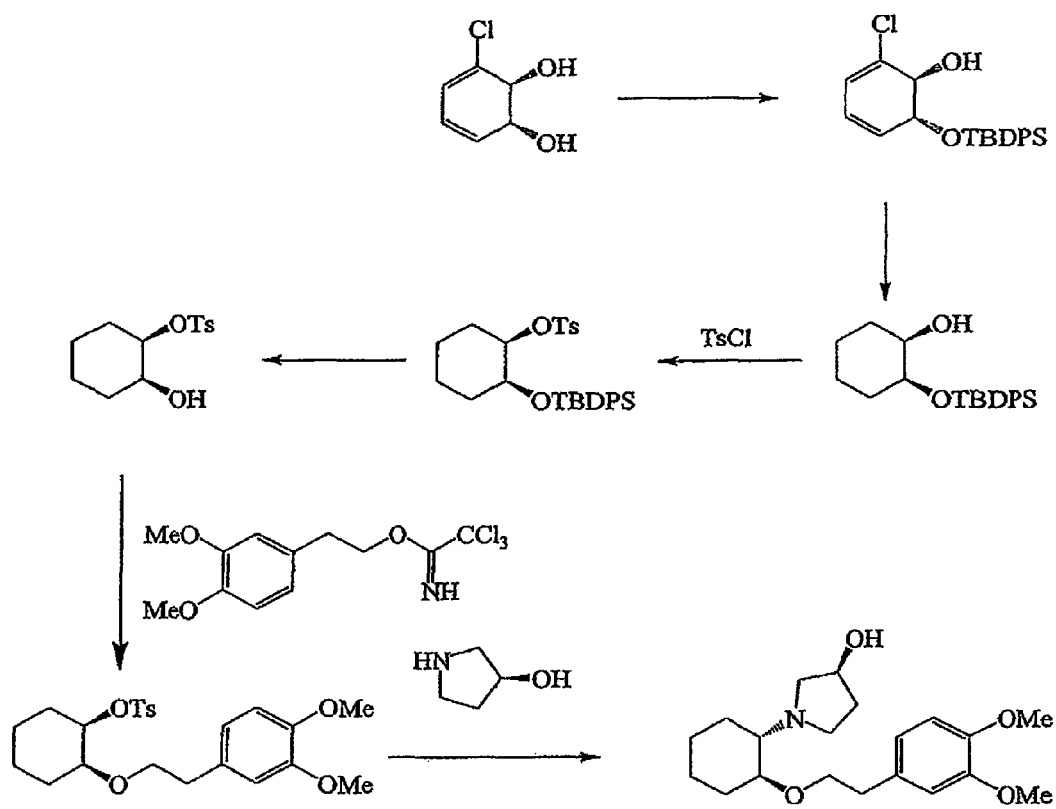

FIG. 152 illustrates a reaction scheme that may be used as a process for preparing a stereoisomerically substantially pure trans-(1S,2S)-aminocyclohexylether compound of formula (81).

Figure 153:
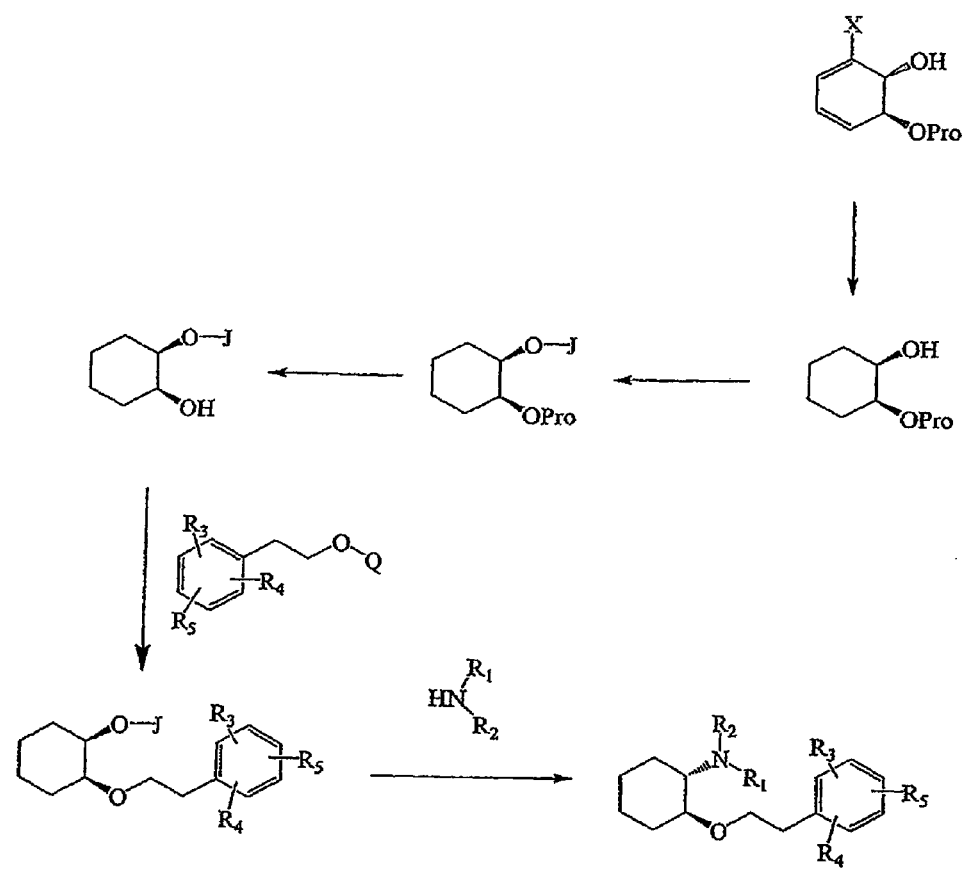

FIG. 153 illustrates a general reaction scheme that may be used as a process for preparing a stereoisomerically substantially pure trans-(1S,2S)-aminocyclohexyl ether compound of formula (75).

Figure 154:
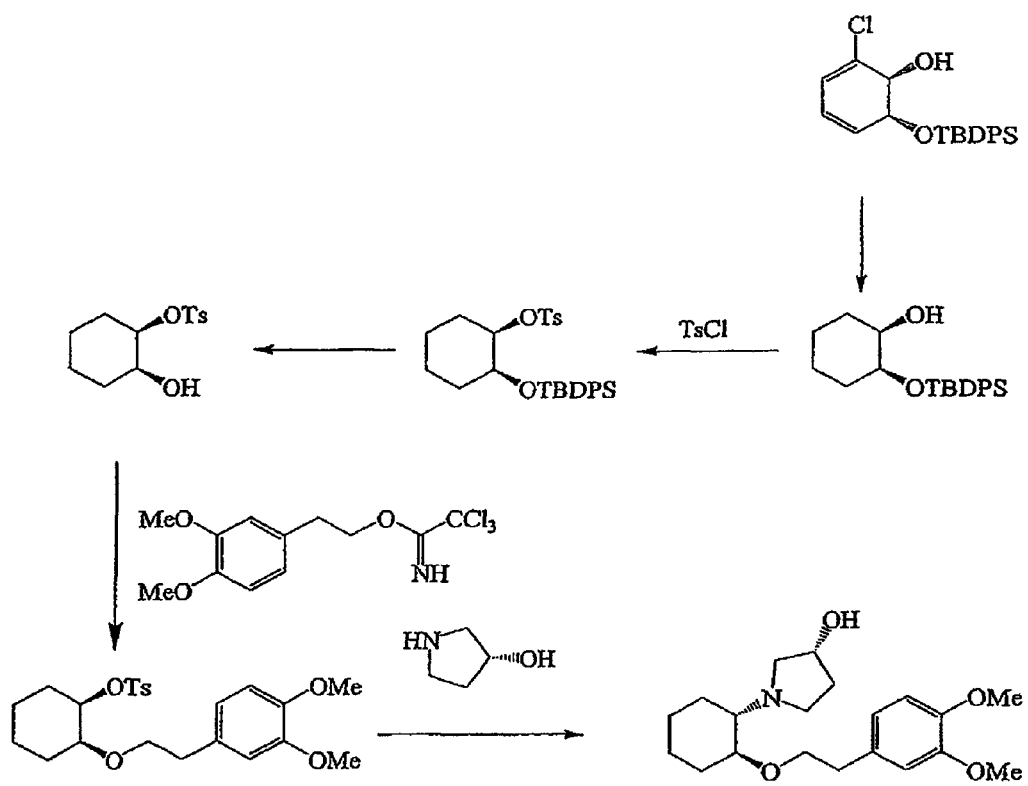

FIG. 154 illustrates a reaction scheme that may be used as a process for preparing a stereoisomerically substantially pure trans-(1S,2S)-aminocyclohexylether compound of formula (79).

Figure 155:
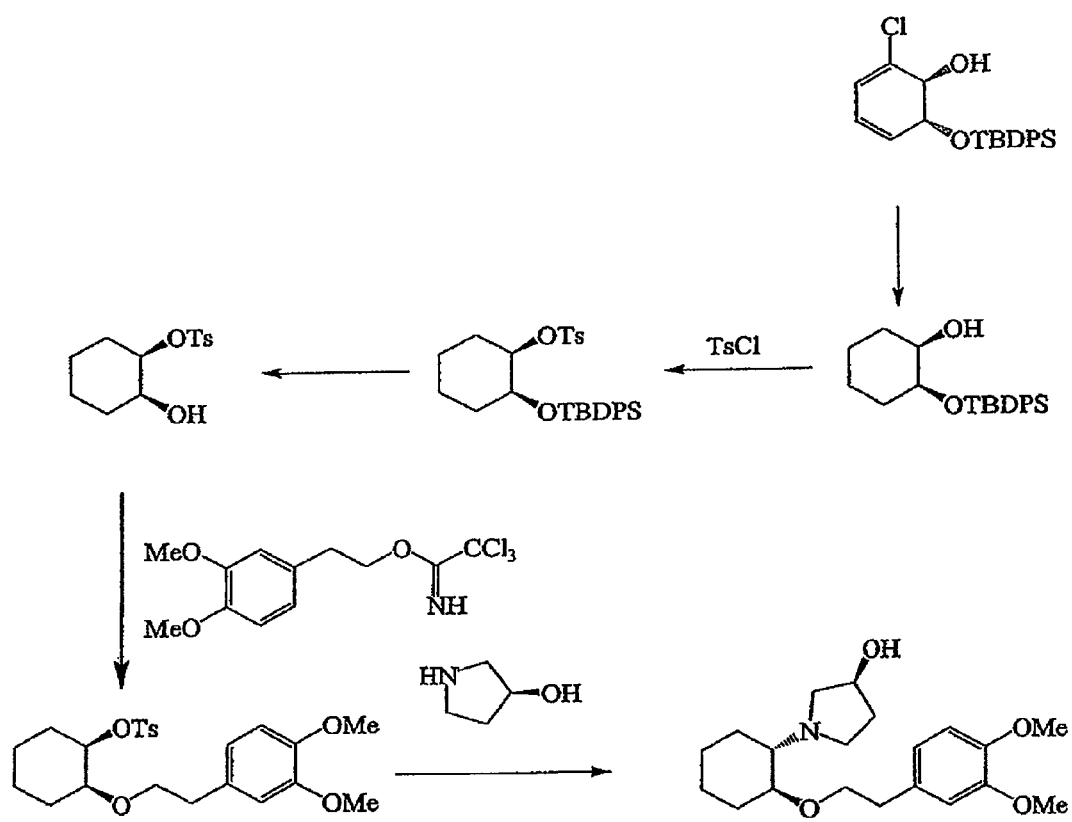

FIG. 155 illustrates a reaction scheme that may be used as a process for preparing a stereoisomerically substantially pure trans-(1S,2S)-aminocyclohexylether compound of formula (81).

Figure 156:
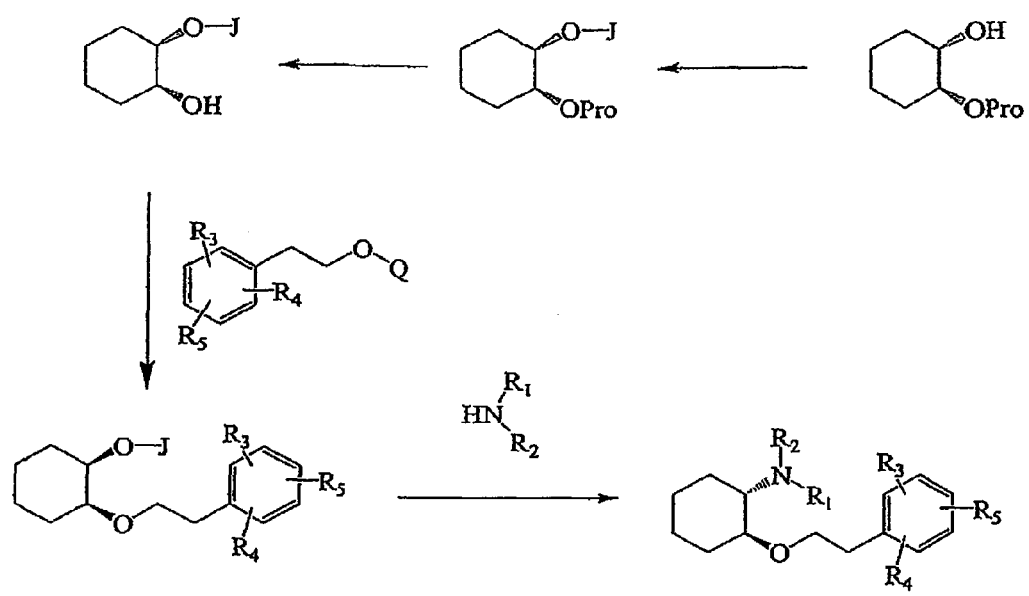

FIG. 156 illustrates a general reaction scheme that may be used as a process for preparing a stereoisomerically substantially pure trans-(1S,2S)-aminocyclohexyl ether compound of formula (75).

Figure 157:
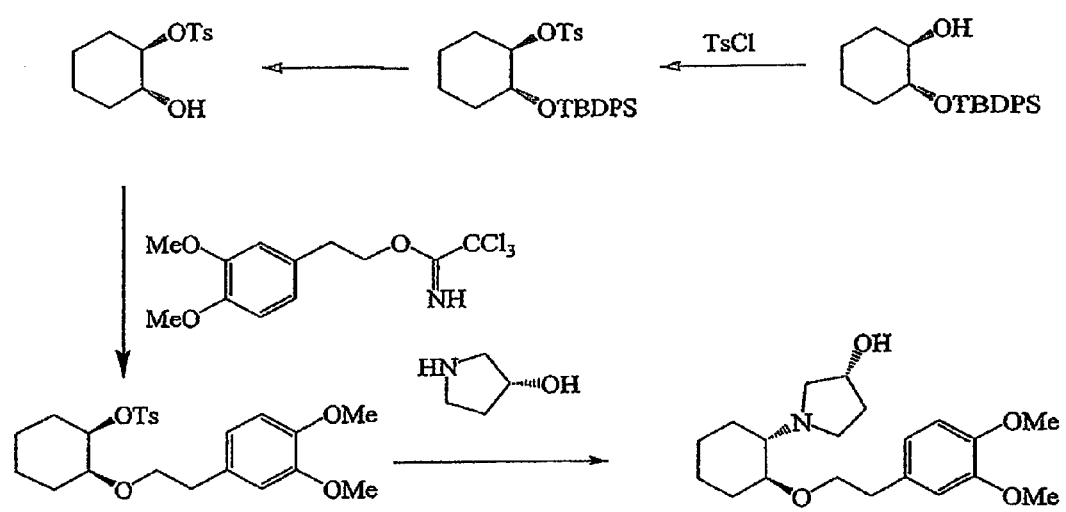

FIG. 157 illustrates a reaction scheme that may be used as a process for preparing a stereoisomerically substantially pure trans-(1S,2S)-aminocyclohexylether compound of formula (79).

Figure 158:
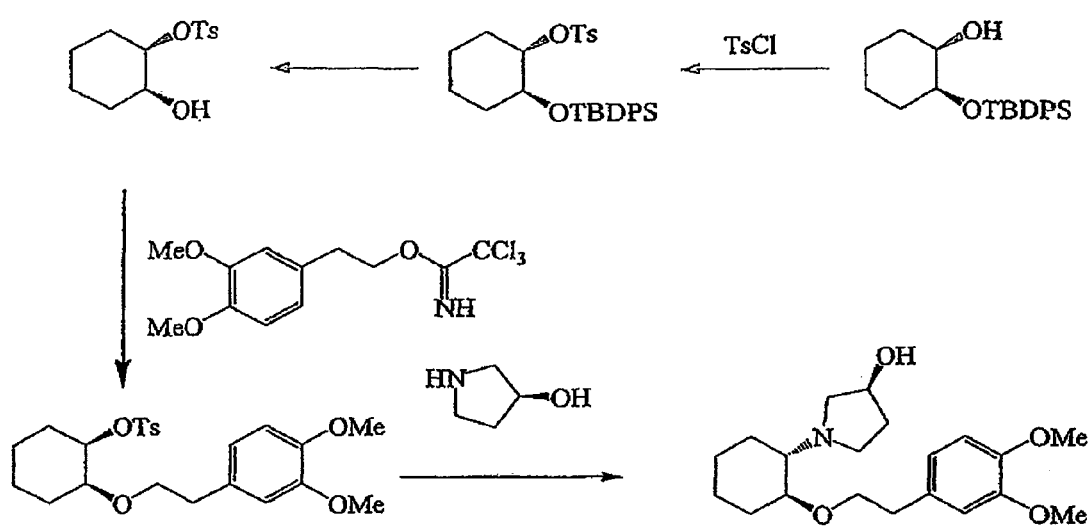

FIG. 158 illustrates a reaction scheme that may be used as a process for preparing a stereoisomerically substantially pure trans-(1S,2S)-aminocyclohexylether compound of formula (81).

Figure 159:
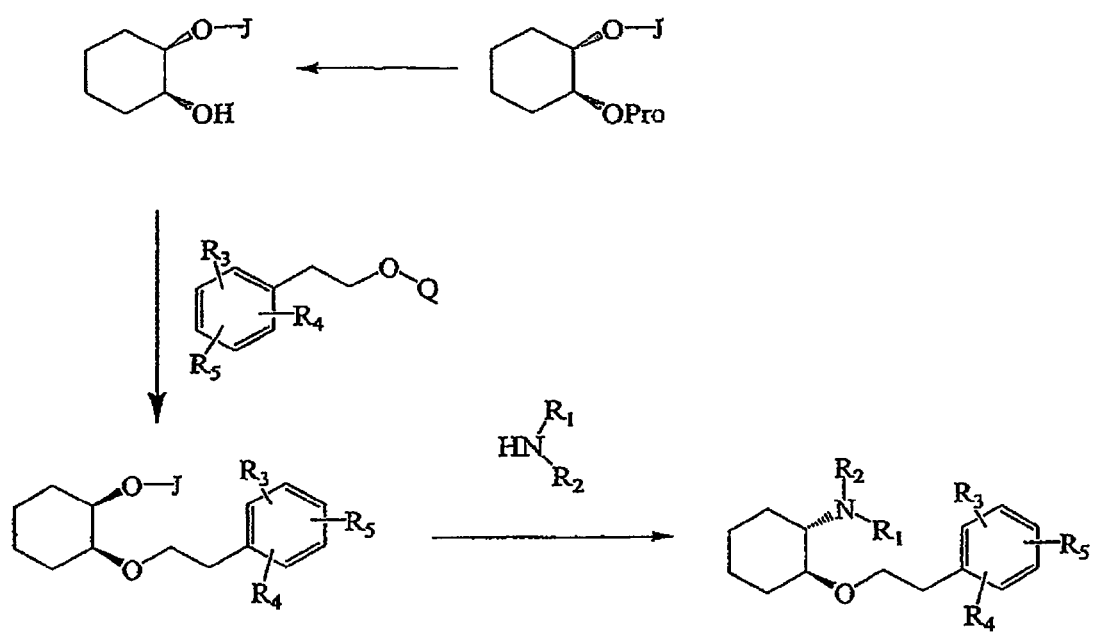

FIG. 159 illustrates a general reaction scheme that may be used as a process for preparing a stereoisomerically substantially pure trans-(1S,2S)-aminocyclohexyl ether compound of formula (75).

Figure 160:
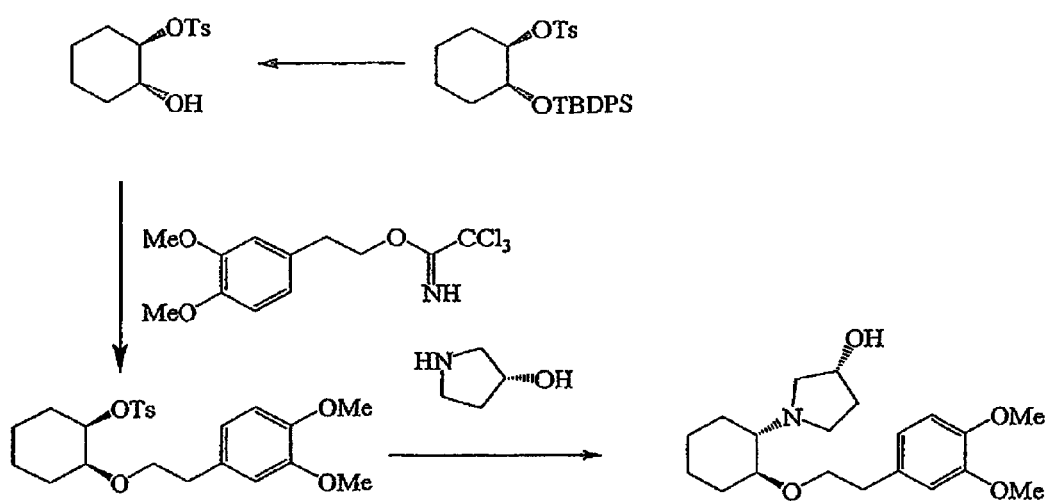

FIG. 160 illustrates a reaction scheme that may be used as a process for preparing a stereoisomerically substantially pure trans-(1S,2S)-aminocyclohexylether compound of formula (79).

Figure 161:
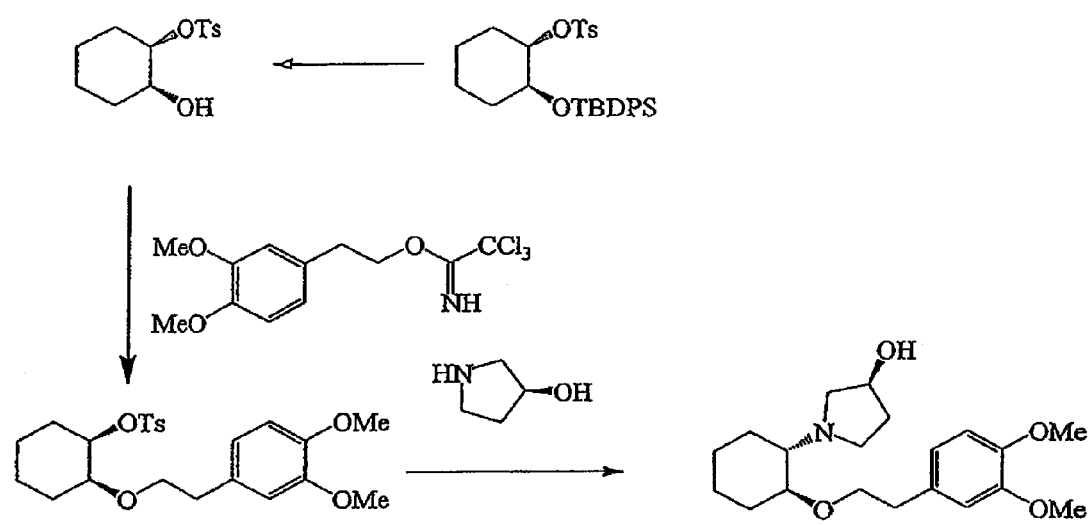

FIG. 161 illustrates a reaction scheme that may be used as a process for preparing a stereoisomerically substantially pure trans-(1S,2S)-aminocyclohexylether compound of formula (81).

Figure 162:
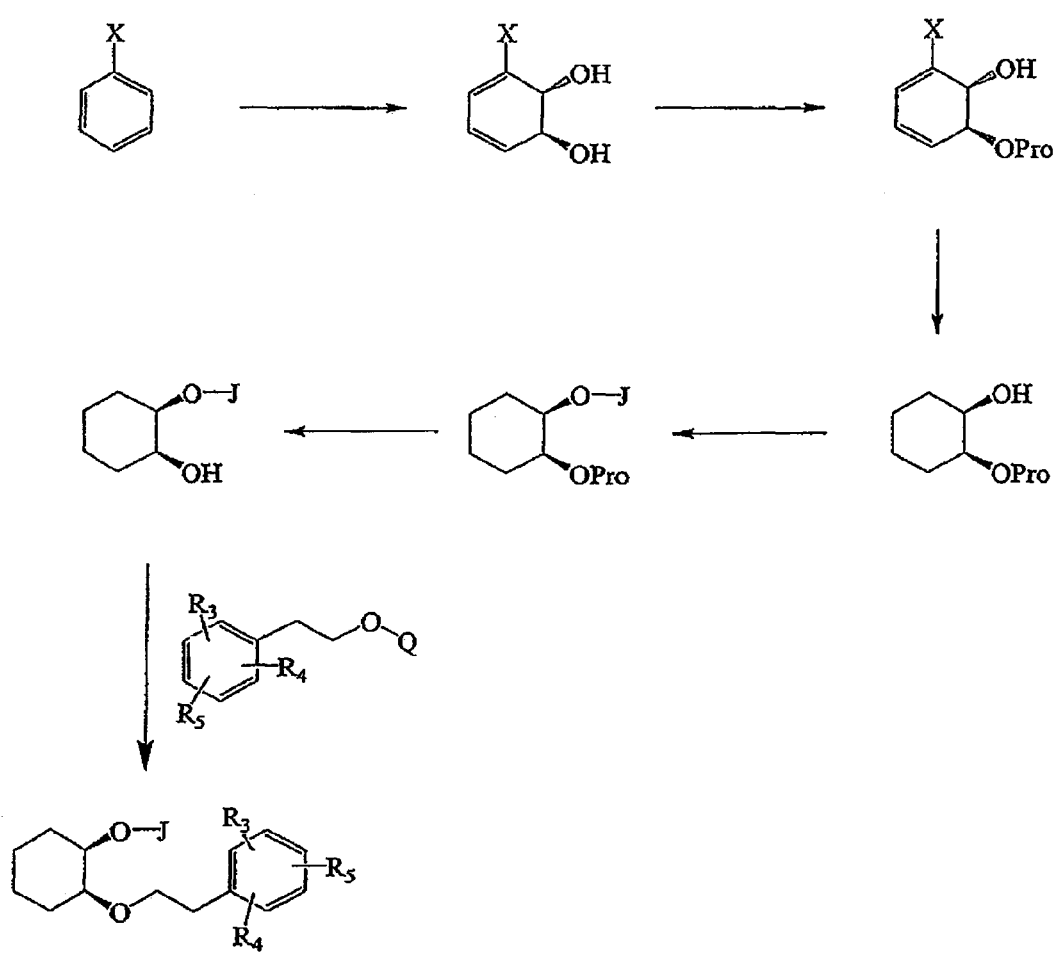

FIG. 162 illustrates a reaction scheme that may be used as a process for preparing a stereoisomerically substantially pure compound of formula (74).

Figure 163:
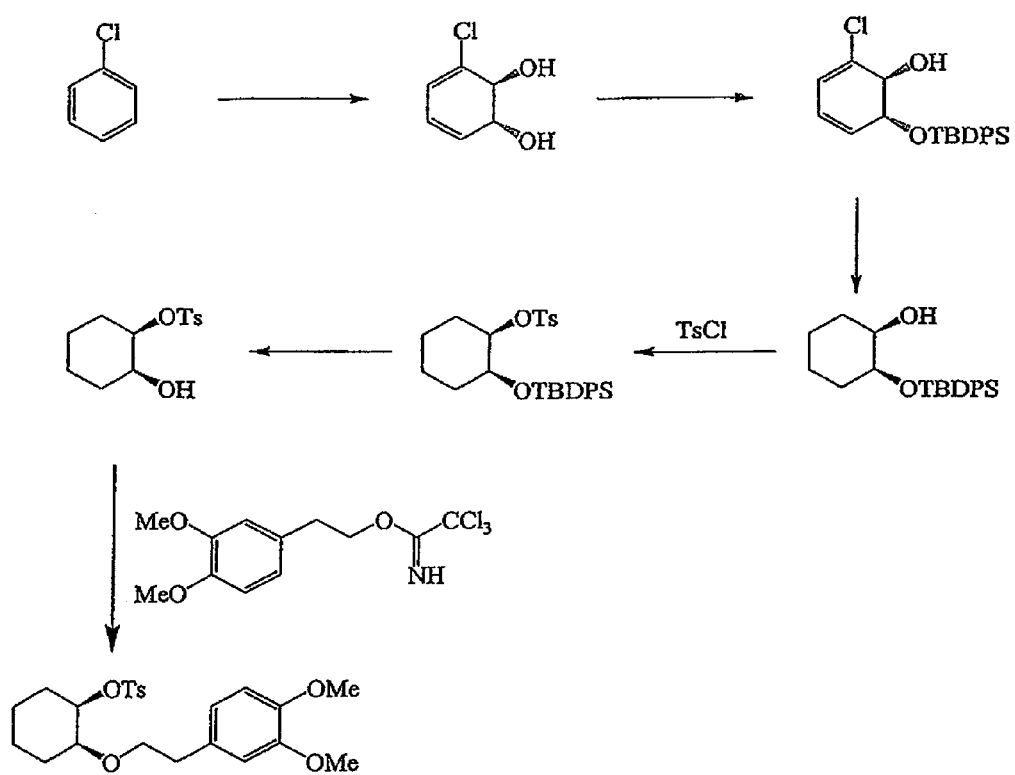

FIG. 163 illustrates a reaction scheme that may be used as a process for preparing a stereoisomerically substantially pure compound of formula (78).

Figure 164:
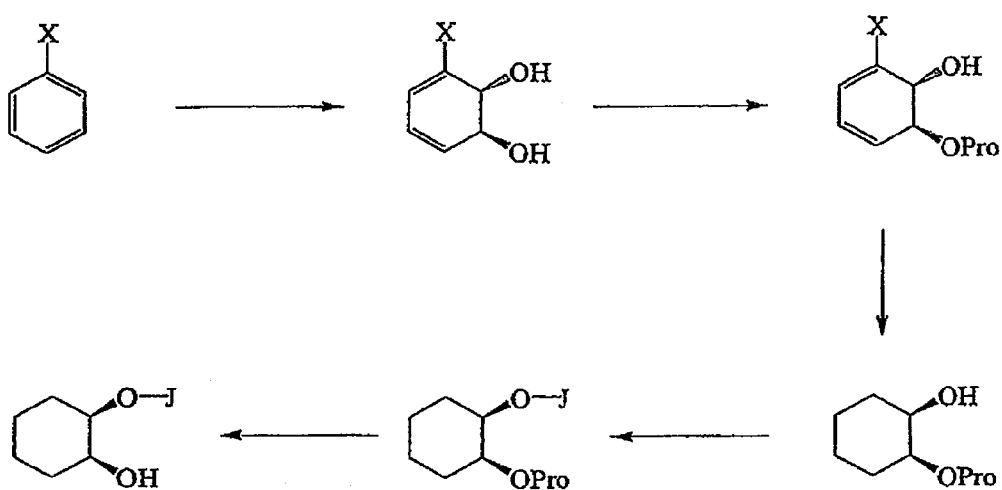

FIG. 164 illustrates a reaction scheme that may be used as a process for preparing a stereoisomerically substantially pure compound of formula (84).

Figure 165:
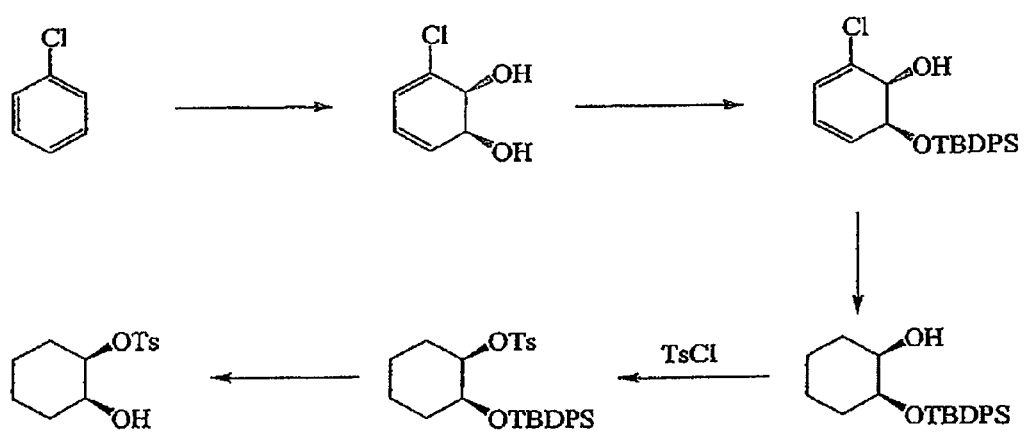

FIG. 165 illustrates a reaction scheme that may be used as a process for preparing a stereoisomerically substantially pure compound of formula (62).

Figure 166:
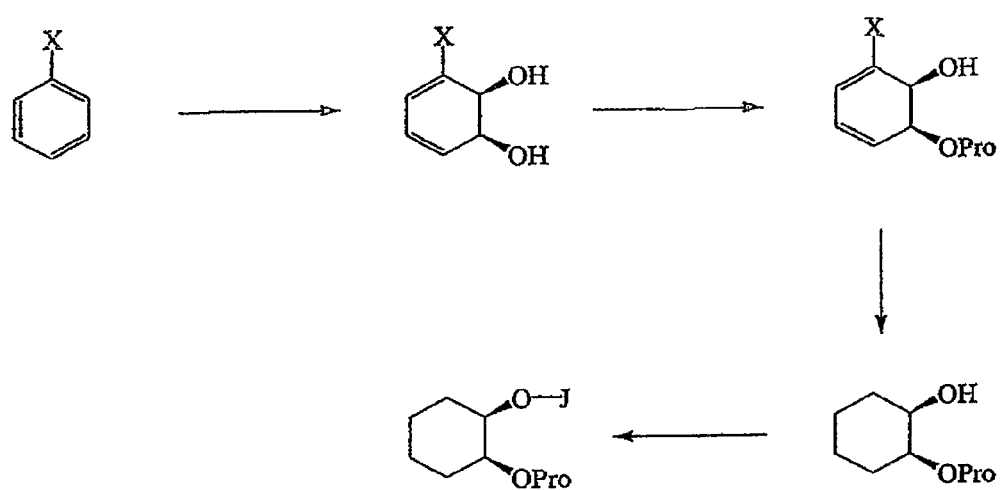

FIG. 166 illustrates a reaction scheme that may be used as a process for preparing a stereoisomerically substantially pure compound of formula (99).

Figure 167:
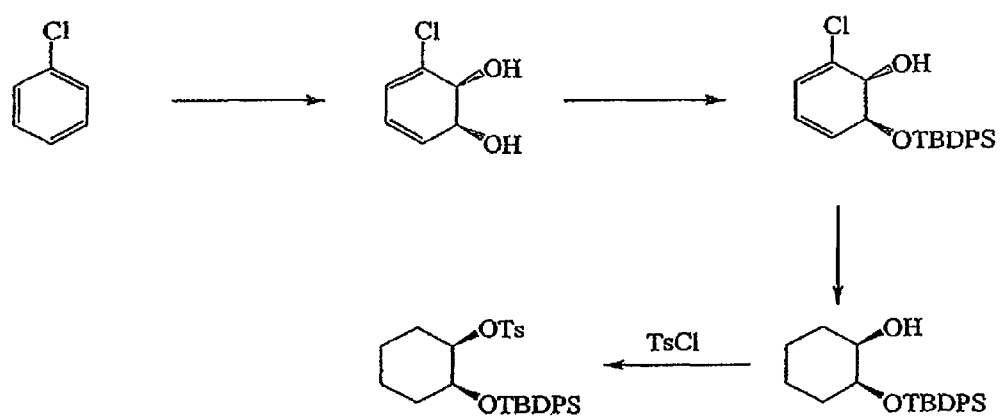

FIG. 167 illustrates a reaction scheme that may be used as a process for preparing a stereoisomerically substantially pure compound of formula (100).

DETAILED DESCRIPTION

As noted above, the present invention is directed to aminocyclohexyl ether compounds of formula such as (IA), (IB), (IC), (ID), or (IE), methods of manufacture thereof, pharmaceutical compositions containing the aminocyclohexyl ether compounds, and various uses for the compounds and compositions. Such uses include the treatment of arrhythmias, ion channel modulation and other uses as described herein.

An understanding of the present invention may be aided by reference to the following definitions and explanation of conventions used herein:

The aminocyclohexyl ether compounds of the invention have an ether oxygen atom at position 1 of a cyclohexane ring, and an amine nitrogen atom at position 2 of the cyclohexane ring, with other positions numbered in corresponding order as shown below in structure (A):

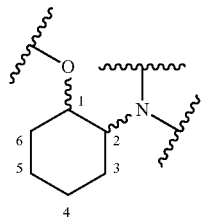

(A)

The bonds from the cyclohexane ring to the 1-oxygen and 2-nitrogen atoms in the above formula may be relatively disposed in either a cis or trans relationship. In a preferred embodiment of the present invention, the stereochemistry of the amine and ether substituents of the cyclohexane ring is either (R,R)-trans or (S,S)-trans. In another preferred embodiment the stereochemistry is either (R,S)-cis or (S,R)-cis.

A wavy bond from a substituent to the central cyclohexane ring indicates that that group may be located on either side of the plane of the central ring. When a wavy bond is shown intersecting a ring, this indicates that the indicated substituent group may be attached to any position on the ring capable of bonding to the substituent group and that the substituent group may lie above or below the plane of the ring system to which it is bound.

Following the standard chemical literature description practice and as used in this patent, a full wedge bond means above the ring plane, and a dashed wedge bond means below the ring plane; one full bond and one dashed bond (i.e., -----) means a trans configuration, whereas two full bonds or two dashed bonds means a cis configuration.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing compounds having the group (B):

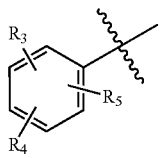

(B)

where the group (B) is intended to encompass groups wherein any ring atom that could otherwise be substituted with hydrogen, may instead be substituted with either $R_3$, $R_4$ or $R_5$, with the proviso that each of $R_3$, $R_4$ and $R_5$ appears once and only once on the ring. Ring atoms that are not substituted with any of $R_3$, $R_4$ or $R_5$ are substituted with hydrogen. In those instances where the invention specifies that a non-aromatic ring is substituted with one or more functional groups, and those functional groups are shown connected to the non-aromatic ring with bonds that bisect ring bonds, then the functional groups may be present at different atoms of the ring, or on the same atom of the ring, so long as that atom could otherwise be substituted with a hydrogen atom.

The compounds of the present invention contain at least two asymmetric carbon atoms and thus exist as enantiomers and diastereomers. Unless otherwise indicated, the present invention includes all enantiomeric and diastereomeric forms of the aminocyclohexyl ether compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers, unless a specific stereoisomer enantiomer or diastereomer is identified, with all isomeric forms being included in the present invention. A racemate or racemic mixture does not imply a 50:50 mixture of stereoisomers. Unless otherwise noted, the phrase "stereoisomerically substantially pure" generally refers to those asymmetric carbon atoms that are described or illustrated in the structural formulae for that compound.

As an example, and in no way limiting the generality of the above, a compound designated with the formula

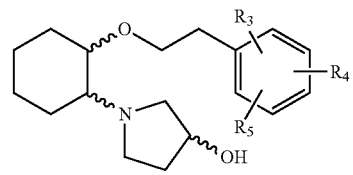

includes at least three chiral centers (the cyclohexyl carbon bonded to the oxygen, the cyclohexyl carbon bonded to the nitrogen, and the pyrrolidinyl carbon bonded to the oxygen) and therefore has at least eight separate stereoisomers, which are (1R,2R)-2-[(3R)-Hydroxypyrrolidinyl]-1-($R_3$, $R_4$ and $R_5$ substituted phenethoxy)-cyclohexane; (1R,2R)-2-[(3S)-Hydroxypyrrolidinyl]-1-($R_3$, $R_4$ and $R_5$ substituted phenethoxy)-cyclohexane; (1S,2S)-2-[(3R)-Hydroxypyrrolidinyl]-1-($R_3$, $R_4$ and $R_5$ substituted phenethoxy)-cyclohexane; (1S,2S)-2-[(3S)-Hydroxypyrrolidinyl]-1-($R_3$, $R_4$ and $R_5$ substituted phenethoxy)-cyclohexane; (1R,2S)-2-[(3R)-Hydroxypyrrolidinyl]-1-($R_3$, $R_4$ and $R_5$ substituted phenethoxy)-cyclohexane; (1R,2S)-2-[(3S)-Hydroxypyrrolidinyl]-1-($R_3$, $R_4$ and $R_5$ substituted phenethoxy)-cyclohexane; (1S, 2R)-2-[(3R)-Hydroxypyrrolidinyl]-1-($R_3$, $R_4$ and $R_5$ substituted phenethoxy)-cyclohexane; and (1S,2R)-2-[(3S)-Hydroxypyrrolidinyl]-1-($R_3$, $R_4$ and $R_5$ substituted phenethoxy)-cyclohexane; and, unless the context makes plain otherwise, as used in this patent a compound of the formula

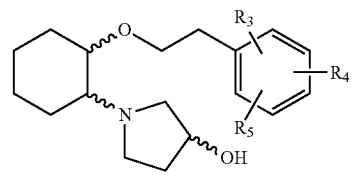

means a composition that includes a component that is either one of the eight pure enantiomeric forms of the indicated compound or is a mixture of any two or more of the pure enantiomeric forms, where the mixture can include any number of the enantiomeric forms in any ratio.

As an example, and in no way limiting the generality of the above, unless the context make plain otherwise as used in this patent a compound designated with the chemical formula (1R,2R)/(1S,2S)-2-[(3R)-Hydroxypyrrolidinyl]-1-(3,4-dimethoxyphenethoxy)-cyclohexane means a composition that includes a component that is either one of the two pure enantiomeric forms of the indicated compound (i.e., (1R,2R)-2-[(3R)-Hydroxypyrrolidinyl]-1-(3,4-dimethoxyphenethoxy)-cyclohexane or (1S,2S)-2-[(3R)-Hydroxypyrrolidinyl]-1-(3,4-dimethoxyphenethoxy)-cyclohexane) or is a racemic mixture of the two pure enantiomeric forms, where the racemic mixture can include any relative amount of the two enantiomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents and/or variables are permissible only if such combinations result in compounds that do not violate the standard rules of chemical valency.

In accordance with the present invention and as used herein, the following terms are defined to have following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like, and include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

"Alkoxy" refers to an oxygen (O)-atom substituted by an alkyl group, for example, alkoxy can include but is not limited to methoxy, which may also be denoted as —$OCH_3$, —OMe or a $C_1$alkoxy.

"Modulating" in connection with the activity of an ion channel means that the activity of the ion channel may be either increased or decreased in response to administration of a compound or composition or method of the present invention. Thus, the ion channel may be activated, so as to transport more ions, or may be blocked (inhibited), so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). Examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of for example formula (IA)" encompass compositions that contain more than one compound of formula (IA).

Compounds of the Present Invention

In one embodiment, the present invention provides a compound of formula (IA), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

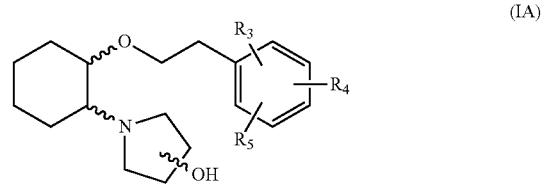

(IA)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof, with the proviso that $R_3$, $R_4$ and $R_5$ cannot all be hydrogen.

In one embodiment, the present invention provides a compound of formula (IA), or a solvate, pharmaceutically acceptable salt thereof, including isolated enantiomeric, diastereomeric and geometric isomers thereof, and mixtures thereof.

In one embodiment, the present invention provides a compound of formula (IA), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In one embodiment, the present invention provides a compound of formula (IA), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In one embodiment, the present invention provides a compound of formula (IA), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IA), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IA), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In one embodiment, the present invention provides a compound of formula (IA), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another embodiment, the present invention provides a compound of formula (IB), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(IB)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof.

In one embodiment, the present invention provides a compound of formula (IB), or a solvate, pharmaceutically acceptable salt thereof, including isolated enantiomeric, diastereomeric and geometric isomers thereof, and mixtures thereof.

In one embodiment, the present invention provides a compound of formula (IB), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In one embodiment, the present invention provides a compound of formula (IB), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In one embodiment, the present invention provides a compound of formula (IB), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IB), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IB), or a solvate, pharmaceutically acceptable salt, ester, amide, complex, chelate, stereoisomer, stereoisomeric mixture, geometric isomer; crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In one embodiment, the present invention provides a compound of formula (IB), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another embodiment, the present invention provides a compound of formula (IC), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(IC)

wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof.

In one embodiment, the present invention provides a compound of formula (IC), or a solvate, pharmaceutically acceptable salt thereof, including isolated enantiomeric, diastereomeric and geometric isomers thereof, and mixtures thereof.

In one embodiment, the present invention provides a compound of formula (IC), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In one embodiment, the present invention provides a compound of formula (IC), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In one embodiment, the present invention provides a compound of formula (IC), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IC), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (IC), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In one embodiment, the present invention provides a compound of formula (IC), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$alkoxy.

In another embodiment, the present invention provides a compound of formula (ID), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

<chemical structure (ID)> wherein, $R_3$, $R_4$ and $R_5$ are independently selected from hydrogen, hydroxy and $C_1$-$C_6$alkoxy, including isolated enantiomeric, diastereomeric and geometric isomers thereof, and mixtures thereof.

In one embodiment, the present invention provides a compound of formula (ID), or a solvate, pharmaceutically acceptable salt thereof, including isolated enantiomeric, diastereomeric and geometric isomers thereof, and mixtures thereof.

In one embodiment, the present invention provides a compound of formula (ID), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In one embodiment, the present invention provides a compound of formula (ID), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from hydroxy and $C_1$-$C_6$alkoxy.

In one embodiment, the present invention provides a compound of formula (ID), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (ID), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are independently selected from $C_1$-$C_6$alkoxy.

In one embodiment, the present invention provides a compound of formula (ID), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_3$ is hydrogen, $R_4$ and $R_5$ are $C_1$alkoxy.

In one embodiment, the present invention provides a compound of formula (ID), or a solvate, pharmaceutically acceptable salt thereof, including isolated enantiomeric, diastereomeric and geometric isomers thereof, and mixtures thereof, wherein, $R_3$ is hydrogen, $R_4$ and $R_5$ are $C_1$ alkoxy.

In another embodiment, the present invention provides a compound of formula (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

<chemical structure (IE)> wherein, $R_4$ and $R_5$ are independently selected from hydrogen, hydroxy and $C_1$-$C_6$alkoxy, including isolated enantiomeric, diastereomeric and geometric isomers thereof, and mixtures thereof.

In one embodiment; the present invention provides a compound of formula (IE), or a solvate, pharmaceutically acceptable salt thereof, including isolated enantiomeric, diastereomeric and geometric isomers thereof, and mixtures thereof.

In one embodiment, the present invention provides a compound of formula (IE), or a solvate, pharmaceutically acceptable salt thereof, wherein, $R_4$ and $R_5$ are independently selected from hydroxy and $C_1$-$C_6$alkoxy, including isolated enantiomeric, diastereomeric and geometric isomers thereof, and mixtures thereof.

In one embodiment, the present invention provides a compound of formula (IE), or a solvate, pharmaceutically acceptable salt thereof, including isolated enantiomeric, diastereomeric and geometric isomers thereof, and mixtures thereof, wherein, $R_4$ and $R_5$ are independently selected from hydroxy and $C_1$-$C_3$alkoxy.

In one embodiment, the present invention provides a compound of formula (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_4$ and $R_5$ are independently selected from $C_1$-$C_6$alkoxy.

In one embodiment, the present invention provides a compound of formula (IE), or a solvate, pharmaceutically acceptable salt thereof, including isolated enantiomeric, diastereomeric and geometric isomers thereof, and mixtures thereof, wherein, $R_4$ and $R_5$ are independently selected from $C_1$-$C_3$alkoxy.

In one embodiment, the present invention provides a compound of formula (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_4$ and $R_5$ are $C_1$alkoxy.

In one embodiment, the present invention provides a compound of formula (IE), or a solvate, pharmaceutically acceptable salt thereof, including isolated enantiomeric, diastereomeric and geometric isomers thereof, and mixtures thereof, wherein, $R_4$ and $R_5$ are $C_1$alkoxy.

In another embodiment, the present invention provides a compound or any salt thereof, or any solvate thereof, or mixture comprising one or more said compounds or any salt thereof, or any solvate thereof, selected from the group consisting of:

| Structure | Chemical name |
| --- | --- |
| 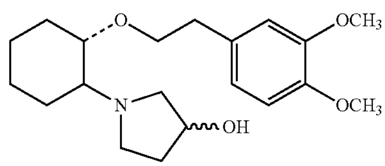 | (1R,2R)/(1S,2S)-2-[(3R)/(3S)-Hydroxypyrrolidinyl]-1-(3,4-dimethoxyphenethoxy)-cyclohexane |
| 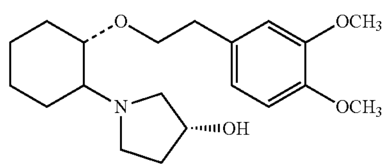 | (1R,2R)/(1S,2S)-2-[(3R)-Hydroxypyrrolidinyl]-1-(3,4-dimethoxyphenethoxy)-cyclohexane |
| 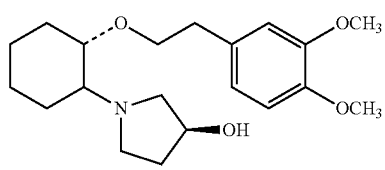 | (1R,2R)/(1S,2S)-2-[(3S)-Hydroxypyrrolidinyl]-1-(3,4-dimethoxyphenethoxy)-cyclohexane |
| 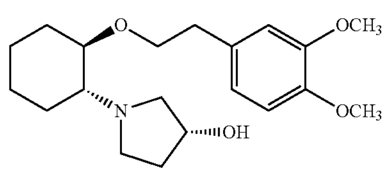 | (1R,2R)-2-[(3R)-Hydroxypyrrolidinyl]-1-(3,4-dimethoxyphenethoxy)-cyclohexane |
| 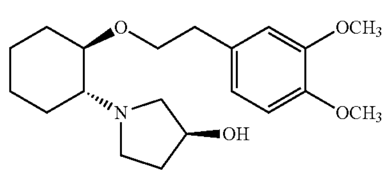 | (1R,2R)-2-[(3S)-Hydroxypyrrolidinyl]-1-(3,4-dimethoxyphenethoxy)-cyclohexane |
| 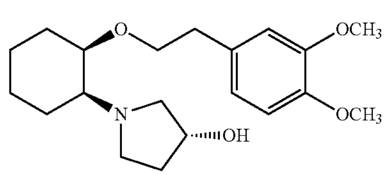 | (1R,2S)-2-[(3R)-Hydroxypyrrolidinyl]-1-(3,4-dimethoxyphenethoxy)-cyclohexane |
| 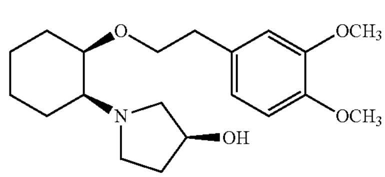 | (1R,2S)-2-[(3S)-Hydroxypyrrolidinyl]-1-(3,4-dimethoxyphenethoxy)-cyclohexane |

-continued

| Structure | Chemical name |
|---|---|
| 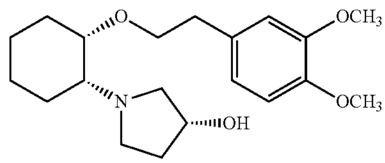 | (1S,2R)-2-[(3R)-Hydroxypyrrolidinyl]-1-(3,4-dimethoxyphenethoxy)-cyclohexane |
| 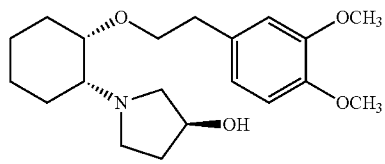 | (1S,2R)-2-[(3S)-Hydroxypyrrolidinyl]-1-(3,4-dimethoxyphenethoxy)-cyclohexane |
| 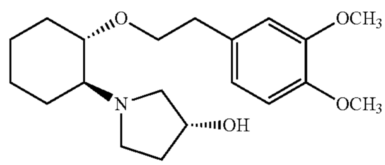 | (1S,2S)-2-[(3R)-Hydroxypyrrolidinyl]-1-(3,4-dimethoxyphenethoxy)-cyclohexane |
| 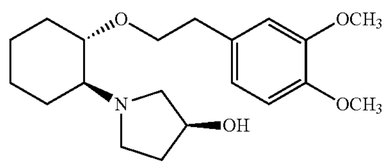 | (1S,2S)-2-[(3S)-Hydroxypyrrolidinyl]-1-(3,4-dimethoxyphenethoxy)-cyclohexane |
| 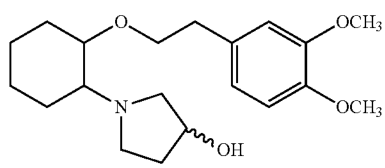 | (1R,2S)/(1S,2R)-2-[(3R)/(3S)-Hydroxypyrrolidinyl]-1-(3,4-dimethoxyphenethoxy)-cyclohexane |

In another embodiment, the present invention provides a composition that includes one or more of the compounds listed in the above table, or includes a solvate or a pharmaceutically acceptable salt of one or more of the compounds listed in the above table. The composition may or may not include additional components as is described elsewhere in detail in this patent.

In another embodiment, the present invention provides a compound, or mixture comprising compounds, or any solvate thereof, selected from the group consisting of:

| Cpd. # | Structure | Chemical name |
|---|---|---|
| 1 | 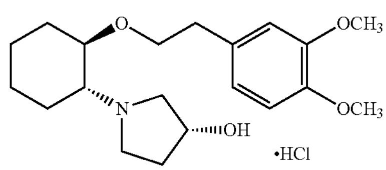 | (1R,2R)-2-[(3R)-Hydroxypyrrolidinyl]-1-(3,4-dimethoxyphenethoxy)-cyclohexane monohydrochloride |
| 2 | 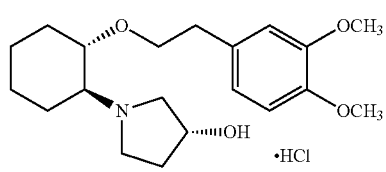 | (1S,2S)-2-[(3R)-Hydroxypyrrolidinyl]-1-(3,4-dimethoxyphenethoxy)-cyclohexane monohydrochloride |

-continued

| Cpd. # | Structure | Chemical name |
|---|---|---|
| 3 | 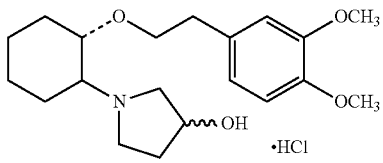 | (1R,2R)/(1S,2S)-2-[(3R)/(3S)-Hydroxypyrrolidinyl]-1-(3,4-dimethoxyphenethoxy)-cyclohexane monohydrochloride |
| 4 | 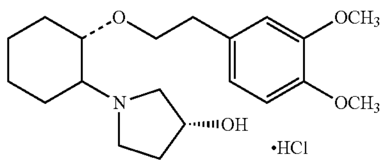 | (1R,2R)/(1S,2S)-2-[(3R)-Hydroxypyrrolidinyl]-1-(3,4-dimethoxyphenethoxy)-cyclohexane monohydrochloride |
| 5 | 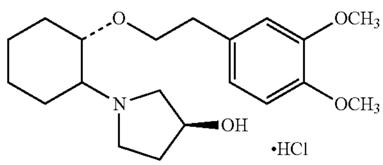 | (1R,2R)/(1S,2S)-2-[(3S)-Hydroxypyrrolidinyl]-1-(3,4-dimethoxyphenethoxy)-cyclohexane monohydrochloride |
| 6 | 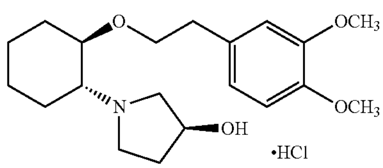 | (1R,2R)-2-[(3S)-Hydroxypyrrolidinyl]-1-(3,4-dimethoxyphenethoxy)-cyclohexane monohydrochloride |
| 7 | 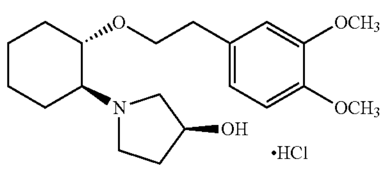 | (1S,2S)-2-[(3S)-Hydroxypyrrolidinyl]-1-(3,4-dimethoxyphenethoxy)-cyclohexane monohydrochloride |

In another embodiment, the present invention provides a composition that includes one or more of the compounds listed in the above table, or includes a solvate of one or more of the compounds listed in the above table. The composition may or may not include additional components as is described elsewhere in detail in this patent.

In one embodiment, the present invention provides a compound which is (1R,2R)-2-[(3R)-Hydroxypyrrolidinyl]-1-(3,4-dimethoxyphenethoxy)-cyclohexane free base or any salt thereof, or any solvate thereof.

In one embodiment, the present invention provides a compound which is (1R,2R)-2-[(3S)-Hydroxypyrrolidinyl]-1-(3,4-dimethoxyphenethoxy)-cyclohexane free base or any salt thereof, or any solvate thereof.

In one embodiment, the present invention provides a compound which is (1S,2S)-2-[(3R)-Hydroxypyrrolidinyl]-1-(3,4-dimethoxyphenethoxy)-cyclohexane free base or any salt thereof, or any solvate thereof.

In one embodiment, the present invention provides a compound which is (1S,2S)-2-[(3S)-Hydroxypyrrolidinyl]-1-(3,4-dimethoxyphenethoxy)-cyclohexane free base or any salt thereof, or any solvate thereof.

In one embodiment, the present invention provides a compound which is (1R,2R)-2-[(3R)-Hydroxypyrrolidinyl]-1-(3,4-dimethoxyphenethoxy)-cyclohexane monohydrochloride, or any solvate thereof.

In one embodiment, the present invention provides a compound which is (1R,2R)-2-[(3S)-Hydroxypyrrolidinyl]-1-(3,4-dimethoxyphenethoxy)-cyclohexane monohydrochloride, or any solvate thereof.

In one embodiment, the present invention provides a compound which is (1S,2S)-2-[(3R)-Hydroxypyrrolidinyl]-1-(3,4-dimethoxyphenethoxy)-cyclohexane monohydrochloride, or any solvate thereof.

In one embodiment, the present invention provides a compound which is (1S,2S)-2-[(3S)-Hydroxypyrrolidinyl]-1-(3,4-dimethoxyphenethoxy)-cyclohexane monohydrochloride, or any solvate thereof.

The present invention also provides protenated versions of all of the compounds described in this patent. That is, for each compound described in this patent, the invention also includes the quaternary protenated amine form of the compound. These quaternary protenated amine forms of the compounds may be present in the solid phase, for example in crystalline or amorphous form, and may be present in solution. These quaternary protenated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Outline of Method of Preparation of Compounds of the Invention

The aminocyclohexyl ether compounds of the present invention contain amino and ether functional groups disposed in a 1,2 arrangement on a cyclohexane ring. Accordingly, the amino and ether functional groups may be disposed in either a cis or trans relationship, relative to one another and the plane of the cyclohexane ring as shown on the page in a two dimensional representation.

The present invention provides synthetic methodology for the preparation of the aminocyclohexyl ether compounds according to the present invention as described herein. The aminocyclohexyl ether compounds described herein may be prepared from aminoalcohols and alcohols by following the general methods described below, and as illustrated in the examples. Some general synthetic processes for aminocyclohexyl ethers have been described in WO 99/50225 and references cited therein. Other processes that may be used for preparing compounds of the present invention are described in the following US provisional patent applications: U.S. 60/476,083, U.S. 60/476,447, U.S. 60/475,884, U.S. 60/475,912 and U.S. 60/489,659, and references cited therein.

Trans compounds of the present invention may be prepared in analogy with known synthetic methodology. In one method, illustrated in FIG. 1, compounds are prepared by a Williamson ether synthesis (Feuer, H.; Hooz, J. Methods of Formation of the Ether Linkage. In *Patai*, Wiley: New York, 1967; pp 445-492) between an activated form of aminoalcohol 4R with the alkoxide of 3,4-dimethoxyphenethyl alcohol in a polar solvent such as dimethoxyethane (ethylene glycol dimethyl ether) (DME) (FIG. 1) that provided the corresponding aminoether 5R in high yield. Subsequent resolution of the diastereomers such as by chromatographic separation (e.g., HPLC) to afford 5RRR and 5SSR followed by hydrogenolysis provided compound 1 and compound 2 respectively.

(1R,2R)-2-[(3S)-Hydroxypyrrolidinyl]-1-(3,4-dimethoxyphenethoxy)cyclohexane free base and the corresponding monohydrochloride (compound 6) and (1S,2S)-2-[(3S)-hydroxypyrrolidinyl]-1-(3,4-dimethoxyphenethoxy)cyclohexane free base and the corresponding monohydrochloride (compound 7) are obtained using a similar synthetic sequence but starting with 3-(S)-hydroxypyrrolidine.

Hydrogenolysis of (1R,2R)/(1S,2S)-2-[(3R)-benzyloxypyrrolidinyl]-1-(3,4-dimethoxyphenethoxy)cyclohexane (5R) provided (1R,2R)/(1S,2S)-2-[(3R)-hydroxypyrrolidinyl]-1-(3,4-dimethoxyphenethoxy)cyclohexane free base and the corresponding monohydrochloride (compound 4). Similarly, starting with 3-(S)-hydroxypyrrolidine instead of 3-(R)-hydroxypyrrolidine and following the same synthetic sequence will afford (1R,2R)/(1S,2S)-2-[(3S)-benzyloxypyrrolidinyl]-1-(3,4-dimethoxyphenethoxy)cyclohexane. The latter on hydrogenolysis will provide (1R,2R)/(1S,2S)-2-[(3S)-hydroxypyrrolidinyl]-1-(3,4-dimethoxyphenethoxy) cyclohexane free base and the corresponding monohydrochloride (compound 5). (1R,2R)/(1S,2S)-2-[(3R)/(3S)-Hydroxypyrrolidinyl]-1-(3,4-dimethoxyphenethoxy)-cyclohexane free base and the corresponding monohydrochloride (compound 3) can also be synthesized by similar process by starting with racemic 3-hydroxypyrrolidine.

FIG. 2 shows a second general methodology by which compounds of the present invention may be prepared. Compounds of formula (IA), (IB), (IC), (ID), or (IE), may be prepared by reduction of the corresponding ketopyrrolidinylcyclohexyl ether compound with $NaBH_4$ in 2-propanol.

Preparation of the starting aminoalcohol 2e requires the preparation of amine 1e, for which suitable method of preparation is illustrated in FIG. 3. 3-Hydroxypyrrolidine 1a was N-protected by carbamoylation with benzylchloroformate to give 1b, Swern oxidation (Mancuso, A. J.; Swern, D. Activated Dimethyl Sulfoxide Useful Reagents for Synthesis. *Synthesis* 1981, 165-185) to 1c followed by ketalisation with ethylene glycol provided 1d which was then hydrogenolyzed to give 1e.

The present invention provides synthetic processes whereby compounds of formula (57) with trans-(1R,2R) configuration for the ether and amino functional groups may be prepared in stereoisomerically substantially pure form. Compounds of formulae (66), (67), (69) and (71) are some of the examples represented by formula (57). The present invention also provides synthetic processes whereby compounds of formulae (52), (53), and (55) may be synthesized in stereoisomerically substantially pure forms. Compounds (61), (62) and (64) are examples of formulae (52), (53) and (55) respectively.

As outlined in FIG. 5, the preparation of a stereoisomerically substantially pure trans aminocyclohexyl ether compound of formula (57) may be carried out by following a process starting from a monohalobenzene (49), wherein X may be F, Cl, Br or I.

In a first step, compound (49) is transformed by well-established microbial oxidation to the cis-cyclohexandienediol (50) in stereoisomerically substantially pure form (T. Hudlicky et al., *Aldrichimica Acta*, 1999, 32, 35; and references cited therein). In a separate step, compound (50) may be selectively reduced under suitable conditions to compound (51) (e.g., $H_2$—$Rh/Al_2O_3$; Boyd et al. *JCS Chem. Commun.* 1996, 45-46; Ham and Coker, *J. Org. Chem.* 1964, 29, 194-198; and references cited therein). In another separate step, the less hindered hydroxy group of formula (51) is selectively converted under suitable conditions into an activated form as represented by formula (52). An "activated form" as used herein means that the hydroxy group is converted into a good leaving group (—O-J) which on reaction with an appropriate nucleophile will result in a substitution product with inversion of the stereochemical configuration. The leaving group may be a mesylate (MsO—) group, a tosylate group (TsO—) or a nosylate (NsO—), or other equivalent good leaving groups. The hydroxy group may also be converted into other suitable leaving groups according to procedures well known in the art. In a typical reaction for the formation of a tosylate, compound (52) is treated with a hydroxy activating reagent such as tosyl chloride (TsCl) in the presence of a base, such as pyridine or triethylamine. The reaction is generally satisfactorily conducted at about 0° C., but may be adjusted as required to maximize the yields of the desired product. An excess of the hydroxy activating reagent (e.g., tosyl chloride), relative to compound (52) may be used to maximally convert the hydroxy group into the activated form. In a separate step, transformation of compound (52) to compound (53) may be effected by hydrogenation and hydrogenolysis in the presence of a catalyst under appropriate conditions. Palladium on activated carbon is one example of the catalysts. Hydrogenolysis of alkyl or alkenyl halide such as (52) may be conducted under basic conditions. The presence of a base such as sodium ethoxide, sodium bicarbonate, sodium acetate or calcium carbonate is some possible examples. The base may be added in one portion or incrementally during the course of the reaction. In a separate step, alkylation of the free hydroxy group in compound (53) to form compound (55) is carried out under appropriate conditions with compound (54), where —O-Q represents a good leaving group on reaction with a hydroxy function with retention of the stereochemical configuration of the hydroxy function in the formation of an ether compound. Trichloroacetimidate is one example for the —O-Q function. For some compound (54), it may be necessary to introduce appropriate protection groups prior to this step being performed. Suitable protecting groups are set forth in, for example, Greene, "Protective Groups in Organic Chemistry", John Wiley & Sons, New York N.Y. (1991).

In a separate step, the resulted compound (55) is treated under suitable conditions with an amino compound of formula (56) to form compound (57) as the product. The reaction may be carried out with or without a solvent and at an appropriate temperature range that allows the formation of the product (57) at a suitable rate. An excess of the amino compound (56) may be used to maximally convert compound (55) to the product (57). The reaction may be performed in the presence of a base that can facilitate the formation of the product. Generally the base is non-nucleophilic in chemical reactivity. When the reaction has proceeded to substantial completion, the product is recovered from the reaction mixture by conventional organic chemistry techniques, and is purified accordingly. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (FIG. 5) generates the compound of formula (57) as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

All publications and patent applications mentioned in this specification are herein incorporated by reference to the same extent as if each individual publication or patent application is specifically and individually incorporated by reference.

In one embodiment, the present invention provides a process for the preparation of a stereoisomerically substantially pure compound of formula (57):

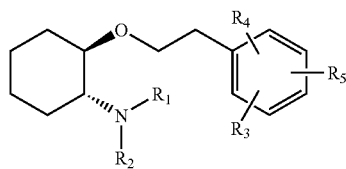

(57)

wherein $R_1$ and $R_2$, when taken together with the nitrogen atom to which they are directly attached in formula (57), form a ring denoted by formula (II):

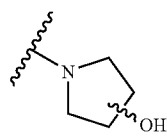

(II)

and $R_3$, $R_4$ and $R_5$ are independently selected from hydrogen, hydroxy and $C_1$-$C_6$alkoxy, with the proviso that $R_3$, $R_4$ and $R_5$ cannot all be hydrogen;

comprising the steps of starting with a monohalobenzene (49), wherein X may be F, Cl, Br or I; and following a reaction sequence as outlined in FIG. 5 under suitable conditions, wherein —O-Q represents a good leaving group on reaction with a hydroxy function with retention of the stereochemical configuration of the hydroxy function in the formation of an ether compound; and —O-J represents a good leaving group on reaction with a nucleophilic reactant with inversion of the stereochemical configuration as shown in FIG. 5 and all the formulae and symbols are as described above.

In another embodiment, the present invention provides a process for the preparation of a stereoisomerically substantially pure compound of formula (66), comprising the steps under suitable conditions as shown in FIG. 6, wherein all the formulae and symbols are as described above. As outlined in FIG. 6, the preparation of a stereoisomerically substantially pure trans aminocyclohexyl ether compound of formula (66) may be carried out by starting with a biotransformation of chlorobenzene (58) to compound (59) by microorganism such as *Pseudomonas putida* 39/D. Experimental conditions for the biotransformation are well established (Organic Synthesis, Vol. 76, 77 and T. Hudlicky et al., *Aldrichimica Acta*, 1999, 32, 35; and references cited therein). In a separate step, compound (59) is selectively reduced under suitable conditions to compound (60) (e.g., $H_2$—Rh/$Al_2O_3$; Boyd et al. *JCS Chem. Commun.* 1996, 45-46; Ham and Coker, *J. Org. Chem.* 1964, 29, 194-198; and references cited therein). In another separate step, the less hindered hydroxy group of formula (60) is selectively converted under suitable conditions into an activated form such as the tosylate (TsO—) of formula (61) (e.g., TsCl in the presence of pyridine). In a separate step, compound (61) is converted to compound (62) by reduction such as hydrogenation and hydrogenolysis in the presence of a catalyst under appropriate conditions. Palladium on activated carbon is one example of the catalysts. The reduction of compound (61) may be conducted under basic conditions e.g., in the presence of a base such as sodium ethoxide, sodium bicarbonate, sodium acetate or calcium carbonate. The base may be added in one portion or incrementally during the course of the reaction. In another separate step, the free hydroxy group in compound (62) is alkylated under appropriate conditions to form compound (64). The trichloroacetimidate (63) is readily prepared from the corresponding alcohol, 3,4-dimethoxyphenethyl alcohol which is commercially available (e.g., Aldrich), by treatment with trichloroacetonitrile. The alkylation of compound (62) by trichloroacetimidate (63) may be carried out in the presence of a Bronsted acid or Lewis acid such as $HBF_4$. In a separate step, the tosylate group of formula (64) is displaced by an amino compound such as 3R-pyrrolidinol (65) with inversion of configuration. 3R-pyrrolidinol (65) is commercially available (e.g., Aldrich) or may be prepared according to published procedure (e.g., *Chem. Ber./Recueil* 1997, 130, 385-397). The reaction may be carried out with or without a solvent and at an appropriate temperature range that allows the formation of the product (66) at a suitable rate. An excess of the amino compound (65) may be used to maximally convert compound (64) to the product (66). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequence described above (FIG. 6) in general generates the compound of formula (66) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (66) may be carried out under suitable conditions by a process as outlined in FIG. 7, comprising the steps of starting from chlorobenzene (58) and following a reaction sequence analogous to the applicable portion (i.e., from compound (58) to compound (64)) that is described in FIG. 6 above leading to compound of formula (64). The latter is reacted under suitable conditions with an amino compound of formula (65A) wherein Bn represents a benzyl protection group of the hydroxy function of 3R-pyrrolidinol to form compound (67). Compound (65A) is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (67) at a suitable rate. An excess of the amino compound (65A) may be used to maximally convert compound (64) to the product (67). The reaction may be performed in the presence of a base that can facilitate the formation of the product. Generally the additional base is non-nucleophilic in chemical reactivity. The benzyl (Bn) protection group of compound (67) may be removed by standard procedure (e.g., hydrogenation in the presence of a catalyst under appropriate conditions). Palladium on activated carbon is one example of the catalysts. Other suitable conditions are as described in Greene, "Protective Groups in Organic Chemistry", John Wiley & Sons, New York N.Y. (1991)). The product is a stereoisomerically substantially pure trans aminocyclohexyl ether compound of formula (66) and is generally formed as the free base. The free base may be converted, if desired, to the monohydrochloride salt by known methodologies, or alternatively, if desired, to other acid addition salts by reaction with an inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (69) may be carried out under suitable conditions by a process as outlined in FIG. 8, comprising the steps of starting from chlorobenzene (58) and following a reaction sequence analogous to the applicable portion that is described in FIG. 6 above leading to compound of formula (64). The latter is reacted with an amino compound of formula (68). Compound (68), 3S-pyrrolidinol, is commercially available (e.g., Aldrich) or may be prepared according to published procedure (e.g., *Chem. Ber./Recueil* 1997, 130, 385-397). The reaction may be carried out with or without a solvent and at an appropriate temperature range that allows the formation of the product (69) at a suitable rate. An excess of the amino compound (68) may be used to maximally convert compound (64) to the product (69). The reaction may be performed in the presence of a base that can facilitate the formation of the product. Generally the additional base is non-nucleophilic in chemical reactivity. The product is a stereoisomerically substantially pure trans aminocyclohexyl ether compound of formula (69) and is formed as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (69) may be carried out under suitable conditions by a process as outlined in FIG. 9, comprising the steps of starting from chlorobenzene (58) and following a reaction sequence analogous to the applicable portion that is described in FIG. 7 above leading to compound of formula (64). The latter is reacted with an amino compound of formula (70) wherein Bn represents a benzyl protection group of the hydroxy function of 3S-pyrrolidinol to form compound (71). Compound (70) is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (71) at a suitable rate. An excess of the amino compound (70) may be used to maximally convert compound (64) to the product (71). The reaction may be performed in the presence of a base that can facilitate the formation of the product. Generally the additional base is non-nucleophilic in chemical reactivity. The benzyl (Bn) protection group of compound (71) may be removed by standard procedure (e.g., hydrogenation in the presence of a catalyst under appropriate conditions). Palladium on activated carbon is one example of the catalysts. Other suitable conditions are as described in Greene, "Protective Groups in Organic Chemistry", John Wiley & Sons, New York N.Y. (1991)). The product is a stereoisomerically substantially pure trans aminocyclohexyl ether compound of formula (69) and is generally formed as the free base. The free base may be converted, if desired, to the monohydrochloride salt by known methodologies, or alternatively, if desired, to other acid addition salts by reaction with an inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (57) may be carried out under suitable conditions by a process as outlined in FIG. 10, comprising the steps of starting with compound of formula (50) and following a reaction sequence analogous to the applicable portion that is described in FIG. 5, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 11, comprising the steps of starting with compound of formula (59) and following a reaction sequence analogous to the applicable portion that is described in FIG. 6, wherein all the formulae and symbols are as described above. 3-Chloro-(1S,2S)-3,5-cyclohexadiene-1,2-diol of formula (59) is a commercially available product (e.g., Aldrich) or synthesized according to published procedure (e.g., *Organic Synthesis*, Vol. 76, 77 and T. Hudlicky et al., *Aldrichimica Acta,* 1999, 32, 35; and references cited therein).

In another embodiment, the preparation of a stereoisomerically substantially pure trans aminocyclohexyl ether compound of formula (66) may be carried out under suitable conditions by a process as outlined in FIG. 12, comprising the steps of starting with compound of formula (59) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 13, comprising the steps of starting with compound of formula (59) and following a reaction sequence analogous to the applicable portion that is described in FIG. 8, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 14, comprising the steps of starting with compound of formula (59) and following a reaction sequence analogous to the applicable portion that is described in FIG. 9, wherein all the formulae and symbols are as described above.

In another embodiment, the preparation of a stereoisomerically substantially pure trans aminocyclohexyl ether compound of formula (57) may be carried out under suitable conditions by a process as outlined in FIG. 15, comprising the steps of starting with compound of formula (51) and following a reaction sequence analogous to the applicable portion that is described in FIG. 5, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 16, comprising the steps of starting with compound of formula (60) and following a reaction sequence analogous to the applicable portion that is described in FIG. 6, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 17, comprising the steps of starting with compound of formula (60) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 18, comprising the steps of starting with compound of formula (60) and following a reaction sequence analogous to the applicable portion that is described in FIG. 8, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 19, comprising the steps of starting with compound of formula (60) and following a reaction sequence analogous to the applicable portion that is described in FIG. 9, wherein all the formulae and symbols are as described above.

In another embodiment, the preparation of a stereoisomerically substantially pure trans aminocyclohexyl ether compound of formula (57) may be carried out under suitable conditions by a process as outlined in FIG. 20, comprising the steps of starting with compound of formula (52) and following a reaction sequence analogous to the applicable portion that is described in FIG. 5, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 21, comprising the steps of starting with compound of formula (61) and following a reaction sequence analogous to the applicable portion that is described in FIG. 6, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 22, comprising the steps of starting with compound of formula (61) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 23, comprising the steps of starting with compound of formula (61) and following a reaction sequence analogous to the applicable portion that is described in FIG. 8, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 24, comprising the steps of starting with compound of formula (61) and following a reaction sequence analogous to the applicable portion that is described in FIG. 9, wherein all the formulae and symbols are as described above.

In another embodiment, the preparation of a stereoisomerically substantially pure trans aminocyclohexyl ether compound of formula (57) may be carried out under suitable conditions by a process as outlined in FIG. 25, comprising the steps of starting with compound of formula (53) and following a reaction sequence analogous to the applicable portion that is described in FIG. 5, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 26, comprising the steps of starting with compound of formula (62) and following a reaction sequence analogous to the applicable portion that is described in FIG. 6, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 27, comprising the steps of starting with compound of formula (62) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 28, comprising the steps of starting with compound of formula (62) and following a reaction sequence analogous to the applicable portion that is described in FIG. 8, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 29, comprising the steps of starting with compound of formula (62) and following a reaction sequence analogous to the applicable portion that is described in FIG. 9, wherein all the formulae and symbols are as described above.

In another embodiment, the preparation of a stereoisomerically substantially pure trans aminocyclohexyl ether compound of formula (57) may be carried out under suitable conditions by a process as outlined in FIG. 30, comprising the steps of starting with compound of formula (55) and following a reaction sequence analogous to the applicable portion that is described in FIG. 5, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 31, comprising the steps of starting with compound of formula (64) and following a reaction sequence analogous to the applicable portion that is described in FIG. 6, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 32, comprising the steps of starting with compound of formula (64) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 33, comprising the steps of starting with compound of formula (64) and following a reaction sequence analogous to the applicable portion that is described in FIG. 8, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 34, comprising the steps of starting with compound of formula (64) and following a reaction sequence analogous to the applicable portion that is described in FIG. 9, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 35, comprising the steps of starting with compound of formula (67) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (69) may be carried out under suitable conditions by a process as outlined in FIG. 36, comprising the steps of starting with compound of formula (71) and following a reaction sequence analogous to the applicable portion that is described in FIG. 9, wherein all the formulae and symbols are as described above.

In another embodiment, the preparation of a stereoisomerically substantially pure compound of formula (55) may be carried out under suitable conditions by a process as outlined in FIG. 37, comprising the steps of starting with compound of formula (49) and following a reaction sequence analogous to the applicable portion that is described in FIG. 5, wherein all the formulae and symbols are as described above.

In another embodiment, the preparation of a stereoisomerically substantially pure compound of formula (64) may be carried out under suitable conditions by a process as outlined in FIG. 38, comprising the steps of starting with compound of formula (58) and following a reaction sequence analogous to the applicable portion that is described in FIG. 6, wherein all the formulae and symbols are as described above.

In another embodiment, the preparation of a stereoisomerically substantially pure trans aminocyclohexyl ether compound of formula (67) may be carried out under suitable conditions by a process as outlined in FIG. 39, comprising the steps of starting with compound of formula (58) and following a reaction sequence analogous to the applicable portion that is described in FIG. 7, wherein all the formulae and symbols are as described above.

In another embodiment, the preparation of a stereoisomerically substantially pure trans aminocyclohexyl ether compound of formula (71) may be carried out under suitable conditions by a process as outlined in FIG. 40, comprising the steps of starting with compound of formula (58) and following a reaction sequence analogous to the applicable portion that is described in FIG. 9, wherein all the formulae and symbols are as described above.

In another embodiment, the preparation of a stereoisomerically substantially pure compound of formula (53) may be carried out under suitable conditions by a process as outlined in FIG. 41, comprising the steps of starting with compound of formula (49) and following a reaction sequence analogous to the applicable portion that is described in FIG. 5, wherein all the formulae and symbols are as described above.

In another embodiment, the preparation of a stereoisomerically substantially pure compound of formula (62) may be carried out under suitable conditions by a process as outlined in FIG. 42, comprising the steps of starting with compound of formula (58) and following a reaction sequence analogous to the applicable portion that is described in FIG. 6, wherein all the formulae and symbols are as described above.

In another embodiment, the preparation of a stereoisomerically substantially pure compound of formula (52) may be carried out under suitable conditions by a process as outlined in FIG. 43, comprising the steps of starting with compound of formula (49) and following a reaction sequence analogous to the applicable portion that is described in FIG. 5, wherein all the formulae and symbols are as described above.

In another embodiment, the preparation of a stereoisomerically substantially pure compound of formula (61) may be carried out under suitable conditions by a process as outlined in FIG. 44, comprising the steps of starting with compound of formula (58) and following a reaction sequence analogous to the applicable portion that is described in FIG. 6, wherein all the formulae and symbols are as described above.

In another embodiment, the present invention provides a compound of formula (52), or a solvate or pharmaceutically acceptable salt thereof; wherein all the formulae and symbols are as described above.

In another embodiment, the present invention provides a compound of formula (53), or a solvate or pharmaceutically acceptable salt thereof; wherein all the formulae and symbols are as described above.

In another embodiment, the present invention provides a compound of formula (54), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (55), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (61), or a solvate or pharmaceutically acceptable salt thereof; wherein all the formulae and symbols are as described above.

In another embodiment, the present invention provides a compound of formula (62), or a solvate or pharmaceutically acceptable salt thereof; wherein all the formulae and symbols are as described above.

In another embodiment, the present invention provides a compound of formula (64), or a solvate or pharmaceutically acceptable salt thereof; wherein all the formulae and symbols are as described above.

In another embodiment, the present invention provides a compound of formula (67), or a solvate or pharmaceutically acceptable salt thereof; wherein all the formulae and symbols are as described above.

In another embodiment, the present invention provides synthetic, processes whereby compounds of formula (75) with trans-(1S,2S) configuration for the ether and amino functional groups may be prepared in stereoisomerically substantially pure form. Compounds of formulae (79), (80), (81) and (82) are some of the examples represented by formula (75). The present invention also provides synthetic processes whereby compounds of formulae (72), (73) and (74) may be synthesized in stereoisomerically substantially pure forms. Compounds (76), (77) and (78) are examples of formulae (72), (73) and (74) respectively.

As outlined in FIG. 45, the preparation of a stereoisomerically substantially pure trans aminocyclohexyl ether compound of formula (75) may be carried out by following a process starting from a monohalobenzene (49), wherein X may be F, Cl, Br or I.

In a first step, compound (49) is transformed by well-established microbial oxidation to the cis-cyclohexandienediol (50) in stereoisomerically substantially pure form (T. Hudlicky et al., Aldrichimica Acta, 1999, 32, 35; and references cited therein). In a separate step, compound (50) may be selectively reduced under suitable conditions to compound (51) (e.g., $H_2$—$Rh/Al_2O_3$; Boyd et al. JCS Chem. Commun. 1996, 45-46; Ham and Coker, J. Org. Chem. 1964, 29, 194-198; and references cited therein). In another separate step, compound (51) is converted to compound (72) by reaction with compound (54) under appropriate conditions, where —O-Q represents a good leaving group on reaction with a hydroxy function with retention of the stereochemical configuration of the hydroxy function in the formation of an ether compound. Trichloroacetimidate is one example for the —O-Q function. For some compound (72), it may be necessary to introduce appropriate protection groups prior to this step being performed. Suitable protecting groups are set forth in, for example, Greene, "Protective Groups in Organic Chemistry", John Wiley & Sons, New York N.Y. (1991).

In a separate step, transformation of compound (72) to compound (73) may be effected by hydrogenation and hydrogenolysis in the presence of a catalyst under appropriate conditions. Palladium on activated carbon is one example of the catalysts. Hydrogenolysis of alkyl or alkenyl halide such as (72) may be conducted under basic conditions. The presence of a base such as sodium ethoxide, sodium bicarbonate, sodium acetate or calcium carbonate is some possible examples. The base may be added in one portion or incrementally during the course of the reaction. In another separate step, the hydroxy group of compound (73) is selectively converted under suitable conditions into an activated form as represented by compound (74). An "activated form" as used herein means that the hydroxy group is converted into a good leaving group (—O-J) which on reaction with an appropriate nucleophile will result in a substitution product with inversion of the stereochemical configuration. The leaving group may be a mesylate (MsO—) group, a tosylate group (TsO—) or a nosylate (NsO—). The hydroxy group may also be converted into other suitable leaving groups according to procedures well known in the art. In a typical reaction for the formation of a tosylate, compound (73) is treated with a hydroxy activating reagent such as tosyl chloride (TsCl) in the presence of a base (e.g., pyridine or triethylamine). The reaction is generally satisfactorily conducted at about 0° C., but may be adjusted as required to maximize the yields of the desired product. An excess of the hydroxy activating reagent (e.g., tosyl chloride), relative to compound (73) may be used to maximally convert the hydroxy group into the activated form.

In a separate step, the resulted compound (74) is treated under suitable conditions with an amino compound of formula (56) to form compound (75) as the product. The reaction may be carried out with or without a solvent and at an appropriate temperature range that allows the formation of the product (75) at a suitable rate. An excess of the amino compound (56) may be used to maximally convert compound (74) to the product (75). The reaction may be performed in the presence of a base that can facilitate the formation of the product. Generally the base is non-nucleophilic in chemical reactivity. When the reaction has proceeded to substantial completion, the product is recovered from the reaction mixture by conventional organic chemistry techniques, and is purified accordingly. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (FIG. 45) generates the compound of formula (75) as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

All publications and patent applications mentioned in this specification are herein incorporated by reference to the same extent as if each individual publication or patent application is specifically and individually incorporated by reference.

In one embodiment, the present invention provides a process for the preparation of a stereoisomerically substantially pure compound of formula (75):

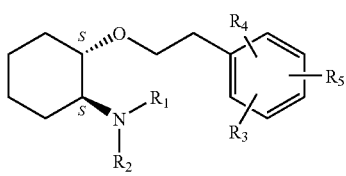
(75)

wherein R$_1$ and R$_2$, when taken together with the nitrogen atom to which they are directly attached in formula (75), form a ring denoted by formula (II):

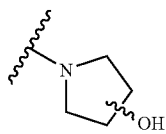
(II)

and R$_3$, R$_4$ and R$_5$ are independently selected from hydrogen, hydroxy and C$_1$-C$_6$alkoxy, with the proviso that R$_3$, R$_4$ and R$_5$ cannot all be hydrogen;
comprising the steps of starting with a monohalobenzene (49), wherein X may be F, Cl, Br or I; and following a reaction sequence as outlined in FIG. 45 under suitable conditions, wherein
—O-Q represents a good leaving group on reaction with a hydroxy function with retention of the stereochemical configuration of the hydroxy function in the formation of an ether compound; and
—O-J represents a good leaving group on reaction with a nucleophilic reactant with inversion of the stereochemical configuration as shown in FIG. 45 and all the formulae and symbols are as described above.

In another embodiment, the present invention provides a process for the preparation of a stereoisomerically substantially pure compound of formula (79), comprising the steps under suitable conditions as shown in FIG. 46, wherein all the formulae and symbols are as described above. As outlined in FIG. 46, the preparation of a stereoisomerically substantially pure trans aminocyclohexyl ether compound of formula (79) may be carried out by starting with a biotransformation of chlorobenzene (58) to compound (59) by microorganism such as *Pseudomonas putida* 39/D. Experimental conditions for the biotransformation are well established (Organic Synthesis, Vol. 76, 77 and T. Hudlicky et al., Aldrichimica Acta, 1999, 32, 35; and references cited therein). In a separate step, compound (59) is selectively reduced under suitable conditions to compound (60) (e.g., H$_2$—Rh/Al$_2$O$_3$; Boyd et al. JCS Chem. Commun. 1996, 45-46; Ham and Coker, J. Org. Chem. 1964, 29, 194-198; and references cited therein). In another separate step, compound (60) is converted to compound (76) by reaction with compound (63) under appropriate conditions. The trichloroacetimidate (63) is readily prepared from the corresponding alcohol, 3,4-dimethoxyphenethyl alcohol which is commercially available (e.g., Aldrich), by treatment with trichloroacetonitrile. The alkylation of compound (60) by trichloroacetimidate (63) may be carried out in the presence of a Bronsted acid or Lewis acid such as HBF$_4$. The reaction temperature may be adjusted as required to maximize the yields of the desired product. In a separate step, compound (76) is converted to compound (77) by reduction such as hydrogenation and hydrogenolysis in the presence of a catalyst under appropriate conditions. Palladium on activated carbon is one example of the catalysts. The reduction of compound (76) may be conducted under basic conditions e.g., in the presence of a base such as sodium ethoxide, sodium bicarbonate, sodium acetate or calcium carbonate. The base may be added in one portion or incrementally during the course of the reaction. In another separate step, the hydroxy group of compound (77) is converted under suitable conditions into an activated form such as the tosylate (TsO—) of formula (78) (e.g., TsCl in the presence of pyridine). In a separate step, the tosylate group of formula (78) is displaced by an amino compound such as 3R-pyrrolidinol (65) with inversion of configuration. 3R-pyrrolidinol (65) is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (79) at a suitable rate. An excess of the amino compound (65) may be used to maximally convert compound (78) to the product (79). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequence described above (FIG. 46) in general generates the compound of formula (79) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (79) may be carried out under suitable conditions by a process as outlined in FIG. 47, comprising the steps of starting from chlorobenzene (58) and following a reaction sequence analogous to the applicable portion (i.e., from compound (58) to compound (78)) that is described in FIG. 46 above leading to compound of formula (78). The latter is reacted under suitable conditions with an amino compound of formula (65A) wherein Bn represents a benzyl protection group of the hydroxy function of 3S-pyrrolidinol to form compound (80). Compound (65A) is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (80) at a suitable rate. An excess of the amino compound (65A) may be used to maximally convert compound (78) to the product (80). The reaction may be performed in the presence of a base that can facilitate the formation of the product. Generally the additional base is non-nucleophilic in chemical reactivity. The benzyl (Bn) protection group of compound (80) may be removed by standard procedure (e.g., hydrogenation in the presence of a catalyst under appropriate conditions. Palladium on activated carbon is one example of the catalysts. Other suitable conditions are as described in Greene, "Protective Groups in Organic Chemistry", John Wiley & Sons, New York N.Y. (1991)). The product is a stereoisomerically substantially pure trans aminocyclohexyl ether compound of formula (79) and is generally formed as the free base. The free base may be converted, if desired, to the monohydrochloride salt by known methodologies, or alternatively, if desired, to other acid addition salts by reaction with an inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (81) may be carried out under suitable conditions by a process as outlined in FIG. 48, comprising the steps of starting from chlorobenzene (58) and following a reaction sequence analogous to the applicable portion that is described in FIG. 46 above leading to compound of formula (78). The latter is reacted with an amino compound of formula (68). Compound (68), 3S-pyrrolidinol, is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (81) at a suitable rate. An excess of the amino compound (68) may be used to maximally convert compound (78) to the product (81). The reaction may be performed in the presence of a base that can facilitate the formation of the product. Generally the additional base is non-nucleophilic in chemical reactivity. The product is a stereoisomerically substantially pure trans aminocyclohexyl ether compound of formula (81) and is formed as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (81) may be carried out under suitable conditions by a process as outlined in FIG. 49, comprising the steps of starting from chlorobenzene (58) and following a reaction sequence analogous to the applicable portion that is described in FIG. 47 above leading to compound of formula (78). The latter is reacted with an amino compound of formula (70) wherein Bn represents a benzyl protection group of the hydroxy function of 3S-pyrrolidinol to form compound (82). Compound (70) is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (82) at a suitable rate. An excess of the amino compound (70) may be used to maximally convert compound (78) to the product (82). The reaction may be performed in the presence of a base that can facilitate the formation of the product. Generally the additional base is non-nucleophilic in chemical reactivity. The benzyl (Bn) protection group of compound (82) may be removed by standard procedure (e.g., hydrogenation in the presence of a catalyst under appropriate conditions. Palladium on activated carbon is one example of the catalysts. Other suitable conditions are as described in Greene, "Protective Groups in Organic Chemistry", John Wiley & Sons, New York N.Y. (1991)). The product is a stereoisomerically substantially pure trans aminocyclohexyl ether compound of formula (81) and is generally formed as the free base. The free base may be converted, if desired, to the monohydrochloride salt by known methodologies, or alternatively, if desired, to other acid addition salts by reaction with inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (75) may be carried out under suitable conditions by a process as outlined in FIG. 50, comprising the steps of starting with compound of formula (50) and following a reaction sequence analogous to the applicable portion that is described in FIG. 45, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 51, comprising the steps of starting with compound of formula (59) and following a reaction sequence analogous to the applicable portion that is described in FIG. 46, wherein all the formulae and symbols are as described above. 3-Chloro-(1S,2S)-3,5-cyclohexadiene-1,2-diol of formula (59) is a commercially available product (e.g., Aldrich) or synthesized according to published procedure (e.g., *Organic Synthesis*, Vol. 76, 77 and T. Hudlicky et al., *Aldrichimica Acta*, 1999, 32, 35; and references cited therein).

In another embodiment, the preparation of a stereoisomerically substantially pure trans aminocyclohexyl ether compound of formula (79) may be carried out under suitable conditions by a process as outlined in FIG. 52, comprising the steps of starting with compound of formula (59) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 53, comprising the steps of starting with compound of formula (59) and following a reaction sequence analogous to the applicable portion that is described in FIG. 48, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 54, comprising the steps of starting with compound of formula (59) and following a reaction sequence analogous to the applicable portion that is described in FIG. 49, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 55, comprising the steps of starting with compound of formula (51) and following a reaction sequence analogous to the applicable portion that is described in FIG. 45, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 56, comprising the steps of starting with compound of formula (60) and following a reaction sequence analogous to the applicable portion that is described in FIG. 46, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 57, comprising the steps of starting with compound of formula (60) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 58, comprising the steps of starting with compound of formula (60) and following a reaction sequence analogous to the applicable portion that is described in FIG. 48, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 59, comprising the steps of starting with compound of formula (60) and following a reaction sequence analogous to the applicable portion that is described in FIG. 49, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 60, comprising the steps of starting with compound of formula (72) and following a reaction sequence analogous to the applicable portion that is described in FIG. 45, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 61, comprising the steps of starting with compound of formula (76) and following a reaction sequence analogous to the applicable portion that is described in FIG. 46, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 62, comprising the steps of starting with compound of formula (76) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 63, comprising the steps of starting with compound of formula (76) and following a reaction sequence analogous to the applicable portion that is described in FIG. 48, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 64, comprising the steps of starting with compound of formula (76) and following a reaction sequence analogous to the applicable portion that is described in FIG. 49, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 65, comprising the steps of starting with compound of formula (73) and following a reaction sequence analogous to the applicable portion that is described in FIG. 45, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 66, comprising the steps of starting with compound of formula (77) and following a reaction sequence analogous to the applicable portion that is described in FIG. 46, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 67, comprising the steps of starting with compound of formula (77) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 68, comprising the steps of starting with compound of formula (77) and following a reaction sequence analogous to the applicable portion that is described in FIG. 48, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 69, comprising the steps of starting with compound of formula (77) and following a reaction sequence analogous to the applicable portion that is described in FIG. 49, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 70, comprising the steps of starting with compound of formula (74) and following a reaction sequence analogous to the applicable portion that is described in FIG. 45, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 71, comprising the steps of starting with compound of formula (78) and following a reaction sequence analogous to the applicable portion that is described in FIG. 46, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 72, comprising the steps of starting with compound of formula (78) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 73, comprising the steps of starting with compound of formula (78) and following a reaction sequence analogous to the applicable portion that is described in FIG. 48, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 74, comprising the steps of starting with compound of formula (78) and following a reaction sequence analogous to the applicable portion that is described in FIG. 49, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 75, comprising the steps of starting with compound of formula (80) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (81) may be carried out under suitable conditions by a process as outlined in FIG. 76, comprising the steps of starting with compound of formula (82) and following a reaction sequence analogous to the applicable portion that is described in FIG. 49, wherein all the formulae and symbols are as described above.

In another embodiment, the preparation of a stereoisomerically substantially pure compound of formula (74) may be carried out under suitable conditions by a process as outlined in FIG. 77, comprising the steps of starting with compound of formula (49) and following a reaction sequence analogous to the applicable portion that is described in FIG. 45, wherein all the formulae and symbols are as described above.

In another embodiment, the preparation of a stereoisomerically substantially pure compound of formula (78) may be carried out under suitable conditions by a process as outlined in FIG. 78, comprising the steps of starting with compound of formula (58) and following a reaction sequence analogous to the applicable portion that is described in FIG. 46, wherein all the formulae and symbols are as described above.

In another embodiment, the preparation of a stereoisomerically substantially pure trans aminocyclohexyl ether compound of formula (80) may be carried out under suitable conditions by a process as outlined in FIG. 79, comprising the steps of starting with compound of formula (58) and following a reaction sequence analogous to the applicable portion that is described in FIG. 47, wherein all the formulae and symbols are as described above.

In another embodiment, the preparation of a stereoisomerically substantially pure trans aminocyclohexyl ether compound of formula (82) may be carried out under suitable conditions by a process as outlined in FIG. 80, comprising the steps of starting with compound of formula (58) and following a reaction sequence analogous to the applicable portion that is described in FIG. 49, wherein all the formulae and symbols are as described above.

In another embodiment, the preparation of a stereoisomerically substantially pure compound of formula (73) may be carried out under suitable conditions by a process as outlined in FIG. 81, comprising the steps of starting with compound of formula (49) and following a reaction sequence analogous to the applicable portion that is described in FIG. 45, wherein all the formulae and symbols are as described above.

In another embodiment, the preparation of a stereoisomerically substantially pure compound of formula (77) may be carried out under suitable conditions by a process as outlined in FIG. 82, comprising the steps of starting with compound of formula (58) and following a reaction sequence analogous to the applicable portion that is described in FIG. 46, wherein all the formulae and symbols are as described above.

In another embodiment, the preparation of a stereoisomerically substantially pure compound of formula (72) may be carried out under suitable conditions by a process as outlined in FIG. 83, comprising the steps of starting with compound of formula (49) and following a reaction sequence analogous to the applicable portion that is described in FIG. 45, wherein all the formulae and symbols are as described above.

In another embodiment, the preparation of a stereoisomerically substantially pure compound of formula (76) may be carried out under suitable conditions by a process as outlined in FIG. 84, comprising the steps of starting with compound of formula (58) and following a reaction sequence analogous to the applicable portion that is described in FIG. 46, wherein all the formulae and symbols are as described above.

In another embodiment, the present invention provides a compound of formula (72), or a solvate or pharmaceutically acceptable salt thereof; wherein all the formulae and symbols are as described above.

In another embodiment, the present invention provides a compound of formula (73), or a solvate or pharmaceutically acceptable salt thereof; wherein all the formulae and symbols are as described above.

In another embodiment, the present invention provides a compound of formula (73), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (74), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (76), or a solvate or pharmaceutically acceptable salt thereof; wherein all the formulae and symbols are as described above.

In another embodiment, the present invention provides a compound of formula (77), or a solvate or pharmaceutically acceptable salt thereof; wherein all the formulae and symbols are as described above.

In another embodiment, the present invention provides a compound of formula (78), or a solvate or pharmaceutically acceptable salt thereof; wherein all the formulae and symbols are as described above.

In another embodiment, the present invention provides a compound of formula (80), or a solvate or pharmaceutically acceptable salt thereof; wherein all the formulae and symbols are as described above.

The present invention provides synthetic processes whereby compounds of formula (57) with trans-(1R,2R) configuration for the ether and amino functional groups may be prepared in stereoisomerically substantially pure form. Compound of formula (66) is an example represented by formula (57). The present invention also provides synthetic processes whereby compounds of formula (75) with trans-(1S,2S) configuration for the ether and amino functional groups may be prepared in stereoisomerically substantially pure form. Compound of formula (79) is an example represented by formula (75). The present invention further provides synthetic processes whereby compounds of formulae (85), (86), (55) and (74) may be synthesized in stereoisomerically substantially pure forms. Compounds (62) and (90) are examples of formula (85). Compounds (87) and (89) are examples of formula (86). Compound (64) is an example of formula (55). Compound (78) is an example of formula (74). The aminocyclohexyl ether compounds of the present invention may be used for medical applications, including, for example, cardiac arrhythmia, such as atrial arrhythmia and ventricular arrhythmia.

As outlined in FIG. 85, the preparation of a stereoisomerically substantially pure trans aminocyclohexyl ether compound of formula (57) may be carried out by following a process starting from a racemic mixture of meso-cis-1,2-cyclohexandiol (83). Compound (83) is commercially available (e.g., Sigma-Aldrich, St. Louis, Mo.) or can be readily synthesized by published methods (e.g., J. E. Taylor et al., *Org. Process Res. & Dev.*, 1998, 2, 147; *Organic Syntheses*, CV6, 342).

In a first step, one of the hydroxy groups of compound (83) is converted under suitable conditions into an activated form as represented by the racemic mixture comprised of formulae (53) and (84). An "activated form" as used herein means that the hydroxy group is converted into a good leaving group (—O-J) which on reaction with an appropriate nucleophile will result in a substitution product with inversion of the stereochemical configuration. The leaving group may be any suitable leaving group on reaction with a nucleophilic reactant with inversion of stereochemical configuration known in the art, including but not limited to compounds disclosed in M. B. Smith and J. March in "March's Advanced Organic Chemistry", Fifth edition, Chapter 10, John Wiley & Sons, Inc., New York, N.Y. (2001). Specific examples of such leaving groups include a mesylate (MsO—) group, a tosylate group (TsO—), a 2-bromophenylsulfonate group, a 4-bromophenylsulfonate group or a nosylate (NsO—) group. The hydroxy group may also be converted into other suitable leaving groups according to procedures well known in the art, using any suitable activating agent, including but not limited to those disclosed in M. B. Smith and J. March in "March's Advanced Organic Chemistry", Fifth edition, Chapter 10, John Wiley & Sons, Inc., New York, N.Y. (2001). In a typical reaction for the formation of a tosylate, compound (83) is treated with a controlled amount of hydroxy activating reagent such as tosyl chloride (TsCl) in the presence of a base, such as pyridine or triethylamine. The reaction may be monitored and is generally satisfactorily conducted at about 0° C., but conditions may be adjusted as required to maximize the yields of the desired product. The addition of other reagents to facilitate the formation of the monotosylates may be advantageously employed (e.g., M. J. Martinelli, et al. "Selective monosulfonylation of internal 1,2-diols catalyzed by di-n-butyltin oxide" *Tetrahedron Letters*, 2000, 41, 3773). The racemic mixture comprises of formulae (53) and (84) is then subjected to a resolution process whereby the two optically active isomers are separated into products that are in stereoisomerically substantially pure form such as (85) and (86), wherein G and $G_1$ are independently selected from hydrogen, $C_1$-$C_8$acyl, or any other suitable functional groups that are introduced as part of the resolution process necessary for the separation of the two isomers. In some situations it may be adequate that the resolution process produces compounds of (85) and (86) of sufficient enrichment in their optical purity for application in the subsequent steps of the synthetic process. Methods for resolution of racemic mixtures are well know in the art (e.g., E. L. Eliel and S. H. Wilen, in *Stereochemistry of Organic Compounds*; John Wiley & Sons: New York, 1994; Chapter 7, and references cited therein). Suitable processes such as enzymatic resolution (e.g., lipase mediated) and chromatographic separation (e.g., HPLC with chiral stationary phase and/or with simulated moving bed technology) are some of the examples that may be applied.

For compound of formula (85) when G is hydrogen, (85) is the same as compound (53) and in a separate reaction step, alkylation of the free hydroxy group in compound (85) to form compound (55) is carried out under appropriate conditions with compound (54), where —O-Q represents a good leaving group on reaction with a hydroxy function with retention of the stereochemical configuration of the hydroxy function in the formation of an ether compound. The leaving group may be any suitable leaving group known in the art, including but not limited to compounds disclosed in Greene, "Protective Groups in Organic Chemistry", John Wiley & Sons, New York N.Y. (1991). Specific examples of -O-Q groups include trichloroacetimidate. For some compound (54), it may be necessary to introduce appropriate protection groups prior to this step being performed. Suitable protecting groups are set forth in, for example, Greene, "Protective Groups in Organic Chemistry", John Wiley & Sons, New York N.Y. (1991). For compound of formula (85) when G is not hydrogen, suitable methods are used to convert (85) to compound (53). For example when G is a $C_2$ acyl function, a mild based-catalyzed methanolysis (G. Zemplen et al., Ber., 1936, 69, 1827) may be used to transform (85) to (53). The latter can then undergo the same reaction with (54) to produce (55) as described above.

In a separate step, the resulted compound (55) is treated under suitable conditions with an amino compound of formula (56) to form compound (57) as the product. The reaction may be carried out with or without a solvent and at an appropriate temperature range that allows the formation of the product (57) at a suitable rate. An excess of the amino compound (56) may be used to maximally convert compound (55) to the product (57). The reaction may be performed in the presence of a base that can facilitate the formation of the product. Generally the base is non-nucleophilic in chemical reactivity. When the reaction has proceeded to substantial completion, the product is recovered from the reaction mixture by conventional organic chemistry techniques, and is purified accordingly. Protective groups may be removed at the appropriate stage of the reaction sequence. Suitable methods are set forth in, for example, Greene, "Protective. Groups in Organic Chemistry", John Wiley & Sons, New York N.Y. (1991).

The reaction sequence described above (FIG. 85) generates the compound of formula (57) as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

In one embodiment, the present invention provides a process for the preparation of a stereoisomerically substantially pure compound of formula (57):

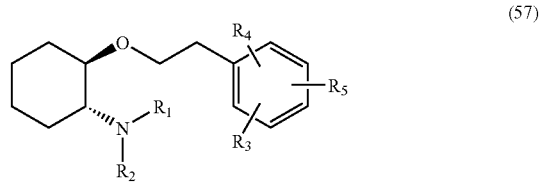

(57)

wherein $R_1$ and $R_2$, when taken together with the nitrogen atom to which they are directly attached in formula (57), form a ring denoted by formula (II):

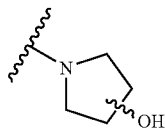

(II)

and $R_3$, $R_4$ and $R_5$ are independently selected from hydrogen, hydroxy and $C_1$-$C_6$alkoxy, with the proviso that $R_3$, $R_4$ and $R_5$ cannot all be hydrogen;

comprising the steps of starting with a monohalobenzene (49), wherein X may be F, Cl, Br or I; and following a reaction sequence as outlined in FIG. 45 under suitable conditions, wherein —O-Q represents a good leaving group on reaction with a hydroxy function with retention of the stereochemical configuration of the hydroxy function in the formation of an ether compound; and —O-J represents a good leaving group on reaction with a nucleophilic reactant with inversion of the stereochemical configuration as shown in FIG. 45 and all the formulae and symbols are as described above, comprising the steps of starting with a compound of formula (83), and following a reaction sequence as outlined in FIG. 85 under suitable conditions, wherein G and $G_1$ are independently selected from hydrogen, $C_1$-$C_8$acyl, or any other suitable functional groups that are introduced as part of the resolution process necessary for the separation of the two isomers;

—O-Q represents a good leaving group on reaction with a hydroxy function with retention of the stereochemical configuration of the hydroxy function in the formation of an ether compound, including, but not limited to, those disclosed in "Protective Groups in Organic Chemistry", John Wiley & Sons, New York N.Y. (1991); and —O-J represents a good leaving group on reaction with a nucleophilic reactant with inversion of the stereochemical configuration, including, but not limited to, those disclosed in "Protective Groups in Organic Chemistry", John Wiley & Sons, New York N.Y. (1991), as shown in FIG. 85 and all the formulae and symbols are as described above.

In another embodiment, the present invention provides a process for the preparation of a stereoisomerically substantially pure compound of formula (66), comprising the steps under suitable conditions as shown in FIG. 86, wherein all the formulae and symbols are as described above. As outlined in FIG. 86, the preparation of a stereoisomerically substantially pure trans aminocyclohexyl ether compound of formula (66) may be carried out by starting with the monotosylation of cis-1,2-cyclohexandiol (83) with TsCl in the presence of $Bu_2SnO$ and triethylamine under suitable conditions (M. J. Martinelli, et al. "Selective monosulfonylation of internal 1,2-diols catalyzed by di-n-butyltin oxide" *Tetrahedron Letters*, 2000, 41, 3773). Initial non-optimized yields of 80-90% have been achieved, and further optimization is being pursued. The resulting racemic mixture of hydroxytosylates comprises of compounds (62) and (87) is subjected to a lipase-mediated resolution process under suitable conditions such as treatment of the racemates (62) and (87) with vinyl acetate (88) in the presence of a lipase derived from *Pseudomonas* sp. (N. Boaz et al., *Tetra. Asymmetry*, 1994, 5, 153) to provide compound (62) and (89). In a separate step, the stereoisomerically substantially pure compound of formula (62) obtained from the resolution process is alkylated under appropriate conditions by treatment with the trichloroacetimidate (63) to form compound (64). Initial non-optimized yields of 60-70% have been achieved, and further optimization is being pursued. The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (62) by trichloroacetimidate (63) may be carried out in the presence of a Lewis acid such as $HBF_4$.

In another separate step, the tosylate group of formula (64) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., Chem. Ber./Recueil 1997, 130, 385-397). The reaction may be carried out with or without a solvent and at an appropriate temperature range that allows the formation of the product (66) at a suitable rate. An excess of the amino compound (65) may be used to maximally convert compound (64) to the product (66). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly. Initial non-optimized yields of approximately 40% have been achieved, and further optimization is being pursued.

In another embodiment, the preparation of a stereoisomerically substantially pure trans aminocyclohexyl ether compound of formula (66) may be carried out under suitable conditions by a process as outlined in FIG. 87, comprising the steps under suitable conditions as shown in FIG. 87, wherein all the formulae and symbols are as described above. As outlined in FIG. 87, the preparation of a stereoisomerically substantially pure trans aminocyclohexyl ether compound of formula (66) may be carried out by starting with the monotosylation of the cis-1,2-cyclohexandiol (83) with TsCl in the presence of $Bu_2SnO$ and triethylamine under suitable conditions (M. J. Martinelli, et al. "Selective monosulfonylation of internal 1,2-diols catalyzed by di-n-butyltin oxide" *Tetrahedron Letters*, 2000, 41, 3773). The resulting racemic mixture of hydroxytosylates comprises of compounds (62) and (87) is subjected to a lipase-mediated resolution process under suitable conditions such as treatment of the racemates (62) and (87) with vinyl acetate (88) in the presence of a lipase derived from *Pseudomonas* sp. (N. Boaz et al., *Tetra. Asymmetry*, 1994, 5, 153) to provide compound (90) and (87).

In a separate step, the stereoisomerically substantially pure compound of formula (90) obtained from the resolution process is subjected to a mild based-catalyzed methanolysis (G. Zemplen et al., Ber., 1936, 69, 1827) to form compound (62). The latter is alkylated under appropriate conditions by treatment with the trichloroacetimidate (63) to form compound (64). The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (88) by trichloroacetimidate (63) may be carried out in the presence of a Lewis acid such as $HBF_4$.

In another separate step, the tosylate group of formula (64) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., Chem. Ber./Recueil 1997, 130, 385-397). The reaction may be carried out with or without a solvent and at an appropriate temperature range that allows the formation of the product (66) at a suitable rate. An excess of the amino compound (65) may be used to maximally convert compound (64) to the product (66). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

In another embodiment, the present invention provides a process for the preparation of a stereoisomerically substantially pure compound of formula (66), comprising the steps under suitable conditions as shown in FIG. 88, wherein all the formulae and symbols are as described above. As outlined in FIG. 88, the preparation of a stereoisomerically substantially pure trans aminocyclohexyl ether compound of formula (66) may be carried out by starting with the monotosylation of the cis-1,2-cyclohexandiol (83) with TsCl in the presence of $Bu_2SnO$ and triethylamine under suitable conditions (M. J. Martinelli, et al. "Selective monosulfonylation of internal 1,2-diols catalyzed by di-n-butyltin oxide" *Tetrahedron Letters,* 2000, 41, 3773). The resulting racemic mixture of hydroxytosylates comprises of compounds (62) and (87) is subjected to a chromatographic resolution process under suitable conditions such as HPLC with an appropriate chiral stationary phase and simulated moving bed technology to provide compounds (62) and (87) in stereoisomerically substantially pure form.

In a separate step, the stereoisomerically substantially pure compound of formula (62) obtained from the resolution process is alkylated under appropriate conditions by treatment with the trichloroacetimidate (63) to form compound (64). The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (62) by trichloroacetimidate (63) may be carried out in the presence of a Lewis acid such as $HBF_4$.

In another separate step, the tosylate group of formula (64) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., Chem. Ber./Recueil 1997, 130, 385-397). The reaction may be carried out with or without a solvent and at an appropriate temperature range that allows the formation of the product (66) at a suitable rate. An excess of the amino compound (65) may be used to maximally convert compound (64) to the product (66). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequences described above (FIG. 86, FIG. 87 and FIG. 88) in general generate the compound of formula (66) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (57) may be carried out under suitable conditions by a process as outlined in FIG. 89, comprising the steps of starting with a racemic mixture comprises of formulae (53) and (84) and following a reaction sequence analogous to the applicable portion that is described in FIG. 85, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 90, comprising the steps of starting with a racemic mixture comprises of formulae (62) and (87) and following a reaction sequence analogous to the applicable portion that is described in FIG. 86, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 91, comprising the steps of starting with a racemic mixture comprises of formulae (62) and (87) and following a reaction sequence analogous to the applicable portion that is described in FIG. 87, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 92, comprising the steps of starting with a racemic mixture comprises of formulae (62) and (87) and following a reaction sequence analogous to the applicable portion that is described in FIG. 88, wherein all the formulae and symbols are as described above.

In another embodiment, the preparation of a stereoisomerically substantially pure trans aminocyclohexyl ether compound of formula (57) may be carried out under suitable conditions by a process as outlined in FIG. 93, comprising the steps of starting with a compound of formula (85) where G is not hydrogen and following a reaction sequence analogous to the applicable portion that is described in FIG. 85, wherein all the formulae and symbols are as described above.

In another embodiment, the preparation of a stereoisomerically substantially pure trans aminocyclohexyl ether compound of formula (66) may be carried out under suitable conditions by a process as outlined in FIG. 94, comprising the steps of starting with a compound of formula (90) and following a reaction sequence analogous to the applicable portion that is described in FIG. 87, wherein all the formulae and symbols are as described above.

In another embodiment, the preparation of a stereoisomerically substantially pure compound of formula (55) may be carried out under suitable conditions by a process as outlined in FIG. 95, comprising the steps of starting with compound of formula (83) and following a reaction sequence analogous to the applicable portion that is described in FIG. 85, wherein all the formulae and symbols are as described above.

In another embodiment, the preparation of a stereoisomerically substantially pure compound of formula (55) may be carried out under suitable conditions by a process as outlined in FIG. 96, comprising the steps of starting with compound of formula (83) and following a reaction sequence analogous to the applicable portion that is described in FIG. 85, wherein all the formulae and symbols are as described above.

In another embodiment, the preparation of a stereoisomerically substantially pure compound of formula (64) may be carried out under suitable conditions by a process as outlined in FIG. 97, comprising the steps of starting with compound of formula (83) and following a reaction sequence analogous to the applicable portion that is described in FIG. 86, wherein all the formulae and symbols are as described above.

In another embodiment, the preparation of a stereoisomerically substantially pure compound of formula (64) may be carried out under suitable conditions by a process as outlined in FIG. 98, comprising the steps of starting with compound of formula (83) and following a reaction sequence analogous to the applicable portion that is described in FIG. 87, wherein all the formulae and symbols are as described above.

In another embodiment, the preparation of a stereoisomerically substantially pure compound of formula (64) may be carried out under suitable conditions by a process as outlined in FIG. 99, comprising the steps of starting with compound of formula (83) and following a reaction sequence analogous to the applicable portion that is described in FIG. 88, wherein all the formulae and symbols are as described above.

In another embodiment, the preparation of stereoisomerically substantially pure compounds of formulae (85) and (86) may be carried out under suitable conditions by a process as outlined in FIG. 100, comprising the steps of starting with compound of formula (83) and following a reaction sequence analogous to the applicable portion that is described in FIG. 85, wherein all the formulae and symbols are as described above.

In another embodiment, the preparation of stereoisomerically substantially pure compounds of formulae (62) and (89) may be carried out under suitable conditions by a process as outlined in FIG. 101, comprising the steps of starting with compound of formula (83) and following a reaction sequence analogous to the applicable portion that is described in FIG. 86, wherein all the formulae and symbols are as described above.

In another embodiment, the preparation of stereoisomerically substantially pure compounds of formulae (90) and (87) may be carried out under suitable conditions by a process as outlined in FIG. 102, comprising the steps of starting with compound of formula (83) and following a reaction sequence analogous to the applicable portion that is described in FIG. 87, wherein all the formulae and symbols are as described above.

In another embodiment, the preparation of stereoisomerically substantially pure compounds of formulae (62) and (87) may be carried out under suitable conditions by a process as outlined in FIG. 103, comprising the steps of starting with compound of formula (83) and following a reaction sequence analogous to the applicable portion that is described in FIG. 88, wherein all the formulae and symbols are as described above.

In another embodiment, the present invention further provides synthetic processes whereby compounds of formula (75) with trans-(1S,2S) configuration for the ether and amino functional groups may be prepared in stereoisomerically substantially pure form. As outlined in FIG. 104, the preparation of a stereoisomerically substantially pure trans aminocyclohexyl ether compound of formula (75) may be carried out by following a process starting from a racemic mixture of meso-cis-1,2-cyclohexandiol (83). Compound (83) is commercially available (e.g., Sigma-Aldrich, St. Louis, Mo.) or can be readily synthesized by published methods (e.g., J. E. Taylor et al., *Org. Process Res. & Dev.*, 1998, 2, 147; *Organic Syntheses*, CV6, 342).

In a first step, one of the hydroxy groups of compound (83) is converted under suitable conditions into an activated form as represented by the racemic mixture comprised of formulae (53) and (84). An "activated form" as used herein means that the hydroxy group is converted into a good leaving group (—O-J) which on reaction with an appropriate nucleophile will result in a substitution product with inversion of the stereochemical configuration. The leaving group may be any suitable leaving group on reaction with a nucleophilic reactant with inversion of stereochemical configuration known in the art, including but not limited to compounds disclosed in M. B. Smith and J. March in "March's Advanced Organic Chemistry", Fifth edition, Chapter 10, John Wiley & Sons, Inc., New York, N.Y. (2001). Specific examples of such leaving groups include a mesylate (MsO—) group, a tosylate group (TsO—), a 2-bromophenylsulfonate group, a 4-bromophenylsulfonate group or a nosylate (NsO—) group. The hydroxy group may also be converted into other suitable leaving groups according to procedures well known in the art, using any suitable activating agent, including but not limited to those disclosed in M. B. Smith and J. March in "March's Advanced Organic Chemistry", Fifth edition, Chapter 10, John Wiley & Sons, Inc., New York, N.Y. (2001). In a typical reaction for the formation of a tosylate, compound (83) is treated with a controlled amount of hydroxy activating reagent such as tosyl chloride (TsCl) in the presence of a base, such as pyridine or triethylamine. The reaction may be monitored and is generally satisfactorily conducted at about 0° C., but conditions may be adjusted as required to maximize the yields of the desired product. The addition of other reagents to facilitate the formation of the monotosylates may be advantageously employed (e.g., M. J. Martinelli, et al. "Selective monosulfonylation of internal 1,2-diols catalyzed by di-n-butyltin oxide" *Tetrahedron Letters*, 2000, 41, 3773). The racemic mixture comprises of formulae (53) and (84) is then subjected to a resolution process whereby the two optically active isomers are separated into products that are in stereoisomerically substantially pure form such as (85) and (86), wherein G and $G_1$ are independently selected from hydrogen, $C_1$-$C_8$acyl, or any other suitable functional groups that are introduced as part of the resolution process necessary for the separation of the two isomers. In some situations it may be adequate that the resolution process produces compounds of (85) and (86) of sufficient enrichment in their optical purity for application in the subsequent steps of the synthetic process. Methods for resolution of racemic mixtures are well know in the art (e.g., E. L. Eliel and S. H. Wilen, in *Stereochemistry of Organic Compounds*; John Wiley & Sons: New York, 1994; Chapter 7, and references cited therein). Suitable processes such as enzymatic resolution (e.g., lipase mediated) and chromatographic separation (e.g., HPLC with chiral stationary phase and/or with simulated moving bed technology) are some of the methods that may be applied.

For compound of formula (86) when $G_1$ is hydrogen, (86) is the same as compound (84) and in a separate reaction step, alkylation of the free hydroxy group in compound (86) to form compound (74) is carried out under appropriate conditions with compound (54), where —O-Q represents a good leaving group on reaction with a hydroxy function with retention of the stereochemical configuration of the hydroxy function in the formation of an ether compound. The leaving group may be any suitable leaving group known in the art, including but not limited to compounds disclosed in Greene, "Protective Groups in Organic Chemistry", John Wiley & Sons, New York N.Y. (1991). Trichloroacetimidate is one example for the —O-Q function. For some compound (54), it may be necessary to introduce appropriate protection groups prior to this step being performed. Suitable protecting groups are set forth in, for example, Greene, "Protective Groups in Organic Chemistry", John Wiley & Sons, New York N.Y.

(1991). For compound of formula (86) when $G_1$ is not hydrogen, suitable methods are used to convert (86) to compound (84). For example when $G_1$ is a $C_2$ acyl function, a mild based-catalyzed methanolysis (G. Zemplen et al., *Ber.*, 1936, 69, 1827) may be used to transform (86) to (84). The latter can then undergo the same reaction with (54) to produce (74) as described above.

In a separate step, the resulted compound (74) is treated under suitable conditions with an amino compound of formula (56) to form compound (75) as the product. The reaction may be carried out with or without a solvent and at an appropriate temperature range that allows the formation of the product (75) at a suitable rate. An excess of the amino compound (56) may be used to maximally convert compound (74) to the product (75). The reaction may be performed in the presence of a base that can facilitate the formation of the product. Generally the base is non-nucleophilic in chemical reactivity. When the reaction has proceeded to substantial completion, the product is recovered from the reaction mixture by conventional organic chemistry techniques, and is purified accordingly. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (FIG. 104) generates the compound of formula (75) as the free base. The free base may be converted, if desired, to the monohydrochloride salt by known methodologies, or alternatively, if desired, to other acid addition salts by reaction with an inorganic or organic acid under appropriate conditions. Acid addition salts can also be prepared metathetically by reaction of one acid addition salt with an acid that is stronger than that giving rise to the initial salt.

In one embodiment, the present invention provides a process for the preparation of a stereoisomerically substantially pure compound of formula (75):

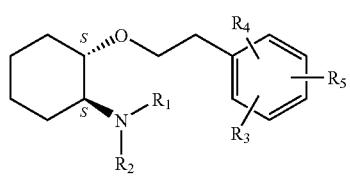

wherein $R_1$ and $R_2$, when taken together with the nitrogen atom to which they are directly attached in formula (75), form a ring denoted by formula (II):

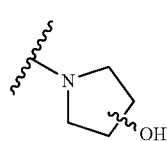

and $R_3$, $R_4$ and $R_5$ are independently selected from hydrogen, hydroxy and $C_1$-$C_6$alkoxy, with the proviso that $R_3$, $R_4$ and $R_5$ cannot all be hydrogen;

comprising the steps of starting with a compound of formula (83), and following a reaction sequence as outlined in FIG. 104 under suitable conditions, wherein G and $G_1$ are independently selected from hydrogen, $C_1$-$C_8$acyl, or any other suitable functional groups that are introduced as part of the resolution process necessary for the separation of the two isomers;

—O-Q represents a good leaving group on reaction with a hydroxy function with retention of the stereochemical configuration of the hydroxy function in the formation of an ether compound, including, but not limited to, those disclosed in "Protective Groups in Organic Chemistry", John Wiley & Sons, New York N.Y. (1991); and —O-J represents a good leaving group on reaction with a nucleophilic reactant with inversion of the stereochemical configuration, including, but not limited to, those disclosed in "Protective Groups in Organic Chemistry", John Wiley & Sons, New York N.Y. (1991), as shown in FIG. 104 and all the formulae and symbols are as described above.

In another embodiment, the present invention provides a process for the preparation of a stereoisomerically substantially pure compound of formula (79), comprising the steps under suitable conditions as shown in FIG. 105, wherein all the formulae and symbols are as described above. As outlined in FIG. 105, the preparation of a stereoisomerically substantially pure trans aminocyclohexyl ether compound of formula (79) may be carried out by starting with the monotosylation of cis-1,2-cyclohexandiol (83) with TsCl in the presence of $Bu_2SnO$ and triethylamine under suitable conditions (M. J. Martinelli, et al. "Selective monosulfonylation of internal 1,2-diols catalyzed by di-n-butyltin oxide" *Tetrahedron Letters*, 2000, 41, 3773). The resulting racemic mixture of hydroxytosylates comprises of compounds (62) and (87) is subjected to a lipase-mediated resolution process under suitable conditions such as treatment of the racemates (62) and (87) with vinyl acetate (88) in the presence of a lipase derived from *Pseudomonas* sp. (N. Boaz et al., *Tetra. Asymmetry*, 1994, 5, 153) to provide compound (87) and (90). In a separate step, the stereoisomerically substantially pure compound of formula (87) obtained from the resolution process is alkylated under appropriate conditions by treatment with the trichloroacetimidate (63) to form compound (78). The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (87) by trichloroacetimidate (63) may be carried out in the presence of a Lewis acid such as $HBF_4$.

In another separate step, the tosylate group of formula (78) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., *Chem. Ber./Recueil* 1997, 130, 385-397). The reaction may be carried out with or without a solvent and at an appropriate temperature range that allows the formation of the product (79) at a suitable rate. An excess of the amino compound (65) may be used to maximally convert compound (78) to the product (79). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

In another embodiment, the preparation of a stereoisomerically substantially pure trans aminocyclohexyl ether compound of formula (79) may be carried out under suitable conditions by a process as outlined in FIG. 106, comprising the steps under suitable conditions as shown in FIG. 106, wherein all the formulae and symbols are as described above. As outlined in FIG. 106, the preparation of a stereoisomerically substantially pure trans aminocyclohexyl ether compound of formula (79) may be carried out by starting with the monotosylation of the cis-1,2-cyclohexandiol (83) with TsCl in the presence of Bu$_2$SnO and triethylamine under suitable conditions (M. J. Martinelli, et al. "Selective monosulfonylation of internal 1,2-diols catalyzed by di-n-butyltin oxide" *Tetrahedron Letters*, 2000, 41, 3773). The resulting racemic mixture of hydroxytosylates comprises of compounds (62) and (87) is subjected to a lipase-mediated resolution process under suitable conditions such as treatment of the racemates (62) and (87) with vinyl acetate (88) in the presence of a lipase derived from *Pseudomonas* sp. (N. Boaz et al., *Tetra. Asymmetry*, 1994, 5, 153) to provide compound (89) and (62).

In a separate step, the stereoisomerically substantially pure compound of formula (89) obtained from the resolution process is subjected to a mild based-catalyzed methanolysis (G. Zemplen et al., *Ber.,* 1936, 69, 1827) to form compound (87). The latter is alkylated under appropriate conditions by treatment with the trichloroacetimidate (63) to form compound (78). The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (87) by trichloroacetimidate (63) may be carried out in the presence of a Lewis acid such as HBF$_4$.

In another separate step, the tosylate group of formula (78) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., Chem. Ber./Recueil 1997, 130, 385-397). The reaction may be carried out with or without a solvent and at an appropriate temperature range that allows the formation of the product (79) at a suitable rate. An excess of the amino compound (65) may be used to maximally convert compound (78) to the product (79). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

In another embodiment, the present invention provides a process for the preparation of a stereoisomerically substantially pure compound of formula (79), comprising the steps under suitable conditions as shown in FIG. 107, wherein all the formulae and symbols are as described above. As outlined in FIG. 107, the preparation of a stereoisomerically substantially pure trans aminocyclohexyl ether compound of formula (79) may be carried out by starting with the monotosylation of the cis-1,2-cyclohexandiol (83) with TsCl in the presence of Bu$_2$SnO and triethylamine under suitable conditions (M. J. Martinelli, et al. "Selective monosulfonylation of internal 1,2-diols catalyzed by di-n-butyltin oxide" Tetrahedron Letters, 2000, 41, 3773). The resulting racemic mixture of hydroxytosylates comprises of compounds (62) and (87) is subjected to a chromatographic resolution process under suitable conditions such as HPLC with an appropriate chiral stationary phase and simulated moving bed technology to provide compounds (62) and (87) in stereoisomerically substantially pure form.

In a separate step, the stereoisomerically substantially pure compound of formula (87) obtained from the resolution process is alkylated under appropriate conditions by treatment with the trichloroacetimidate (63) to form compound (64). The trichloroacetimidate (63) is readily prepared from the corresponding alcohol, 3,4-dimethoxyphenethyl alcohol which is commercially available (e.g., Sigma-Aldrich, St. Louis, Mo.), by treatment with trichloroacetonitrile. The alkylation of compound (87) by trichloroacetimidate (63) may be carried out in the presence of a Lewis acid such as HBF$_4$.

In another separate step, the tosylate group of formula (78) is displaced by an amino compound such as 3R-pyrrolidinol (65) with inversion of configuration. 3R-pyrrolidinol (65) is commercially available (e.g., Sigma-Aldrich, St. Louis, Mo.) or may be prepared according to published procedure (e.g., Chem. Ber./Recueil 1997, 130, 385-397). The reaction may be carried out with or without a solvent and at an appropriate temperature range that allows the formation of the product (79) at a suitable rate. An excess of the amino compound (65) may be used to maximally convert compound (78) to the product (79). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequences described above (FIG. 105, FIG. 106 and FIG. 107) in general generate the compound of formula (79) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (75) may be carried out under suitable conditions by a process as outlined in FIG. 108, comprising the steps of starting with a racemic mixture comprises of formulae (53) and (84) and following a reaction sequence analogous to the applicable portion that is described in FIG. 104, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 109, comprising the steps of starting with a racemic mixture comprises of formulae (62) and (87) and following a reaction sequence analogous to the applicable portion that is described in FIG. 105, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 110, comprising the steps of starting with a racemic mixture comprises of formulae (62) and (87) and following a reaction sequence analogous to the applicable portion that is described in FIG. 106, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 111, comprising the steps of starting with a racemic mixture comprises of formulae (62) and (87) and following a reaction sequence analogous to the applicable portion that is described in FIG. 107, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 112, comprising the steps of starting with a compound of formula (86) where $G_1$ is hydrogen and following a reaction sequence analogous to the applicable portion that is described in FIG. 104, wherein all the formulae and symbols are as described above.

In another embodiment, the preparation of a stereoisomerically substantially pure trans aminocyclohexyl ether compound of formula (75) may be carried out under suitable conditions by a process as outlined in FIG. 113, comprising the steps of starting with a compound of formula (86) where $G_1$ is not hydrogen and following a reaction sequence analogous to the applicable portion that is described in FIG. 104, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 114, comprising the steps of starting with a compound of formula (87) and following a reaction sequence analogous to the applicable portion that is described in FIG. 105, wherein all the formulae and symbols are as described above.

In another embodiment, the preparation of a stereoisomerically substantially pure trans aminocyclohexyl ether compound of formula (79) may be carried out under suitable conditions by a process as outlined in FIG. 115, comprising the steps of starting with a compound of formula (89) and following a reaction sequence analogous to the applicable portion that is described in FIG. 106, wherein all the formulae and symbols are as described above.

In another embodiment, the preparation of a stereoisomerically substantially pure compound of formula (74) may be carried out under suitable conditions by a process as outlined in FIG. 116, comprising the steps of starting with compound of formula (83) and following a reaction sequence analogous to the applicable portion that is described in FIG. 104, wherein all the formulae and symbols are as described above.

In another embodiment, the preparation of a stereoisomerically substantially pure compound of formula (74) may be carried out under suitable conditions by a process as outlined in FIG. 117, comprising the steps of starting with compound of formula (83) and following a reaction sequence analogous to the applicable portion that is described in FIG. 104, wherein all the formulae and symbols are as described above.

In another embodiment, the preparation of a stereoisomerically substantially pure compound of formula (78) may be carried out under suitable conditions by a process as outlined in FIG. 118, comprising the steps of starting with compound of formula (83) and following a reaction sequence analogous to the applicable portion that is described in FIG. 105, wherein all the formulae and symbols are as described above.

In another embodiment, the preparation of a stereoisomerically substantially pure compound of formula (78) may be carried out under suitable conditions by a process as outlined in FIG. 119, comprising the steps of starting with compound of formula (83) and following a reaction sequence analogous to the applicable portion that is described in FIG. 106, wherein all the formulae and symbols are as described above.

In another embodiment, the preparation of a stereoisomerically substantially pure compound of formula (78) may be carried out under suitable conditions by a process as outlined in FIG. 120, comprising the steps of starting with compound of formula (83) and following a reaction sequence analogous to the applicable portion that is described in FIG. 107, wherein all the formulae and symbols are as described above.

In another embodiment, the present invention provides a compound of formula (85), or a solvate or pharmaceutically acceptable salt thereof; wherein all the formulae and symbols are as described above.

In another embodiment, the present invention provides a compound of formula (86), or a solvate or pharmaceutically acceptable salt thereof; wherein all the formulae and symbols are as described above.

In another embodiment, the present invention provides a compound of formula (54), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (55), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (87), or a solvate or pharmaceutically acceptable salt thereof; wherein all the formulae and symbols are as described above.

In another embodiment, the present invention, provides a compound of formula (62), or a solvate or pharmaceutically acceptable salt thereof; wherein all the formulae and symbols are as described above.

In another embodiment, the present invention provides a compound of formula (89), or a solvate or pharmaceutically acceptable salt thereof; wherein all the formulae and symbols are as described above.

In another embodiment, the present invention provides a compound of formula (90), or a solvate or pharmaceutically acceptable salt thereof; wherein all the formulae and symbols are as described above.

In another embodiment, the present invention provides a compound of formula (64), or a solvate or pharmaceutically acceptable salt thereof; wherein all the formulae and symbols are as described above.

In another embodiment, the present invention provides a compound of formula (74), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (78), or a solvate or pharmaceutically acceptable salt thereof; wherein all the formulae and symbols are as described above.

In one embodiment, the present invention provides a process for the preparation of a stereoisomerically substantially pure compound of formula (57):

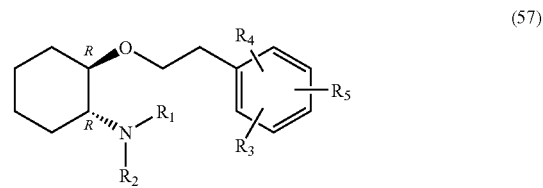

(57)

wherein $R_1$ and $R_2$, when taken together with the nitrogen atom to which they are directly attached in formula (57), form a ring denoted by formula (II):

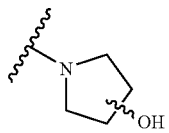

(II)

and $R_3$, $R_4$ and $R_5$ are independently selected from hydrogen, hydroxy and $C_1$-$C_6$alkoxy, with the proviso that $R_3$, $R_4$ and $R_5$ cannot all be hydrogen;

comprising the steps of starting with a monohalobenzene (49), wherein X may be F, Cl, Br or I; and following a reaction sequence as outlined in FIG. 121 under suitable conditions, wherein Pro represents the appropriate protecting group of the hydroxy function with retention of stereochemistry;

—O-Q represents a good leaving group on reaction with a hydroxy function with retention of the stereochemical configuration of the hydroxy function in the formation of an ether compound; and —O-J represents a good leaving group on reaction with a nucleophilic reactant with inversion of the stereochemical configuration as illustrated in FIG. 121 and all the formulae and symbols are as described above.

In another embodiment, the present invention provides a process for the preparation of a stereoisomerically substantially pure compound of formula (66), comprising the steps under suitable conditions as shown in FIG. 122, wherein all the formulae and symbols are as described above. As outlined in FIG. 122, the preparation of a stereoisomerically substantially pure trans aminocyclohexyl ether compound of formula (66) may be carried out by starting with a biotransformation of chlorobenzene (58) to compound (59) by microorganism such as *Pseudomonas putida* 39/D. Experimental conditions for the biotransformation are well established (Organic Synthesis, Vol. 76, 77 and T. Hudlicky et al., *Aldrichimica Acta*, 1999, 32, 35; and references cited therein). In a separate step, the less hindered hydroxy function in compound (59) is selectively monosilylated as compound (95) by reaction with silylating reagent such as t-butyldiphenylsilyl chloride (TBDPSCl) under suitable conditions (e.g., imaidazole in $CH_2Cl_2$) (T. Hudlicky et al., *Aldrichimica Acta*, 1999, 32, 35; S. M. Brown and T. Hudlicky, In Organic Synthesis: Theory and Applications; T. Hudlicky, Ed.; JAI Press: Greenwich, Conn., 1993; Vol. 2, p 113; and references cited therein). In another separate step, compound (95) is converted to compound (96) by reduction such as hydrogenation and hydrogenolysis in the presence of a catalyst under appropriate conditions. Palladium on activated carbon is one example of the catalysts. The reduction of compound (95) may be conducted under basic conditions, e.g., in the presence of a base such as sodium ethoxide, sodium bicarbonate, sodium acetate or calcium carbonate. The base may be added in one portion or incrementally during the course of the reaction. In a separate step, the free hydroxy group in compound (96) is alkylated under appropriate conditions to form compound (97). The trichloroacetimidate (63) is readily prepared from the corresponding alcohol, 3,4-dimethoxyphenethyl alcohol which is commercially available (e.g., Aldrich), by treatment with trichloroacetonitrile. The alkylation of compound (96) by trichloroacetimidate (63) may be carried out in the presence of a Lewis acid such as $HBF_4$. In another separate step, the t-butyldiphenylsilyl (TBDPS) protection group in compound (97) may be removed by standard procedures (e.g., tetrabutylammonium fluoride in tetrahydrofuran (THF) or as described in Greene, "Protective Groups in Organic Chemistry", John Wiley & Sons, New York N.Y. (1991)) to afford the hydroxyether compound (98). In a separate step, the hydroxy group of compound (98) is converted under suitable conditions into an activated form such as the tosylate of formula (64). In another separate step, the tosylate group of formula (64) is displaced by an amino compound such as 3R-pyrrolidinol (65) with inversion of configuration. 3R-pyrrolidinol (65) is commercially available (e.g., Aldrich) or may be prepared according to published procedure (e.g., *Chem. Ber./Recueil* 1997, 130, 385-397). The reaction may be carried out with or without a solvent and at an appropriate temperature range that allows the formation of the product (66) at a suitable rate. An excess of the amino compound (65) may be used to maximally convert compound (64) to the product (66). The reaction may be performed in the presence of a base that can facilitate the formation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequence described above (FIG. 122) in general generates the compound of formula (66) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (69) may be carried out by a process as outlined in FIG. 123, comprising the steps of starting with chlorobenzene (58) and following a reaction sequence under suitable conditions analogous to the applicable portion that is described in FIG. 122 above leading to compound of formula (64). The latter is reacted with an amino compound of formula (68). Compound (68), 3S-pyrrolidinol, is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (69) at a suitable rate. An excess of the amino compound (68) may be used to maximally convert compound (64) to the product (69). The reaction may be performed in the presence of a base that can facilitate the formation of the product. Generally the additional base is non-nucleophilic in chemical reactivity. The product is a stereoisomerically substantially pure trans aminocyclohexyl ether compound of formula (69) and is formed as the free base. The free base may be converted, if desired, to the monohydrochloride salt by known methodologies, or alternatively, if desired, to other acid addition salts by reaction with an inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (57) may be carried out by a process as outlined in FIG. 124, comprising the steps of starting with compound of formula (50) and following a reaction sequence under suitable conditions analogous to the applicable portion that is described in FIG. 121, wherein all the formulae and symbols are as described above.

In another embodiment, the preparation of a stereoisomerically substantially pure trans aminocyclohexyl ether compound of formula (66) may be carried out by a process as outlined in FIG. 125, comprising the steps of starting with compound of formula (59) and following a reaction sequence under suitable conditions analogous to the applicable portion that is described in FIG. 122, wherein all the formulae and symbols are as described above. 3-Chloro-(1S,2S)-3,5-cyclohexadiene-1,2-diol of formula (59) is a commercially available product (e.g., Aldrich) or synthesized according to published procedure (e.g., Organic Synthesis, Vol. 76, 77 and T. Hudlicky et al., *Aldrichimica Acta,* 1999, 32, 35; and references cited therein).

In another embodiment, the preparation of a stereoisomerically substantially pure trans aminocyclohexyl ether compound of formula (69) may be carried out by a process as outlined in FIG. 126, comprising the steps of starting with compound of formula (59) and following a reaction sequence under suitable conditions analogous to the applicable portion that is described in FIG. 123, wherein all the formulae and symbols are as described above.

In another embodiment, the preparation of a stereoisomerically substantially pure trans aminocyclohexyl ether compound of formula (57) may be carried out by a process as outlined in FIG. 127, comprising the steps of starting with compound of formula (91) and following a reaction sequence under suitable conditions analogous to the applicable portion that is described in FIG. 121, wherein all the formulae and symbols are as described above.

In another embodiment, the preparation of a stereoisomerically substantially pure trans aminocyclohexyl ether compound of formula (66) may be carried out by a process as outlined in FIG. 128, comprising the steps of starting with compound of formula (95) and following a reaction sequence under suitable conditions analogous to the applicable portion that is described in FIG. 122, wherein all the formulae and symbols are as described above.

In another embodiment, the preparation of a stereoisomerically substantially pure trans aminocyclohexyl ether compound of formula (69) may be carried out by a process as outlined in FIG. 129, comprising the steps of starting with compound of formula (95) and following a reaction sequence under suitable conditions analogous to the applicable portion that is described in FIG. 123, wherein all the formulae and symbols are as described above.

In another embodiment, the preparation of a stereoisomerically substantially pure trans aminocyclohexyl ether compound of formula (57) may be carried out by a process as outlined in FIG. 130, comprising the steps of starting with compound of formula (92) and following a reaction sequence under suitable conditions analogous to the applicable portion that is described in FIG. 121, wherein all the formulae and symbols are as described above.

In another embodiment, the preparation of a stereoisomerically substantially pure trans aminocyclohexyl ether compound of formula (66) may be carried out by a process as outlined in FIG. 131, comprising the steps of starting with compound of formula (96) and following a reaction sequence under suitable conditions analogous to the applicable portion that is described in FIG. 122, wherein all the formulae and symbols are as described above.

In another embodiment, the preparation of a stereoisomerically substantially pure trans aminocyclohexyl ether compound of formula (69) may be carried out by a process as outlined in FIG. 132, comprising the steps of starting with compound of formula (96) and following a reaction sequence under suitable conditions analogous to the applicable portion that is described in FIG. 123, wherein all the formulae and symbols are as described above.

In another embodiment, the preparation of a stereoisomerically substantially pure trans aminocyclohexyl ether compound of formula (57) may be carried out by a process as outlined in FIG. 133, comprising the steps of starting with compound of formula (93) and following a reaction sequence under suitable conditions analogous to the applicable portion that is described in FIG. 121, wherein all the formulae and symbols are as described above.

In another embodiment, the preparation of a stereoisomerically substantially pure trans aminocyclohexyl ether compound of formula (66) may be carried out by a process as outlined in FIG. 134, comprising the steps of starting with compound of formula (97) and following a reaction sequence under suitable conditions analogous to the applicable portion that is described in FIG. 122, wherein all the formulae and symbols are as described above.

In another embodiment, the preparation of a stereoisomerically substantially pure trans aminocyclohexyl ether compound of formula (69) may be carried out by a process as outlined in FIG. 135, comprising the steps of starting with compound of formula (97) and following a reaction sequence under suitable conditions analogous to the applicable portion that is described in FIG. 123, wherein all the formulae and symbols are as described above.

In another embodiment, the preparation of a stereoisomerically substantially pure trans aminocyclohexyl ether compound of formula (57) may be carried out by a process as outlined in FIG. 136, comprising the steps of starting with compound of formula (94) and following a reaction sequence under suitable conditions analogous to the applicable portion that is described in FIG. 121, wherein all the formulae and symbols are as described above.

In another embodiment, the preparation of a stereoisomerically substantially pure trans aminocyclohexyl ether compound of formula (66) may be carried out by a process as outlined in FIG. 137, comprising the steps of starting with compound of formula (98) and following a reaction sequence under suitable conditions analogous to the applicable portion that is described in FIG. 122, wherein all the formulae and symbols are as described above.

In another embodiment, the preparation of a stereoisomerically substantially pure trans aminocyclohexyl ether compound of formula (69) may be carried out by a process as outlined in FIG. 138, comprising the steps of starting with compound of formula (98) and following a reaction sequence under suitable conditions analogous to the applicable portion that is described in FIG. 123, wherein all the formulae and symbols are as described above.

In another embodiment, the preparation of a stereoisomerically substantially pure compound of formula (55) may be carried out by a process as outlined in FIG. 139, comprising the steps of starting with compound of formula (49) and following a reaction sequence under suitable conditions analogous to the applicable portion that is described in FIG. 121, wherein all the formulae and symbols are as described above.

In another embodiment, the preparation of a stereoisomerically substantially pure compound of formula (64) may be carried out by a process as outlined in FIG. 140, comprising the steps of starting with compound of formula (58) and following a reaction sequence under suitable conditions analogous to the applicable portion that is described in FIG. 122, wherein all the formulae and symbols are as described above.

In another embodiment, the preparation of a stereoisomerically substantially pure compound of formula (94) may be carried out by a process as outlined in FIG. 141, comprising the steps of starting with compound of formula (49) and following a reaction sequence under suitable conditions analogous to the applicable portion that is described in FIG. 121, wherein all the formulae and symbols are as described above.

In another embodiment, the preparation of a stereoisomerically substantially pure compound of formula (98) may be carried out by a process as outlined in FIG. 142, comprising the steps of starting with compound of formula (58) and following a reaction sequence under suitable conditions analogous to the applicable portion that is described in FIG. 122, wherein all the formulae and symbols are as described above.

In another embodiment, the preparation of a stereoisomerically substantially pure compound of formula (93) may be carried out by a process as outlined in FIG. 143, comprising the steps of starting with compound of formula (49) and following a reaction sequence under suitable conditions analogous to the applicable portion that is described in FIG. 121, wherein all the formulae and symbols are as described above.

In another embodiment, the preparation of a stereoisomerically substantially pure compound of formula (97) may be carried out by a process as outlined in FIG. 144, comprising the steps of starting with compound of formula (58) and following a reaction sequence under suitable conditions analogous to the applicable portion that is described in FIG. 122, wherein all the formulae and symbols are as described above.

In another embodiment, the preparation of a stereoisomerically substantially pure compound of formula (92) may be carried out by a process as outlined in FIG. 145, comprising the steps of starting with compound of formula (49) and following a reaction sequence under suitable conditions analogous to the applicable portion that is described in FIG. 121, wherein all the formulae and symbols are as described above.

In another embodiment, the preparation of a stereoisomerically substantially pure compound of formula (96) may be carried out by a process as outlined in FIG. 146, comprising the steps of starting with compound of formula (58) and following a reaction sequence under suitable conditions analogous to the applicable portion that is described in FIG. 122, wherein all the formulae and symbols are as described above.

In another embodiment, the present invention provides a compound of formula (92), or a solvate or pharmaceutically acceptable salt thereof; wherein all the formulae and symbols are as described above.

In another embodiment, the present invention provides a compound of formula (54), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (93), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (94), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (55), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (96), or a solvate or pharmaceutically acceptable salt thereof; wherein all the formulae and symbols are as described above.

In another embodiment, the present invention provides a compound of formula (63), or a solvate or pharmaceutically acceptable salt thereof; wherein all the formulae and symbols are as described above.

In another embodiment, the present invention provides a compound of formula (97), or a solvate or pharmaceutically acceptable salt thereof; wherein all the formulae and symbols are as described above.

In another embodiment, the present invention provides a compound of formula (98), or a solvate or pharmaceutically acceptable salt thereof; wherein all the formulae and symbols are as described above.

In another embodiment, the present invention provides a compound of formula (64), or a solvate or pharmaceutically acceptable salt thereof; wherein all the formulae and symbols are as described above.

The present invention provides synthetic processes whereby compounds of formula (75) with trans-(1S,2S) configuration for the ether and amino functional groups may be prepared in stereoisomerically substantially pure form. Compounds of formulae (79) and (81) are some of the examples represented by formula (75). The present invention also provides synthetic processes whereby compounds of formulae (92), (99), (84) and (74) may be synthesized in stereoisomerically substantially pure forms. Compounds (96), (100), (62) and (78) are examples of formulae (92), (99), (84) and (74), respectively.

As outlined in FIG. 147, the preparation of a stereoisomerically substantially pure trans aminocyclohexyl ether compound of formula (75) may be carried out by following a process starting with a monohalobenzene (49), wherein X may be F, Cl, Br or I.

In a first step, compound (49) is transformed by well-established microbial oxidation to the cis-cyclohexandienediol (50) in stereoisomerically substantially pure form (T. Hudlicky et al., Aldrichimica Acta, 1999, 32, 35; and references cited therein). In a separate step, the less hindered hydroxy function in compound (50) may be selectively monoprotected as compound (91) where Pro represents the appropriate protecting group of the hydroxy function with retention of stereochemistry (T. Hudlicky et al., *Aldrichimica Acta*, 1999, 32, 35; S. M. Brown and T. Hudlicky, In Organic Synthesis: Theory and Applications; T. Hudlicky, Ed.; JAI Press: Greenwich, Conn., 1993; Vol. 2, p 113; and references cited therein). Tri-alkyl-silyl groups such as tri-isopropyl-silyl (TIPS) and t-butyldimethylsilyl (TBDMS) and alkyl-diaryl-silyl groups such as t-butyldiphenylsilyl (TBDPS) are some of the possible examples for Pro. Suitable reaction conditions are set forth in, for example, Greene, "Protective Groups in Organic Chemistry", John Wiley & Sons, New York N.Y. (1991). In a separate step, conversion of compound (91) to compound (92) may be effected by hydrogenation and hydrogenolysis in the presence of a catalyst under appropriate conditions. Palladium on activated carbon is one example of the catalysts. Hydrogenolysis of alkyl or alkenyl halide such as (91) may be conducted under basic conditions. The presence of a base such as sodium ethoxide, sodium bicarbonate, sodium acetate or calcium carbonate is some possible examples. The base may be added in one portion or incrementally during the course of the reaction. In a separate step, the free hydroxy group of compound (92) is converted into an activated form as represented by formula (99) under suitable conditions. An "activated form" as used herein means that the hydroxy group is converted into a good leaving group (—O-J). The leaving group may be a mesylate (MsO—) group, a tosylate group (TsO—) or a nosylate (NsO—). The hydroxy group may also be converted into other suitable leaving groups according to procedures well known in the art. In a typical reaction for the formation of a tosylate, compound (92) is treated with a hydroxy activating reagent such as tosyl chloride (TsCl) in the presence of a base, such as pyridine or triethylamine. The reaction is generally satisfactorily conducted at about 0° C., but may be adjusted as required to maximize the yields of the desired product. An excess of the hydroxy activating reagent (e.g., tosyl chloride), relative to compound (92) may be used to maximally convert the hydroxy group into the activated form. In a separate step, removal of the protecting group (Pro) in compound (99) by standard procedures (e.g., tetrabutylammonium fluoride in tetrahydrofuran or as described in Greene, "Protective Groups in Organic Chemistry", John Wiley & Sons, New York N.Y. (1991)) affords compound (84). In a separate step, alkylation of the free hydroxy group in compound (84) to form compound (74) is carried out under appropriate conditions with compound (54), where —O-Q represents a good leaving group on reaction with a hydroxy function with retention of the stereochemical configuration of the hydroxy function in the formation of an ether compound. Trichloroacetimidate is one example for the —O-Q function. For some compound (54), it may be necessary to introduce appropriate protection groups prior to this step being performed. Suitable protecting groups are set forth in, for example, Greene, "Protective Groups in Organic Chemistry", John Wiley & Sons, New York N.Y. (1991).

In a separate step, the resulted compound (74) is treated under suitable conditions with an amino compound of formula (56) to form compound (75) as the product. The reaction may be carried out with or without a solvent and at an appropriate temperature range that allows the formation of the product (75) at a suitable rate. An excess of the amino compound (56) may be used to maximally convert compound (74) to the product (75). The reaction may be performed in the presence of a base that can facilitate the formation of the product. Generally the base is non-nucleophilic in chemical reactivity. When the reaction has proceeded to substantial completion, the product is recovered from the reaction mixture by conventional organic chemistry techniques, and is purified accordingly. Protective groups may be removed at the appropriate stage of the reaction sequence. Suitable methods are set forth in, for example, Greene, "Protective Groups in Organic Chemistry", John Wiley & Sons, New York N.Y. (1991).

The reaction sequence described above (FIG. 147) generates the compound of formula (75) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid that is stronger than that giving rise to the initial salt.

All publications and patent applications mentioned in this specification are herein incorporated by reference to the same extent as if each individual publication or patent application is specifically and individually incorporated by reference.

In one embodiment, the present invention provides a process for the preparation of a stereoisomerically substantially pure compound of formula (75):

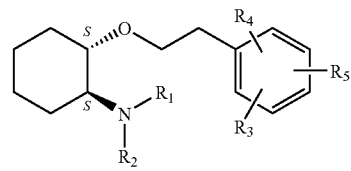

wherein $R_1$ and $R_2$, when taken together with the nitrogen atom to which they are directly attached in formula (75), form a ring denoted by formula (II):

and $R_3$, $R_4$ and $R_5$ are independently selected from hydrogen, hydroxy and $C_1$-$C_6$alkoxy, with the proviso that $R_3$, $R_4$ and $R_5$ cannot all be hydrogen;

comprising the steps of starting with a monohalobenzene (49), wherein X may be F, Cl, Br or I; and following a reaction sequence as outlined in FIG. 147 under suitable conditions, wherein Pro represents the appropriate protecting group of the hydroxy function with retention of stereochemistry;

—O-Q represents a good leaving group on reaction with a hydroxy function under suitable conditions with retention of the stereochemical configuration of the hydroxy function in the formation of an ether compound; and —O-J represents a good leaving group on reaction with a nucleophilic reactant under suitable conditions with inversion of the stereochemical configuration as illustrated in FIG. 147 and all the formulae and symbols are as described above.

In another embodiment, the present invention provides a process for the preparation of a stereoisomerically substantially pure compound of formula (79), comprising the steps under suitable conditions as shown in FIG. 148, wherein all the formulae and symbols are as described above. As outlined in FIG. 148, the preparation of a stereoisomerically substantially pure trans aminocyclohexyl ether compound of formula (79) may be carried out by starting with a biotransformation of chlorobenzene (49) to compound (59) by microorganism such as *Pseudomonas putida* 39/D. Experimental conditions for the biotransformation are well established (*Organic Synthesis*, Vol. 76, 77 and T. Hudlicky et al., *Aldrichimica Acta*, 1999, 32, 35; and references cited therein). In a separate step, the less hindered hydroxy function in compound (59) is selectively monosilylated as compound (95) by reaction with silylating reagent such as t-butyldiphenylsilyl chloride (TBDP-SCl) under suitable conditions (e.g., imaidazole in $CH_2Cl_2$) (T. Hudlicky et al., *Aldrichimica Acta*, 1999, 32, 35; S. M. Brown and T. Hudlicky, In Organic Synthesis: Theory and Applications; T. Hudlicky, Ed.; JAI Press: Greenwich, Conn., 1993; Vol. 2, p 113; and references cited therein). In another separate step, compound (95) is converted to compound (96) by reduction such as hydrogenation and hydrogenolysis in the presence of a catalyst under appropriate conditions. Palladium on activated carbon is one example of the catalysts. The reduction of compound (95) may be conducted under basic conditions e.g., in the presence of a base such as sodium ethoxide, sodium bicarbonate, sodium acetate or calcium carbonate. The base may be added in one portion or incrementally during the course of the reaction. In a separate step, the hydroxy group of compound (96) is converted under suitable conditions into an activated form such as the tosylate of formula (100) by treatment with tosyl chloride (TsCl) in the presence of pyridine. In another separate step, the t-butyldiphenylsilyl (TBDPS) protection group in compound (100) may be removed by standard procedures (e.g., tetrabutylammonium fluoride in tetrahydrofuran or as described in Greene, "Protective Groups in Organic Chemistry", John Wiley & Sons, New York N.Y. (1991)) to afford the hydroxytosylate compound (62). In a separate step, the free hydroxy group in compound (62) is alkylated under appropriate conditions to form compound (78). The trichloroacetimidate (63) is readily prepared from the corresponding alcohol, 3,4-dimethoxyphenethyl alcohol which is commercially available (e.g., Aldrich), by treatment with trichloroacetonitrile. The alkylation of compound (62) by trichloroacetimidate (63) may be carried out in the presence of a Lewis acid such as $HBF_4$. In another separate step, the tosylate group of formula (78) is displaced by an amino compound such as 3R-pyrrolidinol (65) with inversion of configuration. 3R-pyrrolidinol (65) is commercially available (e.g., Aldrich) or may be prepared according to published procedure (e.g., *Chem. Ber./Recueil* 1997, 130, 385-397). The reaction may be carried out with or without a solvent and at an appropriate temperature range that allows the formation of the product (79) at a suitable rate. An excess of the amino compound (65) may be used to maximally convert compound (78) to the product (79). The reaction may be performed in the presence of a base that can facilitate the formation and isolation of the product. Generally the additional base is non-nucleophilic in chemical reactivity. When the reaction has proceeded to substantial completion, the desired product is recovered from the reaction mixture by conventional organic chemistry techniques, and is purified accordingly.

The reaction sequence described above (FIG. 148) in general generates the compound of formula (79) as the free base. The free base may be converted, if desired, to the monohydrochloride salt by known methodologies, or alternatively, to other acid addition salts by reaction with an inorganic or organic acid under appropriate conditions. Acid addition salts can also be prepared metathetically by reaction of one acid addition salt with an acid addition salt with an acid that is stronger than that giving rise to the initial salt.

In another embodiment, the preparation of a stereoisomerically substantially pure trans aminocyclohexyl ether compound of formula (81) may be carried out by a process as outlined in FIG. 149, comprising the steps of starting with chlorobenzene (58) and following a reaction sequence under suitable conditions analogous to the applicable portion that is described in FIG. 148 above leading to compound of formula (78). The latter is reacted with an amino compound of formula (68). Compound (68), 3S-pyrrolidinol, is commercially available (e.g., Aldrich) or may be prepared according to published procedure (e.g., Chem. Ber./Recueil 1997, 130, 385-397). The reaction may be carried out with or without a solvent and at an appropriate temperature range that allows the formation of the product (81) at a suitable rate. An excess of the amino compound (68) may be used to maximally convert compound (78) to the product (81). The reaction may be performed in the presence of a base that can facilitate the formation of the product. Generally the additional base is non-nucleophilic in chemical reactivity. The product is a stereoisomerically substantially pure trans aminocyclohexyl ether compound of formula (81) and is formed as the free base. The free base may be converted, if desired, to the monohydrochloride salt by known methodologies, or alternatively, to other acid addition salts by reaction with an inorganic or organic acids under appropriate conditions. Acid addition salts can also be prepared metathetically by reaction of one acid addition salt with an acid that is stronger than that giving rise to the initial salt.

In another embodiment, the preparation of a stereoisomerically substantially pure trans aminocyclohexyl ether compound of formula (75) may be carried out by a process as outlined in FIG. 150, comprising the steps of starting with compound of formula (50) and following a reaction sequence under suitable conditions analogous to the applicable portion that is described in FIG. 147, wherein all the formulae and symbols are as described above.

In another embodiment, the preparation of a stereoisomerically substantially pure trans aminocyclohexyl ether compound of formula (79) may be carried out by a process as outlined in FIG. 151, comprising the steps of starting with compound of formula (59) and following a reaction sequence under suitable conditions analogous to the applicable portion that is described in FIG. 148, wherein all the formulae and symbols are as described above. 3-Chloro-(1S,2S)-3,5-cyclohexadiene-1,2-diol of formula (59) is a commercially available product (e.g., Aldrich) or synthesized according to published procedure (e.g., Organic Synthesis, Vol. 76, 77 and T. Hudlicky et al., Aldrichimica Acta, 1999, 32, 35; and references cited therein).

In another embodiment, the preparation of a stereoisomerically substantially pure trans aminocyclohexyl ether compound of formula (81) may be carried out by a process as outlined in FIG. 152, comprising the steps of starting with compound of formula (59) and following a reaction sequence under suitable conditions analogous to the applicable portion that is described in FIG. 149, wherein all the formulae and symbols are as described above.

In another embodiment, the preparation of a stereoisomerically substantially pure trans aminocyclohexyl ether compound of formula (75) may be carried out by a process as outlined in FIG. 153, comprising the steps of starting with compound of formula (91) and following a reaction sequence under suitable conditions analogous to the applicable portion that is described in FIG. 147, wherein all the formulae and symbols are as described above.

In another embodiment, the preparation of a stereoisomerically substantially pure trans aminocyclohexyl ether compound of formula (79) may be carried out by a process as outlined in FIG. 154, comprising the steps of starting with compound of formula (95) and following a reaction sequence under suitable conditions analogous to the applicable portion that is described in FIG. 148, wherein all the formulae and symbols are as described above.

In another embodiment, the preparation of a stereoisomerically substantially pure trans aminocyclohexyl ether compound of formula (81) may be carried out by a process as outlined in FIG. 155, comprising the steps of starting with compound of formula (95) and following a reaction sequence under suitable conditions analogous to the applicable portion that is described in FIG. 149, wherein all the formulae and symbols are as described above.

In another embodiment, the preparation of a stereoisomerically substantially pure trans aminocyclohexyl ether compound of formula (75) may be carried out by a process as outlined in FIG. 156, comprising the steps of starting with compound of formula (92) and following a reaction sequence under suitable conditions analogous to the applicable portion that is described in FIG. 147, wherein all the formulae and symbols are as described above.

In another embodiment, the preparation of a stereoisomerically substantially pure trans aminocyclohexyl ether compound of formula (79) may be carried out by a process as outlined in FIG. 157, comprising the steps of starting with compound of formula (96) and following a reaction sequence under suitable conditions analogous to the applicable portion that is described in FIG. 148, wherein all the formulae and symbols are as described above.

In another embodiment, the preparation of a stereoisomerically substantially pure trans aminocyclohexyl ether compound of formula (81) may be carried out by a process as outlined in FIG. 158, comprising the steps of starting with compound of formula (96) and following a reaction sequence under suitable conditions analogous to the applicable portion that is described in FIG. 149, wherein all the formulae and symbols are as described above.

In another embodiment, the preparation of a stereoisomerically substantially pure trans aminocyclohexyl ether compound of formula (75) may be carried out by a process as outlined in FIG. 159, comprising the steps of starting with compound of formula (99) and following a reaction sequence under suitable conditions analogous to the applicable portion that is described in FIG. 147, wherein all the formulae and symbols are as described above.

In another embodiment, the preparation of a stereoisomerically substantially pure trans aminocyclohexyl ether compound of formula (79) may be carried out by a process as outlined in FIG. 160, comprising the steps of starting with compound of formula (100) and following a reaction sequence under suitable conditions analogous to the applicable portion that is described in FIG. 148, wherein all the formulae and symbols are as described above.

In another embodiment, the preparation of a stereoisomerically substantially pure trans aminocyclohexyl ether compound of formula (81) may be carried out by a process as outlined in FIG. 161, comprising the steps of starting with compound of formula (100) and following a reaction sequence under suitable conditions analogous to the applicable portion that is described in FIG. 149, wherein all the formulae and symbols are as described above.

In another embodiment, the preparation of a stereoisomerically substantially pure compound of formula (74) may be carried out by a process as outlined in FIG. 162, comprising the steps of starting with compound of formula (49) and following a reaction sequence under suitable conditions analogous to the applicable portion that is described in FIG. 147, wherein all the formulae and symbols are as described above.

In another embodiment, the preparation of a stereoisomerically substantially pure compound of formula (78) may be carried out by a process as outlined in FIG. 163, comprising the steps of starting with compound of formula (58) and following a reaction sequence under suitable conditions analogous to the applicable portion that is described in FIG. 148, wherein all the formulae and symbols are as described above.

In another embodiment, the preparation of a stereoisomerically substantially pure compound of formula (84) may be carried out by a process as outlined in FIG. 164, comprising the steps of starting with compound of formula (49) and following a reaction sequence under suitable conditions analogous to the applicable portion that is described in FIG. 147, wherein all the formulae and symbols are as described above.

In another embodiment, the preparation of a stereoisomerically substantially pure compound of formula (62) may be carried out by a process as outlined in FIG. 165, comprising the steps of starting with compound of formula (58) and following a reaction sequence under suitable conditions analogous to the applicable portion that is described in FIG. 148, wherein all the formulae and symbols are as described above.

In another embodiment, the preparation of a stereoisomerically substantially pure compound of formula (99) may be carried out by a process as outlined in FIG. 166, comprising the steps of starting with compound of formula (49) and following a reaction sequence under suitable conditions analogous to the applicable portion that is described in FIG. 147, wherein all the formulae and symbols are as described above.

In another embodiment, the preparation of a stereoisomerically substantially pure compound of formula (100) may be carried out by a process as outlined in FIG. 167, comprising the steps of starting with compound of formula (58) and following a reaction sequence under suitable conditions analogous to the applicable portion that is described in FIG. 148, wherein all the formulae and symbols are as described above.

In another embodiment, the present invention provides a compound of formula (92), or a solvate or pharmaceutically acceptable salt thereof; wherein all the formulae and symbols are as described above.

In another embodiment, the present invention provides a compound of formula (99), or a solvate or pharmaceutically acceptable salt thereof; wherein all the formulae and symbols are as described above.

In another embodiment, the present invention provides a compound of formula (84), or a solvate or pharmaceutically acceptable salt thereof; wherein all the formulae and symbols are as described above.

In another embodiment, the present invention provides a compound of formula (54), or a solvate or pharmaceutically acceptable salt thereof; wherein all the formulae and symbols are as described above with the proviso that $R_3$, $R_4$ and $R_5$ cannot all be hydrogen.

In another embodiment, the present invention provides a compound of formula (74), or a solvate or pharmaceutically acceptable salt thereof; wherein all the formulae and symbols are as described above with the proviso that when $R_3$, $R_4$ and $R_5$ are all hydrogen then J is not a methanesulfonyl group.

In another embodiment, the present invention provides a compound of formula (96), or a solvate or pharmaceutically acceptable salt thereof; wherein all the formulae and symbols are as described above.

In another embodiment, the present invention provides a compound of formula (100), or a solvate or pharmaceutically acceptable salt thereof; wherein all the formulae and symbols are as described above.

In another embodiment, the present invention provides a compound of formula (62), or a solvate or pharmaceutically acceptable salt thereof; wherein all the formulae and symbols are as described above.

In another embodiment, the present invention provides a compound of formula (63), or a solvate or pharmaceutically acceptable salt thereof; wherein all the formulae and symbols are as described above.

In another embodiment, the present invention provides a compound of formula (78), or a solvate or pharmaceutically acceptable salt thereof; wherein all the formulae and symbols are as described above.

The reaction sequences described above (FIG. 1 and FIG. 2) generate the aminocyclohexyl ether compounds of the present invention as the free base initially. The free base may be converted, if desired, to the monohydrochloride salt by known methodologies, or alternatively, if desired, to other acid addition salts by reaction with the appropriate inorganic or organic acids. Acid addition salts can also be prepared metathetically by reaction of one acid addition salt with an acid that is stronger than that giving rise to the initial salt.

It is recognized that there may be one or more chiral centers in the compounds used within the scope of the present invention and thus such compounds will exist as various stereoisomeric forms. Applicants intend to include all the various stereoisomers within the scope of the invention. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention. Pure enantiomeric forms if produced may be isolated by preparative chiral HPLC. The free base may be converted if desired, to the monohydrochloride salt by known methodologies, or alternatively, if desired, to other acid addition salts by reaction with other inorganic or organic acids. Acid addition salts can also be prepared metathetically by reacting one acid addition salt with an acid that is stronger than that of the anion of the initial salt.

The present invention also encompasses the pharmaceutically acceptable salts, esters, amides, complexes, chelates, solvates; crystalline or amorphous forms, metabolites, metabolic precursors or prodrugs of the compounds of the present invention. Pharmaceutically acceptable esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmakokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, Design of Prodrugs, (1985). Those skilled in the art are well-versed in the preparation of prodrugs and are well-aware of its meaning.

The present invention also encompasses the pharmaceutically acceptable complexes, chelates, metabolites, or metabolic precursors of the compounds of the present invention. Information about the meaning these terms and references to their preparation can be obtained by searching various databases, for example Chemical Abstracts and the U.S. Food and Drug Administration (FDA) website. Documents such as the followings are available from the FDA: Guidance for Industry, "In Vivo Drug Metabolism/Drug Interaction Studies— Study Design, Data Analysis, and Recommendations for Dosing and Labeling", U.S. Department of Health and Human Services, Food and Drug Administration, Center for Drug Evaluation and Research (CDER), Center for Biologics Evaluation and Research (CBER), November 1999. Guidance for Industry, "In Vivo Drug Metabolism/Drug Interaction Studies in the DRUG DEVELOPMENT PROCESS: STUDIES IN VITRO", U.S. Department of Health and Human Services, Food and Drug Administration, Center for Drug Evaluation and Research (CDER), Center for Biologics Evaluation and Research (CBER), April 1997.

The synthetic procedures described herein, especially when taken with the general knowledge in the art, provide sufficient guidance to those of ordinary skill in the art to perform the synthesis, isolation, and purification of the compounds of the present invention.

Compositions and Modes of Administration

In other embodiments, the present invention provides a composition or medicament that includes one or more compounds, selected from any of the compounds or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, described above, in combination with a pharmaceutically acceptable carrier, diluent or excipient, and further provides a method for the manufacture of such a composition or medicament.

In other embodiments, the present invention provides a composition or medicament that includes one or more compounds according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

In other embodiments, the present invention provides a composition or medicament that includes one or more compounds according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

In other embodiments, the present invention provides a composition or medicament that includes one or more compounds, selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof;

in combination with a pharmaceutically acceptable carrier, diluent or excipient, and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

in combination with a pharmaceutically acceptable carrier, diluent or excipient, and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane free base or any salt thereof, or any solvate thereof; in combination with a pharmaceutically acceptable carrier, diluent or excipient, and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with a pharmaceutically acceptable carrier, diluent or excipient, and further provides a method for the manufacture of such a composition or medicament.

In other embodiments, the present invention provides a composition or medicament that includes one or more compounds of the present invention according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, in combination with appropriate amounts of sodium chloride USP, citric acid USP, sodium hydroxide NF and water for injection USP; and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof; in combination with appropriate amounts of sodium chloride USP, citric acid USP, sodium hydroxide NF and water for injection USP; and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP; and further provides a method for the manufacture of such a composition or medicament.

In other embodiments, the present invention provides a composition or medicament that includes one or more compounds of the present invention according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, in combination with appropriate amounts of sodium chloride USP, citric acid USP, sodium hydroxide NF and water for injection USP that resulted in an isotonic intravenous solution of said compound at a concentration of about 0.1 mg/ml to 100 mg/ml in sodium citrate of about 1 to 400 mM at a pH of about 7.5 to 4.0; and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof; in combination with appropriate amounts of sodium chloride USP, citric acid USP, sodium hydroxide NF and water for injection USP that resulted in an isotonic intravenous solution of said compound at a concentration of about 0.1 mg/ml to 100 mg/ml in sodium citrate of about 1 to 400 mM at a pH of about 7.5 to 4.0; and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP that resulted in an isotonic intravenous solution of said compound at a concentration of about 0.1 mg/ml to 100 mg/ml in sodium citrate of about 1 to 400 mM at a pH of about 7.5 to 4.0; and further provides a method for the manufacture of such a composition or medicament.

In other embodiments, the present invention provides a composition or medicament that includes one or more compounds of the present invention according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, in combination with appropriate amounts of sodium chloride USP, citric acid USP, sodium hydroxide NF and water for injection USP that resulted in an isotonic intravenous solution of said compound at a concentration of about 5 mg/ml to 80 mg/ml in sodium citrate of about 10 to 80 mM at a pH of about 6.5 to 4.5; and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof; in combination with appropriate amounts of sodium chloride USP, citric acid USP, sodium hydroxide NF and water for injection USP that resulted in an isotonic intravenous solution of said compound at a concentration of about 5 mg/ml to 80 mg/ml in sodium citrate of about 10 to 80 mM at a pH of about 6.5 to 4.5; and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP that resulted in an isotonic intravenous solution of said compound at a concentration of about 5 mg/ml to 80 mg/ml in sodium citrate of about 10 to 80 mM at a pH of about 6.5 to 4.5; and further provides a method for the manufacture of such a composition or medicament.

In other embodiments, the present invention provides a composition or medicament that includes one or more compounds of the present invention according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, in combination with appropriate amounts of sodium chloride USP, citric acid USP, sodium hydroxide NF and water for injection USP that resulted in an isotonic intravenous solution of said compound at a concentration of about 10 mg/ml to 40 mg/ml in sodium citrate of about 20 to 60 mM at a pH of about 6 to 5; and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof; in combination with appropriate amounts of sodium chloride USP, citric acid USP, sodium hydroxide NF and water for injection USP that resulted in an isotonic intravenous solution of said compound at a concentration of about 10 mg/ml to 40 mg/ml in sodium citrate of about 20 to 60 mM at a pH of about 6 to 5; and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP that resulted in an isotonic intravenous solution of said compound at a concentration of about 10 mg/ml to 40 mg/ml in sodium citrate of about 20 to 60 mM at a pH of about 6 to 5; and further provides a method for the manufacture of such a composition or medicament.

In other embodiments, the present invention provides a composition or medicament that includes one or more compounds of the present invention according to formula (IA), (IB), (IC), (ID), or (IE), or a solvate, pharmaceutically acceptable salt, stereoisomer, stereoisomeric mixture, geometric isomer, crystalline or amorphous form, or metabolite thereof, in combination with appropriate amounts of sodium chloride USP, citric acid USP, sodium hydroxide NF and water for injection USP that resulted in an isotonic intravenous solution of said compound at a concentration of about 20 mg/ml in sodium citrate of about 40 mM at a pH of about 5.5; and further provides a method for the manufacture of such a composition or medicament.

In other embodiments, the present invention provides a composition or medicament that includes one or more compounds, selected from the group consisting of:

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof; in combination with appropriate amounts of sodium chloride USP, citric acid USP, sodium hydroxide NF and water for injection USP that resulted in an isotonic intravenous solution of said compound at a concentration of about 20 mg/ml in sodium citrate of about 40 mM at a pH of about 5.5; and further provides a method for the manufacture of such a composition or medicament.

In other embodiments, the present invention provides a composition or medicament that includes a compound which is (1R,2R)-2-[(3R)-Hydroxypyrrolidinyl]-1-(3,4-dimethoxyphenethoxy)-cyclohexane monohydrochloride, or any solvate thereof; in combination with appropriate amounts of sodium chloride USP, citric acid USP, sodium hydroxide NF and water for injection USP that resulted in an isotonic intravenous solution of said compound at a concentration of about 20 mg/ml in sodium citrate of about 40 mM at a pH of about 5.5; and further provides a method for the manufacture of such a composition or medicament.

In another embodiment, the present invention provides compositions which include a compound of the present invention in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a compound of the present invention, in admixture with a pharmaceutically acceptable carrier, excipient or diluent. The invention further provides a pharmaceutical composition containing an effective amount of compound of the present invention, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a compound of the present invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydroxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active aminocyclohexyl ether compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocyclohexyl ether compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert and may be selected from, for example, sugar, shellac, and other enteric coating agents. Alternatively, the active ingredients may be encased in a gelatin capsule or cachet.

The composition in solid or liquid form may include an agent which binds to the aminocyclohexyl ether compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment and/or prevention of arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease, dementia and other mental disorders, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer or other diseases. Other agents known to cause libido enhancement, analgesia or local anesthesia may be combined with compounds of the present invention.

The compositions may be prepared by methodology well known in the pharmaceutical art. The aminocyclohexyl ether compounds of the present invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the aminocyclohexyl ether compound of the present invention with water, and preferably buffering agents, so as to form a solution. The water is preferably sterile pyrogen-free water. A surfactant may be added to facilitate the formation of a homogeneous solution or suspension. Surfactants are compounds that non-covalently interact with the aminocyclohexyl ether compound so as to facilitate dissolution or homogeneous suspension of the aminocyclohexyl ether compound in the aqueous delivery system. Surfactants are desirably present in aqueous compositions of the invention because the aminocyclohexyl ether compounds according to the present invention may be hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

Other Compositions

The present invention also provides kits that contain a pharmaceutical composition which includes one or more compounds of the above formulae. The kit also includes instructions for the use of the pharmaceutical composition for modulating the activity of ion channels, for the treatment of arrhythmia or for the production of analgesia and/or local anesthesia, and for the other utilities disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Pharmacological Embodiments

In other embodiments, the present invention provides one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above, for use in methods for modulating ion channel activity in a warm-blooded animal or for modulating ion channel activity in vitro. In one version of this embodiment, the warm-blooded animal in which the ion channel activity is modulated is a mammal; in one version, the warm-blooded animal is a human; in one version, the warm-blooded animal is a farm animal.

In other embodiments, the present invention provides one or more compounds, selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above, for, use in methods for modulating ion channel activity in a warm-blooded animal or for modulating ion channel activity in vitro.

In one version of this embodiment, the warm-blooded animal in which the ion channel activity is modulated is a mammal; in one version, the warm-blooded animal is a human; in one version, the warm-blooded animal is a farm animal.

As disclosed within the present invention, a variety of cardiac pathological conditions may be treated and/or prevented by the use of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above. These compounds of the present invention are ion channel modulating compounds that either singly or together with one or more additional compounds are able to selectively modulate certain ionic currents. The ion currents referred to herein are generally cardiac currents and more specifically, are the sodium currents and early repolarising currents.

Early repolarising currents correspond to those cardiac ionic currents which activate rapidly after depolarization of membrane voltage and which effect repolarisation of the cell.

Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The pathological conditions that may be treated and/or prevented by the present invention may include, but are not limited to, various cardiovascular diseases.

The cardiac pathological conditions that may be treated and/or prevented by the present invention may include, but are not limited to, arrhythmias such as the various types of atrial and ventricular arrhythmias, e.g., atrial fibrillation, atrial flutter, ventricular fibrillation, ventricular flutter.

In one embodiment, the present invention provides ion channel modulating compounds that can be used to selectively inhibit cardiac early repolarising currents and cardiac sodium currents.

In another embodiment, the present invention provides ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation.

In other embodiments, the present invention provides a method for modulating ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating ion channel activity in an in vitro setting comprising administering in vitro an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the activity/conductance of ion channel in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the activity/conductance of ion channel in an in vitro setting comprising administering in vitro an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating potassium ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating voltage-gated potassium ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating cardiac sodium currents activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for modulating cardiac early repolarising currents and cardiac sodium currents ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the cardiac early repolarising currents referred to in the present invention comprise ionic currents which activate rapidly after depolarisation of membrane voltage and which effect repolarisation of the cell.

In other embodiments, the cardiac early repolarising currents referred to in the present invention comprise the cardiac transient outward potassium current ($I_{to}$) and/or the ultrarapid delayed rectifier current ($I_{Kur}$).

In other embodiments, the cardiac transient outward potassium current ($I_{to}$) and/or the ultrarapid delayed rectifier current ($I_{Kur}$) referred to in the present invention comprise at least one of the Kv4.2, Kv4.3, Kv2.1, Kv1.4 and Kv1.5 currents.

In other embodiments, the present invention provides a method for treating and/or preventing arrhythmia in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial arrhythmia in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular arrhythmia in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial fibrillation in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular fibrillation in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial flutter in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular flutter in a warm-blooded animal comprising administering to a warm-blooded animal in need thereof, an effective amount of one or more compounds of the present invention such as those according to formula (IA), (IB), (IC), (ID), or (IE), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing arrhythmia in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing atrial arrhythmia in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing ventricular arrhythmia in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing atrial fibrillation in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing ventricular fibrillation in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing atrial flutter in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

In another embodiments, the present invention provides a method for treating and/or preventing ventricular flutter in a warm-blooded animal comprising administering to a warm-blooded animal in need thereof, an effective amount of one or more compounds of the present invention such as those selected from the group consisting of:

(1R,2R)/(1S,2S)-2-[(3R)/(3S)-Hydroxypyrrolidinyl]-1-(3,4-dimethoxyphenethoxy)-cyclohexane free base or any salt thereof, or any solvate thereof;

(1R,2R)/(1S,2S)-2-[(3R)-Hydroxypyrrolidinyl]-1-(3,4-dimethoxyphenethoxy)-cyclohexane free base or any salt thereof, or any solvate thereof;

(1R,2R)/(1S,2S)-2-[(3S)-Hydroxypyrrolidinyl]-1-(3,4-dimethoxyphenethoxy)-cyclohexane free base or any salt thereof, or any solvate thereof;

(1R,2R)-2-[(3R)-Hydroxypyrrolidinyl]-1-(3,4-dimethoxyphenethoxy)-cyclohexane free base or any salt thereof, or any solvate thereof;

(1R,2R)-2-[(3S)-Hydroxypyrrolidinyl]-1-(3,4-dimethoxyphenethoxy)-cyclohexane free base or any salt thereof, or any solvate thereof;

(1S,2S)-2-[(3R)-Hydroxypyrrolidinyl]-1-(3,4-dimethoxyphenethoxy)-cyclohexane free base or any salt thereof, or any solvate thereof;

(1S,2S)-2-[(3S)-Hydroxypyrrolidinyl]-1-(3,4-dimethoxyphenethoxy)-cyclohexane free base or any salt thereof, or any solvate thereof;

(1R,2S)-2-[(3R)-Hydroxypyrrolidinyl]-1-(3,4-dimethoxyphenethoxy)-cyclohexane free base or any salt thereof, or any solvate thereof;

(1R,2S)-2-[(3S)-Hydroxypyrrolidinyl]-1-(3,4-dimethoxyphenethoxy)-cyclohexane free base or any salt thereof, or any solvate thereof;

(1S,2R)-2-[(3R)-Hydroxypyrrolidinyl]-1-(3,4-dimethoxyphenethoxy)-cyclohexane free base or any salt thereof, or any solvate thereof;

(1S,2R)-2-[(3S)-Hydroxypyrrolidinyl]-1-(3,4-dimethoxyphenethoxy)-cyclohexane free base or any salt thereof, or any solvate thereof;

(1R,2S)/(1S,2R)-2-[(3R)/(3S)-Hydroxypyrrolidinyl]-1-(3,4-dimethoxyphenethoxy)-cyclohexane free base or any salt thereof, or any solvate thereof; or a composition or medicament that includes said compound or mixture comprising compounds as described above.

As noted above, the present invention provides for utilizing the compounds described above in in vitro and in vivo methods. In one embodiment, ion channels, such as cardiac potassium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating and/or preventing a variety of diseases or disorders caused by defective or inadequate function of the ion channels. The compounds of the invention are found to have significant activity in modulating various ion channel activity both in vivo and in vitro.

In one embodiment, the present invention provides a compound of the present invention or a composition containing said compound, for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems.

In one embodiment, the invention provides a compound of the present invention such as those according to formula (IA), (IB), (IC), (ID) or (IE), or composition containing said compound, for use in methods for either modulating activity of ion channel(s) in a warm-blooded animal or for modulating activity of ion channel(s) in vitro, wherein said ion channel(s) correspond to some of the cardiac and/or neuronal ion channels that are responsible for one or more early repolarising currents comprising those which activate rapidly after membrane depolarisation and which effect repolarisation of the cells.

In another embodiment, of the present invention, the above-mentioned early repolarising currents comprise the transient outward potassium current ($I_{to}$ for cardiac or $I_A$ for neuronal) and/or the ultrarapid delayed rectifier current ($I_{Kur}$); and include at least one of the Kv4.2, Kv4.3, Kv2.1, Kv1.3, Kv1.4 and Kv1.5 currents.

In another embodiment, the present invention provides a compound of the present invention such as those according to formula (IA), (IB), (IC), (ID) or (IE), or composition containing said compound, for use in methods for either modulating activity of ion channel(s) in a warm-blooded animal or for modulating activity of ion channel(s) in vitro, wherein said ion channel(s) correspond to either the cardiac or neuronal ion channel(s) that are responsible for Kv1.5 current.

In yet another embodiment, the present invention provides a compound of the present invention such as those according to formula (IA), (IB), (IC), (ID) or (IE), or composition containing said compound, for use in methods for either modulating activity of ion channel(s) in a warm-blooded animal or for modulating activity of ion channel(s) in vitro, wherein said ion channel(s) correspond to the potassium channel that are responsible for Kv4.2 current.

Furthermore, the voltage-activated sodium ion channels comprise the $Na_v1$, $Na_v2$ or $Na_v3$ series and may be present in cardiac, neuronal, skeletal muscle, central nervous and/or peripheral nervous systems (e.g., hH1Na).

For cardiac sodium channels, in studies on ion channels in isolated human atrial myocytes, compounds of the present invention have been shown to produce frequency-dependent blockade of cardiac sodium channels. In these studies enhanced blockade of cardiac sodium channels was observed at faster rates of stimulation with sodium block increasing several-fold during rapid stimulation rates. These protocols have been designed to mimic the short recovery intervals during fibrillation.

As noted earlier, modulating the activity of an ion channel as used above may imply but does not limit to blocking or inhibiting the conductance of the current through the ion channel.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of the present invention, or a composition containing a compound of the present invention is administered to a warm-blooded animal in need thereof. Some of the diseases and conditions to which the compounds, compositions and methods of the present invention may be applied are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g., diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia; myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease, dementia and other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

Furthermore, the present invention provides a method for producing analgesia or local anesthesia in a warm-blooded animal which includes administering to a warm-blooded animal in need thereof an effective amount of a compound of the present invention or a pharmaceutical composition containing said compound. These methods may be used to relieve or forestall the sensation of pain in a warm-blooded animal.

The invention further provides a method for enhancing libido in a warm-blooded animal which includes administering to a warm-blooded animal in need thereof an effective amount of a compound of the present invention or a pharmaceutical composition containing said compound. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

Furthermore, the present invention provides a method in an in vitro setting, wherein a preparation that contains ion channels is contacted with an effective amount of an aminocyclohexyl ether compound of the invention. Suitable preparations containing cardiac sodium channels and/or cardiac, potassium channels include cells isolated from cardiac tissue as well as cultured cell lines. The step of contacting includes, for example, incubation of ion channels with a compound under conditions and for a time sufficient to permit modulation of the activity of the channels by the compound.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocyclohexyl ether compound of the invention may be co-administered with epinephrine in order to induce local anesthesia.

In order to assess whether a compound has a desired pharmacological activity with the present invention, it may be subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P—R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle as applied to the shaved back of a guinea pig (*Cavia porcellus*) is assessed following subcutaneous administration of sufficient (50 µl, 10 mg/ml) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing may be carried out at intervals for up to 8 hours or more post-administration. The sites of bleb formation are examined after 24 hours to check for skin abnormalities consequent to local administration of test substances or of the vehicle used for preparation of the test solutions.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" each refers to diethyl ether; "h." refers to hours; "min." refers to minutes; "GC" refers to gas chromatography; "v/v" refers to volume per volume; and ratios are weight ratios unless otherwise indicated.

EXAMPLE 1

(1R,2R)-2-[(3R)-Hydroxypyrrolidinyl]-1-(3,4-dimethoxyphenethoxy)cyclohexane monohydrochloride (Compound 1)

Figure 1:
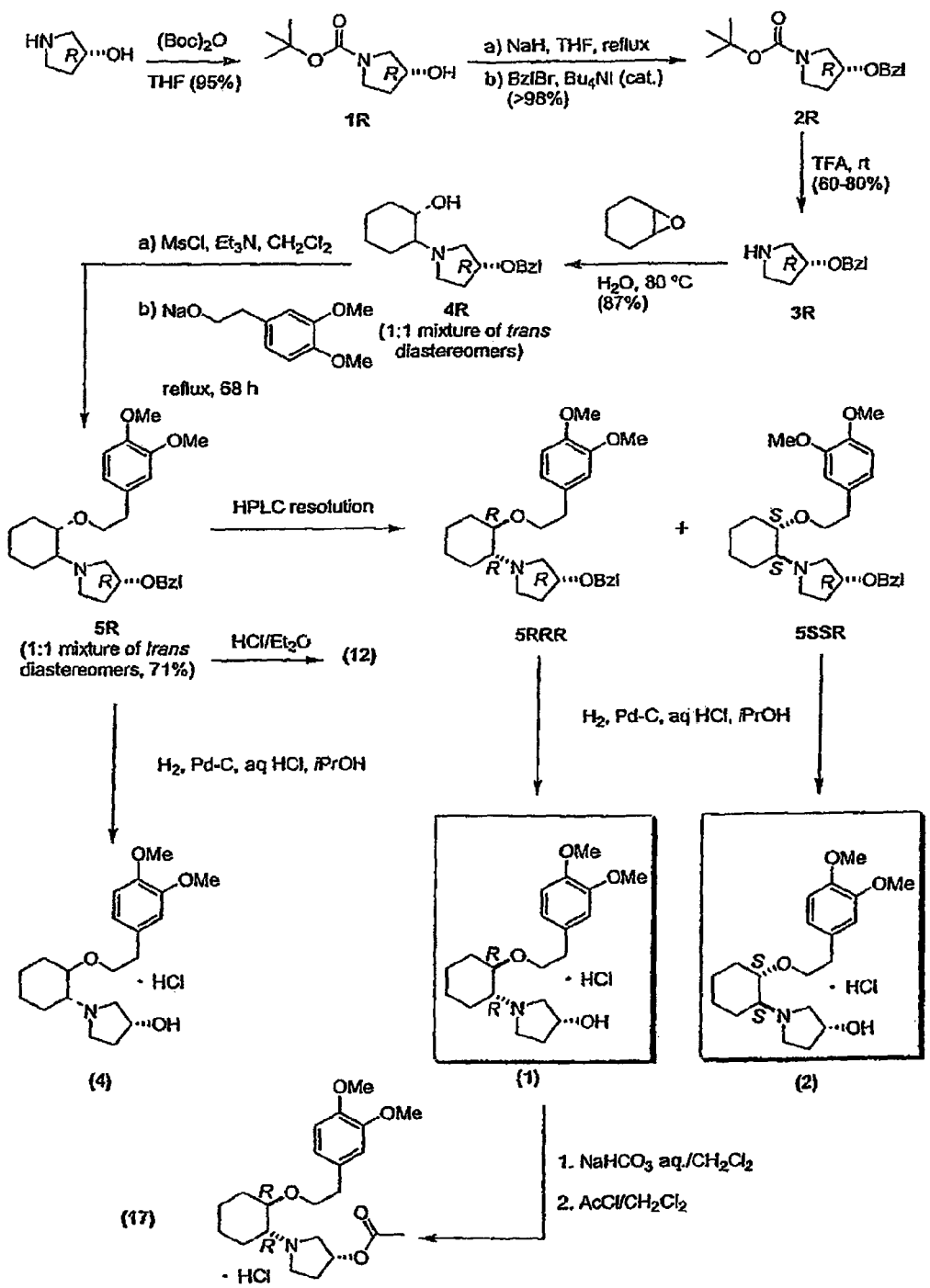
FIG. 1 illustrates a reaction sequence whereby the following aminocyclohexyl ether compounds of the present invention may be synthesized.

The reaction scheme for the preparation of compound 1 described herein is illustrated in FIG. 1.

Preparation of Intermediates

N-tert-Butoxycarbonyl-3R-pyrrolidinol (1R)

To a cold (0° C.) stirred solution of (R)-3-pyrrolidinol (20.6 g, 236 mmol; Omega cat. # HP-2113) in anhydrous THF (800 mL) was added dropwise a solution of di-tert-butyldicarbonate (56.7 g, 260 mmol, Aldrich cat. #20, 524-9) in THF (200 mL), and the resultant solution was stirred at room temperature for 18 h. Concentration in vacuo of the reaction mixture and short-path distillation in vacuo of the clear yellow residue gave 1R (42 g, 95% yield) as clear and colourless oil, which crystallized on standing.

Characterization: $R_f$ 0.58 (CHCl$_3$-MeOH, 4:1, v/v), NMR (200 MHz, CDCl$_3$) δ 4.4 (br s, 1H), 3.5-3.2 (m, 4H), 2.5 (br s, 1H), 2.0-1.9 (m, 2H), 1.4 (s, 9H); $^{13}$C NMR (75 MHz, CDCl$_3$) δ 154.7, 79.3, 70.6, 69.8, 54.1, 53.9, 43.9, 43.4, 33.8, 33.3, 28.4; IR (film) 3411, 1678 cm$^{-1}$; EIMS m/z (relative intensity) 187 (M$^+$, 8), 169 (M-H$_2$O, 0.5), 132 (25); 114 (39), 87 (13), 57 (100); FIRMS m/z calcd for C$_9$H$_{17}$NO$_3$ (M$^+$) 187.12081. found 187.12084.

N-tert-Butoxycarbonyl-3R-benzyloxypyrrolidine (2R)

A suspension of sodium hydride (8.08 g, 269 mmol, 80%, Aldrich cat. #25, 399-5) in anhydrous THF (100 mL) was stirred, allowed to settle and the supernatant was discarded.

The grey residue was washed with THF (2×50 mL) and then re-suspended in THF (700 mL). To the cold (0° C.), stirred suspension of sodium hydride was added dropwise a solution of 1R (41.7 g, 223 mmol) in THF (200 mL) and the resultant mixture was refluxed for 1 h. After the reaction mixture had cooled to room temperature, benzyl bromide (26.5 mL, 223 mmol) and tetrabutylammonium iodide (8.20 g, 22.3 mmol, Aldrich cat. #14,077-5) were successively added. The mixture was stirred at room temperature for 18 h and then concentrated under reduced pressure. To the residue was added brine (300 mL) and water (50 mL), and the pH of the resultant mixture was adjusted to neutrality with 1M aq HCl. This mixture was extracted with hexane (100 mL), and the hexane extract was dried ($MgSO_4$ anhydr) and concentrated under reduced pressure to give 64.3 g (>98% yield) of a yellow oil, which was shown by GC analysis to consist almost exclusively of the desired product. A small amount of the oil was subjected to flash column chromatography on silica gel eluted with hexane-ethyl acetate (3:1) to give 2R as a colourless oil, which crystallized on standing.

Characterization of 2R: $R_f$ 0.58 ($CHCl_3$-MeOH, 4:1, v/v), $^1H$ NMR (400 MHz, $CDCl_3$) δ 7.35-7.25 (m, 5H), 4.58-4.47 (m, 2H), 4.12 (br s, 1H), 3.55-3.40 (m, 4H), 2.10-2.00 (m, 1H), 2.00-1.90 (m, 1H), 1.48 (s, 9H); $^{13}C$ NMR (75 MHz, $CDCl_3$) δ 154.5, 138.0, 128.3, 127.6, 79.1, 77.7, 76.8, 70.8, 51.4, 50.7, 44.0, 43.6, 31.4, 30.4, 28.4; IR (film) 2975, 1691, 1410 $cm^{-1}$; HRMS m/z calcd for $C_{16}H_{23}NO_3$ (M) 277.16779. found 277.16790.

3R-Benzyloxypyrrolidine (3R)

A mixture of trifluoroacetic acid (50 mL, Aldrich cat. #T6, 220-0) and 2R (20 g, 72 mmol) was stirred at room temperature for 1 h and then concentrated under reduced pressure. The residue was taken up in water (250 mL) and the resultant acidic aqueous solution was extracted with $Et_2O$ (2×150 mL). To the acidic aqueous layer was carefully added in portions solid $NaHCO_3$ until saturation. The basic aqueous solution was then extracted with $CH_2Cl_2$ (2×150 mL) and the combined organic extracts were dried ($Na_2SO_4$ anhydr). Evaporation of the solvent in vacuo yielded 8.0 g of 3R (62% yield).

Characterization of 3R: $R_f$ 0.24 ($CHCl_3$-MeOH, 9:1, v/v), NMR (400 MHz, $CDCl_3$) δ 7.40-7.17 (m, 5H), 4.43 (s, 2H), 4.09-4.03 (m, 1H), 3.10-2.98 (m, 2H), 2.85-2.70 (m, 2H), 2.46 (s, 1H), 1.90-1.78 (m, 2H); IR (film) 3400, 1452, 1100, 1068 $cm^{-1}$.

(1R,2R)/(1S,2S)-1-[(3R)-benzyloxypyrrolidinyl]cyclohexan-2-ol (4R)

A mixture of cyclohexene oxide (12.5 mL, 120.9 mmol, Aldrich cat. #C10, 250-4), 3R (14.3 g, 80.6 mmol) and water (6 mL) was heated at 80° C. for 9.5 h, after which GC analysis revealed complete consumption of 3R. The reaction mixture was allowed to cool to room temperature and diluted with water (140 mL). By the addition of 1M aq HCl (55 mL), the pH was adjusted to 4.6 and the mixture was extracted with $Et_2O$ (2×200 mL). After the aqueous layer was adjusted to pH 12.5 by the addition of 40% aq NaOH (NaCl may be added to effect separation into 2 clear layers), it was extracted with $Et_2O$ (1×400 mL, 1×200 mL). The combined $Et_2O$ extracts (from basic aqueous layer) were dried ($Na_2SO_4$ anhydr), and concentrated under reduced pressure and then in vacuo at 55° C. with stirring, to give 4R as an orange oil (15.9 g, 72%) of 96% purity (GC).

Characterization of 4R: $R_f$ 0.24 (EtOAc-i$PrNH_2$, 98:2, v/v); $^1H$ NMR (200 MHz, $CDCl_3$) δ 7:4-7.2 (m, 5H), 4.5 (s, 2H), 4.2-4.0 (m, 1H), 3.9 (br s, 1H), 3.4-3.2 (m, 1H), 3.0-2.5 (m, 4H), 2.4 (t, J 10 Hz, 1H), 2.2-1.9 (m, 2H), 1.9-1.6 (m, 4H), 1.3-1.1 (m, 4H); $^{13}C$ NMR (75 MHz, $CDCl_3$) δ 138.30, 128.35, 127.61, 127.55, 77.98, 77.71, 71.07, 71.01, 70.52, 70.45, 64.96, 64.89, 54.16, 52.74, 46.83, 45.43, 33.24, 31.53, 31.34, 25.20, 24.13, 21.40, 21.33; IR (film) 3450 (broad) $cm^{-1}$.

(1R,2R)/(1S,2S)-2-[(3R)-Benzyloxypyrrolidinyl]-1-(3,4-dimethoxyphenethoxy)cyclohexane (5R)

(a) To a cold (0° C.), stirred solution of 4R (32.7 g, 88% purity by GC analysis, 104 mmol) and $Et_3N$ (13.8 g, 135 mmol, Aldrich cat. #13, 206-3) in $CH_2Cl_2$ (210 mL) was added dropwise methanesulfonyl chloride (15.8 g, 135 mmol, Aldrich cat. #M880-0). The reaction mixture was stirred at 0° C. for 30 min. and then at room temperature for 2 hours 15 min. The reaction mixture was then washed with a 1:1 mixture of $H_2O$-saturated aq $NaHCO_3$ (200 mL). The aqueous layer was extracted with $CH_2Cl_2$ (1×200 mL, 2×150 mL) and the organic extracts were combined and dried over sodium sulfate. Concentration of the organic layer in vacuo yielded the crude mesylate as a viscous oil, which was stirred under high vacuum for 3 h to removal residual traces of volatile material, and then used in the next step without further purification.

(b) To a suspension of NaH (3.75 g, 80% dispersion in mineral oil, 125 mmol, Aldrich cat. #25, 399-5) in anhydrous ethylene glycol dimethyl ether (350 mL) was added a solution of 3,4-dimethoxyphenethyl alcohol (23.2 g, 125 mmol, Aldrich cat. #19, 765-3) in ethylene glycol dimethyl ether (100 mL). The resultant mixture was then stirred at room temperature for 2 h to complete formation of the sodium alkoxide.

A solution of mesylate (see part a above) in anhydrous ethylene glycol dimethyl ether (100 mL) was added quickly to the alkoxide mixture (see part b above) and the resultant mixture was refluxed under argon for 17 h. The reaction mixture was allowed to cool to room temperature and then quenched with water (200 mL), followed by concentration under reduced pressure. The resultant aqueous solution was diluted with water (400 mL) and its pH was adjusted to pH 0.5 by the addition of 10% aq HCl. To remove unreacted 3,4-dimethoxyphenethyl alcohol, the acidic aqueous layer was extracted with $Et_2O$ (2×600 mL). The pH of the aqueous solution was then adjusted to pH 6.3 by the addition of 5M aq NaOH and the resultant aqueous layer was extracted with $Et_2O$ (600 mL). To the aqueous layer was added $Et_2O$ (600 mL), the pH was adjusted to 6.4 and the layers were separated. This operation was repeated for pH adjustments to 6.5 and 6.7. The ether extracts following pH adjustments 6.3-6.7 were combined, concentrated under reduced pressure to a volume of ~800 mL, and dried ($Na_2SO_4$ anhydr). Removal of solvent in vacuo yielded 34.4 g (95% purity by GC analysis) of the title compound as a brown oil. Purification of this material by flash column chromatography on silica gel eluted with a gradient solvent system of hexane-EtOAc (6.6:1→2:1) containing 0.5% v/v i-$PrNH_2$ gave the diastereomeric mixture 5R as a yellow oil (70% yield) in two fractions: 7.9 g (97% purity by GC analysis) and 25.5 g (95% purity by GC analysis).

Characterization: $R_f$ 0.14 (hexanes-EtOAc, 2:1 containing 0.5% i-$PrNH_2$); $^{13}C$ NMR (100 MHz, $CDCl_3$) δ 148.94, 147.59, 138.77, 132.30, 128.30, 127.62, 127.42, 120.90, 112.77, 111.55, 79.18, 78.07, 70.93, 69.82, 63.93, 57.46, 56.02, 55.90, 49.22, 36.59, 31.37, 28.70, 26.97, 23.08, 22.82; EIMS m/z (relative intensity) 440 (M+, 2) 333 (15) 274 (67) 165 (40) 91 (100).

Resolution of (1S,2S)- and (1R,2R)-2-[(3R)-benzyloxypyrrolidinyl]-1-(3,4-dimethoxyphenethoxy)cyclohexanes (5RRR and 5SSR)

The diastereomeric mixture 5R was separated using a Prochrom 110 HPLC equipped with a column body of 110 mm internal diameter, a bed length of 850 mm, and a maximum bed length of 400 mm (packed column). The column was packed with Kromasil silica (10 micron, 100 angstrom, normal phase). 5RRR was isolated with a diastereoselectivity of 99.5% and chemical purity of 97%.

Preparation of Compound (1), (1R,2R)-2-[(3R)-Hydroxypyrrolidinyl]-1-(3,4-dimethoxyphenethoxy)cyclohexane monohydrochloride To a 500 mL Erlenmeyer flask equipped with a 24/40 joint at 22° C. and charged with a stirred solution of 5RRR (12.7 mmol) in isopropyl alcohol (70 mL, HPLC grade from EM science, cat. No. PX1838-1) was added dropwise a solution of hydrochloric acid (5 mL, 37%, Aldrich #25,814-8). After the solution was stirred for 10 minutes, Pd—C catalyst (1.5 g, 10%, Adrich #20,569-9) was added and the reaction vessel was equipped with a gas inlet adapter (24/40 joint, Kontes cat. no. KT185030-2440) connected to a water aspirator. The reaction flask was evacuated by water aspiration for 1 min and then charged with $H_2$ via a balloon attached to the gas inlet. After the reaction mixture was stirred vigorously for 1 h at 22° C. under a positive pressure of $H_2$, TLC and GC analysis indicated total consumption of substrate and clean conversion into the desired product. The reaction mixture was filtered through a Celite 545® (Fisher)-packed column (45 mm in diameter and 35 mm in height, pre-wet with methanol under suction to rid air pockets and to ensure efficient charcoal trapping during filtration) and the Pd—C catalyst was well rinsed with methanol (3×40 mL). The acidic methanolic solution was concentrated under reduced pressure azeotropically with benzene or toluene to give a residue which was stirred vigorously in ethyl acetate over 1-2 days to facilitate formation of a solid or crystals.

Characterization: m.p. 144-150° C.; $R_f$ 0.37 (AcOEt/iso-PrNH2, 95:5); IR 1514, 1263, 1111 $cm^{-1}$; MS (ES) m/z 350.5; $^{13}C$ NMR (75 MHz, $CDCl_3$) δ 148.84, 147.57, 131.10, 120.54, 112.14, 111.26, 69.41, 68.81, 67.51, 66.32, 59.48, 55.88, 52.35, 35.80, 32.32, 30.06, 28.05, 24.23, 22.95; Calcd for $C_{20}H_{31}NO_4·HCl$: C, 62.24%; H, 8.36%; N, 3.63%. Found: C, 62.00%; H, 8.42%; N, 3.57%; $[α]_D$ −46.7° (c 1.52, $CH_3OH$); $[α]_D$ −39.6° (c 1.00, $CHCl_3$)

Preparation of Single Crystals of Compound 1 for X-Ray Crystallography

Compound 1 (200 mg) was dissolved in warm EtOH (3 mL) and then the solution was allowed to evaporate slowly at room temperature for 3 days. Crystals had formed and further evaporation of the remaining solvent (~1 mL) for another 2 days provided suitable crystals for X-Ray diffraction measurements. The sample was stored under Argon.

X-Ray Structure Determination of Compound 1
Experimental
Data Collection

A clear platelet crystal of $C_{20}H_{32}NO_4Cl$ having approximate dimensions of 0.25×0.20×0.04 mm was mounted on a glass fiber. All measurements were made on an ADSC CCD area detector coupled with a Rigaku AFC7 diffractometer with graphite monochromated Mo—Kα radiation.

Cell constants and an orientation matrix for data collection corresponded to a monoclinic cell with dimensions:

$a = 8.4333(7)$Å

$b = 9.4675(9)$Å  $β = 93.125(7)°$ $c = 12.581(1)$Å

$V = 1003.0(1)$Å$^3$

For Z=2 and F.W.=385.93, the calculated density is 1.28 g/cm$^3$. Based on the systematic absences of:

$0k0: k±2n$ a statistical analysis of intensity distribution, and the successful solution and refinement of the structure, the space group was determined to be:

$P2_1 (\#4)$

The data were collected at a temperature of −100±1° C. to a maximum 2θ value of 50.2°. Data were collected in 0.50° oscillations with 60.0 second exposures. A sweep of data was done using ω oscillations from −18.0 to 23.0° at χ=−90.0°. A second sweep was performed using φ oscillations from 0.0 to 190.0° at χ=−90.0°. The crystal-to-detector distance was 39.68 mm. The detector swing angle was −5.50°.

Data Reduction

Of the 7703 reflections which were collected, 3390 were unique ($R_{int}$=0.053, Friedels not merged); equivalent reflections were merged. Data were collected and processed using d*TREK[1]. Net intensities and sigmas were derived as follows:

$$F^2 = [Σ(P_i - mB_{ave})]·Lp$$

where $P_i$ is the value in counts of the i$^{th}$ pixel
m is the number of pixels in the integration area
$B_{ave}$ is the background average
Lp is the Lorentz and polarization factor $$B_{ave} = Σ(B_j)/n$$

where n is the number of pixels in the background area
$B_j$ is the value of the j$^{th}$ pixel in counts $$σ^2(F^2_{hkl}) = [(ΣP_i) + m((Σ(B_{ave} - B_j)^2)/(n-1))]·Lp·\text{errmul} + (\text{erradd}·F^2)^2$$

where erradd=0.05
errmul=1.40

The linear absorption coefficient, µ, for Mo—Kα radiation is 2.1 cm$^{-1}$. An empirical absorption correction was applied which resulted in transmission factors ranging from 0.73 to 1.00. The data were corrected for Lorentz and polarization effects.

Structure Solution and Refinement

The structure was solved by direct methods[2] and expanded using Fourier techniques[3]. The non-hydrogen atoms were refined anisotropically. This configuration was chosen based on the results of a parallel refinement of both possible configurations, and was further confirmed by the refined Flack parameter. Hydrogen atoms involved in hydrogen-bonding were refined isotropically, the rest were included in fixed positions. The final cycle of full-matrix least-squares refinement[4] on F$^2$ was based on 3390 observed reflections and 242 variable parameters and converged (largest parameter shift was 0.00 times its esd) with unweighted and weighted agreement factors of:

$$R1 = \Sigma ||Fo| - |Fc||/\Sigma |Fo| = 0.057$$

$$wR2 = [\Sigma(w(Fo^2 - Fc^2)^2)/\Sigma w(Fo^2)^2]^{1/2} = 0.082$$

The standard deviation of an observation of unit weight[5] was 0.97. The weighting scheme was based on counting statistics. Plots of $\Sigma w\,(|Fo|-|Fc|)^2$ versus $|Fo|$, reflection order in data collection, $\sin\theta/\lambda$ and various classes of indices showed no unusual trends. The maximum and minimum peaks on the final difference Fourier map corresponded to 0.30 and $-0.32$ $e^-/Å^3$, respectively.

Neutral atom scattering factors were taken from Cromer and Waber[6]. Anomalous dispersion effects were included in Fcalc[7]; the values for $\Delta f'$ and $\Delta f''$ were those of Creagh and McAuley[8]. The values for the mass attenuation coefficients are those of Creagh and Hubbell[9]. All calculations were performed using the teXsan[10] crystallographic software package of Molecular Structure Corporation.

REFERENCES (1) d*TREK: Area Detector Software. Version 4.13. Molecular Structure Corporation. (1996-1998).

(2) SIR97: Altomare, A., Burla, M. C., Cammalli, G. Cascarano, M., Giacovazzo, C., Guagliardi, A, Moliterni, A. G. G., Polidori, G., Spagna, A. SIR97: a new tool for crystal structure determination and refinement. (1990). J. Appl. Cryst., 32, 115-119.

(3) DIRDIF94: Beurskens, P. T., Admiraal, G., Beurskens, G., Bosman, W. P., de Gelder, R., Israel, R. and Smits, J. M. M. (1994). The DIRDIF-94 program system, Technical Report of the Crystallography Laboratory, University of Nijmegen, The Netherlands.

(4) Least Squares function minimized:

$$\Sigma w(F_o^2 - F_c^2)^2$$

(5) Standard deviation of an observation of unit weight:

$$[\Sigma w(F_o^2 - F_c^2)^2/(N_o - N_v)]^{1/2}$$

where:

$N_o$=number of observations $N_v$=number of variables (6) Cromer, D. T. & Waber, J. T.; "International Tables for X-ray Crystallography", Vol. IV, The Kynoch Press, Birmingham, England, Table 2.2 A (1974).

(7) Ibers, J. A. & Hamilton, W. C.; Acta Crystallogr., 17, 781 (1964).

(8) Creagh, D. C. & McAuley, W. J.; "International Tables for Crystallography", Vol C, (A. J. C. Wilson, ed.), Kluwer Academic Publishers, Boston, Table 4.2.6.8, pages 219-222 (1992).

(9) Creagh, D. C. & Hubbell, J. H.; "International Tables for Crystallography", Vol C, (A. J. C. Wilson, ed.), Kluwer Academic Publishers, Boston, Table 4.2.4.3, pages 200-206 (1992).

(10) teXsan for Windows version 1.06: Crystal Structure Analysis Package, Molecular Structure Corporation (1997-9).

| EXPERIMENTAL DETAILS | |
|---|---|
| A. Crystal Data | |
| Empirical Formula | $C_{20}H_{32}NO_4Cl$ |
| Formula Weight | 385.93 |
| Crystal Color, Habit | clear, platelet |
| Crystal Dimensions | 0.25 × 0.20 × 0.04 mm |
| Crystal System | monoclinic |
| Lattice Type | Primitive |
| Lattice Parameters | a = 8.4333(7) Å |
| | b = 9.4675(9) Å |
| | c = 12.581(1) Å |
| | β = 93.125(7)° |
| | V = 1003.0(1) Å³ |
| Space Group | $P2_1$ (#4) |
| Z value | 2 |
| $D_{calc}$ | 1.278 g/cm³ |
| $F_{000}$ | 416.00 |
| μ(MoKα) | 2.15 cm⁻¹ |
| B. Intensity Measurements | |
| Detector | ADSC Quantum 1 CCD |
| Goniometer | Rigaku AFC7 |
| Radiation | MoKα (λ = 0.71069 Å) |
| | graphite monochromated |
| Detector Aperture | 94 mm × 94 mm |
| Data Images | 462 exposures @ 60.0 seconds |
| ω oscillation Range (χ = −90.0) | −18.0-23.0° |
| φ oscillation Range (χ = −90.0) | 0.0-190.0° |
| Detector Position | 39.68 mm |
| Detector Swing Angle | −5.50° |
| $2\theta_{max}$ | 50.2° |
| No. of Reflections Measured | Total: 7703 |
| | Unique: 3390 ($R_{int}$ = 0.053, Friedels not merged) |
| Corrections | Lorentz-polarization |
| | Absorption/decay/scaling |
| | (trans. factors: 0.7295-1.0000) |
| C. Structure Solution and Refinement | |
| Structure Solution | Direct Methods (SIR97) |
| Refinement | Full-matrix least-squares on F² |
| Function Minimized | $\Sigma\,w\,(Fo^2 - Fc^2)^2$ |
| Least Squares Weights | $1/\sigma^2(Fo^2) = 4Fo^2/\sigma^2(Fo^2)$ |
| Anomalous Dispersion | All non-hydrogen atoms |
| No. Observations (I > 0.00σ(I)) | 3390 |
| No. Variables | 242 |
| Reflection/Parameter Ratio | 14.01 |
| Residuals (refined on F², all data): R1; wR2 | 0.057; 0.082 |
| Goodness of Fit Indicator | 0.97 |
| Max Shift/Error in Final Cycle | 0.00 |
| No. Observations (I > 3.00σ(I)) | 2624 |
| Residuals (refined on F > 3.00σ(I)): R1; wR2 | 0.033; 0.038 |
| Maximum peak in Final Diff. Map | 0.30 $e^-/Å^3$ |
| Minimum peak in Final Diff. Map | −0.32 $e^-/Å^3$ |

X-Ray Structure of Compound 1

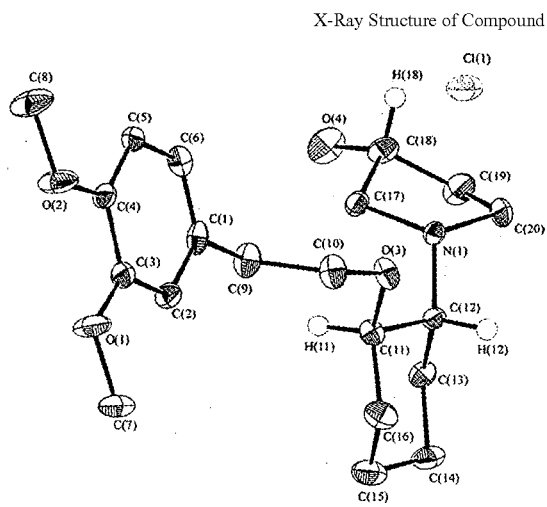

The results of the X-ray structure determination for compound 1 confirmed the absolute configuration and structural assignment as (1R,2R)-2-[(3R)-Hydroxypyrrolidinyl]-1-(3,4-dimethoxyphenethoxy)-cyclohexane monohydrochloride. By inference and spectroscopic analyses, the absolute configuration and structural assignment for compound 2, compound 3, compound 4, compound 5, compound 6 and compound 7 are confirmed accordingly.

EXAMPLE 2

(1S,2S)-2-[(3R)-Hydroxypyrrolidinyl]-1-(3,4-dimethoxyphenethoxy)cyclohexane monohydrochloride (Compound 2)

5SSR, (1S,2S)-2-[(3R)-benzyloxypyrrolidinyl]-1-(3,4-dimethoxyphenethoxy)cyclohexane was prepared and resolved according to Example 1. Compound 2 was then obtained from 5SSR using the procedure described above in example 1 with respect to the preparation of Compound 1.

Characterization: Calcd for $C_{20}H_{31}NO_4 \cdot HCl$: C, 62.24; H, 8.36; N, 3.63. Found: C, 62.20; H, 8.46; N, 3.55; $[\alpha]_D$+26.69° (c 13.04 g/L, $CHCl_3$)

EXAMPLE 3

(1R,2R)/(1S,2S)-2-[(3R)/(3S)-Hydroxypyrrolidinyl]-1-(3,4-dimethoxyphenethoxy)-cyclohexane monohydrochloride (Compound 3)

Preparation of Intermediates

N-Benzyloxycarbonyl-3-pyrrolidinol (1b). To a cold (−60° C.) solution of 1a (20.0 g, 225 mmol) and $Et_3N$ (79 mL, 560 mmol) in $CH_2Cl_2$ (200 mL) was added dropwise a solution of benzyl chloroformate (34 mL, 225 mmol) in $CH_2Cl_2$ (80 mL). After the addition was completed within 45 min, the reaction mixture (a yellow suspension) was allowed to warm up to room temperature and was stirred under argon at room temperature overnight. The reaction mixture was then quenched with 1M HCl aq (350 mL) and the organic layer was collected. The acidic aqueous layer was extracted with $CH_2Cl_2$ (2×150 mL) and the combined organic layers were dried. Evaporation in vacuo of the solvent provided 59.6 g of pale yellow oil, which was further pumped under high vacuum for 15 min to yield 58.2 g (17% over theoretical yield) of 1b suitable for the next step without any further purification. $R_f$ 0.42 (EtOAc-iPrNH$_2$, 98:2, v/v); NMR (200 MHz, $CDCl_3$) δ 7.40-7.30 (m, 5H), 5.10 (s, 2H), 4.40 (br s, 1H), 3.60-3.40 (m, 4H), 2.80 (d, J 15 Hz, 1H), 2.00-1.90 (m, 2H); $^{13}$C NMR (50 MHz, APT, $CDCl_3$) δ 137.0 (+), 128.5 (−), 127.5 (−), 71.0 (−), 70.0 (−), 66.5 (+), 55.0 (+), 54.5 (+), 44.0 (+), 43.5 (+), 34.0 (+), 33.5 (+); IR (film) 3415 (broad), 1678 cm$^{-1}$.

N-Benzyloxycarbonyl-3-pyrrolidinone (1c). To a chilled (−60° C.) solution of oxalyl chloride (23 mL, 258.6 mmol) in $CH_2Cl_2$ (400 mL) was added dropwise a solution of DMSO (36.7 mL, 517.3 mmol) in $CH_2Cl_2$ (20 mL) at such a rate to keep the temperature below −40° C. The reaction mixture was then stirred at −60° C. for 15 min. Then a solution of 1b (58.2 g, no more than 225 mmol) in $CH_2Cl_2$ (80 mL) was added dropwise, keeping the reaction mixture temperature below −50° C. The reaction mixture was then stirred at −60° C. for 30 min before adding $Et_3N$ (158.3 mL, 1.125 mol). The resulting mixture was allowed to warm up to room temperature and then washed with water (600 mL), 1M HCl aq (580 mL) and water (400 mL). The organic layer was dried and concentrated in vacuo to leave 54.5 g of amber oil, which was further pumped under high vacuum with stirring at room temperature for 25 min to give 52 g (5.6% over theoretical yield) of 1c suitable for the next step without any further purification. $R_f$ 0.81 (EtOAc-iPrNH$_2$, 98:2, v/v); $^1$H NMR (200 MHz, $CDCl_3$) δ 7.40-7.30 (m, 5H), 5.20 (s, 2H), 3.90-3.80 (m, 4H), 2.60 (t, J 7 Hz, 2H); $^{13}$C NMR (50 MHz, APT, $CDCl_3$) δ 136.0 (+), 128.5 (−), 128.0 (−), 67.0 (+), 52.5 (+), 42.5 (+), 36.5 (+); IR (film) 1759, 1708 cm$^{-1}$.

7-Benzyloxycarbonyl-1,4-dioxa-7-azaspiro[4.4]nonane (1d). A mixture of 1c (52 g, no more than 225 mmol) and ethylene glycol (18.8 mL, 337.4 mmol) in toluene (180 mL) with a catalytic amount of p-TsOH.H$_2$O (1.0 g, 5.4 mmol) was refluxed in a Dean & Stark apparatus for 16 h. The reaction mixture was then diluted with more toluene (250 mL) and washed with saturated NaHCO$_3$ aq (150 mL) and brine (2×150 mL). The combined aqueous layers were back-extracted with toluene (100 mL). The combined organic layers were dried and concentrated in vacuo to leave 79.6 g of dark oil. The crude product was dissolved in EtOH (500 mL), and running it through a bed of activated carbon (80 g), decolorized the resultant solution. The charcoal was washed with more EtOH (1000 mL) and toluene (500 mL). The filtrate was concentrated in vacuo and further pumped under high vacuum for 1 h to yield 63.25 g (6.8% over theoretical yield) of 1d suitable for the next step without any further purification. $R_f$ 0.78 (EtOAc-iPrNH$_2$, 98:2, v/v); NMR (200 MHz, $CDCl_3$) δ 7.40-7.20 (m, 5H), 5.20 (s, 2H), 4.00 (s, 4H), 3.60-3.50 (m, 2H), 3.50-3.40 (m, 2H), 2.10-2.00 (m, 2H); $^{13}$C NMR (50 MHz, APT, $CDCl_3$) δ 137.0 (+), 128.5 (−), 128 (−), 67.0 (+), 65.0 (+), 5.5 (+), 45.0 (+), 34.5 (+); IR (film) 1703 cm$^{-1}$.

1,4-Dioxa-7-azaspiro[4.4]nonane (1e). A mixture of 1d (34.8 g, no more than 124 mmol) and 10% Pd—C (14 g) in EtOH (90 mL) was hydrogenolyzed (60 psi) in a Parr shaker apparatus at room temperature for 1.5 h. The catalyst was filtered off, the solvent was evaporated in vacuo and the residue was pumped under high vacuum for 20 min to yield 1e (15.9 g, quant. yield). $R_f$ 0.14 (EtOAc-iPrNH$_2$, 95:5, v/v); $^1$H NMR (200 MHz, $CDCl_3$) δ 4.00 (s, 4H), 3.10 (t, J 7 Hz, 2H), 2.90 (s, 2H), 2.00 (t, J 7 Hz, 2H); $^{13}$C NMR (50 MHz, APT, $CDCl_3$) δ 64.5 (+), 55.0 (+), 45.5 (+), 37.0 (+); IR (film) 3292 cm$^{-1}$.

(1R,2R)/(1S,2S)-1-(1,4-Dioxa-7-azaspiro[4.4]non-7-yl) cyclohexan-2-ol (2e). A mixture of 1e (23.5 g, no more than 182 mmol), cyclohexene oxide (23 mL, 220 mmol) and water (8 mL) was heated at 80° C. for 2 h. The reaction mixture was then partitioned between 40% NaOH aq (60 mL) and Et$_2$O (120 mL). The basic aqueous layer was extracted twice more with Et$_2$O (2×120 mL). The combined organic extracts were dried and concentrated in vacuo. The residue was then heated under high vacuum at 50° C. for 1 h with stirring (to remove the excess of cyclohexene oxide) to yield 32.8 g of 2e (79% yield). R$_f$ 0.33 (EtOAc-iPrNH$_2$, 98:2, v/v); $^{13}$C NMR (50 MHz, APT, CDCl$_3$) δ 115.5 (+), 70.0 (−), 65.0 (−), 64.5 (+), 57.0 (+), 46.5 (+), 36.0 (+), 33.5 (+), 25.0 (+), 24.0 (+), 21.5 (+); IR (film) 3457 cm$^{-1}$.

(1R,2R)/(1S,2S)-1-[1,4-Dioxa-7-azaspiro[4.4]non-7-yl]-2-(3,4-dimethoxy phenoxy)cyclohexane in Et$_2$O (80 mL) was treated with ethereal HCl. The solvent was evaporated in vacuo and the residue was taken up with Et$_2$O and triturated. (1R,2R)/(1S,2S)-1-[1,4-Dioxa-7-azaspiro[4.4]non-7-yl]-2-(3,4-dimethoxyphenoxy)cyclohexane monohydrochloride was precipitated from a mixture of CH$_2$Cl$_2$-Et$_2$O A solution of (1R,2R)/(1S,2S)-1-[1,4-Dioxa-7-azaspiro[4.4]non-7-yl]-2-(3,4-dimethoxy phenoxy)cyclohexane with 6 M HCl aq (50 mL) in 2-butanone (200 mL) was refluxed for 12 h. The butanone was evaporated in vacuo and the residual aqueous solution was diluted to 250 mL with water. The aqueous solution was extracted with Et$_2$O (2×200 mL) and then with CH$_2$Cl$_2$ (2×200 mL). The pooled CH$_2$Cl$_2$ extracts were dried and the solvent was evaporated in vacuo. The residual oil was azeotropically dried with toluene. The resulting sticky product was triturated in Et$_2$O (500 mL), the resultant solid was collected and solubilized in a small amount of CH$_2$Cl$_2$ (~10 mL), then addition of a large quantity of Et$_2$O (~400 mL) triggered recrystallization. The solid was collected, dried under high vacuum for 3 h to yield (1R,2R)/(1S,2S)-1-(3,4-Dimethoxyphenethoxy)-2-(3-ketopyrrolidinyl)cyclohexane monohydrochloride (Compound 18)(1.9 g, 56% yield)

$^1$H NMR (400 MHz, free base, CDCl$_3$) δ 6.70 (m, 3H, Ar), 3.85 (2s, 6H, 2×CH$_3$O), 3.80-1.10 (m, 20H, aliph); $^{13}$C NMR (75 MHz, APT, free base, CDCl$_3$) δ 215.21 (+), 148.57 (+), 147.27 (+), 131.64 (+), 120.61 (−), 112.11 (−), 111.03 (−), 79.40 (−), 69.43 (+), 63.64 (−), 58.90 (+), 55.76 (−), 55.70 (−), 48.00 (+), 37.63 (+), 36.31 (+), 29.00 (+), 27.07 (+), 23.54 (+), 23.01 (+); HRMS (EI) mass calcd for C$_{20}$H$_{29}$O$_4$N: 347.20966. found: 347.21046 (21.1%); Anal. (C$_{20}$H$_{30}$O$_4$NCl) H, N; C: calcd 62.57. found, C, 60.32.

Preparation of (1R,2R)/(1S,2S)-1-(3,4-Dimethoxyphenethoxy)-2-(3-(R/S)-hydroxy pyrrolidinyl)cyclohexane monohydrochloride (Compound 3)

To a chilled (0° C.) suspension of sodium borohydride (1.53 g, 40 mmol) in isopropanol (60 mL) was added slowly a solution of Compound 18 (6.14 g, 16 mmol) in isopropanol (40 mL). The resultant mixture was stirred at 0° C. for another 30 min and then was allowed to warm up to room temperature for 1 h. The reaction mixture was cooled to 0° C. again and slowly hydrolyzed with 1 M HCl aq (80 mL). The reaction mixture was allowed to warm up to room temperature and was stirred overnight. The organic solvent was evaporated in vacuo, the residual aqueous layer was diluted with water to 150 mL and extracted with diethyl ether (1×150 mL) and dichloromethane (3×150 mL). The combined dichloromethane extracts were concentrated to 120 mL and treated with 0.25 M aq sodium hydroxide (100 mL). The aqueous layer was separated and extracted twice more with dichloromethane (2×150 mL). The combined dichloromethane extracts were dried over sodium sulfate and evaporated in vacuo. Purification by dry-column chromatography (ethyl acetate-hexanes, 2:1 to 4:1, +0.5% v/v isopropylamine) provided 2.0 g (36% yield) of the title compound as a free base. 1.9 g of the free base was partitioned between dichloromethane (24 mL) and 0.5 M HCl aq (24 mL). The aqueous layer was separated and extracted thrice more with dichloromethane (3×24 mL). The combined dichloromethane extracts were dried over sodium sulfate and the solvent was evaporated in vacuo. Azeotropic distillation with benzene (2×25 mL) and drying under high vacuum provided the title compound as an off-white hygroscopic solid (1.58 g). $^1$H NMR (400 MHz, free base, CDCl$_3$) δ 6.80-6.70 (m, 3H, Ar), 4.20-1.10 (m, 22H, Aliph), 3.80 (2×s, 6H, 2×CH$_3$O); $^{13}$C NMR (75 MHz, APT, free base, CDCl$_3$) δ 148.56 (+), 147.25 (+), 131.83 (+), 120.66 (−), 112.25 (−), 111.00 (−), 79.30 (−), 79.11 (−), 70.96 (−), 70.73 (−), 69.62 (+), 69.50 (+), 63.28 (−), 59.67 (+), 59.35 (+), 55.80 (−), 55.71 (−), 48.70 (+), 48.44 (+), 36.35 (+), 34.33 (+), 34.17 (+), 28.81 (+), 28.76 (+), 27.09 (+), 27.03 (+), 23.30 (+), 23.22 (+), 22.92 (+), 22.86 (+); HRMS (EI) mass calcd for C$_{20}$H$_{31}$N$_2$O: 349.22531. found: 349.22578 (100%); HPLC (Zorbax Extend C18, 150×4.6 mmm, 5µ; 20-70% acetonitrile: 10 mM phosphate buffer (pH 2.5)) 95.8%; CE 99.8%.

EXAMPLE 4

(1R,2R)/(1S,2S)-2-[(3R)-Hydroxypyrrolidinyl]-1-(3,4-dimethoxyphenethoxy)-cyclohexane monohydrochloride (Compound 4)

(1R,2R)/(1S,2S)-2-[(3R)-benzyloxypyrrolidinyl]-1-(3,4-dimethoxy phenethoxy)cyclohexane was prepared according to Example 1. The title compound was formed by hydrogenolysis of (1R,2R)/(1S,2S)-2-[(3R)-benzyloxypyrrolidinyl]-1-(3,4-dimethoxyphenethoxy)cyclohexane under the conditions described in Example 1.

EXAMPLE 5

(1R,2R)/(1S,2S)-2-[(3S)-Hydroxypyrrolidinyl]-1-(3,4-dimethoxyphenethoxy)-cyclohexane monohydrochloride (Compound 5)

(1R,2R)/(1S,2S)-2-[(3S)-benzyloxypyrrolidinyl]-1-(3,4-dimethoxy phenethoxy)-cyclohexane was prepared according to Example 1. The title compound was prepared by hydrogenolysis of (1R,2R)/(1S,2S)-2-[(3S)-benzyloxypyrrolidinyl]-1-(3,4-dimethoxyphenethoxy)-cyclohexane under the conditions described in Example 1.

EXAMPLE 6

(1R,2R)-2-[(3S)-Hydroxypyrrolidinyl]-1-(3,4-dimethoxyphenethoxy)cyclohexane monohydrochloride (Compound 6)

(1R,2R)-2-[(3S)-Hydroxypyrrolidinyl]-1-(3,4-dimethoxyphenethoxy)cyclohexane monohydrochloride (compound 6) was prepared according to the method of Example 1, but starting from 3-(S)-hydroxypyrrolidine.

EXAMPLE 7

(1S,2S)-2-[(3S)-hydroxypyrrolidinyl]-1-(3,4-dimethoxyphenethoxy)cyclohexane monohydrochloride (Compound 7)

(1S,2S)-2-[(3S)-hydroxypyrrolidinyl]-1-(3,4-dimethoxyphenethoxy)cyclohexane monohydrochloride (compound 7) was prepared according to the method of Examples 1 and 2, but starting from 3-(S)-hydroxypyrrolidine.

COMPARATIVE EXAMPLE 8

(1R,2R)/(1S,2S)-1-(3,4-Dimethoxyphenethoxy)-2-(1,4-dioxa-7-azaspiro[4,4]non-7-yl)cyclohexane monohydrochloride (Compound 9)

To a chilled (0° C.) solution of 2e (4.62 g, 20 mmol) and triethylamine (2.64 g, 26 mmol) in dichloromethane (40 mL) was added dropwise methanesulfonyl chloride (3.0 g, 26 mmol). The reaction mixture was stirred at 0° C. for 45 min and then at room temperature for 2 h. The reaction mixture was then washed with a mixture of water-saturated sodium bicarbonate aq (1:1, v/v, 30 mL). The aqueous layer was collected and back-extracted with dichloromethane (2×30 mL). The combined organic extracts were dried over sodium sulfate and the solvent was evaporated in vacuo to yield the crude mesylate suitable for the next step without any further purification.

To sodium hydride (0.72 g, 80% dispersion in mineral oil, 24 mmol) suspended in DME (20 mL) was added a solution of 3,4-dimethoxyphenethyl alcohol (4.46 g, 24 mmol) in DME (20 mL). The resulting mixture was then stirred at room temperature for 2 h.

The mesylate in DME (40 mL) was added quickly to the alkoxide and the resultant mixture was refluxed under argon for 20 h. The cooled reaction mixture was quenched with water (60 mL) and the organic solvent was evaporated in vacuo. The residual aqueous solution was acidified with 10% HCl aq to pH 0.3 and extracted with diethyl ether (2×75 mL). The aqueous layer was collected, basified to pH 7.0 with 5 M NaOH aq and extracted with diethyl ether (3×70 mL). The combined diethyl ether extracts were dried over sodium sulfate and the solvent was evaporated in vacuo to yield 7.1 g (89% yield) of the title compound as a free base.

The free amine (0.58 g, 1.48 mmol) was partitioned between dichloromethane (8 mL) and 0.5 M HCl aq (8 mL). The aqueous layer was collected and extracted twice more with dichloromethane (2×8 mL). The combined organic layers were dried over sodium sulfate and concentrated in vacuo to yield 0.62 g (98% yield) of the title compound. $R_f$ 0.13 (EtOAc-hexanes, 1:4, v/v, +0.5% v/v iPrNH$_2$); $^1$H NMR (400 MHz, free amine, CDCl$_3$) δ 6.75 (m, 3H, Ar), 3.86-1.16 (m, 24H, Aliph); $^{13}$C NMR (75 MHz, APT, free amine, CDCl$_3$) δ 148.59 (+), 147.2 (+), 131.95 (+), 120.74 (−), 115.24 (+), 112.26 (−), 111.04 (−), 79.10 (−), 69.78 (+), 64.22 (+), 64.00 (−), 60.48 (+), 55.84 (−), 55.74 (−), 49.92 (+), 36.48 (+), 35.84 (+), 28.60 (+), 26.92 (+), 23.01 (+), 22.74 (+); HRMS (EI) mass calcd for C$_{22}$H$_{33}$NO$_5$: 391.23587. found: 391.23546 (100%); HPLC (Zorbax Extend C18, 150×4.6 mm, 5 μl; 20-7-% acetonitrile:10 mM phosphate buffer (pH 2.5)) 84.2%; CE 98.5%.

COMPARATIVE EXAMPLE 9

(1R,2R)/(1S,2S)-1-(3,4-Dimethoxyphenethoxy)-2-(pyrrolidinyl)cyclohexane monohydrochloride (Compound 10)

Pyrrolidine (10.5 g, 148 mmol), cyclohexene oxide (15 mL, 148 mmol) and water (5 mL) were refluxed under nitrogen for 7 h. The cooled, orange mixture was partitioned between saturated sodium hydroxide aq (150 mL) and diethyl ether (150 mL). The aqueous layer was back-washed with diethyl ether (75 mL) and the combined diethyl ether layers were dried over sodium sulfate. The diethyl ether was removed in vacuo the residual oil was vacuum distilled (bp 51° C. at full vacuum) to give (1R,2R)/(1S,2S)-2-(Pyrrolidinyl)cyclohexan-1-ol (21.9 g, 87%). $^{13}$C NMR (50 MHz, APT, CDCl$_3$) δ 70.47 (−), 64.82 (−), 47.44 (+), 33.15 (+), 25.11 (+), 24.23 (+), 24.00 (+), 21.12 (+).

To a chilled (0° C.) solution of (1R,2R)/(1S,2S)-2-(Pyrrolidinyl)cyclohexan-1-ol (1.7 g, 10 mmol), triethylamine (1.8 mL, 13 mmol) in dichloromethane (50 mL) was added neat methanesulfonyl chloride (1.0 mL, 13 mmol). The resultant mixture was stirred at 0° C. for another 45 min and then was allowed to warm up to room temperature for 3 h. The reaction mixture was diluted with dichloromethane (50 mL) and washed with water (2×50 mL). The combined washings were back-extracted with dichloromethane (50 mL) and dried over sodium sulfate. Evaporation in vacuo of the solvent yielded the crude mesylate suitable for the next step without further purification.

To NaH (0.33 g, 11 mmol) in DME (15 mL) was added a solution of 3,4-dimethoxyphenethyl alcohol (2.0 g, 11 mmol) in DME (15 mL). The resultant mixture was stirred for 2 h at room temperature under argon.

The mesylate in DME (20 mL) was added to the alkoxide and the resultant reaction mixture was refluxed for 3 h. The solvent was evaporated in vacuo, the residue was taken up with water (100 mL) and the pH was adjusted to pH 1 with 1 M HCl aq. The acidic aqueous solution was then extracted with diethyl ether (100 mL) and the pH was adjusted to pH 13. Extraction with diethyl ether (2×100 mL) provided the free base of the title compound. Treatment with ethereal hydrogen chloride followed by trituration in diethyl ether yielded 1.0 g (27% yield) of the title compound as hydrochloride salt. $^1$H NMR (400 MHz, CDCl$_3$) δ 11.60 (br s, 1H, HN$^+$), 6.70 (m, 3H, Ar), 3.80 (2×d, 2×6H, CH$_3$O), 3.70-1.05 (m, 22H, Aliph); $^{13}$C NMR (75 MHz, APT, CDCl$_3$) δ 148.72 (+), 147.41 (+), 131.32 (+), 120.69 (−), 112.04 (−), 111.07 (−), 77.82 (−), 68.83 (+), 66.94 (−), 55.87 (−), 53.12 (+), 51.76 (+), 35.92 (+), 30.25 (+), 28.30 (+), 24.34 (+), 23.44 (+), 23.01 (+), 22.13 (+); MS (+LSIMS) M$^+$+H 334 (100%); Anal. (C$_{20}$H$_{32}$O$_3$NCl) H, N; C: calcd, 64.94. found, 63.04.

COMPARATIVE EXAMPLE 10

(1R,2R)-1-(3-(R)-Acetyloxypyrrolidinyl)-2-(3,4-dimethoxyphenethoxy) cyclohexane monohydrochloride (Compound 17)

Acetyl chloride (5 mL; 70.31 mmol) was added dropwise into a solution of (3R)-1-{(1R,2R)-2-[2-(3,4-dimethoxyphenyl)ethoxy]cyclohexyl}pyrrolidin-3-ol free base (2.12 g; 5.49 mmol) in methylene chloride (50 mL) at 1° C. The reaction was allowed to reach room temperature overnight. The reaction was followed by TLC and visualized by iodine. The $R_f$ of (1R,2R)-1-(3-(R)-acetyloxypyrrolidinyl)-2-(3,4-dimethoxyphenethoxy)cyclohexane is 0.36 in methanol-methylene chloride (0.5:95, v/v). The excess of acetyl chloride and the solvent were removed under reduced pressure and DCM (30 mL) was added to the remaining mixture. The organic layer was washed with a saturated solution of sodium bicarbonate (30 mL), dried over magnesium sulfate and concentrated to yield the free base acetate (1.3 g, 4.35 mmol) in 61% yield.

COMPARATIVE EXAMPLE 11

(1R,2S)/(1S,2R)-1-(3-(R/S)-Hydroxypyrrolidinyl)-2-(1-naphthalenethoxy)cyclohexane monohydrochloride (Compound 25)

Preparation of Intermediate Compound (1R,2S)/(1S,2R)-1-(3-Ketopyrrolidinyl)-2-(1-naphthalenethoxy)cyclohexane monohydrochloride To a flask containing $Mg(ClO_4)_2$ (2.14 g, 0.95 mmol) vacuum flame-dried, cooled and charged with argon, was added via cannula a solution of 1-naphthaleneethanol (21.6 g, 125 mmol) in $CH_3CN$ (15 mL). The resultant mixture was refluxed until all material had dissolved and then cyclohexene oxide (1.0 g, 10 mmol) was added over a period of 2.5 h. The reaction mixture was then refluxed for 16 h, cooled to room temperature and partitioned between water (150 mL), saturated $NaHCO_3$ aq (50 mL) and $Et_2O$ (100 mL). The aqueous layer was collected and extracted twice with $Et_2O$ (2×100 mL). The combined $Et_2O$ extracts were back-washed with brine (50 ml), dried and concentrated in vacuo to yield 25.2 g of crude material, which solidified upon standing. The excess 1-naphthaleneethanol was recovered by successive recrystallizations in $Et_2O$-hexanes (1:1, v/v). The resultant mother liquor (7.5 g) obtained after 3 recrystallizations was purified by chromatography using a mixture of EtOAc-hexanes (1:5, v/v, +0.5% v/v $iPrNH_2$) to provide 1.5 g (55% yield) of crude (1R,2R)/(1S,2S)-2-(1-naphthalenethoxy)cyclohexan-1-ol, which was used in the next step without further purification.

To a suspension of pyridinium chlorochromate (PCC) (4.78 g, 22.2 mmol) in $CH_2Cl_2$ (35 mL) was added at once a solution of (1R,2R)/(1S,2S)-2-(1-naphthalenethoxy)cyclohexan-1-ol (1.5 g, 5.5 mmol) in $CH_2Cl_2$ (5 mL). The resultant dark brown mixture was stirred at room temperature for 16 h, and then filtered through a plug of silica gel topped with $Na_2SO_4$. The plug was further rinsed with $Et_2O$ (3×40 mL) and the filtrate was concentrated in vacuo to yield 2.0 g of crude material. The crude material was applied to a dry column of silica gel and eluted with a mixture of EtOAc-hexanes (1:6, v/v, +0.5% v/v $iPrNH_2$) to yield 1.0 g of (2R/2S)-2-(1-Naphthalenethoxy)cyclohexan-1-one (68% yield). $^{13}C$ NMR (50 MHz, APT, $CDCl_3$) δ 203.0 (+), 135.0 (+), 134.0 (+), 132 (+), 129.0 (−), 127.0 (−), 125.5 (−), 125.0 (−), 123.5 (−), 113.0 (−), 83.0 (−), 70.0 (+), 40.0 (+), 34.5 (+), 33.5 (+), 28.0 (+), 23.0 (+); IR (film) 1720 $cm^{-1}$.

(2R/2R)-2-(1-Naphthalenethoxy)cyclohexan-1-one (1.0 g, 3.7 mmol), 2e (1.2 g, 9.3 mmol) and poly(4-vinylpyridine) or PVP (0.4 g) in benzene (10 mL) were refluxed in a Dean-stark apparatus for 5 h. The cooled reaction mixture was then quickly transferred to a Parr shaker apparatus, Pd on activated carbon (0.2 g) was added and the mixture was hydrogenated for 16 h. The catalyst was removed by filtration, the filtrate was concentrated in vacuo and the resultant crude material (cis-trans, 87:13, area %/GC) was purified by dry-column chromatography with a mixture of EtOAc-hexanes (1:2, v/v, +0.5% v/v $iPrNH_2$) to provide 1.0 g (70% yield) of (1R,2S)/(1S,2R)-1-(1,4-dioxo-7-azaspiro[4.4]non-7-yl)-2-(1-naphthalenethoxy)cyclohexane, which was refluxed with 6 M HCl aq (20 mL) in 2-butanone (80 mL) for 16 h. The cooled reaction mixture was concentrated in vacuo and the residue was diluted with water (90 mL). The aqueous solution was then extracted with $Et_2O$ (2×50 mL) and $CH_2Cl_2$ (3×70 mL). The combined $CH_2Cl_2$ extracts were dried and the solvent was evaporated in vacuo. Trituration in $Et_2O$ provided (1R,2S)/(1S,2R)-1-(3-Ketopyrrolidinyl)-2-(1-naphthalenethoxy) cyclohexane monohydrochloride (0.82 g, 84% yield). mp 176-178° C.; $^1H$ NMR (400 MHz, $CDCl_3$) δ 12.53 (br s, 1H, $HN^+$), 8.06-7.32 (m, 7H, Ar), 4.05-1.16 (m, 20H, aliph); $^{13}C$ NMR (75 MHz, APT, $CDCl_3$) δ 204.19 (+), 204.02 (+), 134.99 (+), 134.90 (+), 133.65 (+), 131.94 (+), 131.85 (+), 128.71 (−), 127.12 (−), 127.04 (−), 125.92 (−), 125.84 (−), 125.53 (−), 125.45 (−), 123.75 (−), 123.68 (−), 72.49 (−), 71.79 (−), 68.39 (+), 68.24 (+), 65.50 (−), 64.92 (−), 54.73 (+), 54.33 (+), 48.86 (+), 48.22 (+), 35.56 (+), 35.12 (+), 32.91 (+), 26.81 (+), 26.77 (+), 24.00 (+), 22.53 (+), 21.97 (+), 18.3 (+); HRMS (EI) mass Anal. ($C_{22}H_{28}NO_2Cl$) C, H, N.

Preparation of (Compound 25), (1R,2R)/(1S,2R)-1-(3-(R/S)-Hydroxypyrrolidinyl)-2-(1-naphthalenethoxy)cyclohexane monohydrochloride To a solution of (1R,2S)/(1S,2R)-1-(3-Ketopyrrolidinyl)-2-(1-naphthalenethoxy)cyclohexane monohydrochloride (0.55 g, 1.5 mmol) in isopropanol (15 mL) was added portionwise sodium borohydride (0.3 g, 7.9 mmol). The resultant reaction mixture was stirred at room temperature for 16 h. The reaction mixture was quenched with 6 M HCl aq (4 mL) for 2 h and then concentrated in vacuo. The residual solid was taken up with dichloromethane (20 mL), the insoluble was filtered off and washed once more with dichloromethane (20 mL) and the combined filtrates were treated with ethereal hydrogen chloride (20 mL). The solvents were evaporated in vacuo and the residual oil was triturated in diethyl ether (80 mL) to yield 0.32 g (57% yield) of a hygrospcopic solid. $^1H$ NMR (400 MHz, $CDCl_3$) δ 10.30 (br s, 1H, $HN^+$), 8.10-7.30 (m, 7H, Ar), 5.40-1.00 (m, 22H, Aliph); $^{13}C$ NMR (75 MHz, APT, $CDCl_3$) δ 135.15 (+), 133.59 (+), 131.92 (+), 128.53 (−), 127.05 (−), 126.85 (−), 125.80 (−), 125.40 (−), 123.87 (−), 72.51 (−), 72.17 (−), 68.81 (−), 68.76 (−), 68.57 (+), 66.41 (−), 66.25 (−), 65.19 (−), 59.75 (+), 59.08-58.68 (+), 50.43-49.82 (+), 33.02 (+), 32.98 (+), 26.75 (+), 23.96 (+), 22.93-22.42 (+), 18.23 (+); MS ($ES^+$) $M^++H$ 340.1 (100%); HPLC (Zorbax Extend C18, 150×4.6 mm, 5μ; 20-70% acetonitrile: 10 mM phosphate buffer (pH 2.5)) 96.7%; CE 98.7%.

COMPARATIVE EXAMPLE 12

(1R,2R)/(1S,2S)-[2-(4-Morpholinyl)-1-(2-Naphthenethoxy)]Cyclohexane Monohydrochloride (Compound 30)

(i) Morpholine (5 mL, 57 mmol), cyclohexene oxide (5.8 mL, 57 mmol) and water (3 mL) were refluxed for 1.5 h. GC analysis showed the reaction to be complete. The cooled mixture was partitioned between saturated NaOH solution (50 mL) and ether (75 mL). The aqueous layer was back-washed with ether (30 mL) and the combined ether layers were dried over sodium sulfate. The ether was removed in vacuo to leave a yellow oil (9.83 g). The crude product, (1R,2R)/(1S,2S)-[2-(4-morpholinyl)]cyclohexanol, was purified by vacuum distillation (b.p. 75-80° C. at full vacuum) to give a clear liquid (8.7 g). Yield 82.5%.

(ii) To a chilled (0° C.) solution of (1R,2R)/(1S,2S)-[2-(4-morpholinyl)]cyclohexanol (6.0 g, 32.4 mmol) and triethylamine (6.8 mL, 48 mmol) in dichloromethane (100 mL) was added via cannula a solution of methanesulfonyl chloride (3.10 mL, 40 mmol) in dichloromethane (50 mL). The addition was completed in 10 min., the reaction mixture was stirred for another hour at 0° C. and then at room temperature for 4 hours. The dichloromethane mixture was washed with water (2×50 mL) and the combined aqueous washings back extracted with dichloromethane (50 mL). The combined organic layers were dried over sodium sulfate and concentrated in vacuo to provide 8.5 g (100% yield) of the crude mesylate.

(iii) To sodium hydride, 80% oil dispersion previously washed with hexanes (3×20 mL), (1.24 g, 51.6 mmol) in dry dimethylformamide (50 mL) was added via cannula a solution of 2-naphthenethanol (6.8 g, 40 mmol) in dry dimethylformamide (50 mL). Addition was followed by gas evolution and, as the reaction mixture was stirred at room temperature, it began to gel. The mesylate as prepared in (ii) above was dissolved in dimethylformamide (50 mL) and the resulting solution was added quickly via cannula to the slurry of alcoholate. The reaction mixture was heated to 80° C. and then the temperature reduced to 40° C. The resulting yellow solution was poured into ice-water (1500 mL) and extracted with ethyl acetate (3×300 mL). The combined organic extracts were backwashed with a saturated aqueous solution of sodium chloride (500 mL) and dried over sodium sulfate. Evaporation of the solvent in vacuo provided 13.4 g of an amber oil which was dissolved in water (150 mL) and the pH of the solution was adjusted to pH 2 with aqueous 1M HCl. The acidic aqueous solution was extracted with ethyl ether (2×100 mL) and then basified to pH 10 with 50% sodium hydroxide aqueous solution. The basic aqueous solution was extracted with ethyl ether (2×100 mL), the combined organic layers were dried over sodium sulfate and concentrated in vacuo to leave 7.16 g of the crude free aminoether. The crude product was purified by chromatography on silica gel 60 (70-230 mesh) with a mixture of ethyl acetate-chloroform (1:1, v/v) as eluent to yield 4.37 g of the pure free base. The product was dissolved in ethyl ether (80 mL) and converted to the monohydrochloride salt by adding saturated solution of HCl in ethyl ether (80 mL). An oil came out of the solution, the solvent was evaporated in vacuo and the residue dissolved in the minimum amount of warm ethyl alcohol, addition of a large volume of ethyl ether triggered crystallization. The crystals were collected to afford 3.83 g (31% yield) of the title compound, m.p. 158-160° C.

COMPARATIVE EXAMPLE 13

(1R,2R)/(1S,2S)-[2-(4-Morpholinyl)-1-(4-Bromophenethoxy)]Cyclohexane Monohydrochloride (Compound 32)

(i) The starting trans-aminocyclohexanol is prepared according to comparative example 12.

(ii) To a chilled (0° C.) solution of (±)-trans-[2-morpholinyl]cyclohexanol (3.0 g, 16.2 mmol) and triethylamine (3.4 mL, 24 mmol) in dichloromethane (25 mL) was added via cannula a solution of methanesulfonyl chloride (1.55 mL, 20.0 mmol) in dichloromethane (25 mL). The addition was completed in 5 min., the reaction mixture was stirred for another hour at 0° C. and then at room temperature for 2 hours. The reaction mixture was diluted with dichloromethane (50 mL) and washed with water (2×50 mL) and the combined aqueous washings back extracted with dichloromethane (25 mL). The combined organic layers were dried over sodium sulfate and concentrated in vacuo to provide 4.7 g of the crude mesylate.

(iii) To sodium hydride, 80% oil dispersion, previously washed with hexanes (3×10 mL), (0.62 g, 25.8 mmol) in dry dimethylformamide (25 mL) was added via cannula a solution of 4-bromophenethylalcohol (4.0 g, 20 mmol) in dimethylformamide (50 mL). Addition was followed by evolution of gas and the reaction mixture was stirred at room temperature for 4 hours. The mesylate as prepared in (ii) above was dissolved in dry dimethylformamide (50 mL) and the resulting solution was added quickly (3 min.) via cannula to the slurry of alcoholate. The reaction mixture was heated to 80° C. for 2 hours, then the temperature was reduced to 35° C. and the reaction stirred overnight. The reaction mixture was poured into ice-water (800 mL) and extracted with ethyl acetate (3×200 mL). The combined organic extracts were backwashed with a saturated aqueous solution of sodium chloride (150 mL) and dried over sodium sulfate. Evaporation of the solvent in vacuo provided 7.4 g of an oil which was dissolved in ether (80 mL) was treated with a saturated solution of HCl in ether. An oil came out of solution, the solvent was evaporated in vacuo and the residue was dissolved in water (100 mL). The acidic aqueous solution was extracted with ethyl ether (2×50 mL) and then basified to pH 10 with 50% sodium hydroxide aqueous solution. The basic aqueous solution was extracted with ethyl ether (2×50 mL), the combined organic layers were dried over sodium sulfate and concentrated in vacuo to leave 3.67 g of the crude free amino ether. The crude product was purified by chromatography on silica gel 60 (70-230 mesh) with a mixture of ethyl acetate-dichloromethane (1:1, v/v) as eluent to provide the pure free base. The product was dissolved in ethyl ether (30 mL) and converted to the monohydrochloride salt by adding a saturated solution of HCl in ethyl ether (30 mL). The solvent was evaporated and the residue dissolved in the minimum amount of ethyl alcohol, addition of a large volume of ethyl ether triggered crystallization. The crystals were collected to afford 1.31 g of the title compound, m.p. 148-151° C.

COMPARATIVE EXAMPLE 14

(1R,2R)/(1S,2S)-2-(3-Ketopyrrolidinyl)-1-(2,6-dichlorophenethoxy)cyclohexane monohydrochloride (Compound 41)

(vi) To a chilled (0° C.) solution of (1R,2R)/(1S,2S)-2-(1,4-dioxa-7-azaspiro[4.4]non-7-yl)cyclohexanol (2e) (27.77 g, 120 mmol) and triethylamine (22 mL, 156 mmol) in dichloromethane (240 mL) was added methanesulfonyl chloride (12.32 mL, 156 mmol). The reaction mixture was stirred at 0° C. for 45 min. and then at room temperature for 3 hours. The reaction mixture was washed with water (2×100 mL) and the combined washings were back-extracted with dichloromethane (120 mL). The combined organic extracts were dried over sodium sulfate and the solvent was evaporated in vacuo to yield the crude mesylate which was further pumped under high vacuum for 4 hours prior to use in step (ix) below.

(vii) 2,6-Dichlorophenethyl alcohol: a suspension of lithium aluminum hydride (13.75 g, 365.75 mmol) in anhydrous diethyl ether (500 mL) was added via a powder addition funnel 2,6-dichlorophenylacetic acid (50 g, 243.75 mmol). The resulting reaction mixture was refluxed for 16 hours and then quenched by slow addition of a sodium sulfate saturated aqueous solution (25 mL). The resulting slurry was stirred for 3 hours and then filtered, the insoluble was carefully washed with diethyl ether (2×100 mL). The combined ether filtrates were dried over sodium sulfate and the solvent was evaporated in vacuo to yield 38.6 g (85% yield) of the title compound.

(viii) To sodium hydride (144 mmol, 4.32 g, 80% oil dispersion) in anhydrous ethylene glycol dimethyl ether (80 mL) was added a solution of 2,6-dichlorophenethyl alcohol (27.65 g, 144 mmol) in anhydrous ethylene glycol dimethyl ether (80 mL). The resulting mixture was stirred at room temperature under argon atmosphere for 4 hours.

(ix) (1R,2R)/(1S,2S)-2-[1,4-Dioxa-7-azaspiro[4.4]non-7-yl]-1-(2,6-dichlorophenethoxy)cyclohexane: The mesylate from (vi) in anhydrous ethylene glycol dimethyl ether (80 mL) was added quickly to the alkoxide mixture (viii) and the resulting mixture was readily refluxed for 66 hours. The cooled reaction mixture was poured into water (200 mL) and the organic solvent was evaporated in vacuo. The residual aqueous solution was diluted with more water to a volume of 700 mL, acidified to pH 0.5 with 6M HCl aqueous solution and extracted with diethyl ether (2×600 mL). The pH of the aqueous layer was adjusted to pH 5.9 and then the aqueous solution was extracted with diethyl ether (700 mL). The organic extract was dried over sodium sulfate and the solvent was evaporated in vacuo to yield 34.0 g of the title compound (70% yield).

(x) (1R,2R)/(1S,2S)-2-(3-Ketopyrrolidinyl)-1-(2,6-dichlorophenethoxy)cyclohexane monohydrochloride: A mixture of (1R,2R)/(1S,2S)-2-[1,4-Dioxa-7-azaspiro[4.4]non-7-yl]-1-(2,6-dichlorophenethoxy)cyclohexane (15.85 g, 38.9 mmol, step ix) and 6M HCl aqueous solution (100 mL) in 2-butanone (400 mL) was refluxed for 16 hours. The cooled reaction mixture was diluted with water (100 mL) and the organic solvent was evaporated in vacuo. The organic layer was further diluted with water (400 mL), extracted with diethyl ether (500 mL) and with dichloromethane (2×600 mL). The combined dichloromethane extracts were dried over sodium sulfate and the solvent was evaporated in vacuo. Azeotropic distillation with toluene provided the title compound which was further dried under high vacuum for 15 min. The hydrochloride salt was crystallized by triturating in diethyl ether, the crystals were collected and recrystallized from a mixture of ethanol-diethyl ether to yield 11.85 g of pure product (77% yield), having the correct elemental analysis.

COMPARATIVE EXAMPLE 15

(1R,2R)/(1S,2S)-2-(3-Acetoxypyrrolidinyl)-1-(1-naphthenethoxy)cyclohexane monohydrochloride (Compound 43)

(i) (1R,2R)/(1S,2S)-2-(3-Hydroxypyrrolidinyl)-1-(1-naphthenethoxy)cyclohexane monohydrochloride: To a chilled (0° C.) solution of sodium borohydride in isopropanol (20 mL) was added a solution of (1R,2R)/(1S,2S)-2-(3-ketopyrrolidinyl)-1-(1-naphthenethoxy)cyclohexane monohydrochloride (1.4 g, 3.75 mmol) in isopropanol (30 mL). The resulting mixture was stirred at 0° C. for 15 min. and then 30 min. at room temperature. The reaction was quenched by addition of water, the reaction mixture was evaporated to dryness and the residue was washed with dichloromethane (2×20 mL). The dichloromethane washings were dried over sodium sulfate and the solvent was evaporated in vacuo to yield the title compound.

(ii) (1R,2R)/(1S,2S)-2-(3-Acetoxypyrrolidinyl)-1-(1-naphthenethoxy)cyclohexane monohydrochloride: The intermediate alcohol (i) was then refluxed in acetic anhydride (15 mL) for 2 hours. The excess acetic anhydride was removed in vacuo; the residue was taken up with water (100 mL) and extracted with diethyl ether (2×30 mL). The aqueous solution was basified to pH 8.0 and extracted with diethyl ether (3×50 mL). The combined organic extracts were dried over sodium sulfate and concentrated in vacuo. The residual oil was dissolved in a small amount of dichloromethane and a large volume of diethyl ether was added in order to trigger crystallization of 1.0 g (65% yield) of the title compound

COMPARATIVE EXAMPLE 16

(1R,2R)/(1S,2S)-2-(3-Thiazolidinyl)-1-(2,6-dichlorophenethoxy)cyclohexane monohydrochloride (Compound 48)

(i) (1R,2R)/(1S,2S)-2-(3-Thiazolidinyl)cyclohexanol: To anhydrous magnesium perchlorate (12.93 g, 53.3 mmol) was added a solution of cyclohexene oxide (6.1 mL, 58.6 mmol) in anhydrous acetonitrile (25 mL) and the resulting mixture was stirred at room temperature for 20 min. Then a solution of thiazolidine (5.16 g, 55.0 mmol) in anhydrous acetonitrile was added and the reaction mixture was heated at 35° C. for 16 hours. The reaction mixture was concentrated in vacuo and the residue was partitioned between water (350 mL) and diethyl ether (350 mL). The aqueous layer was separated and extracted once more with diethyl ether (350 mL). The combined organic extracts were dried over sodium sulfate and concentrated in vacuo to provide the crude product. The crude aminoalcohol was purified by dry-column chromatography with a mixture of ethyl acetate-hexanes (1:1, v/v) as eluent to yield 4.83 g (47% yield) of the title compound.

(ii) To a chilled (0° C.) solution of (1R,2R)/(1S,2S)-2-(3-thiazolidinyl)cyclohexanol (3.17 g, 16.9 mmol) and triethylamine (3.08 mL, 22.0 mmol) in dichloromethane (30 mL) was added dropwise methanesulfonyl chloride (1.74 mL, 22.0 mmol). The reaction mixture was stirred at 0° C. for one hour and then at ambient temperature for 3 hours. The reaction mixture was diluted with dichloromethane (20 mL) and washed with water (2×30 mL). The combined washings were back-extracted with dichloromethane (25 mL) and the combined organic extracts were dried over sodium sulfate. Evaporation of the solvent in vacuo yielded the mesylate suitable for the next step without any further purification.

(iii) To sodium hydride, 80% oil dispersion (608 mg, 20.28 mmol) in ethylene glycol dimethyl ether (30 mL) was added a solution of 2,6-dichlorophenethyl alcohol (3.87 g, 20.28 mmol, example 4, step vii) in ethyleneglycol dimethyl ether (15 mL). The resulting mixture was stirred at room temperature under argon atmosphere for 2 hours.

(iv) (1R,2R)/(1S,2S)-2-(3-Thiazolidinyl)-1-(2,6-dichlorophenethoxy)cyclohexane monohydrochloride: The mesylate (ii) in ethylene glycol dimethyl ether (15 mL) was added quickly to the alkoxide (iii) and the reaction mixture was refluxed for 40 hours. The cooled reaction mixture was poured into water (100 mL) and the organic solvent was evaporated in vacuo. The residual aqueous solution was diluted with more water (100 mL) and the pH was adjusted to pH 1.5. The acidic aqueous solution was extracted with diethyl ether (3×100 mL), the combined organic extracts were dried over sodium sulfate and the solvent was removed in vacuo to provide the crude free base. The product was purified by dry-column chromatography with a mixture of ethyl acetate-hexanes (1:10, v/v) as eluent to yield 2.4 g of the crude free aminoether. The pure product (1.0 g) was converted to the hydrochloride salt by treatment with ethereal HCl and the resulting salt was recrystallized from a mixture of acetone-diethyl ether to yield 0.69 g of the title compound.

COMPARATIVE EXAMPLE 17

(1R,2R)/(1S,2S)-2-(3-Ketopyrrolidinyl)-1-(2,2-diphenylethoxy)cyclohexane monohydrochloride (Compound 47)

(vi) To a chilled (0° C.) solution of (1R,2R)/(1S,2S)-2-(1,4-dioxa-7-azaspiro[4.4]non-7-yl)cyclohexanol (2e) (2.0 g, 8.8 mmol) and triethylamine (2.1 mL, 15 mmol) in dichloromethane (30 mL) was added methanesulfonyl chloride (0.9 mL, 11.44 mmol). The reaction mixture was stirred at 0° C. for 45 min. and then at room temperature for 3 hours. The reaction mixture was diluted with dichloromethane (25 mL), washed with water (2×25 mL) and the combined washings were back-extracted with dichloromethane (25 mL). The combined organic extracts were dried over sodium sulfate and the solvent was evaporated in vacuo to yield the crude mesylate which was further pumped under high vacuum for 30 min. prior to use in step (ix) below.

(vii) (2,2-Diphenyl)ethyl alcohol: To lithium aluminum hydride (2.85 g, 23.56 mmol) in anhydrous diethyl ether (150 mL) was added, as a powder, diphenylacetic acid (5.0 g, 56 mmol). The resulting reaction mixture was gently refluxed for one hour. The reaction was quenched with sodium sulfate saturated aqueous solution and the resulting precipitate was filtered off. The filtrate was concentrated in vacuo to yield 4.0 g (86% yield) of the title compound.

(viii) To sodium hydride, previously washed with hexanes, (253 mg, 10.56 mmol) in suspension in ethylene glycol dimethyl ether (15 mL) was added a solution of 2,2-diphenylethyl alcohol (2.09 g, 10.56 mmol, step vii) in ethylene glycol dimethyl ether (15 mL). The resulting mixture was stirred at room temperature under argon atmosphere for 30 min.

(ix) (1R,2R)/(1S,2S)-2-(1,4-Dioxa-7-azaspiro[4.4]non-7-yl)-1-(2,2-diphenylethoxy)cyclohexane: The mesylate from (vi) in ethylene glycol dimethyl ether (20 mL) was added quickly to the alkoxide (viii) and the reaction mixture was refluxed for 5 days. The cooled reaction mixture was concentrated in vacuo, the residue was taken up with water (50 mL) and the pH was adjusted to pH 1.0 with 6M HCl aqueous solution. The acidic aqueous solution was extracted with diethyl ether (2×50 mL), the aqueous layer was collected and basified to pH 6.0. Extraction with diethyl ether (2×50 mL) followed by drying over sodium sulfate and evaporation of the solvent in vacuo yielded 1.55 g (43% yield) of the title compound.

(x) (1R,2R)/(1S,2S)-2-(3-Ketopyrrolidinyl)-1-(2,2-diphenylethoxy)cyclohexane monohydrochloride: A mixture of (1R,2R)/(1S,2S)-2-(1,4-dioxa-7-azaspiro[4.4]non-7-yl)-1-(2,2-diphenylethoxy)cyclohexane (1.55 g, 3.8 mmol) in 6M HCl-butanone(1:4, v/v, 50 mL) was refluxed for 2 hours. The butanone was evaporated in vacuo and the residue was taken up with water (50 mL). The aqueous solution was extracted with diethyl ether (2×50 mL); the aqueous layer was collected and extracted with dichloromethane (2×50 mL). The combined dichloromethane extracts were dried over sodium sulfate and concentrated in vacuo to yield the crude title compound. The product was crystallized by triturating in diethyl ether and reprecipitated from a mixture of dichloromethane-diethyl ether to yield 1.21 g (80% yield) of the title compound, having the correct elemental analysis.

General Experimental Procedures

Melting points were determined on a Fisher-Johns apparatus and are uncorrected. NMR spectra were acquired in the indicated solvent on a Brucker AC-200, Varian XL-300, Brucker AV-300 or AV-400. Mass spectra were recorded for EI on a Kratos MS50, for FAB/LSIMS on a Kratos Concept IIHQ and for ES on a Micromass (Waters) Quattro (I) MSMS, connected to a HP1090 Series 2 LC (Agilent), controlled by Masslynx version 3.3 software. Elemental analyses were performed on an Element Analyzer 1108 by D. & H. Malhow, University of Alberta, Edmonton, AB. Where analyses are indicated only by symbols of the elements, analytical results were within ±0.4% of the theoretical values. Whenever elemental analyses were not available, purity was determined by HPLC and capillary electrophoresis (CE). HPLC analyses were performed using a Gilson HPLC system (Gilson, Middleton, Wis.) with UV detection at 200 nm. A $C_{18}$ column with 150×4.6 mm, 5μ particle size was used. The mobile phase was delivered isocratically or as a gradient at a flow rate of 1 mL/min and consisted of a combination of phosphate buffer (low or high pH) and acetonitrile. Samples were prepared at ~100 μg/mL in mobile phase and 20 μL were injected into the HPLC. Purity was expressed in area %. CE analyses were performed using a P/ACE System MDQ (Beckman Coulter, Fullerton, Calif.). Uncoated silica capillaries with 60 (50 to detector) cm length and 75 μm internal diameter were used. The run buffer used was 100 mM sodium phosphate (pH 2.5). The separation voltage was either 23 or 25 kV (normal polarity) and the capillary cartridge temperature was maintained at 20° C. Samples (~0.5 mg/mL in water) were injected by pressure at 0.5 psi for 6 seconds. Detection was by UV at 200 or 213 nm. Purity was expressed in area %. IR were recorded on a Perkin-Elmer 983G spectrophotometer. Optical rotations were performed by F. Hoffman-La Roche Ltd (CH, Basel). Thin layer chromatography (TLC) was performed on E. Merck, TLC aluminum sheets 20×20 cm, Silica gel 60 $F_{254}$ plates. Flash chromatography[41] was performed on E.M. Science silica gel 60 (70-230 mesh). Dry flash chromatography[42] was performed with Sigma silica gel type H. Chromatotron chromatography (Harisson Research, USA) was performed on 4 mm plate with EM Science silica gel 60P $F_{254}$ with Gypsum or aluminum oxide 60P $F_{254}$ with Gypsum (type E). Preparative HPLC were performed on a Waters Delta Prep 4000 with a cartridge column (porasil, 10 μm, 125 Å, 40 mm×100 mm). GC analyses were performed on a Hewlett Packard HP 6890 equipped with 30 m×0.25 mm×0.25 μm capillary column HP-35 (crosslinked 35% PH ME siloxane) and a flame-ionization detector. High-boiling solvents (DMF, DMSO) were Sure/Seal™ from Aldrich, and tetrahydrofuran (THF) and ethylene glycol dimethyl ether (DME) were distilled from sodium-benzophenone ketyl. Organic extracts were dried with $Na_2SO_4$ unless otherwise noted. All moisture sensitive reactions were performed in dried glassware under a nitrogen or argon atmosphere.

Biological Activity Data

Assessment of Antiarrhythmic Efficacy

Antiarrhythmic efficacy may be assessed by investigating the effect of a compound on the incidence of cardiac arrhythmias in anesthetized rats subjected to coronary artery occlusion. Rats weighing 200-300 gms are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22:656 (1988) (see Table 1).

TABLE 1

| Score | Description |
|---|---|
| 0 | 0-49 VPBs |
| 1 | 50-499 VPBs |
| 2 | >499 VPBs and/or 1 episode of spontaneously reverting VT or VF |
| 3 | >1 episode of VT or VF or both (>60 s total combined duration) |
| 4 | VT or VF or both (60-119 s total combined duration) |
| 5 | VT or VF or both (>119 s total combined duration) |
| 6 | fatal VF starting at >15 min after occlusion |
| 7 | fatal VF starting at between 4 min and 14 min 59 s after occlusion |
| 8 | fatal VF starting at between 1 min and 3 min 59 s after occlusion |
| 9 | fatal VF starting <1 min after occlusion |

Where:
VPB = ventricular premature beats
VT = ventricular tachycardia
VF = ventricular fibrillation Rats are excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

Table 4, column 6 shows the $ED_{50}AA$ result of tests of the compounds 1 to 7 according to the invention in micromol/kg/min. Table 5, column 6 shows the $ED_{50}AA$ result of tests of the comparative examples compounds 8 to 48 in micromol/kg/min.

Measurement of Cardiovascular and Behavioral Effects

Preparative surgery is performed in Sprague Dawley rats weighing 200-300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 guage needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 μmol/kg/min (at 1 ml/hr). This rate is doubled every 5 minutes until one of the following effects is observed:
 a) partial or complete convulsions
 b) severe arrhythmias
 c) bradycardia below 120 beats/min
 d) hypotension below 50 mmHg
 e) the dose exceeds 32 times the initial starting dose (i.e., 64 μmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lipsmacking, wet dog shake etc.) occurred are recorded.

Blood Samples

Estimates of plasma concentrations of the test compound are determined by removing a 0.5 ml blood sample at the end of the experiment. Blood samples are centrifuged for 5 min at 4600×g and the plasma decanted. Brain tissue samples are also extracted and kept frozen (−20° C.) along with the plasma samples for chemical analysis.

Data Analysis

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P-R interval and QRS interval indicate cardiac sodium channel blockade while the increase in Q-T interval indicates cardiac potassium channel blockade.

Electrophysiological Test (In Vivo)

This experiment determines the potency of the test compound for its effects on haemodynamic and electrophysiological parameters under non-ischemic conditions.

Methods

Surgical Preparation

Male Sprague-Dawley rats weighing between 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 ml/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in μA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×1T and 0.2 msec pulse width); VTt is the minimum pulse current (in μA) to evoke a sustained episode of VT (0.2 msec pulse width and 50

Hz) (Howard, P. G. and Walker, M. J. A., *Proc. West. Pharmacol. Soc.* 33:123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R-R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

Experimental Protocol

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 ml/hr/300 g (i.e., 0.5 µmol/kg/min). Each infusion dose is doubled (in rate) every 5 minutes. All experiments are terminated at 32 ml/hr/300 g (i.e., 32 µmol/kg/min). Electrical stimulation protocols are initiated during the last two minutes of each infusion level.

Data Analyses

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

Canine Vagal-AF Model

General Methods

Mongrel dogs of either sex weighing 15-49 kg are anesthetized with morphine (2 mg/kg im initially, followed by 0.5 mg/kg IV every 2 h) and α-chloralose (120 mg/kg IV followed by an infusion of 29.25 mg/kg/h; St.-Georges et al., 1997). Dogs are ventilated mechanically with room air supplemented with oxygen via an endotracheal tube at 20 to 25 breaths/minute with a tidal volume obtained from a nomogram. Arterial blood gases are measured and kept in the physiological range ($SAO_2$>90%, pH 7.30-7.45). Catheters are inserted into the femoral artery for blood pressure recording and blood gas measurement, and into both femoral veins for drug administration and venous sampling. Catheters are kept patent with heparinized 0.9% saline solution. Body temperature is maintained at 37-40° C. with a heating blanket.

The heart is exposed via a medial thoracotomy and a pericardial cradle is created. Three bipolar stainless steel, Teflon™-coated electrodes are inserted into the right atria for recording and stimulation, and one is inserted into the left atrial appendage for recording. A programmable stimulator (Digital Cardiovascular Instruments, Berkeley, Calif.) is used to stimulate the right atrium with 2 ms, twice diastolic threshold pulses. Two stainless steel, Teflon™-coated electrodes are inserted into the left ventricle, one for recording and the other for stimulation. A ventricular demand pacemaker (GBM 5880, Medtronics, Minneapolis, Minn.) is used to stimulate the ventricles at 90 beats/minute when (particular during vagal-AF) the ventricular rate became excessively slow. A P23 ID transducer, electrophysiological amplifier (Bloom Associates, Flying Hills, Pa.) and paper recorder (Astromed MT-95000, Toronto, ON, Canada) are used to record ECG leads II and III, atrial and ventricular electrograms, blood pressure and stimulation artefacts. The vagi are isolated in the neck, doubly-ligated and divided, and electrodes inserted in each nerve (see below). To block changes in β-adrenergic effects on the heart, nadolol is administered as an initial dose of 0.5 mg/kg iv, followed by 0.25 mg/kg IV every two hours.

Atrial Fibrillation Model

Drug effects to terminate sustained AF maintained during continuous vagal nerve stimulation are assessed. Unipolar hook electrodes (stainless steel insulated with Teflon™, coated except for the distal 1-2 cm) are inserted via a 21 gauge needle within and parallel to the shaft of each nerve. In most experiments, unipolar stimuli are applied with a stimulator (model DS-9F, Grass Instruments, Quincy, Mass.) set to deliver 0.1 ms square-wave pulses at 10 Hz and a voltage 60% of that required to produce asystole. In some experiments, bipolar stimulation is used. The voltage required to produce asystole ranged between 3-20 volts. Under control conditions, a short burst of rapid atrial pacing (10 Hz, four times diastolic threshold) is delivered to induce AF which is ordinarily sustained for more than 20 minutes. The vagal stimulation voltage is adjusted under control conditions, and then readjusted after each treatment to maintain the same bradycardic effect. AF is defined as rapid (>500 minute under control conditions), irregular atrial rhythm with varying electrogram morphology.

Measurement of Electrophysiological Variables and Vagal Response

Diastolic threshold current is determined at a basic cycle length of 300 ms by increasing the current 0.1 mA incrementally until stable capture is obtained. For subsequent protocols current is set to twice diastolic threshold. Atrial and ventricular ERP is measured with the extrastimulus method, over a range of S1S2 intervals at a basic cycle length of 300 ms. A premature extrastimulus S2 is introduced every 15 basic stimuli. The S1S2 interval is increased in 5 ms increments until capture occurred, with the longest S1S2 interval consistently failing to produce a propagated response defining ERP. Diastolic threshold and ERP are determined in duplicate and averaged to give a single value. These values are generally within 5 ms. The interval between the stimulus artefact and the peak of the local electrogram is measured as an index of conduction velocity. AF cycle length (AFCL) is measured during vagal-AF by counting the number of cycles (number of beats—1) over a 2-second interval at each of the atrial recording sites. The three AFCLs measurements are averaged to obtain an overall mean AFCL for each experimental condition.

The stimulus voltage-heart rate relationship for vagal nerve stimulation is determined under control conditions in most experiments. The vagal nerves are stimulated as described above with various voltages to determine the voltage which caused asystole (defined as a sinus pause greater than 3 seconds). The response to vagal nerve stimulation is confirmed under each experimental condition and the voltage adjusted to maintain the heart rate response to vagal nerve stimulation constant. In cases in which is not possible to produce asystole, vagal nerve stimulation is adjusted to a voltage which allowed two 20-minute episodes of vagal-AF to be maintained under control conditions (see below).

Experimental Protocols

One of the experimental groups studied is summarized in Table 3. Each dog received only one drug at doses indicated in Table 3. The first series of experiments are dose ranging studies, followed by blinded study in which 1-3 doses are given. All drugs are administered IV via an infusion pump, with drug solutions prepared freshly in plastic containers on the day of the experiment. Vagal stimulation parameters are defined under control conditions as described above, and maintenance of AF during 20 minutes of vagal nerve stimulation under control conditions is verified. After the termination of AF, the diastolic threshold and ERP of the atrium and ventricle are determined. Subsequently, these variables are reassessed in the atrium under vagal nerve stimulation. Electrophysiological testing usually took 15-20 minutes. The heart rate response to vagal nerve stimulation is confirmed and the vagal-AF/electrophysiological testing protocol is repeated. A pre-drug blood sample is obtained and vagal-AF reinstituted. Five minutes later, one of the treatments is administered at doses shown in Table 2. The total dose is infused over 5 minutes and a blood sample obtained immediately thereafter. No maintenance infusion is given. If AF terminated within 15 minutes, the electrophysiological measurements obtained under control conditions are repeated and a blood sample is obtained. If AF is not terminated by the first dose (within 15 minutes), a blood sample is obtained and vagal stimulation is discontinued to allow a return to sinus rhythm. The electrophysiological measurements are repeated and a third and final blood sample for this dose is obtained. AF is reinitiated and the vagal-AF/drug infusion/electrophysiological testing protocol is repeated until AF is terminated by the drug.

Statistical Analysis

Group data are expressed as the mean±SEM. Statistical analysis is carried out for effective doses for AFCL, and ERP using a t-test with a Bonferroini correction for multiple comparisons. Drug effects on blood pressure, heart rate, diastolic threshold and ECG intervals are assessed at the median dose for termination of AF. Two tailed tests are used and a p<0.05 is taken to indicate statistical significance.

TABLE 2

EXPERIMENTAL GROUPS AND DOSES OF DRUGS

| Drug | Dose range tested (µmol/kg) | Effective doses for terminating AF (µmol/kg) | Mean dose required for termination of AF (µmol/kg) | Median dose required for termination of AF (µmol/kg) |
|---|---|---|---|---|
| Flecainide | 1.25-10 | 4-2.5; 1-10 | 4 ± 2 | 2.5 |

A single drug was administered to each dog over the dose range specified until AF was terminated. The number of dogs in which AF was terminated at each dose is shown (number of dogs-dose, in µmol/Kg). The mean±SEM as well as the median dose required to terminate AF is shown. Each dog received only one drug.

Compounds of the present invention may be evaluated by this method. The effectiveness of flecainide as a control in the present study was comparable to that previously reported.

Canine Sterile Pericarditis Model

This model has been used to characterize the mechanisms of AF and atrial flutter (AFL). Waldo and colleagues have found that AF depends on reentry and that the site of termination is usually an area of slowed conduction. This canine model is prepared by dusting the exposed atria with talcum powder followed by "burst" pacing the atria over a period of days after recovery. AF is inducible two days after surgery, however, by the fourth day after surgical preparation; sustainable atrial flutter is the predominant inducible rhythm. The inducibility of AF at day 2 is somewhat variable, such that only 50% of dogs may have sustained AF (generally <60 minutes) for a requisite of 30 minutes. However, the sustainable atrial flutter that evolves by the fourth day is inducible in most preparations. Atrial flutter is more readily "mapped" for purposes of determining drug mechanisms. Inducibility of AF subsides after the fourth day post-surgery, similar to the AF that often develops following cardiac surgery that the sterile pericarditis model mimics. There may be an inflammatory component involved in the etiology of post-surgery AF that would provide a degree of selectivity to an ischaemia or acid selective drug. Similarly, while coronary artery bypass graft (CABG) surgery is performed to alleviate ventricular ischaemia, such patients may also be at risk for mild, atrial ischaemia due to coronary artery disease (CAD). While atrial infarcts are rare, there has been an association between AV nodal artery stenosis and risk for AF following CABG surgery. Surgical disruption of the autonomic innervation of the atria may also play a role in AF following CABG.

Methods

Studies are carried out in a canine model of sterile percarditis to determine the potency and efficacy of compounds of the present invention in terminating atrial fibrillation/flutter. Atrial flutter or fibrillation was induced 2 to 4 days after creation of sterile pericarditis in adult mongrel dogs weighing 19 kg to 25 kg. In all instances, the atrial fibrillation or flutter lasted longer than 10 minutes.

Creation of the Sterile Pericarditis Atrial Fibrillation/Flutter Model

The canine sterile pericarditis model is created as previously described. At the time of surgery, a pair of stainless steel wire electrodes coated with FEP polymer except for the tip (O Flexon, Davis and Geck) are sutured on the right atrial appendage, Bachman's bundle and the posteroinferior left atrium close to the proximal portion of the coronary sinus. The distance between each electrode of each pair is approximately 5 mm. These wire electrodes are brought out through the chest wall and exteriorized posteriorly in the interscapular region for subsequent use. At the completion of surgery, the dogs are given antibiotics and analgesics and then are allowed to recover. Postoperative care included administration of antibiotics and analgesics.

In all dogs, beginning on postoperative day 2, induction of stable atrial fibrillation/flutter is attempted in the conscious, non-sedated state to confirm the inducibility and the stability of atrial fibrillation/flutter and to test the efficacy of the drugs. Atrial pacing is performed through the electrodes sutured during the initial surgery. On postoperative day 4, when stable atrial flutter is induced, the open-chest study is performed.

For the open-chest study, each dog is anesthetized with pentobarbital (30 mg/kg IV) and mechanically ventilated with 100% oxygen by use of a Boyle model 50 anesthesia machine (Harris-Lake, Inc.). The body temperature of each dog is kept within the normal physiological range throughout the study with a heating pad. With the dog anesthetized, but before the chest is opened, radiofrequency ablation of the His bundle is performed to create complete atrioventricular (AV) block by standard electrode catheter techniques. This is done to minimize the superimposition of atrial and ventricular complexes during subsequent recordings of unipolar atrial electrograms after induction of atrial flutter. After complete AV block is created, an effective ventricular rate is maintained by pacing of the ventricles at a rate of 60 to 80 beats per minute with a Medtronic 5375 Pulse Generator (Medtronic Inc.) to deliver stimuli via the electrodes sutured to the right ventricle during the initial surgery.

Determination of Stimulus Thresholds and Refractory Periods During Pacing

For the induction of AF/AFL, one of two previously described methods is used: (1) introduction of one or two premature atrial beats after a train of 8 paced atrial beats at a cycle length of 400 ms, 300 ms, 200 ms, or 150 ms, or (2) rapid atrial Pacing for Periods of 1 to 10 seconds at rates incrementally faster by 10 to 50 beats per minute than the spontaneous sinus rate until atrial flutter is induced or there is a loss of 1:1 atrial capture. Atrial pacing is performed from either the right atrial appendage electrodes or the posteroinferior left atrial electrodes. All pacing is performed using stimuli of twice threshold for each basic drive train with a modified Medtronic 5325 programmable, battery-powered stimulator with a pulse width of 1.8 ms.

After the induction of stable atrial fibrillation/flutter (lasting longer than 10 minutes), the atrial fibrillation/flutter cycle length is measured and the initial mapping and analysis are performed to determine the location of the atrial fibrillation/flutter reentrant circuit. Atrial flutter is defined as a rapid atrial rhythm (rate, >240 beats per minute) characterized by a constant beat-to-beat cycle length, polarity, morphology, and amplitude of the recorded bipolar electrograms.

Drug Efficacy Testing Protocol

1. Effective refractory periods (ERPs) are measured from three sites: right atrial appendage (RAA), posterior left atrium (PLA), and Bachman's Bundle (BB), at two basic cycle lengths 200 and 400 ms.

2. Pace induce A-Fib or AFL. This is attempted for one hour. If no arrhythmia is induced, no further study is done on that day.

3. If induced, AF must have been sustained for 10 minutes. Then a waiting period is allowed for spontaneous termination or 20 minutes, whichever came first.

4. AF is then reinduced and 5 minutes is allowed before starting drug infusion.

5. Drug is then infused in a bolus over 5 minutes.

6. If AF terminated with the first dose then a blood sample is taken and ERP measurements are repeated.

7. Five minutes is allowed for the drug to terminate. If there is no termination then the second dose is given over 5 minutes.

8. After termination and ERPs are measured, a second attempt to reinduce AF is tried for a period of ten minutes.

9. If reinduced and sustained for 10 minutes, a blood sample is taken and the study repeated from #3 above.

10. If no reinduction, then the study is over.

Compounds of the present invention may be evaluated by this method.

Assessment of Pain Blockage

CD-1 mice (20-30 g) are restrained in an appropriate holder. A tourniquet is placed at the base of the tail and a solution of the test compound (50 µl, 5 mg/ml) is injected into the lateral tail vein. The tourniquet is removed 10 min after the injection. Suitable dilutions of compound solution are used to obtain an $ED_{50}$ for pain blockade at various times after injection. Pain responses are assessed by pin prick at regular intervals up to 4 hours post injection and the duration of pain blockage is recorded for three animals for each test compound solution. Compounds of the present invention may be evaluated according to the method described.

In Vitro Assessment of Inhibition Activity of Ion Channel Modulating Compounds on Different Cardiac Ionic Currents Cell Culture:

The relevant cloned ion channels (e.g., cardiac hH1Na, Kv1.4, Kv1.5, Kv4.2, Kv2.1, HERG etc.) are studied by transient transfection into HEK cells using the mammalian expression vector pCDNA3. Transfections for each channel type are carried out separately to allow individual study of the ion channel of interest. Cells expressing channel protein are detected by cotransfecting cells with the vector pHook-1 (Invitrogen, San Diego, Calif., USA). This plasmid encoded the production of an antibody to the hapten phOX, which when expressed is displayed on the cell surface. Equal concentrations of individual channel and pHook DNA are incubated with 10× concentration of lipofectAce in Modified Eagle's Medium (MEM, Canadian Life Technologies) and incubated with parent HEK cells plated on 25 mm culture dishes. After 3-4 hours the solution is replaced with a standard culture medium plus 20% fetal bovine serum and 1% antimycotic. Transfected cells are maintained at 37° C. in an air/5% $CO^2$ incubator in 25 mm Petri dishes plated on glass coverslips for 24-48 hours to allow channel expression to occur. 20 min prior to experiments, cells are treated with beads coated with phOX. After 15 min, excess beads are ished off with cell culture medium and cells which had beads stuck to them are used for electrophysiological tests.

Solutions:

For whole-cell recording the control pipette filling solution contained (in mM): KCl, 130; EGTA, 5; MgCl2, 1; HEPES, 10; Na2ATP, 4; GTP, 0.1; and is adjusted to pH 7.2 with KOH. The control bath solution contained. (in mM): NaCl, 135; KCl, 5; sodium acetate, 2.8; MgCl2, 1; HEPES, 10; CaCl2, 1; and is adjusted to pH 7.4 with NaOH. The test ion channel modulating compound is dissolved to 10 mM stock solutions in water and used at concentrations between 0.5 and 100 µM.

Electrophysiological Procedures:

Coverslips containing cells are removed from the incubator before experiments and placed in a superfusion chamber (volume 250 µl) containing the control bath solution at 22 C to 23 C. All recordings are made via the variations of the patch-clamp technique, using an Axopatch 200A amplifier (Axon Instruments, CA). Patch electrodes are pulled from thin-walled borosilicate glass (World Precision Instruments; FL) on a horizontal micropipette puller, fire-polished, and filled with appropriate solutions. Electrodes had resistances of 1.0-2.5 µohm when filled with control filling solution. Analog capacity compensation is used in all whole cell measurements. In some experiments, leak subtraction is applied to data. Membrane potentials have not been corrected for any junctional potentials that arose between the pipette and bath solution. Data are filtered at 5 to 10 kHz before digitization and stored on a microcomputer for later analysis using the pClamp6 software (Axon Instruments, Foster City, Calif.). Due to the high level of expression of channel cDNA's in HEK cells, there is no need for signal averaging. The average cell capacitance is quite small, and the absence of ionic current at negative membrane potentials allowed faithful leak subtraction of data.

Data Analysis:

The concentration-response curves for changes in peak and steady-state current produced by the test compound are computer-fitted to the Hill equation:

$$f = 1 - 1/[1 + (IC_{50}/[D])^n] \quad [1]$$

where f is the fractional current (f=Idrug/Icontrol) at drug concentration [D]; $IC_{50}$ is the concentration producing half-maximal inhibition and n is the Hill coefficient.

Compounds of the present invention may be evaluated by this method. The results show that compounds of the present invention tested have different degree of effectiveness in blocking various ion channels. Block is determined from the decrease in peak hH1 $Na^+$ current, or in steady-state Kv1.5 and integrated Kv4.2 current in the presence of drug. To record $Na^+$ current, cells are depolarized from the holding potential of −100 mV to a voltage of −30 mV for 10 ms to fully open and inactivate the channel. To record Kv1.5 and Kv4.2 current, cells are depolarized from the holding potential of −80 mV to a voltage of +60 mV for 200 ms to fully open the channel. Currents are recorded in the steady-state at a range of drug concentrations during stimulation every 4 s. Reduction in peak current ($Na^+$ channel), steady-state current (Kv1.5 channel) or integrated current (Kv4.2) at the test potential of −30 mV ($Na^+$ channel) or +60 mV (Kv1.5 and Kv4.2 channel) is normalized to control current, then plotted against the concentration of test compound. Data are averaged from 4-6 cells. Solid lines are fit to the data using a Hill equation. The $IC_{50}$ values for some of the compounds of the present invention on various ion channels studied are summarized in the following table (Table 3):

TABLE 3

| Compound # | Kv1.5 | hERG | Kv4.2 | H1Na | Kv2.1 |
|---|---|---|---|---|---|
| 1 | 3.2 | 7 | 50 | 18.6 | |
| 2 | 6 | | 20 | 36.4 | |
| 3 | 5 | | 35 | 30.3 | |
| 6 | 6 | | 20 | 25.4 | |
| 7 | 6 | | 35 | 37.2 | |

The activity of other compounds of the present invention to modulate various ionic currents of interest may be similarly studied.

Assessment of Proarrhythmia (Torsade de Pointes) Risk of Ion Channel Modulating Compounds in Primates Methods
General Surgical Preparation:

All studies are carried out in male *Macaca fascicularis* weighing between 4 and 5.5 kg. Animals are fasted over night and pre-medicated with ketamine (10 mg/kg im). Both saphenous veins are cannulated and a saline drip instituted to keep the lines patent. Halothane anaesthesia (1.5% in oxygen) is administered via a face mask. Lidocaine spray (10% spray) is used to facilitate intubation. After achieving a sufficient depth of anaesthesia, animals are intubated with a 4 or 5 French endotracheal tube. After intubation halothane is administered via the endotracheal tube and the concentration is reduced to 0.75-1%. Artificial respiration is not used and all animals continue to breathe spontaneously throughout the experiment. Blood gas concentrations and blood pH are measured using a blood gas analyser (AVO OPTI I). The femoral artery is cannulated to record blood pressure.

Blood pressure and a modified lead II ECG are recorded using a MACLAB 4S recording system paired with a Macintosh PowerBook (2400c/180). A sampling rate of 1 kHz is used for both signals and all data is archived to a Jazz disc for subsequent analysis.

Vagal Nerve Stimulation:

Either of the vagi is isolated by blunt dissection and a pair of electrodes inserted into the nerve trunk. The proximal end of the nerve is crushed using a vascular clamp and the nerve is stimulated using square wave pulses at a frequency of 20 Hz with a 1 ms pulse width delivered from the MACLAB stimulator. The voltage (range 2-10V) is adjusted to give the desired bradycardic response. The target bradycardic response is a reduction in heart rate by half. In cases where a sufficient bradycardic response could not be obtained, 10 µg/kg neostigmine iv is administered. This dose of neostigmine is also given after administration of the test drug in cases where the test drug has vagolytic actions.

Test Compounds:

A near maximum tolerated bolus dose of the test compound, infused (iv) over 1 minute, is used to assess the risk of torsade de pointer caused by each test compound. The actual doses vary slightly depending on the animals' weight. Clofilium, 30 µmol/kg, is used as a positive comparison (control) for these studies. The expectation is that a high dose of drug would result in a high incidence of arrhythmias. The test compounds are dissolved in saline immediately before administration.

Experimental Protocol:

Each animal receives a single dose of a given drug iv. Before starting the experiment, two 30 second episodes of vagal nerve stimulation are recorded. A five minute rest period is allowed between episodes and before starting the experiment. The test solution is administered as an iv bolus at a rate of 5 ml/minute for 1 minute using an infusion pump (total volume 5 ml). ECG and blood pressure responses are monitored continuously for 60 minutes and the occurrence of arrhythmias is noted. The vagal nerve is stimulated for 30 seconds at the following times after injection of the drug: 30 seconds, 2, 5, 10, 15, 20, 25, 30 and 60 minutes.

Blood samples (1 ml total volume) are taken from each treated animal at the following times after drug administration: 30 seconds, 5, 10, 20, 30 and 60 minutes as well as 3, 6, 24 and 48 hours. Blood samples taken up to 60 minutes after drug administration are arterial while those taken after this time are venous. Samples are centrifuged, the plasma decanted and frozen. Samples are kept frozen before analysis of plasma concentration of the drug and potassium.

Statistics:

The effect of drugs on blood pressure, heart rate and ECG intervals are described as the mean±SEM for a group size of "n."

Compounds of the present invention may be evaluated by this method.

Determination of CNS Toxicity

In order to assess the activity of ion channel compounds in vivo it is important to know the maximum tolerated dose. Here CNS toxicity was assessed by investigating the minimum dose of a compound which induces partial or complete convulsions in conscious rats. The procedure avoids using lethality as an end point as well as avoiding unnecessary suffering as the experiment is terminated if this appears likely. Should the drug precipitate a life threatening condition (e.g., severe hypotension or cardiac arrhythmias) the animals are sacrificed via an overdose of pentobarbital.

Rats weighing 200-250 g were anaesthetized with pentobarbital anesthetic and subjected to preparative surgery. The femoral artery was cannulated for measurement of blood pressure and withdrawal of blood samples. The femoral vein was cannulated for injection of drugs. ECG leads were inserted into the subcutaneous muscle layer in the region of the heart and in the region near the base of the neck and shoulder. All cannulae and ECG leads were exteriorized in the mid scalpular region. To alleviate post-operative pain narcotics and local anesthetics were used. Animals were returned to a recovery cage for at least 24 hours before commencing the experiment. Infusion of the compound was then commenced via the femoral vein cannula. The initial rate of infusion was set at 2.0 micromole/kg/min at a rate of 1 ml/hr. The infusion rate was doubled every minute until partial or complete convulsions were observed. The maximum infusion rate used was 64 micromole/kg/min. Rates were continuously monitored and end time an infusion rate noted.

Table 4, column 4 describes the results of test for the compounds described therein as values of a given infusion rate in micromole/kg/min. (convulsion dose) which is the minimum infusion rate at which partial or complete convulsions are observed. Table 4, column 5 gives the results of the test for the described compounds as values of the cumulative convulsion dose which is the total amount of drug infused at the point that partial or complete convulsions are first observed.

Similarly, Table 5, column 4 describes the results of test for the comparative example compounds described therein as values of a given infusion rate in micromole/kg/min. (convulsion dose) which is the minimum infusion rate at which partial or complete convulsions are observed. Table 5, column 5 gives the results of the test for the described comparative example compounds as values of the cumulative convulsion dose which is the total amount of drug infused at the point that partial or complete convulsions are first observed.

Determination of Therapeutic Index

The therapeutic index for the compounds 1 to 7 (Table 4) according to the invention and comparative example compounds 8 to 49 (Table 5) was calculated using formula the following:

Cumulative convulsion dose/(20×ED$_{50}$AA)

Tables 4 and 5, column 7, give the calculated value for the therapeutic index of the compounds described therein.

TABLE 4

| Cpd No. | Structure | Chemical name | Convulsion dose (umol/kg/g/min) | cum conv dose (umol/kg) | ED$_{50}$AA (umol/kg/min) | Therapeutic index* |
|---|---|---|---|---|---|---|
| 1 | 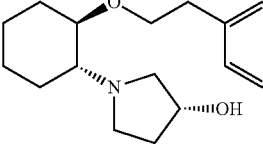 | (1R,2R)-2-[(3R)-Hydroxy-pyrrolidinyl]-1-(3,4-dimethoxy-phenethoxy)-cyclohexane monohydrochloride | 64 | 507 | 1.4 | 18.1 |
| 2 | 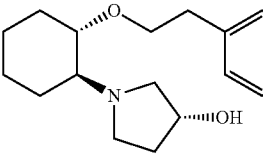 | (1S,2S)-2-[(3R)-Hydroxy-pyrrolidinyl]-1-(3,4-dimethoxy-phenethoxy)-cyclohexane monohydrochloride | 64 | 500.67 | 1.2 | 20.9 |
| 3 | 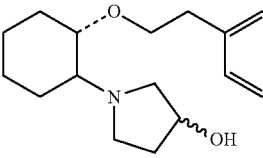 | (1R,2R)/(1S,2S)-2-[(3R)/(3S)-Hydroxy-pyrroldinyl]-1-(3,4-dimethoxy-phenethoxy)-cyclohexane monohydrochloride | 64 | 502 | 1.3 | 19.3 |
| 4 | 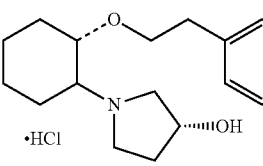 | (1R,2R)/(1S,2S)-2-[(3R)-Hydroxy-pyrrolidinyl]-1-(3,4-dimethoxy-phenethoxy)-cyclohexane monohydrochloride | 64 | 502 | 0.8 | 31.4 |
| 5 | 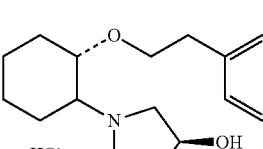 | (1R,2R)/(1S,2S)-2-[(3S)-Hydroxy-pyrrolidinyl]-1-(3,4-dimethoxy-phenethoxy)-cyclohexane monohydrochloride | 64 | 438 | 0.7 | 31.3 |

TABLE 4-continued

| Cpd No. | Structure | Chemical name | Convulsion dose (umol/kg/g/min) | cum conv dose (umol/kg) | ED$_{50}$A A (umol/kg/min) | Therapeutic index* |
|---|---|---|---|---|---|---|
| 6 | (structure) ·HCl | (1R,2R)-2-[(3S)-Hydroxy-pyrrolidinyl]-1-(3,4-dimethoxy-phenethoxy)-cyclohexane monohydrochloride | 64 | 472.24 | 1.6 | 14.8 |
| 7 | (structure) ·HCl | (1S,2S)-2-[(3S)-Hydroxy-pyrrolidinyl]-1-(3,4-dimethoxy-phenethoxy)-cyclohexane monohydrochloride | 64 | 451.67 | 0.9 | 25.1 |

As shown by Table 4 above, the compounds according to the present invention, having the specified dimethoxyphenylethoxy group at position 1 of the cyclohexyl ring and hydroxypyrrolidine group at position 2 of the cyclohexyl ring, exhibit low CNS toxicity together with high antiarrhythmic activity. The experimental results recited above clearly indicate the compounds of the present invention for the effective treatment of arrhythmia. Whereas comparative example compounds 8 to 22 containing only the specified dimethoxyphenylethoxy group at position 1 of the cyclohexyl ring and comparative example compounds 23 to 29 having only the specified hydroxypyrrolidine group at position 2 of the cyclohexyl ring, exhibit both higher CNS toxicity together with lower antiarrhythmic activity when compared with the compounds of the present invention (compounds 1 to 7 shown in Table 4). Accordingly, the therapeutic indexes of the compounds of the present invention are much better. Additional comparative example compounds 30 to 48 correspond to the examples described in WO 99/50225. The test results with these compounds again showed higher CNS toxicity together with lower antiarrhythmic activity than the compounds of the present invention.

TABLE 5

| Comparative Example Cpd No. | Structure | Chemical name | Convulsion dose (umol/kg/min) | cum conv dose (umol/kg) | ED50 AA (umol/kg/min) | Therapeutic index |
|---|---|---|---|---|---|---|
| 8 | (structure) ·HCl | 4-{(1R,2R)/(1S,2S)-2-[2-(3,4-dimethoxy-phenyl)ethoxy]cyclohexyl}morpholine hydrochloride | 16 | 113 | 1.5 | 3.8 |
| 9 | (structure) ·HCl | 7-{(1R,2R)/(1S,2S)-2-[2-(3,4-dimethoxy-phenyl)-ethoxy]cyclohexyl}-1,4-dioxa-7-azaspiro[4.4]nonane hydrochloride | 16 | 91.33 | 1.6 | 2.9 |
| 10 | (structure) ·HCl | 1-{(1R,2R)/(1S,2S)-2-[2-(3,4-dimethoxy-phenyl)-ethoxy]cyclohexyl}-pyrrolidine hydrochloride | 21.33 | 118 | 1.33 | 4.4 |

TABLE 5-continued

| Comparative Example Cpd No. | Structure | Chemical name | Convulsion dose (umol/ kg/ min) | cum conv dose (umol/ kg) | ED50 AA (umol kg/ min) | Therapeutic index |
|---|---|---|---|---|---|---|
| 11 | 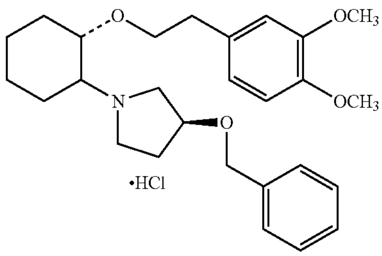 | (3S)-3-benzyloxy-1-{(1R,2R)/(1S,2S)-2-[2-(3,4-dimethoxy-phenyl)-ethoxy]cyclo-hexyl}-pyrrolidine hydrochloride | 8 | 38.13 | 0.5 | 3.8 |
| 12 | 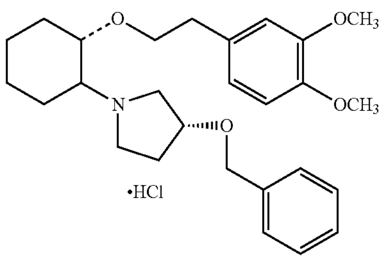 | (3R)-3-benzyloxy-1-{(1R,2R)/(1S,2S)-2-[2-(3,4-dimethoxy-phenyl)-ethoxy]cyclohexyl}-pyrrolidine hydrochloride | 8 | 51.1 | 1 | 2.6 |
| 13 | 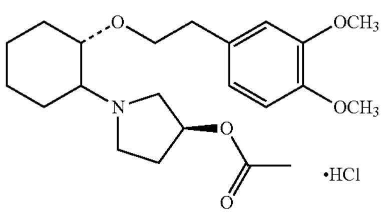 | (3S)-1-{(1R,2R)/(1S,2S)-2-[2-(3,4-dimethoxy-phenyl)-ethoxy]cyclohexyl}-pyrrolidin-3-yl acetate hydrochloride | 8 | 51.9 | 1.3 | 2 |
| 14 | 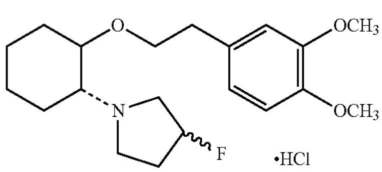 | (3R)/(3S)-1-{(1R,2R)/(1S,2S)-2-[2-(3,4-dimethoxy-phenyl)-ethoxy]cyclohexyl}-3-fluoro-pyrrolidine hydrochloride | 10.67 | 63.33 | 1.4 | 2.3 |
| 15 | 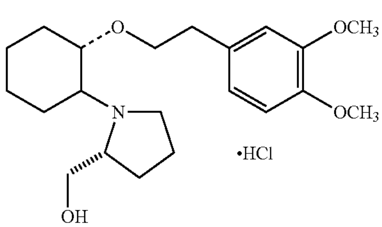 | {(2R)-1-{(1R,2R)/(1S,2S)-2-[2-(3,4-dimethoxy-phenyl)-ethoxy]cyclohexyl}-pyrrolidin-2-yl}methanol hydrochloride | 16 | 142.33 | 0.8 | 8.9 |
| 16 | 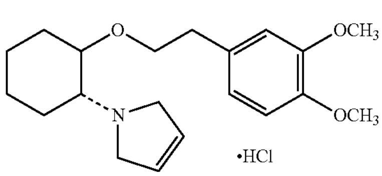 | 1-{(1R,2R)/(1S,2S)-2-[2-(3,4-dimethoxy-phenyl)-ethoxy]cy chlohexyl}-2,5-dihydro-1H-pyrrole hydrochloride | 8 | 44.4 | 2.4 | 0.9 |

TABLE 5-continued

| Comparative Example Cpd No. | Structure | Chemical name | Convulsion dose (umol/kg/min) | cum conv dose (umol/kg) | ED50 AA (umol/kg/min) | Therapeutic index |
|---|---|---|---|---|---|---|
| 17 | 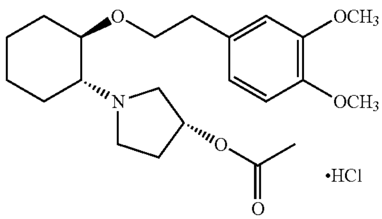 | (3R)-1-{(1R,2R)-2-[2-(3,4-dimethoxyphenyl)-ethoxy]cyclohexyl}-pyrrolidin-3-yl acetate hydrochloride | 13.33 | 74.3 | 2.1 | 1.8 |
| 18 | 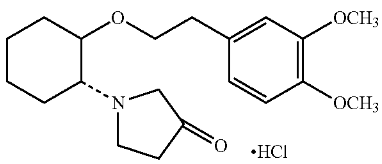 | 1-{(1R,2R)(1S,2S)-2-[2-(3,4-dimethoxyphenyl)-ethoxy]cyclohexyl}-pyrrolidin-3-one hydrochloride | 32 | 235 | 4.5 | 2.6 |
| 19 | 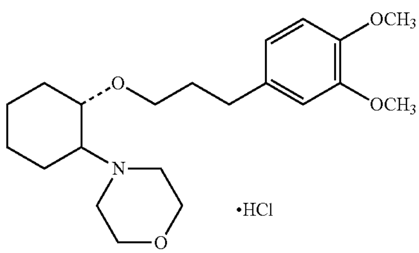 | 4-{(1R,2R)/(1S,2S)-2-[3-(3,4-dimethoxyphenyl)-propoxy]cyclohexyl} morpholine hydrochloride | 16 | 109 | 1.5 | 3.6 |
| 20 | 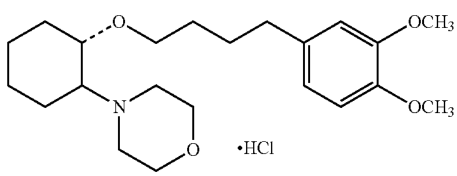 | 4-{(1R,2R)/(1S,2S)-2-[4-(3,4-dimethoxyphenyl)-butoxy]cyclohexyl} morpholine hydrochloride | 10.7 | 66.8 | 1.5 | 2.2 |
| 21 | 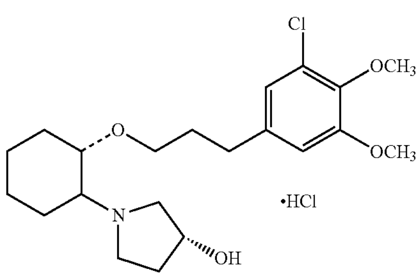 | (3R)-1-{(1R,2R)/(1S,2S)-2-[3-(3-chloro-4,5-dimethoxyphenyl)-propoxy]cyclohexyl} pyrrolidin-3-ol hydrochloride | 13.33 | 90.9 | 0.6 | 7.6 |
| 22 | 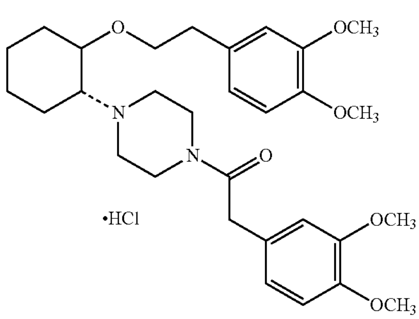 | 1-[(3,4-dimethoxyphenyl)acetyl]-4-{(1R,2R)/(1S,2S)-2-[2-(3,4-dimethoxyphenyl)-ethoxy]cyclohexyl}-piperazine hydrochloride | 21.33 | 133 | 0.6 | 11.1 |

TABLE 5-continued

| Comparative Example Cpd No. | Structure | Chemical name | Convulsion dose (umol/kg/min) | cum conv dose (umol/kg) | ED50 AA (umol kg/min) | Therapeutic index |
|---|---|---|---|---|---|---|
| 23 | 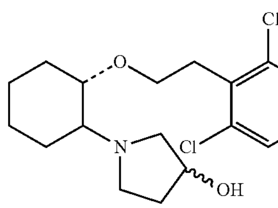 | (3R)/(3S)-1-{(1R,2R)/(1S,2S)-2-[2-(2,6-dichlorophenyl)-ethoxy]cyclohexyl}-pyrrolidin-3-ol hydrochloride | 8 | 65 | 0.6 | 5.4 |
| 24 | 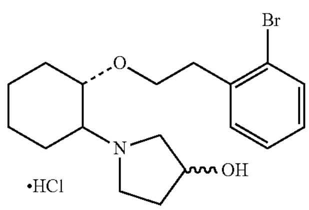 | (3R)/(3S)-1-{(1R,2R)/(1S,2S)-2-[2-(2-bromophenyl)-ethoxy]cyclohexyl}-pyrrolidin-3-ol hydrochloride | 13 | 67 | 0.4 | 8.4 |
| 25 | 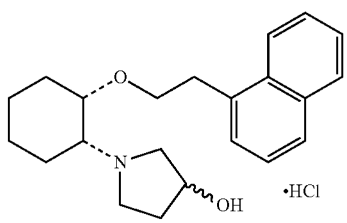 | (3R)/(3S)-1-{(1R,2S)/(1S,2R)-2-[2-(1-naphthyl)ethoxy]-cyclohexyl}-pyrrolidin-3-ol hydrochloride | 16 | 70 | 0.4 | 8.8 |
| 26 | 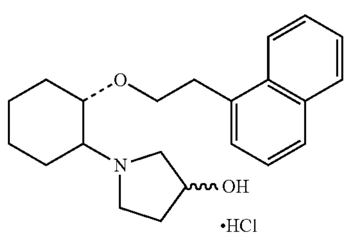 | (3R)/(3S)-1-{(1R,2R)/(1S,2S)-2-[2-(1-naphthyl)ethoxy]-cyclohexyl}-pyrrolidin-3-ol hydrochloride | 8 | 67.33 | 0.78 | 4.3 |
| 27 | 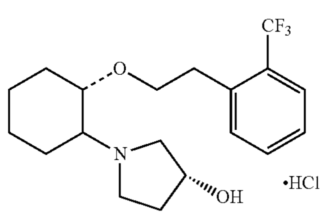 | (3R)-1-{(1R,2R)/(1S,2S)-2-[2-(2-Trifluoromethyl-phenyl)ethoxy]-cyclohexyl}-pyrrolidin-3-ol hydrochloride | 16 | 101.93 | 0.7 | 7.3 |
| 28 | 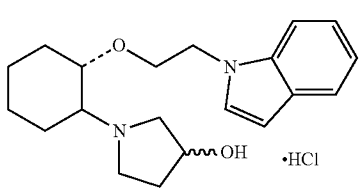 | (3R)/(3S)-1-{(1R,2R)/(1S,2S)-2-[2-(1H-indol-1-yl)ethoxy]cyclohexyl}-pyrrolidin-3-ol hydrochloride | 16 | 113 | 0.6 | 9.4 |

TABLE 5-continued

| Comparative Example Cpd No. | Structure | Chemical name | Convulsion dose (umol/kg/min) | cum conv dose (umol/kg) | ED50 AA (umol kg/min) | Therapeutic index |
|---|---|---|---|---|---|---|
| 29 | 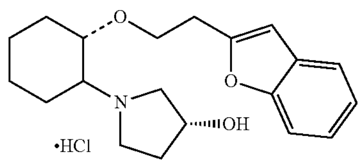 | (3R)-1-{(1R,2R)/(1S,2S)-2-[2-(1-benzofuran-2-yl)ethoxy]-cyclohexyl}-pyrrolidin-3-ol hydrochloride | 10.67 | 65.67 | 1 | 3.3 |
| 30 | 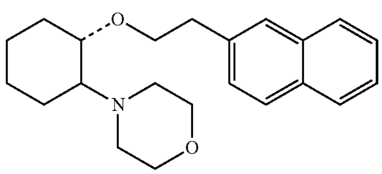 | (1R,2R)/(1S,2S)-[2-(4-morpholinyl)-1-(2-naphthenethoxy)]-cyclohexane | 13.3 | 85 | 0.8 | 5.3 |
| 31 | 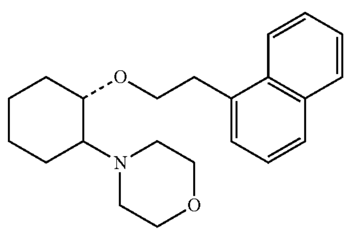 | (1R,2R)/(1S,2S)-[2-(4-morpholinyl)-1-(1-naphthenethoxy)]-cyclohexane | 16 | 93 | 1 | 4.7 |
| 32 | 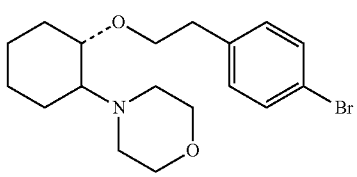 | (1R,2R)/1S,2S)-[2-(4-morpholinyl)-1-(4-bromo-phenethoxy)]-cyclohexane | 12 | 91 | 2.1 | 2.2 |
| 33 | 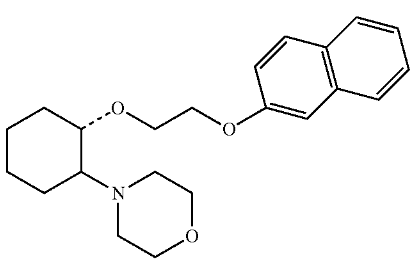 | (1R,2R)/(1S,2S)-[2-(4-morpholinyl)-1-[2-(2-naphthoxy)ethoxy]]-cyclohexane | 8 | 61.63 | 2 | 1.5 |
| 34 | 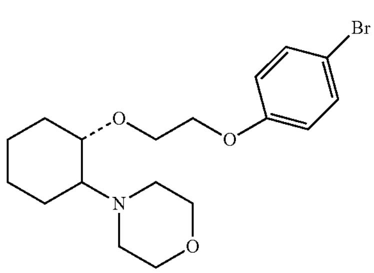 | (1R,2R)/(1S,2S)-[2-(4-morpholinyl)-1-[2-(4-bromo-phenoxy)-ethoxy]]cyclohexane | 10.7 | 83 | 3 | 1.4 |

TABLE 5-continued

| Comparative Example Cpd No. | Structure | Chemical name | Convulsion dose (umol/kg/min) | cum conv dose (umol/kg) | ED50 AA (umol kg/min) | Therapeutic index |
|---|---|---|---|---|---|---|
| 35 | 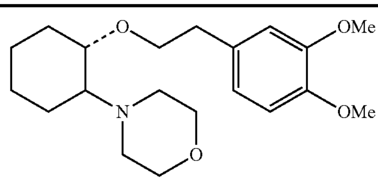 | (1R,2R)/(1S,2S)-[2-(4-morpholinyl)-1-(3,4-dimethoxyphenethoxy)]-cyclohexane | 16 | 113 | 4 | 1.4 |
| 36 | 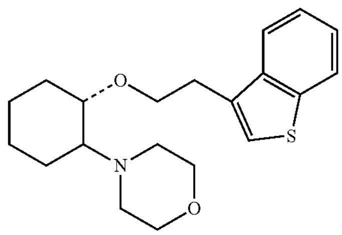 | (1R,2R)/(1S,2S)-[2-(4-morpholinyl)-1-(2-(benzo[b]thiophen-3-yl)]cyclohexane | 8 | 65 | 1 | 3.3 |
| 37 | 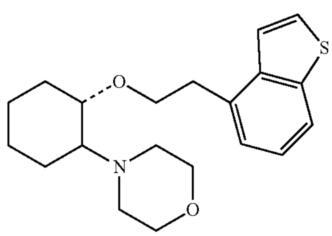 | (1R,2R)/(1S,2S)-[2-(4-morpholinyl)-1-(2-(benzo[b]thiophen-4-yl)]cyclohexane | 8 | 54 | 1 | 2.7 |
| 38 | 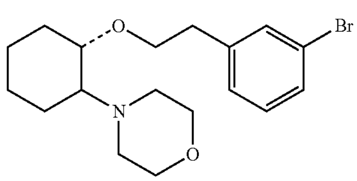 | (1R,2R)/(1S,2S)-[2-(4-morpholinyl)-1-(3-bromophenethoxy)]-cyclohexane | 16 | 131 | 2 | 3.3 |
| 39 | 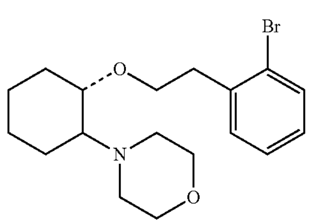 | (1R,2R)/(1S,2S)-[2-(4-morpholinyl)-1-(2-bromophenethoxy)]-cyclohexane | 16 | 125 | 1 | 6.3 |
| 40 | 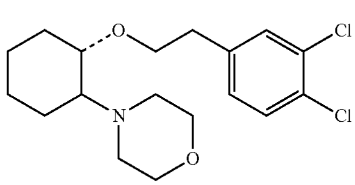 | (1R,2R)/(1S,2S)-2-(4-morpholinyl)-1-(3,4-dichlorophenethoxy)cyclohexane | 16 | 118 | 1.5 | 3.9 |
| 41 | 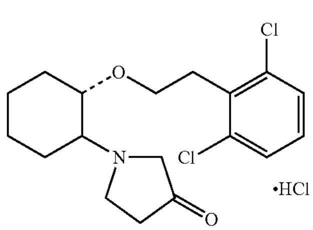 | (1R,2R)/(1S,2S)-2-(3-ketopyrrolidinyl)-1-(2,6-dichlorophenethoxy)cyclohexane monohydrochloride | 32 | 190 | 1.1 | 8.6 |

TABLE 5-continued

| Comparative Example Cpd No. | Structure | Chemical name | Convulsion dose (umol/kg/min) | cum conv dose (umol/kg) | ED50 AA (umol kg/min) | Therapeutic index |
|---|---|---|---|---|---|---|
| 42 | 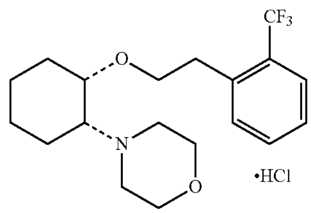 | (1R,2S)/(1S,2R)-2-(4-morpholinyl)-1-[(2-trifluoromethyl)-phenethoxy]-cyclohexane monohydrochloride | 16 | 102 | 1.4 | 3.6 |
| 43 | 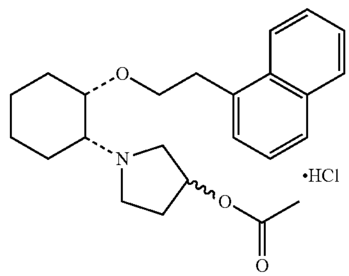 | (1R,2R)/(1S,2S)-2-(3-acetoxy pyrrolidinyl)-1-(1-naphthenethoxy)cyclohexane monohydrochloride | 8 | 65 | 1.4 | 2.3 |
| 44 | 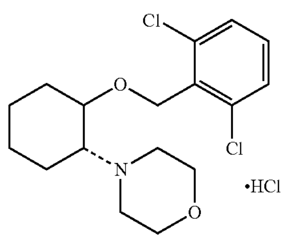 | (1R,2R)/(1S,2S)-2-(4-morpholinyl)-1-[(2,6-dichlorophenyl)methoxy]cyclohexane monohydrochloride | 16 | 97 | 1.8 | 2.7 |
| 45 | 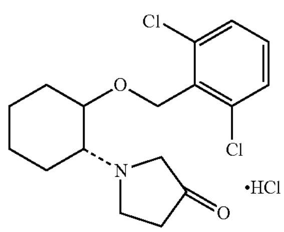 | (1R,2R)/(1S,2S)-2-(3-ketopyrrolidinyl)-1-[(2,6-dichlorophenyl)methoxy]cyclohexane monohydrochloride | 32 | 214 | 2.1 | 5.1 |
| 46 | 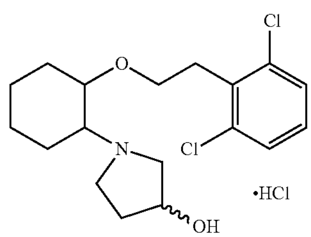 | (1R,2R)/(1S,2S)-2-(3-hydroxypyrrolidinyl)-1-(2,6-dichlorophenethoxy)cyclohexane monohydrochloride | 8 | 65 | 0.6 | 5.4 |
| 47 | 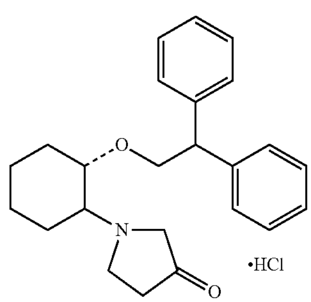 | (1R,2R)/(1S,2S)-2-(3-ketopyrrolidinyl)-1-(2,2-diphenylethoxy)cyclohexane monohydrochloride | 21 | 155 | 2.5 | 3.1 |

TABLE 5-continued

| Comparative Example Cpd No. | Structure | Chemical name | Convulsion dose (umol/ kg/ min) | cum conv dose (umol/ kg) | ED50 AA (umol kg/ min) | Therapeutic index |
|---|---|---|---|---|---|---|
| 48 | 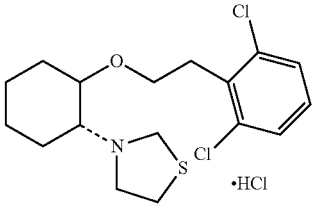 | (1R,2R)/(1S,2S)-2-(3-thiazolidinyl)-1-(2,6-dichlorophenethoxy)cyclohexane monohydrochloride | 43 | 331 | 6.5 | 2.5 |

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited by the specific embodiments and examples contained in this patent.

What is claimed is:

1. A method of stereoselectively making an aminocyclohexyl ether comprising:

reacting a compound of formula (55),

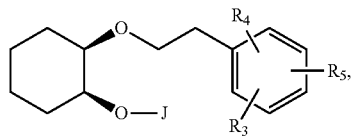
(55)

or a compound of formula (74),

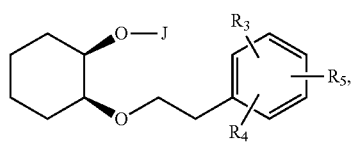
(74)

with a compound of formula (56),

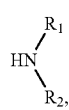
(56)

to form a compound of formula (57),

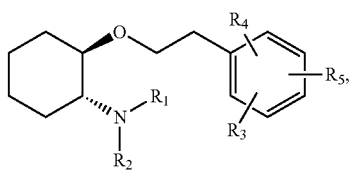
(57)

or a compound of formula (75),

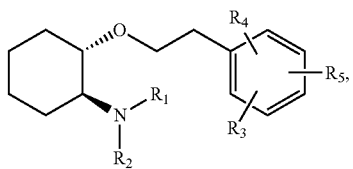
(75)

respectively, wherein $R_1$ and $R_2$, when taken together with the nitrogen atom to which they are directly attached in formula (57) or (75), form a ring denoted by formula (II):

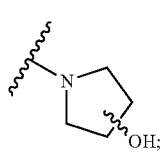
(II)

wherein the method further comprises making the compound of formula (74) or formula (55) by activating a compound of formula (73),

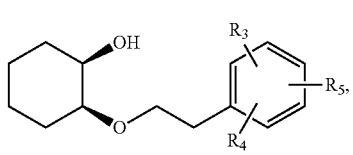
(73)

or a compound of formula (94),

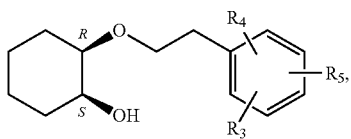
(94)

with a hydroxy activating reagent to form the compound of formula (74) or the compound of formula (55), respectively;

wherein the method further comprises making a compound of formula (73) by hydrogenating and hydrogenolyzing a compound of formula (72),

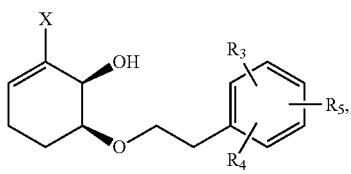
(72)

to form the compound of formula (73);

wherein the method further comprises making a compound of formula (72) by alkylating a compound of formula (51),

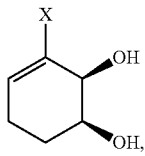
(51)

with a compound of formula (54),

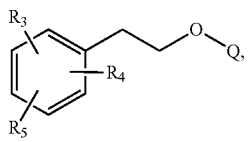
(54)

to form the compound of formula (72);
wherein X is a halide;
wherein O-J is a leaving group;
wherein $R_3$, $R_4$ and $R_5$ are independently selected from hydrogen, hydroxy, and $C_1$-$C_6$alkoxy, with the proviso that $R_3$, $R_4$ and $R_5$ cannot all be hydrogen; and
wherein O-Q is a leaving group that reacts with —OH in the compound of formula (51) to form the compound of formula (72), such that the stereochemical configuration of the compound of formula (51) is retained in the compound of formula (72).

2. A method of making a compound of compound of formula (93):

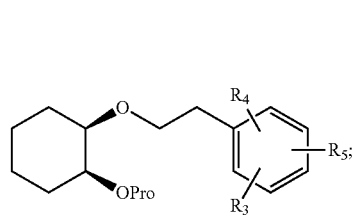
(93)

wherein the method comprises:

alkylating a compound of formula (92),

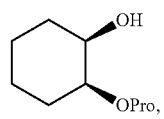
(92)

with a compound of formula (54),

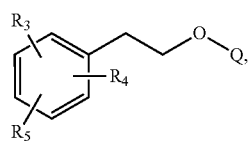
(54)

to form the compound of formula (93);

wherein the method further comprises making a compound of formula (92) by hydrogenating and hydrogenolyzing a compound of formula (91),

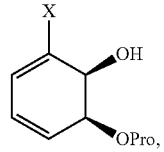
(91)

to form the compound of formula (92);
wherein Pro is a protecting group;
wherein X is a halide;
wherein $R_3$ $R_4$ and $R_5$ are independently selected from hydrogen, hydroxy, and $C_1$-$C_6$alkoxy, with the proviso that $R_3$, $R_4$ and $R_5$ cannot all be hydrogen; and
wherein O-Q is a leaving group that reacts with —OH in the compound of formula (92) to form the compound of formula (93), such that the stereochemical configuration of the compound of formula (92) is retained in the compound of formula (93).

3. A method of stereoselectively making an aminocyclohexyl ether comprising:

reacting a compound of formula (55),

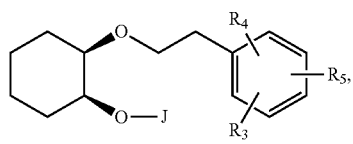
(55)

or a compound of formula (74),

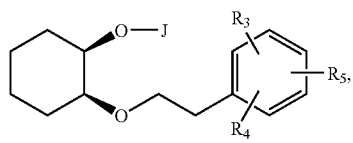
(74)

with a compound of formula (56),

(56)

to form a compound of formula (57),

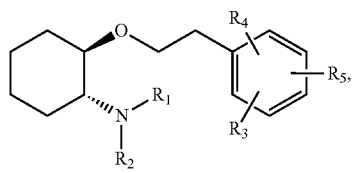
(57)

or a compound of formula (75),

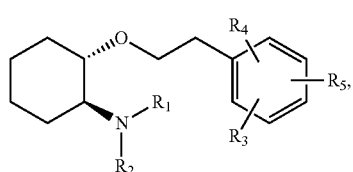
(75)

respectively, wherein $R_1$ and $R_2$, when taken together with the nitrogen atom to which they are directly attached in formula (57) or (75), form a ring denoted by formula (II):

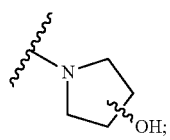
(II)

and wherein the method further comprises making a compound of formula (55) or formula (74) by alkylating a compound of formula (53),

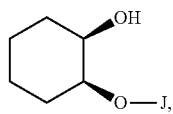
(53)

or a compound of formula (84),

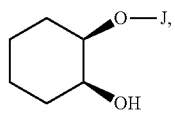
(84)

with a compound of formula (54),

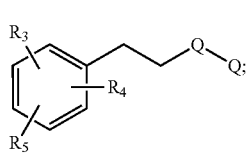
(54)

to form the compound of formula (55) or the compound of formula (74); respectively; and optionally protecting the compound of formula (53) or the compound of formula (84), before said alkylating step;

wherein O-Q is a leaving group that reacts with —OH in formula (53) or formula (84) to form the compound of formula (55) or the compound of formula (74), such that the stereochemical configuration of the compound of formula (53) or the compound of formula (84) is retained in the compound of formula (55) or the compound of formula (74), respectively;

wherein the method further comprises making the compound of formula (53) by hydrogenating and hydrogenolyzing a compound of formula (52),

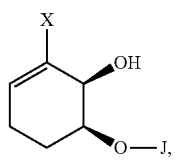
(52)

to form the compound of formula (53);
wherein X is a halide;
wherein O-J is a leaving group; and
wherein $R_3$, $R_4$ and $R_5$ are independently selected from hydrogen, hydroxy, and $C_1$-$C_6$alkoxy, with the proviso that $R_3$, $R_4$ and $R_5$ cannot all be hydrogen.

4. The method of claim 3, wherein the method further comprises making a compound of formula (52):

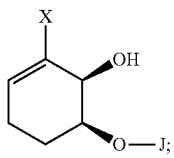

(52)

wherein the method comprises:
activating a compound of formula (51),

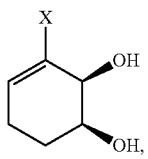

(51)

with a hydroxy activating reagent to form the compound of formula (52);
wherein X is a halide; and
wherein O-J is a leaving group.

5. A method of making an aminocyclohexyl ether comprising:
reacting a compound of formula (55),

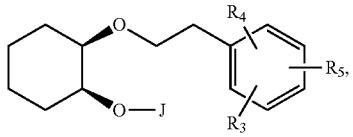

(55)

or a compound of formula (74),

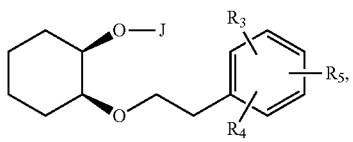

(74)

with a compound of formula (56),

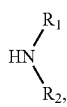

(56)

to form a compound of formula (57),

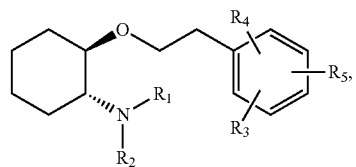

(57)

or a compound of formula (75),

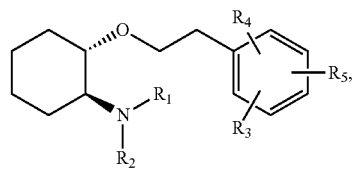

(75)

respectively,
wherein $R_1$ and $R_2$, when taken together with the nitrogen atom to which they are directly attached in formula (57) or (75), form a ring denoted by formula (II):

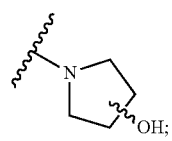

(II)

and
wherein the method further comprises stereoselectively making the aminocyclohexyl ether of formula (57) by
(a) hydrogenating and hydrogenolyzing a compound of formula (91),

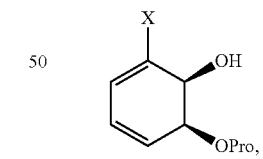

(91)

to form a compound of formula (92),

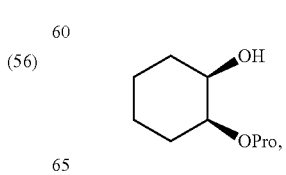

(92)

wherein Pro is a protecting group and X is a halide;

(b) alkylating the compound of formula (92) with a compound of formula (54),

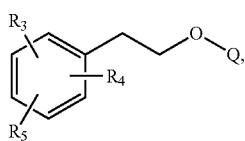
(54)

wherein $R_3$, $R_4$ and $R_5$ are as defined above and O-Q is a leaving group that reacts with the hydroxy group in formula (92) to form a compound of formula (93),

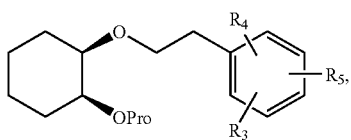
(93)

such that the stereochemical configuration of the compound of formula (92) is retained in the compound of formula (93);

(c) deprotecting the compound of formula (93) to form a compound of formula (94),

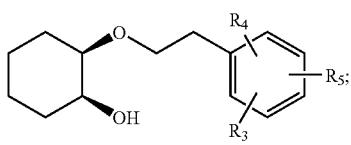
(94)

(d) activating the compound of formula (94) to form a compound of formula (55),

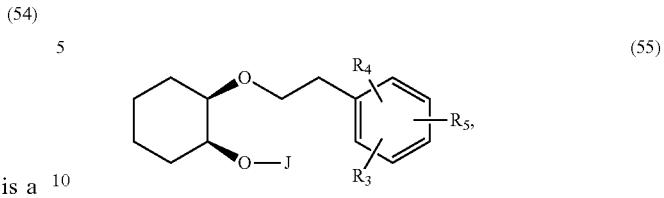
(55)

wherein O-J is a leaving group; and (e) reacting the compound of formula (55) with a compound of formula (56),

(56)

wherein $R_1$ and $R_2$ are as defined above, to form the aminocyclohexyl ether of formula (57);

wherein $R_3$, $R_4$ and $R_5$ are independently selected from hydrogen, hydroxy and $C_1$-$C_6$alkoxy, with the proviso that $R_3$, $R_4$ and $R_5$ cannot all be hydrogen; and wherein O-J is a leaving group.

\* \* \* \* \*

UNITED STATES PATENT AND TRADEMARK OFFICE
CERTIFICATE OF CORRECTION

PATENT NO. : 8,163,938 B2
APPLICATION NO. : 12/833423
DATED : April 24, 2012
INVENTOR(S) : Grace Jung et al.

It is certified that error appears in the above-identified patent and that said Letters Patent is hereby corrected as shown below:

Title Page, Item (56):
"Amin et al., "RPR 101821, a New Potent Cholesterol-lowering Agent. Inhibition of Squalene Synthase and 7-Dehydrocholesterol Reductase", Naunyn-Schmiedeberg's Arch Pharmacol 353:233-240, 1996" should read, --Amin et al., "RPR 101821, a New Potent Cholesterol-lowering Agent: Inhibition of Squalene Synthase and 7-Dehydrocholesterol Reductase", Naunyn-Schmiedeberg's Arch Pharmacol 353:233-240, 1996--.

Title Page 2, Item (56):
"Beatch et al., "RSD1235, a Novel Atrial-Selective Antiarrhythmic Drug, Shows Rapid and Extensive Oral Absorption in Man", 12$^{th}$ International Congress on Cardiovascular Pharmacotherapy, May 7-10, 2003, Barcelona, Spain." should read, --Beatch et al., "RSD1235, A Novel Atrial-Selective Antiarrhythmic Drug, Shows Rapid and Extensive Oral Absorption in Man", 12$^{th}$ International Congress on Cardiovascular Pharmacotherapy, May 7-10, 2003, Barcelona, Spain.--.

Column 162, Line 60:
"wherein $R_3R_4$ and $R_5$ are independently selected from" should read, --wherein $R_3$, $R_4$ and $R_5$ are independently selected from--.

Column 164, Lines 35-40:

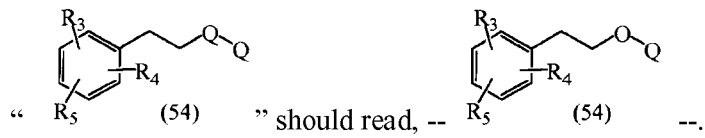

Column 165, Line 4:
"wherein $R_3R_4$ and $R_5$ are independently selected from" should read, --wherein $R_3$, $R_4$ and $R_5$ are independently selected from--.

Signed and Sealed this
Twelfth Day of March, 2013

Teresa Stanek Rea
*Acting Director of the United States Patent and Trademark Office*